(12) United States Patent
Margulies et al.

(10) Patent No.: US 10,281,459 B2
(45) Date of Patent: May 7, 2019

(54) PROTEIN BIOSENSORS, CROSS REACTIVE SENSOR ARRAYS AND METHODS OF USE THEREOF

(71) Applicant: YEDA RESEARCH AND DEVELOPMENT CO. LTD., Rehovot (IL)

(72) Inventors: David Margulies, Rehovot (IL); Leila Motiei, Rehovot (IL); Zohar Pode, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 690 days.

(21) Appl. No.: 14/754,785

(22) Filed: Jun. 30, 2015

(65) Prior Publication Data
US 2015/0362490 A1 Dec. 17, 2015

Related U.S. Application Data

(63) Continuation-in-part of application No. PCT/IL2013/051102, filed on Dec. 31, 2013.
(Continued)

(51) Int. Cl.
*C07K 7/06* (2006.01)
*G01N 33/58* (2006.01)
(Continued)

(52) U.S. Cl.
CPC .......... *G01N 33/53* (2013.01); *C07D 417/06* (2013.01); *C07D 417/14* (2013.01); *C07F 9/6541* (2013.01); *C07K 7/06* (2013.01); *G01N 33/582* (2013.01); *C09K 11/06* (2013.01); *C09K 2211/1029* (2013.01); *C09K 2211/1037* (2013.01); *G01N 33/573* (2013.01);
(Continued)

(58) Field of Classification Search
CPC .... G01N 33/53; G01N 33/582; C07D 417/06; C07D 417/14; C07F 9/6541; C07K 7/06
See application file for complete search history.

(56) References Cited

U.S. PATENT DOCUMENTS 7,939,313 B2 * 5/2011 Heyduk ................ C12N 15/111
435/287.2
2011/0210017 A1 9/2011 Lai et al.

FOREIGN PATENT DOCUMENTS

EP 2320230 A1 5/2011
WO WO 2002/022882 A2 3/2002
(Continued)

OTHER PUBLICATIONS

Green et al. (Biochemistry, 1996, 35:14413-14424) (Year: 1996).*
(Continued)

*Primary Examiner* — Jeremy C Flinders
(74) *Attorney, Agent, or Firm* — Mark S. Cohen; Pearl Cohen Zedek Latzer Baratz LLP

(57) ABSTRACT

The present invention is directed to fluorescent protein biosensors based on oligonucleotide cross reactive sensor arrays including a selective and a non-selective protein surface binding domain for protein detection. Interaction of different protein isoforms with the sensors of this invention yields a unique optical signature for each protein. The unique optical signature allows differentiating between closely related protein isoforms and diagnosing diseases and disorders associated with the proteins also in biofluids.

36 Claims, 34 Drawing Sheets
Specification includes a Sequence Listing.

Related U.S. Application Data

(60) Provisional application No. 61/747,426, filed on Dec. 31, 2012.

(51) Int. Cl.

| | | |
|---|---|---|
| G01N 33/53 | (2006.01) | |
| C07D 417/06 | (2006.01) | |
| C07D 417/14 | (2006.01) | |
| C07F 9/6541 | (2006.01) | |
| G01N 33/574 | (2006.01) | |
| G01N 33/573 | (2006.01) | |
| C09K 11/06 | (2006.01) | |

(52) U.S. Cl.
CPC ..... *G01N 33/574* (2013.01); *G01N 2333/918* (2013.01); *G01N 2333/91177* (2013.01); *G01N 2333/96494* (2013.01)

(56) References Cited

FOREIGN PATENT DOCUMENTS

| WO | WO 2003/014375 A2 | 2/2003 |
|---|---|---|
| WO | WO 2007/100392 A2 | 9/2007 |

OTHER PUBLICATIONS

Alhamdani et al. "Oncoproteomic profiling with antibody microarrays", Genome Med. Jul. 6, 2009;1(7):68.
Anslyn "Supramolecular analytical chemistry", J Org Chem. Feb. 2, 2007;72(3):687-99.
Arai et al. "Fluorescent "Turn-on" system utilizing a quencher-conjugated peptide for specific protein labeling of living cells", Biochem Biophys Res Commun. Jan. 7, 2011; 404(1):211-6.
Baldini et al. "Pattern-based detection of different proteins using an array of fluorescent protein surface receptors", J Am Chem Soc. May 12, 2004;126(18):5656-7.
Behera et al. "Cyanine Dyes: Self Aggregation and Behaviour in Surfactants. A Review", J. Surface Sci. Technol., 2007, vol. 23, No. 1-2, pp. 1-31, 2007.
Biver et al. "Cyanine dyes as intercalating agents: kinetic and thermodynamic studies on the DNA/Cyan40 and DNA/CCyan2 systems", Biophys J. Jul. 2005;89(1):374-83.
Collins et al. "Pattern-based peptide recognition", Chemistry. 2007;13(17):4700-8.
Dajani et al. "Development of a rapid and sensitive immunofluorometric assay for glutathione S-transferase A", Clin Chem. May 2001;47(5):867-73.
De et al. "Sensing of proteins in human serum using conjugates of nanoparticles and green fluorescent protein", Nat Chem. Sep. 2009;1(6):461-5.
Deligeorgiev et al. "Synthesis of novel cyanine dyes containing carbamoylethyl component—Noncovalent labels for nucleic acids detection", Dyes and Pigments vol. 74, Issue 2, 2007, pp. 320-328.
Fei et al. "Thiazole Orange derivatives: synthesis, fluorescence properties, and labeling cancer cells", Bioorg Med Chem. Jan. 15, 2009;17(2):585-91.
Fei et al. "Synthesis and Crystal Structure of Thiazole Orange Derivative", Journal of Chemical Crystallography Aug. 2011, vol. 41, Issue 8, pp. 1232-1236.
Feng et al. "A graphene oxide-peptide fluorescence sensor tailor-made for simple and sensitive detection of matrix metalloproteinase 2", Chem Commun (Camb). Oct. 14, 2011;47(38):10680-2.
Fletcher et al. "Targeting protein-protein interactions by rational design: mimicry of protein surfaces", J R Soc Interface. Apr. 22, 2006;3(7):215-33.
Grate et al. "Laser-mediated, site-specific inactivation of RNA transcripts", Proc Natl Acad Sci U S A. May 25, 1999;96(11):6131-6.
Habig et al. "Glutathione S-transferases. The first enzymatic step in mercapturic acid formation", J Biol Chem. Nov. 25, 1974;249(22):7130-9.
Hanash "Harnessing immunity for cancer marker discovery", Nature Biotechnology 21, 37-38 (2003).
Hoque et al. "Induction of glutathione S-transferase in biofilms and germinating spores of Mucor hiemalis strain EH5 from cold sulfidic spring waters", Appl Environ Microbiol. Apr. 2007;73(8):2697-707.
International Search for PCT Application No. PCT/IL2013/051102 dated Mar. 20, 2014.
International Search for PCT Application No. PCTIL2013051099 dated Apr. 1, 2014.
Jochum et al. "Glutathione-S-transferase subtypes α and π as a tool to predict and monitor graft failure or regeneration in a pilot study of living donor liver transplantation", Eur J Med Res. Jan. 27, 2011;16(1):34-40.
Kapanidis et al. "Site-specific incorporation of fluorescent probes into protein: hexahistidine-tag-mediated fluorescent labeling with (Ni(2+):nitrilotriacetic Acid (n)-fluorochrome conjugates", J Am Chem Soc. Dec. 5, 2001;123(48):12123-5.
Khoudoli et al. "Optimisation of the two-dimensional gel electrophoresis protocol using the Taguchi approach", Proteome Sci. Sep. 9, 2004;2(1):6.
Kolusheva et al. "Color fingerprinting of proteins by calixarenes embedded in lipid/polydiacetylene vesicles", J Am Chem Soc. Oct. 18, 2006;128(41):13592-8.
Lombard et al. "Assays of matrix metalloproteinases (MMPs) activities: a review", Biochimie. Mar.-Apr. 2005;87(3-4):265-72.
Margulies et al. "Combinatorial protein recognition as an alternative approach to antibody-mimetics", Curr Opin Chem Biol. Dec. 2010;14(6):705-12.
Margulies et al. "Protein recognition by an ensemble of fluorescent DNA G-quadruplexes", Angew Chem Int Ed Engl. 2009;48(10):1771-4.
McIlwain et al. "Glutathione S-transferase polymorphisms: cancer incidence and therapy", Oncogene. Mar. 13, 2006;25(11):1639-48.
Miranda et al. "Array-based sensing with nanoparticles: 'chemical noses' for sensing biomolecules and cell surfaces", Curr Opin Chem Biol. Dec. 2010;14(6):728-36.
Miranda et al. "Array-based sensing of proteins using conjugated polymers", J Am Chem Soc. Aug. 15, 2007;129(32):9856-7.
Moerke "Fluorescence Polarization (FP) Assays for Monitoring Peptide-Protein or Nucleic Acid-Protein Binding", Curr Protoc Chem Biol. Dec. 1, 2009;1(1):1-15.
Ogoshi et al. "Chemical Sensors Based on Cyclodextrin Derivatives", Sensors 2008, 8, 4961-4982.
Owicki "Fluorescence polarization and anisotropy in high throughput screening: perspectives and primer", J Biomol Screen. Oct. 2000;5(5):297-306.
Olympus Microscopy Resource Center Solvent Effects on Fluorescence Emission, 2012; downloaded from: http://www.olympusmicro.com/primer/java/jablonski/solventeffects/index.html.
Pei et al. "Light-up properties of complexes between thiazole orange-small molecule conjugates and aptamers", Nucleic Acids Res. May 2009;37(8):e59.
Pietras et al. "PDGF receptors as cancer drug targets", Cancer Cell. May 2003; 3(5):439-43.
Qi et al. "Fluorescence Polarization Binding Assay for Aspergillus fumigatus Virulence Factor UDP-Galactopyranose Mutase", Enzyme Res. 2011;2011:513905.
Reddy et al. "Protein "fingerprinting" in complex mixtures with peptoid microarrays", Proc Natl Acad Sci U S A. Sep. 6, 2005;102(36):12672-7.
Rout et al. "Medication detection by a combinatorial fluorescent molecular sensor", Angew Chem Int Ed Engl. Dec. 7, 2012;51(50):12477-81.
Silva et al. "Experimental and computational investigation of unsymmetrical cyanine dyes: understanding torsionally responsive fluorogenic dyes", J Am Chem Soc. May 2, 2007;129(17):5710-8.
Soh "Selective Chemical Labeling of Proteins with Small Fluorescent Molecules Based on Metal-Chelation Methodology", Sensors 2008, 8(2), 1004-1024.

(56) References Cited

OTHER PUBLICATIONS

Stewart et al. "Identifying protein variants with cross-reactive aptamer arrays", Chembiochem. Sep. 5, 2011;12(13):2021-4.

Stoehlmacher et al. "Association between glutathione S-transferase P1, T1, and M1 genetic polymorphism and survival of patients with metastatic colorectal cancer", J Natl Cancer Inst. Jun. 19, 2002;94(12):936-42.

Takahashi et al. "Molecular subclassification of kidney tumors and the discovery of new diagnostic markers", Oncogene. Oct. 2, 2003;22(43):6810-8.

Tsuchida et al. "Elevation of the placental glutathione S-transferase form (GST-pi) in tumor tissues and the levels in sera of patients with cancer", Cancer Res. Sep. 15, 1989;49(18):5225-9.

Tsuchida et al. "Glutathione transferases and cancer", Crit Rev Biochem Mol Biol. 1992; 27(4-5):337-84.

Ueda et al. "Current and prospective applications of metal ion-protein binding", J Chromatogr A. Feb. 21, 2003;988(1):1-23.

Venkatraman et al. "Fluorogenic probes for monitoring peptide binding to class II MHC proteins in living cells", Nat Chem Biol. Apr. 2007;3(4):222-8.

Wright et al. "Differential receptors create patterns that distinguish various proteins", Angew Chem Int Ed Engl. Oct. 7, 2005;44(39):6375-8.

Yang et al. "Detection of MMP activity in living cells by a genetically encloded surface-displayed FRET sensor", Biochimica et Biophysica Acta 1773 (2007) 400-407.

You et al. "Detection and identification of proteins using nanoparticle-fluorescent polymer 'chemical nose' sensors", Nat Nanotechnol. May 2007;2(5):318-23.

Zhi-Qiang et al. "Specific survivin dual fluorescence resonance energy transfer molecular beacons for detection of human bladder cancer cells", Acta Pharmacol Sin. Dec. 2011;32(12):1522-8. doi: 10.1038/aps.2011.122. Epub Oct. 24, 2011.

Zhou et al. "Pattern recognition of proteins based on an array of functionalized porphyrins", J Am Chem Soc. Feb. 22, 2006;128(7):2421-5.

\* cited by examiner

SEQUENCE LISTING

```
<160> NUMBER OF SEQ ID NOS: 20

<210> SEQ ID NO 1
<211> LENGTH: 6
<212> TYPE: DNA
<213> ORGANISM: Artificial Sequence
<220> FEATURE:
<223> OTHER INFORMATION: Oligodeoxyribose nucleotide

<400> SEQUENCE: 1 tagtac                                                                    6

<210> SEQ ID NO 2
<211> LENGTH: 17
<212> TYPE: DNA
<213> ORGANISM: Artificial Sequence
<220> FEATURE:
<223> OTHER INFORMATION: Oligodeoxyribose nucleotide

<400> SEQUENCE: 2
cgcaagacga gcgaggc                                                       17

<210> SEQ ID NO 3
<211> LENGTH: 17
<212> TYPE: DNA
<213> ORGANISM: Artificial Sequence
<220> FEATURE:
<223> OTHER INFORMATION: Oligodeoxyribose nucleotide
```

```
<400> SEQUENCE: 3
gcctcgctcg tcttgcg                                                    17

<210> SEQ ID NO 4
<211> LENGTH: 6
<212> TYPE: DNA
<213> ORGANISM: Artificial Sequence
<220> FEATURE:
<223> OTHER INFORMATION: Oligodeoxyribose nucleotide

<400> SEQUENCE: 4 gtacta                                                                 6

<210> SEQ ID NO 5
<211> LENGTH: 9
<212> TYPE: PRT
<213> ORGANISM: Artificial Sequence
<220> FEATURE:
<223> OTHER INFORMATION: Peptide Sequence

<400> SEQUENCE: 5

Lys Phe Asp Ser Glu Phe Asp Ser Glu
1               5

<210> SEQ ID NO 6
<211> LENGTH: 9
<212> TYPE: PRT
<213> ORGANISM: Artificial Sequence
<220> FEATURE:
<223> OTHER INFORMATION: Peptide Sequence

<400> SEQUENCE: 6

Lys Ser Thr Gly Val Ser Thr Gly Val
1               5

<210> SEQ ID NO 7
<211> LENGTH: 8
<212> TYPE: PRT
<213> ORGANISM: Artificial Sequence
<220> FEATURE:
<223> OTHER INFORMATION: Peptide Sequence

<400> SEQUENCE: 7

Tyr Gly Glu Gly Glu Phe Asn Lys
1               5

<210> SEQ ID NO 8
<211> LENGTH: 9
<212> TYPE: PRT
<213> ORGANISM: Artificial Sequence
<220> FEATURE:
<223> OTHER INFORMATION: Peptide Sequence

<400> SEQUENCE: 8

Lys Gly Pro Leu Ala Ser Glu Ser Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Peptide Sequence

<400> SEQUENCE: 9
```

Lys Gly Arg Val Gly Ala Val Ser Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Peptide Sequence

<400> SEQUENCE: 10

Thr Ser Pro Val Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Peptide Sequence

<400> SEQUENCE: 11

Lys Ile Arg Gln Lys
1               5

<210> SEQ ID NO 12
<211> LENGTH: 6
<212> TYPE: PRT
<213> ORGANISM: Artificial Sequence
<220> FEATURE:
<223> OTHER INFORMATION: Peptide Sequence

<400> SEQUENCE: 12

Lys Lys Arg Gln Lys Phe
1               5

<210> SEQ ID NO 13
<211> LENGTH: 5
<212> TYPE: PRT
<213> ORGANISM: Artificial Sequence
<220> FEATURE:
<223> OTHER INFORMATION: Peptide Sequence

<400> SEQUENCE: 13

Glu Gly Asp Phe Asn
1               5

<210> SEQ ID NO 14
<211> LENGTH: 7
<212> TYPE: PRT
<213> ORGANISM: Artificial Sequence
<220> FEATURE:
<223> OTHER INFORMATION: Peptide Sequence

<400> SEQUENCE: 14

Leu Tyr Ala Thr Gln Gly Asp
1               5

<210> SEQ ID NO 15
<211> LENGTH: 7
<212> TYPE: PRT
<213> ORGANISM: Artificial Sequence
<220> FEATURE:
<223> OTHER INFORMATION: Peptide Sequence

<400> SEQUENCE: 15

Ile Ser Tyr Val Glu Gly Thr

```
<210> SEQ ID NO 16
<211> LENGTH: 8
<212> TYPE: PRT
<213> ORGANISM: Artificial Sequence
<220> FEATURE:
<223> OTHER INFORMATION: Peptide Sequence

<400> SEQUENCE: 16

Leu Tyr Thr Ala Val Ser Leu Gly
1               5

<210> SEQ ID NO 17
<211> LENGTH: 12
<212> TYPE: PRT
<213> ORGANISM: Artificial Sequence
<220> FEATURE:
<223> OTHER INFORMATION: Peptide Sequence

<400> SEQUENCE: 17

Pro Gly Gly Ser Thr Pro Val Ser Ser Ala Asn Met
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Peptide Sequence

<400> SEQUENCE: 18

Ala Ile Pro Val Ser Arg Glu Glu Lys
1               5

<210> SEQ ID NO 19
<211> LENGTH: 8
<212> TYPE: PRT
<213> ORGANISM: Artificial Sequence
<220> FEATURE:
<223> OTHER INFORMATION: Peptide Sequence

<400> SEQUENCE: 19

Ile Glu Ala Asp Lys Gly Ile Asp
1               5

<210> SEQ ID NO 20
<211> LENGTH: 8
<212> TYPE: PRT
<213> ORGANISM: Artificial Sequence
<220> FEATURE:
```

<223> OTHER INFORMATION: Peptide Sequence

<400> SEQUENCE: 20

Ser Thr Ala Phe Ala Tyr Gly Lys
1               5

PROTEIN BIOSENSORS, CROSS REACTIVE SENSOR ARRAYS AND METHODS OF USE THEREOF

CROSS-REFERENCE TO RELATED APPLICATIONS

This application is a Continuation-In-Part of PCT Application Number PCT/IL2013/051102, filed Dec. 31, 2013; which claims priority of U.S. Provisional Application Ser. No. 61/747,426, filed Dec. 31, 2012; both of which are herein incorporated by reference in their entirely.

FIELD OF THE INVENTION

The present invention is directed to molecular biosensors based on oligonucleotide cross reactive sensor arrays including a selective and a non-selective protein surface binding domain for protein detection. Interaction of different protein isoforms with the sensors of this invention yields a unique optical signature for each protein. The unique optical signature allows differentiating between closely related protein isoforms and diagnosing diseases and disorders associated with the proteins also in biofluids.

BACKGROUND OF THE INVENTION

Fluorescent molecular sensors have become valuable tools in the analytical biosciences owing to their sensitive detection mode, down to the level of a single molecule, the feasibility of naked eye visualization, their versatility, and their small size, which enable them to penetrate the cell membrane and track the rise and fall of various bio-analytes within living cells. Although fluorescent sensors that utilize photo-induced electron transfer (PET), electronic energy transfer (EET) (or fluorescence resonance energy transfer (FRET)), and internal charge transfer (ICT) processes have been developed and used to detect various proteins, most of them suffer from a high background signal that complicates their use in complex biochemical mixtures and within cells.

Extensive efforts have been taken to develop non-reductionist approaches to disease diagnosis. Profiling the expression of multiple proteins, rather than detecting individual protein analytes, has been explored as a means of improving diagnostic accuracy and better understanding the parameters affecting disease states. Potential techniques for proteome-wide analysis include two-dimensional gel electrophoresis, mass spectrometry, and antibody microarrays.

A promising method for obtaining multiplexed protein analysis involves the use of antibodies, which can bind and detect the proteins of interest with high affinity and selectivity. This approach has found widespread applications in medical diagnosis, however, the need for producing an antibody for each target and for using stepwise protocols, in addition to their high cost, relative instability and the difficulties associated with quantifications hamper high-throughput analysis.

Cross-reactive sensor arrays, inspired by the mammalian olfactory system, have recently emerged as an alternative detection method that may address these limitations. When the "nose/tongue" approach is used, proteins can be rapidly differentiated using an array of non-selective synthetic receptors that, in combination, generate a unique optical "fingerprint" upon interacting with each protein. Unlike antibody arrays, which operate according to the "lock-and key" paradigms, arrays that rely on "differential sensing" do not require manufacturing multiple antibodies or using technically challenging procedures. As a result, such systems can straightforwardly discriminate among multiple different proteins as well as profile protein mixtures in blood or urine, which may indicate of disease states.

Despite the numerous advantages of pattern-generating arrays, applications for this technology in medical diagnostics are largely limited by the difficulty of non-selective receptors to operate within biological mixtures. Human serum contains more than 20,000 proteins, of which only ~20 proteins constitute about 99% of the serum protein mass. Thus, although such systems can effectively discriminate among combinations and concentrations of abundant serum proteins, in their current form, they cannot be applied for detecting most disease biomarkers.

Matrix Metalloproteases (MMPs) family of enzymes comprising more than 20 zinc-dependent endopeptidases that share a similar, zinc-dependent binding site, and are capable of degrading virtually every component of the extracellular matrix (ECM). These isozymes can be divided into several subgroups, based on their structures or preferential substrates, which include, among others, collagen, gelatin, and various extracellular matrix proteins.

Owing to their role in tumor growth, metastasis, and angiogenesis, MMPs are considered as important therapeutic targets for treating human cancers. In addition, high levels of members of the MMP family in serum, urine, or tissue have been identified in a variety of human cancers, including breast, pancreatic, bladder, colorectal, ovarian, and prostate cancer (MMP-1 is identified in breast cancer, lung cancer and colorectal cancer; MMP-2 is identified in pancreas cancer, bladder cancer, colorectal cancer, ovarian cancer, prostate cancer and brain cancer; MMP-7 is identified in pancreas cancer, lung cancer and colorectal cancer; MMP-9 is identified in breast cancer, pancreas cancer, bladder cancer, lung cancer, colorectal cancer, ovarian cancer, prostate cancer and brain cancer). Thus, MMPs are considered to be promising biomarkers for different cancers, both for diagnostic and prognostic purposes.

Human Glutathione S-Transferases (GSTs) are a family of widely distributed enzymes that play a role in cell detoxification by catalyzing the conjugation of γ-L-glutamyl-L-cysteinylglycine (gluthation) to a broad range of electrophilic endo toxines and xenobiotics that are subsequently excreted from the cell. This activity is a crucial part of a self-defense mechanism that protects the organism from toxic and sometimes carcinogenic species.

Human soluble GSTs can be mainly subdivided into 7 classes, namely, α (A), μ (M), π (P), θ (T), σ (S), κ (K), and ω (O), which share a similar GST binding domain but differ in their surface characteristics as well as in their tissue distribution (FIG. 1D). Comparative analysis of GST expression in normal and diseased tissues or serum has shown a clear correlation between their expression profiles and disease states. For example, abnormal tissue expression of GST α (A) has been associated with an increased risk for colorectal cancer, ovarian cancer, and clear cell renal cell carcinoma. μ (M) class expression alteration was detected in cases of lung, colon, and bladder cancer, whereas the π (P) class isozymes are overexpressed in the majority of human tumors.

Moreover, several metabolic conditions led to excretion of GST proteins into urine or the blood circulation. For instance, the presence of GST-A in urine or in blood plasma is an early biomarker for hepatocellular damage, whereas elevated serum levels of GST-P is an indicator of various cancers (breast, lung and gastric cancers). GST-A1 is an indicator for colorectal, prostate, breast and lung cancers.

GST-A2 is an indicator for prostate and lung cancers. GST-M1 is an indicator for prostate and breast cancers. An issue of high importance is distinguishing between combinations of several GST subtypes in urine. For example, measurements of GST-A and GST-P in urine provide information about the site of renal tubular injury. In addition, a combination of plasma α and π levels was proposed as a tool to predict and monitor graft failure or regeneration following living donor liver transplantation.

Fibroblast Growth Factors (FGFs) are a family comprising 22 heparin-binding proteins whose over-expression is associated with different types of cancers. Pattern-based detection arrays, specific for this class of proteins, could therefore facilitate their differentiation and, more importantly, might be able to distinguish between medicinally relevant samples involving different combinations or concentrations of FGFs.

Estrogen Receptors (ERα) have been mainly implicated in the development and progression of breast cancer, where much research has focused on identifying alterations within the coding sequence of these receptors in clinical samples. Mutations within ERα have been identified in several different diseases, indicating that the most common technique for determining tumor ER status, namely, immunohistochemical assays or ligand binding assays, might not be efficient for identifying ERs with abnormal ligand binding capacity or reduced functionality. Therefore, pattern-based detection arrays, specific for ERs, might serve as an additional tool for characterizing ER biomarkers.

There is a need for an integrated sensing method, which utilizes both the "lock and key" and "differential sensing" strategies for discriminating among low concentration protein biomarkers in biological mixtures. With this approach cross-reactive sensor arrays can be "tuned" to generate patterns that reflect the composition of specific protein groups, even in the presence of highly abundant serum proteins or within human urine.

The above examples not only stress the importance of developing methods for high-throughput protein analysis in biological fluids but also highlight GSTs, MMPs FGFs and ERs as potential biomarkers for detecting early stages of various diseases, including cancer.

SUMMARY OF THE INVENTION

In one embodiment, this invention is directed to an oligodeoxyribose nucleotide (ODN) derivatives duplex, which consists of:
a first ODN derivative comprising a first ODN sequence, at least one selective protein binder and a donor or acceptor; and
a second ODN derivative comprising a second ODN sequence, which is complementary to the first ODN sequence, at least one non-selective protein surface binder and a donor or acceptor; wherein if one ODN derivative comprises a donor, the other one comprises an acceptor, and wherein at least one of the donor or acceptor is a fluorophore.

In another embodiment, the selective protein binder is marimastat, ethacrynic acid (EA), bis ethacrynic acid, Ni-nitrilotriacetic acid (Ni-NTA), bis-Ni-NTA, tris-Ni-NTA, PDGF-BB aptamer, heparin derivative, FGF aptamer, or estrogen.

In another embodiment, the non-selective protein surface binder comprises a peptide tripod, represented by the structure of formula A:

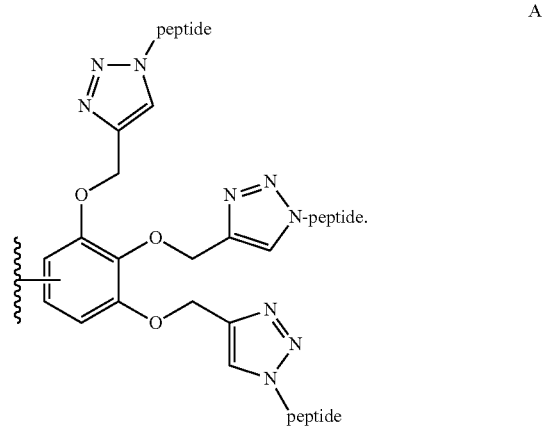

In another embodiment, the first ODN derivative of the oligodeoxyribose nucleotide (ODN) derivatives duplex is represented by the structure of formula IA, IB or IC:

$$\text{ODN1-}X^2\text{—}Y\text{—}X^1\text{—}(R^1)_k \quad \text{(IA)};$$

$$Y\text{—}X^2\text{—}\text{ODN1-}X^1\text{—}(R^1)_k \quad \text{(IB)};$$

$$\text{ODN1-}X^2\text{—}R^1\text{—}X^1\text{—}(Y)_k \quad \text{(IC)};$$

wherein ODN1, $X^2$, $R^1$, $X^1$, Y, and k are defined below.

In another embodiment, the second ODN derivative is represented by the structure of formula IIA, IIB or IIC:

$$\text{ODN2-}X^{2'}\text{—}Y'\text{—}X^{1'}\text{—}R^{1'} \quad \text{(IIA)};$$

$$Y'\text{—}X^{2'}\text{-ODN2-}X^{1'}\text{—}R^{1'} \quad \text{(IIB)};$$

$$\text{ODN2-}X^{2'}\text{—}R^{1'}\text{—}(X^{1'}\text{—}Y')_{k'} \quad \text{(IIC)};$$

wherein ODN2, $X^{2'}$, $R^{1'}$, $X^{1'}$, Y', k' are defined below.

In another embodiment, the first ODN derivative of formula IA is represented by the structure of formula III:

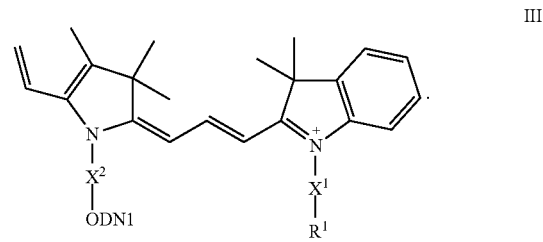

In another embodiment, the second ODN derivative of formula IIA is represented by the structure of formula IV:

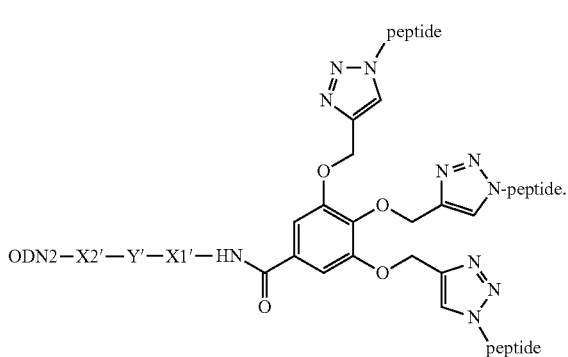

In another embodiment, the second ODN derivative of formula IIC is represented by the structure of formula V:

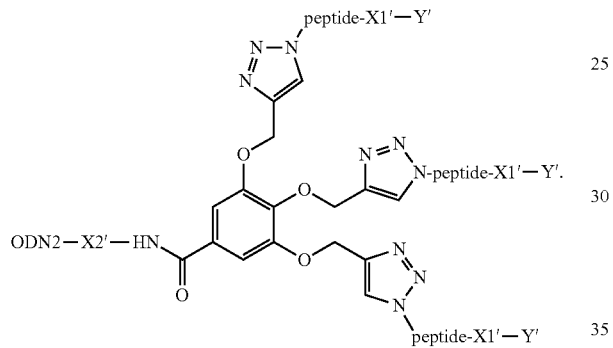

In another embodiment, the first ODN derivative of the oligodeoxyribose nucleotide (ODN) to derivatives duplex is represented by the structure of formula IIIA, IIIB or IIIC:

ODN1-[(PEG)$_m$-(P)$_n$]$_v$—X$^2$—Y—(P)$_q$—(Split)[X$^1$—R$^1$]$_t$  (IIIA);

Y—X$^2$—ODN1-[(PEG)$_m$-(P)$_n$]$_v$—(Split)[X$^1$—R$^1$]$_t$  (IIIB);

ODN1-[(PEG)$_m$-(P)$_n$]$_v$—X$^2$—(Split)[R$^1$—X$^1$—Y]$_t$  (IIIC);

wherein ODN1, PEG, P, X$^2$, R$^1$, X$^1$, Y(Split), n, m, v, q, and t are defined below.

In another embodiment, the second ODN derivative of the oligodeoxyribose nucleotide (ODN) derivatives duplex is represented by the structure of formula IVA, IVB or IVC:

ODN2-[(PEG)$_{m'}$—(P)$_{n'}$]$_{v'}$—X$^{2'}$—Y'—(P)$_{q'}$—X$^{1'}$-(Q)(R$^{1'}$)$_k$  (IVA);

Y'—X$^{2'}$-ODN2-[(PEG)$_{m'}$—(P)$_{n'}$]$_{v'}$—X$^{1'}$-(Q)(R$^{1'}$)$_k$  (IVB);

ODN2-[(PEG)$_{m'}$—(P)$_{n'}$]$_{v'}$—X$^{2'}$-(Q)[R$^{1'}$—X$^{1'}$—Y']$_k$  (IVC);

wherein ODN2, PEG, P, X$^{2'}$, R$^{1'}$, X$^{1'}$, Y', Q, p, n', m', v', q', and k are defined below.

In another embodiment, this invention is directed to a method of differentiating between proteins and/or protein isoforms in a biological medium comprising:
(i) Incubating an array of complementary two oligodeoxyribose nucleotide (ODN) derivatives duplexes with a biological medium comprising said proteins and/or protein isoforms;

wherein each of said duplexes is the oligodeoxyribose nucleotide (ODN) derivatives duplex of this invention, wherein the non-selective protein surface binder comprises a peptide tripod, represented by the structure of formula A as defined herein above and wherein said "peptide" is different for each ODN derivative duplex;

wherein binding said protein and/or protein isoforms with each of said duplexes results in a conformational change of said duplex and thereby to a unique optical signature for each duplex; and (ii) measuring said optical signature obtained by said binding of step (i);

thereby, differentiating between proteins and/or protein isoforms in said biological medium.

In another embodiment, this invention is directed to a method of diagnosing a disease or disorder in a subject, wherein said diagnosis comprises detection of a protein biomarker; said method comprises:
(i) collecting a biological sample from a subject;
(ii) optionally isolating components from said biological sample;
(iii) incubating an array of complementary oligodeoxyribose nucleotide (ODN) derivatives duplexes with said biological sample;

wherein each of said duplexes is the oligodeoxyribose nucleotide (ODN) derivatives duplex of this invention, wherein the non-selective protein surface binder comprises a peptide tripod, represented by the structure of formula A as defined herein above and wherein said "peptide" is different for each ODN derivative duplex;

wherein binding of said protein biomarker with each of said duplexes results in a conformational change of said duplex and thereby to a unique optical signature for each duplex;

(iv) measuring said optical signature obtained by said binding of step (iii); and
(v) identifying said protein biomarker in said sample based on the measurement of a unique optical signature, which characterizes the specific protein biomarker;
wherein said protein biomarker being characteristic of a disease or disorder;
thereby, diagnosing a disease or disorder in a subject.

In another embodiment, the protein is matrix metalloproteases (MMPs) protein and its isoforms, glutathione S-Transferase (GSTs) protein and its isoforms, platelet derived growth factor, Histidine-tag proteins, estrogen receptor, or fibroblast growth factor (FGF).

In another embodiment, the disease or disorder is breast cancer, lung cancer, colorectal cancer, pancreatic cancer, bladder cancer, ovarian cancer, prostate cancer, brain cancer, clear cell renal cell carcinoma, gastric cancer, renal tubular injury or any combination thereof.

In one embodiment, this invention is directed to a protein sensor, said sensor comprises an array of synthetic receptors, wherein each of said synthetic receptors comprises the ODN derivative duplex of this invention, and wherein said synthetic receptors differ from each other in their non-selective protein surface binder.

In another embodiment, the non-selective protein surface binder comprises a peptide tripod, represented by the structure of formula A:

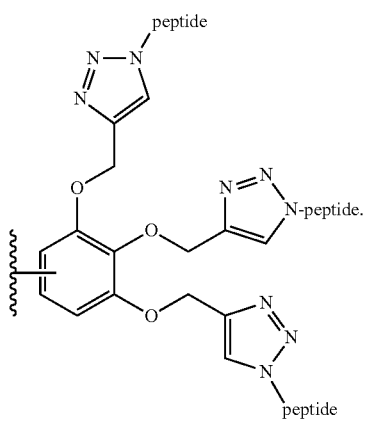

In one embodiment, this invention is directed to a method for the preparation of a compound comprising a non-selective tripodal protein surface binder, said method comprises the following steps:

a. conjugation of compound of the formula:

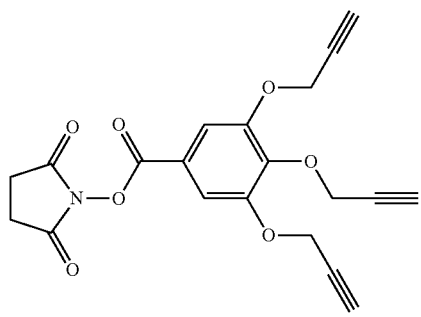 [SMILES: C#CCOc1cc(C(=O)ON2C(=O)CCC2=O)cc(OCC#C)c1OCC#C]

to an amino derivatized compound; and b. conjugation of the product resulting from step a to an azido-modified peptide using the copper-catalyzed Huisgen 1,3-dipolar cycloaddition (the "click reaction").

In one embodiment, this invention is directed to a protein sensor, said sensor comprises a non-selective protein surface binder represented by the structure of formula A:

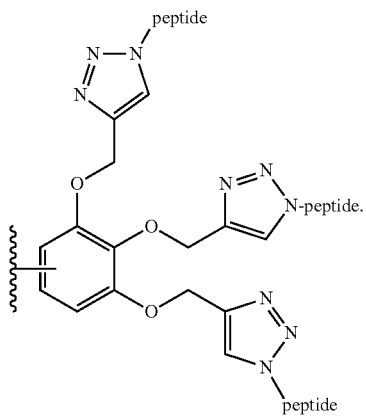

In another embodiment, the protein sensor further comprises a selective protein binder. In another embodiment, the protein sensor further comprises a fluorophore. In another embodiment, the protein sensor further comprises a donor and an acceptor, wherein at least one of the donor or acceptor is a fluorophore. In another embodiment, each donor or acceptor is attached to or in close proximity to one of the selective and non-selective binders of said sensor.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

(FIG. 1B) Binding to different protein isoforms (a-d) is expected to induce different conformations, leading to distinct FRET efficiencies. (FIG. 1C) Schematic representation of different FRET efficiency levels (isoform b vs. c). (FIG. 1D) electrostatic mapping of the GST isoforms A1, A2, M1, and P1.

(FIG. 2C) Representative structure of a peptide. Sequences of the peptides are listed in Table 1.

(FIG. 5B) PCA mapping of the GST isozymes discriminated by the array. (a) GST-A1, (b) GST-M1, (c) GSTA1-GST-P1, (d) GST-A2, and (e) GST-P1 where the squares and circles represent the replicates in buffer and in the spiked protein solution, respectively. The spiked protein solution contained transferrin (150 nM), haptoglobin mixed type (150 nM), IgG (150 nM), a1-acid-glycoprotein (150 nM), APOA1 (150 nM), leptin (100 nM), FGF-21 (100 nM), thyroglobulin (100 nM). The experiments in buffer solutions were carried out using 20 nM of each receptor and 150 nM of GST isozymes. In the spiked protein solution, final concentrations of the receptors and GST isozymes were 26 nM and 300 nM, respectively.

(FIG. 7B) Change in the fluorescence intensities of receptor 3 (20 nM) upon addition of GST isoforms and the control proteins. Final concentration of GST isoforms and the control proteins were as follow: each GST (150 nM), FGF-21 (1 μM), APOA1 (500 nM), IgA (1 μM), Transferrin (500 nM), leptin (1 μM), α₁-acid glycoprotein (1 μM), IgG (500 nM), and heptaglobin (1 μM).

FIG. 11A depicts a schematic differential molecular beacons (MBs) consisting of two weakly associated oligonucleotides (ODNs). ODN 1 is appended with a fluorophore and a selective protein binder, whereas ODN2 is modified with a quencher and a non-selective protein surface binder. Binding to an isoform with a complementary surface (isoform I) will decrease the signal, whereas binding to an isoform with different surface characteristics (isoform II) will not affect the emission. FIG. 11B depicts an array of MBs involving different protein surface binders that can generate different patterns for each isoform.

FIGS. 12A and 12B are two different designs of molecular beacons of this invention, wherein the position of the quencher/fluorophore are different in respect to the oligonucleotide.

FIG. 13A depicts a synthetic scheme of the non-selective binder (ODN-39). FIG. 13B depicts a synthetic scheme of a MMP selective binder (ODN-49). FIG. 13C depicts a synthetic scheme of a GST selective binder possessing one ethacrynic acid (EA) derivative (ODN-51). FIG. 13D depicts a synthetic scheme of a GST selective binder possessing two EA derivatives (ODN-53).

FIGS. 15A-15D provide initial velocity analysis of the hydrolysis of a fluorogenic substrate by the active form of (A) MMP-1, (B) MMP-2, (C) MMP-7, and (D) MMP-9. FIG. 15E presents fluorescence polarization analysis of ODN-49 binding to MMP-7.

FIG. 19B depicts a fluorescence response of a single MB to the presence of MMP-7, VEGF, and PDGF (80 nM each). The MBs are assembled from ODN-49 (20 nM) and ODN-39-P1 (5 μM). P1, P5 and P6 refer to different peptides.

FIGS. 21C and 21D present the corresponding PCA plots.

FIG. 22A depicts a synthetic scheme of the non-selective protein surface binder (ODN-56). FIG. 22B depicts a synthetic scheme of a GST selective binder (ODN-58).

Figure 1A:
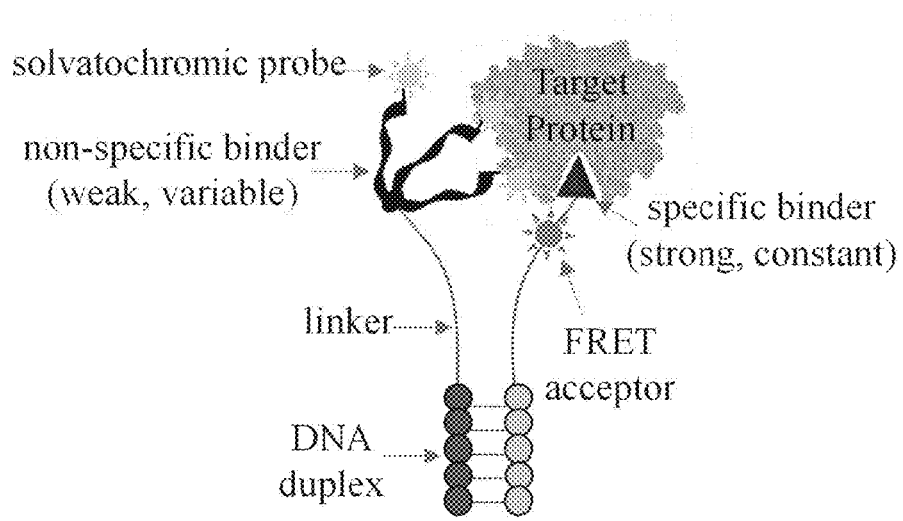
FIG. 1A-1D depicts (FIG. 1A) A schematic representation of synthetic protein receptors with dual interaction modes. The selective binder appended with a fluorophore (Cy3) and a selective recognition element (triangle) provides the molecule with high affinity and selectivity toward a particular protein family. The non-selective protein surface binder appended with a fluorescent donor (dansyl) varies between the different receptors.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

This invention is directed to an integrated sensing scheme, which utilizes both the "lock and key" and "differential sensing" strategies for discriminating among low concentration protein biomarkers in biological mixtures. With this approach cross-reactive sensor arrays can be "tuned" to generate patterns that reflect the composition of specific protein groups, even in the presence of highly abundant serum proteins or within human urine.

Accordingly, this invention is directed to an array of synthetic receptors that can discriminate among closely related proteins (e.g. Glutathione S-Transferase (GST) isozymes, matrix metalloproteases MMPs), in biological media (e.g. human serum, human urine).

Figures 1B, 1C:
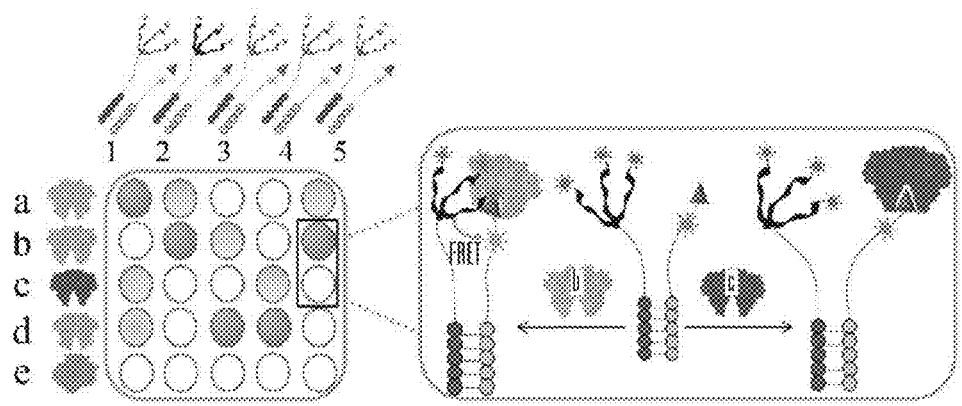
Figure 1D:
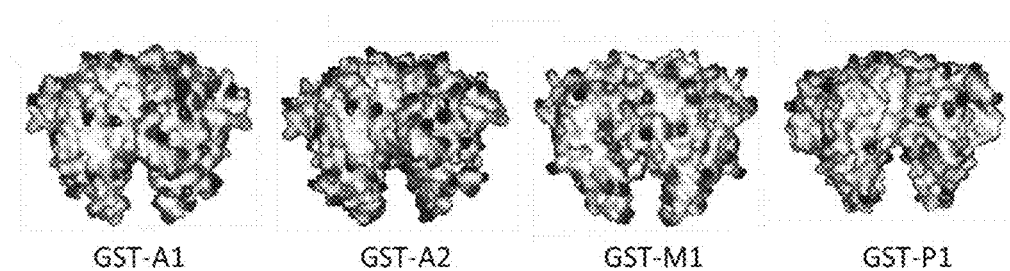

According to this invention, hetero-multivalency and binding cooperatively are used to create a cross-reactive sensor array with selectivity toward specific protein groups (FIG. 1A-1D). As shown in FIG. 1A, each fluorescent receptor in the array is self-assembled from two complementary oligonucleotides (ODNs) appended with distinct protein recognition motifs: selective or non-selective. On the one hand, these receptors bind particular protein groups with high affinity and selectivity. On the other hand, they possess a non-selective binding domain that respond differently to closely related isoforms, therefore generating unique signal pattern for each isoform. The selective binder can be a synthetic inhibitor, a natural ligand or an aptamer that is selective toward a specific protein group, but also broad spectrum. In other words, this unit can strongly interact with multiple isoforms of a particular protein family (e.g. ethacrynic acid (EA), a broad-spectrum inhibitor of GSTs; Marimastat, a broad spectrum inhibitor of MMPs). Because this binder is maintained in all different duplexes (FIG. 1B), it provides the receptors with high affinity and selectivity toward a small set of protein biomarkers. The non-selective binding domain (FIG. 1A), on the other hand, is a relatively weak binder that varies among the different receptors (FIG. 1B). In one embodiment, the non selective binder contains a tripodal peptide group with a large surface area of 750-1500 $Å^{-2}$, typical for synthetic protein surface receptors and protein-protein interaction. By systematically modifying the non selective binder's sequence and length one can obtain a library of protein surface binders with distinct physico-chemical properties.

Generating an array of duplexes, which differ only in their protein surface binders (FIG. 1B), results in an analytical device in which all the receptors can bind to a particular protein family. However, each non-selective binder in the array (e.g. tripodal peptide) is expected to interact differently with the surfaces of distinct isoforms (FIG. 1A-1D, isoform a vs. b).

Distinct optical "fingerprint" for different protein isoforms (e.g. GSTs, MMPs) can be generated by modifying the selective and non-selective binders with solvatochromic fluorescent donors and a fluorescent acceptor, respectively (FIG. 1A). In this way, different family members could be differentiated using e.g. fluorescence resonance energy transfer (FRET) efficiency (which is sensitive to the distance and orientation), owing to changes that occur in the distance between the donor and acceptors and/or the local environment of the solvatochromic probes (FIG. 1C). Notably, because binding cooperatively between the weak and strong binders can only occur with proteins that possess the specific recognition domain (FIG. 1B, proteins a-d), other proteins which lack this site should not affect the emission of the array (FIG. 1B, protein e).

In one embodiment, the non-selective protein surface binder peptides connected to one oligonucleotide derivative are labeled with solvatochromic fluorophore, (e.g. dansyl), whose emission spectrum overlaps the excitation spectrum of Cy3 which is incorporated into the complementary oligonucleotide derivative in the vicinity of the selective binder (e.g. EA molecule, Marimastat). In another embodiment, the oligonucleotide derivative which is connected to the non-selective binder peptides is labeled with dabcyl whose emission spectrum overlaps the excitation spectrum of fluorescein (FAM) which is incorporated into the complementary oligonucleotide derivative.

In one embodiment, this invention is directed to an oligodeoxyribose nucleotide (ODN) derivatives duplex, which consists of a first ODN derivative comprising a first ODN sequence, at least one selective protein binder and a donor or acceptor; and a second ODN derivative comprising a second ODN sequence, which is complementary to the first ODN sequence, at least one non-selective protein surface binder and a donor or acceptor; wherein if one ODN derivative comprise a donor, the other one comprises an acceptor, and wherein at least one of the donor or acceptor is a fluorophore.

The "selective binder" is any compound or derivative that can binds particular protein or protein groups with high affinity and selectivity. In one embodiment, the selective binder is a synthetic inhibitor, a natural ligand or an aptamer that is selective toward a specific protein group, but also broad spectrum which binds particular protein groups with high affinity and selectivity. In another embodiment, the selective protein binder of this invention is any selective protein binder known in the art. In another embodiment, the selective protein binder is marimastat, ethacrynic acid (EA), bis ethacrynic acid, Ni-nitrilotriacetic acid (Ni-NTA), bis-Ni-NTA, tris-Ni-NTA, platelet-derived growth factor-BB homodimer (PDGF-BB) aptamer, heparin derivative, fibroblast growth factor (FGF) aptamer, estrogen, or derivatives thereof wherein the term "derivative" includes but not limited to alkyl derivatives, amide derivatives, carboxy derivatives, and the like. In another embodiment, the selective protein binder is DNA aptamar, peptide binder to fibronectin (e.g., VGVMYEYVPQVT), Ethacrynic acid (EA), Modified Marimastat, DNA or RNA aptamer, $Ni^{+2}$-NTA, bis-$Ni^{+2}$-NTA, peptide aldehydes (for example, Ac-WEHD-CHO or Ac-DEVD-CHO or Z-VAD-FMK), peptide binder to β-amyloid (for example, KLVFF), suberoylanilide hydroxamic acid (SAHA) derivative, estrogen, estrone or estriol, or any combination thereof. In another embodiment, a selective protein binder is any molecule that can target different type of fusion proteins that contain certain protein tags such as: a polyhistidine tag, (e.g., 6×His-tag, 10×His-tag), tetra cysteine peptide (CCPGCC, TC tag), etc. In one embodiment, the selective binder comprises a His-tag binder. In another embodiment, the selective binder of this invention comprises Ni-nitrilotriacetic acid (Ni-NTA), bis-Ni-NTA, or tris-Ni-NTA. In another embodiment, the selective binder of this invention comprises a derivative of Ni-nitrilotriacetic acid (Ni-NTA), bis-Ni-NTA, or tris-Ni-NTA.

In another embodiment, marimastat is selective to matrix metalloproteases (MMPs) protein and to its isoforms. In another embodiment, ethacrynic acid (EA) is selective to glutathione S-Transferase (GSTs) protein and its isoforms. In another embodiment, bis ethacrynic acid, is selective to glutathione S-Transferase (GSTs) protein and its isoforms. In another embodiment Ni-nitrilotriacetic acid (Ni-NTA) is selective to His-tag protein. In another embodiment bis-Ni-nitrilotriacetic acid (Bis-Ni-NTA) is selective to His-tag protein. In another embodiment tris-Ni-nitrilotriacetic acid (tris-Ni-NTA) is selective to His-tag protein. In another embodiment, PDGF-BB is selective to platelet derived growth factor. In another embodiment, heparin or FGF aptamer BB is selective to fibroblast growth factor (FGF). In another embodiment, estrogen is selective to estrogen receptor (ERα, ERβ). In another embodiment, suberoylanilide hydroxamic acid (SAHA) derivative is selective to Histone deacetylases (HDACs). In another embodiment, peptide binder to β-amyloid (e.g., KLVFF) is selective to β-amyloid. In another embodiment, peptide aldehydes (e.g., Ac-WEHD-CHO or Ac-DEVD-CHO or Z-VAD-FMK) are selective to Caspases. In another embodiment, $Ni^{+2}$-NTA or bis-$Ni^{+2}$-NTA are selective to His-tagged Protein. In another embodiment, DNA or RNA aptamers are selective to PSA. In another embodiment, peptide binders to fibronectin (e.g., VGVMYEYVPQVT) are selective to Firbronectin. In another embodiment, DNA aptamers are selective to Lysosyme. In another embodiment, $R^1$ of formula IA, IB and IC as described herein below is a selective protein binder derivative, including alkyl derivatives, amide derivatives, carboxy derivatives, and the like.

A "non-selective protein surface binder" which can also be referred to herein as a "protein surface receptor", is a functionalized amino acid sequence or peptide groups that react non-selectively, with complementary protein surfaces based on their size, topology and electrostatic potential. By systematically modifying the non-selective binder's sequence and length one can obtain a library of protein surface binders with distinct physicochemical properties. In one embodiment, the non-selective protein surface binder is a relatively weak binder that varies among the different receptors. In one embodiment, the non-selective binder contains a tripodal peptide group with a large surface area of 750-1500 $Å^{\circ 2}$, typical for synthetic protein surface receptors and protein-protein interaction. Each non-selective binder (e.g. tripodal peptide) is expected to interact differently with the surfaces of distinct proteins of interest (POI). In another embodiment, the non-selective protein surface binder is a peptide. In another embodiment, the non-selective protein surface binder comprises at least one peptide. In another embodiment, the non-selective protein surface binder comprises three peptides. In another embodiment, the non-selective protein surface binder is a tripodal peptides having a surface of 750-1500 $Å^2$. In another embodiment, the non-selective binder comprises at least one peptide as listed in Table 1.

In another embodiment, the non-selective protein surface binder comprises a peptide tripod, represented by the structure of formula A:

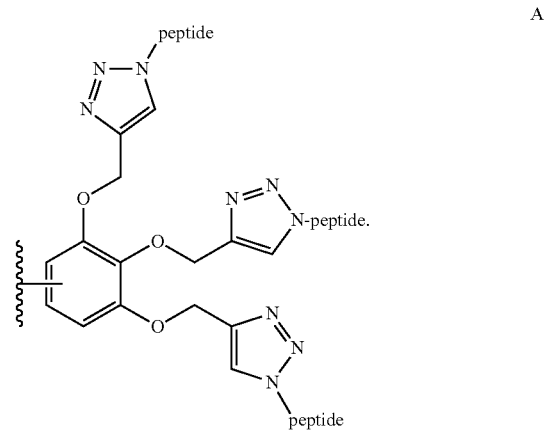

In another embodiment, the peptides comprised in the non-selective protein surface binder of formula A are all the same. In another embodiment, the peptides comprised in the non-selective protein surface binder of formula A are different. In another embodiment, the peptides comprised in the non-selective protein surface binder of formula A comprise between 2 to 30 amino acid sequences. In another embodiment, the peptides comprise between 5 to 15 amino acid sequences. In another embodiment, the peptides comprise between 5 to 10 amino acid sequences. In another embodiment, the peptides further comprise linkers which link between the amino acid sequence of the peptide and the compound to which they are attached. In another embodiment, the peptides are attached to the N atoms of the compound through linkers. In another embodiment, the linker is a substituted or unsubstituted linear or branched alkyl chain of 1-50 carbon atoms, substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof. In another embodiment, the linker is a $C_1$-$C_6$ alkyl. In another embodiment, the linker is a propyl (i.e., —$CH_2$—$CH_2$—$CH_2$—). In another embodiment the peptides comprise the sequence as described in Table 1, Example 1. In another embodiment the peptides comprise the sequence as described in Table 3, Example 8. In another embodiment the peptides comprises the sequence as described in Table 5, Example 16. In another embodiment the peptide includes amino acid sequence interrupted by a donor or an acceptor, or substituted by a donor or an acceptor. In another embodiment, the donor or acceptor is covalently bonded to a lysine residue (K).

In some embodiments, the oligodeoxyribose nucleotide (ODN) derivatives of this invention include a first ODN derivative comprising a first ODN sequence and a second ODN derivative comprising a second ODN sequence. The first and second ODN sequences are complementary. In some embodiments, the ODN sequences of this invention are commercially available sequences. In some embodiments the sequences include between 3-100 oligodeoxyribose nucleotides. In one embodiment the sequences include between 3-50 oligodeoxyribose nucleotides. In one embodiment the sequences include between 3-20 oligodeoxyribose nucleotides. In some embodiments the sequences include between 10-50 oligodeoxyribose nucleotides. In some embodiments the sequences include between 3 and 8 oligodeoxyribose nucleotides. In some embodiments the sequences include 6 oligodeoxyribose nucleotides. In some embodiments the sequences include between 10 and 20 oligodeoxyribose nucleotides. In some embodiments the sequences include 17 oligodeoxyribose nucleotides. In some embodiments, ODN sequences of more than 10 oligodeoxyribose nucleotides form stable duplexes (i.e., of high Tm). In another embodiment, ODN sequences of less than 10 oligodeoxyribose nucleotides form weak duplexes (i.e., of low Tm). In one embodiment, the ODN sequence of the weak duplex is TAGTAC (Seq ID. 1). In another embodiment, the ODN sequence of the stable duplex is CGCAAGACGAGCGAGGC (Seq. ID. 2).

In some embodiments, the ODN sequences can be replaced with peptide nucleic acid (PNA) sequences. Accordingly, it is understood that the term "ODN sequence" as used hereinabove, encompasses both oligodeoxyribose nucleotide (ODN) sequence and peptide nucleic acid sequence (PNA).

In one embodiment, this invention is directed to a peptide nucleic acid oligomer (PNA) derivatives duplex, which consists of a first PNA derivative comprising a first PNA sequence, at least one selective protein binder and a donor or acceptor; and a second PNA derivative comprising a second PNA sequence, which is complementary to the first PNA sequnce, at least one non-selective protein surface binder and a donor or acceptor; wherein if one PNA derivative comprise a donor, the other one comprises an acceptor, and wherein at least one of the donor or acceptor is a fluorophore. In another embodiment, the non-selective protein surface binder comprises a peptide tripod, represented by the structure of formula A:

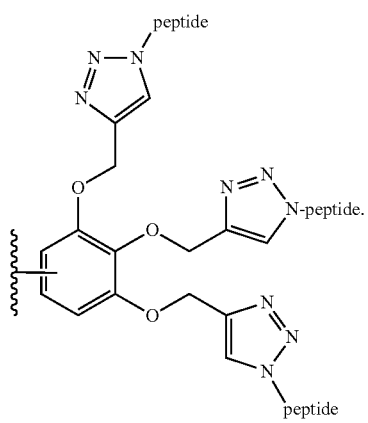

In one embodiment, this invention is directed to a device for protein sensing, or a protein sensor, which comprises an array of duplexes as described hereinabove, wherein the duplexes in the array vary in the peptide sequences which are comprised in their non-selective protein surface binders.

In one embodiment, this invention is directed to a protein sensor, said sensor comprises a non-selective tripodal protein surface binder represented by the structure of formula A:

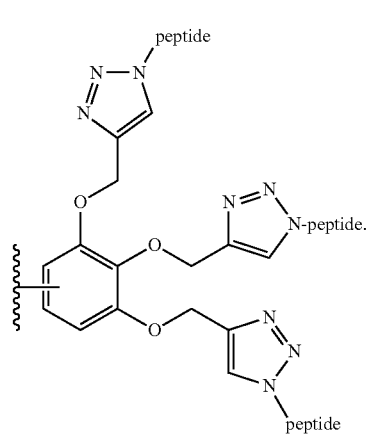

In another embodiment, the protein sensor further comprises a selective protein binder. In another embodiment, the protein sensor further comprises a fluorophore. In another embodiment, the protein sensor further comprises a donor and an acceptor, wherein at least one of the donor or acceptor is a fluorophore. In another embodiment, each donor or acceptor is attached to or in close proximity to one of the selective and non-selective binders of said sensor. In another embodiment, the sensor is used for discriminating between closely related proteins in a biological medium. In another embodiment, "peptide" of formula A refers to an amino acid sequence. In another embodiment, "peptide" refers to an amino acid sequence attached to a linker.

In one embodiment, this invention is directed to a compound, said compound comprises a non-selective tripodal protein surface binder represented by the structure of formula A:

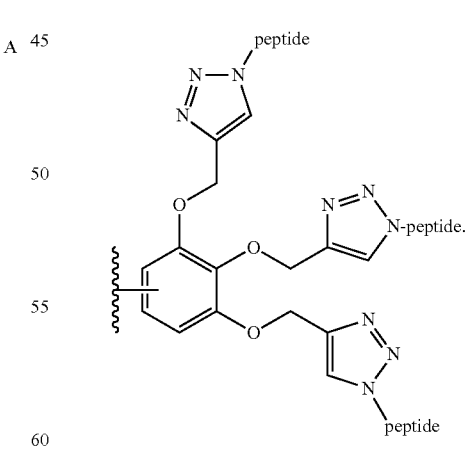

In another embodiment, the compound is a sensor for proteins (i.e., protein sensor). In another embodiment, the compound further comprises a selective protein binder. In another embodiment, the compound further comprises a fluorophore. In another embodiment, the compound further comprises a donor and an acceptor, wherein at least one of the donor or acceptor is a fluorophore. In another embodiment, each donor or acceptor is attached to or in close proximity to one of the selective and non-selective binders of said sensor. In another embodiment, "peptide" of formula A refers to an amino acid sequence. In another embodiment, "peptide" refers to an amino acid sequence attached to a linker.

In some embodiments, this invention is directed to complementary two oligodeoxyribose nucleotide (ODN) derivatives duplex, which consists of a first ODN and a second ODN derivative, wherein said first ODN derivative is represented by the structure of formula IA, IB or IC:

  (IA);

  (IB);

  (IC);

and said second ODN derivative is represented by the structure of formula IIA, IIB or IIC

  (IIA);

  (IIB);

  (IIC);

wherein ODN1 consists of a first oligodeoxyribose nucleotide sequence and ODN2 consists of a second oligodeoxyribose nucleotide sequence, wherein said the second ODN sequence is complementary to said first ODN sequence;

$X^1$, $X^{1'}$, $X^2$ and $X^{2'}$ are each independently a linker or a bond.

Y and Y' is a donor or acceptor, wherein at least one of said donor or acceptor is a fluorophore, wherein if Y is a donor then Y' is an acceptor and vice versa;

k is an integer between 1 and 5;

$R^1$ is a selective protein binder; and $R^{1'}$ is a non-selective protein surface binder.

In one embodiment, $X^1$, $X^{1'}$, $X^2$ and $X^{2'}$ are each independently a bond. In another embodiment, $X^1$, $X^{1'}$, $X^2$ and $X^{2'}$ are each independently a linker.

In another embodiment, the linker is a hydrophilic linker. In another embodiment, the linker is flexible linker.

In another embodiment, the linker comprises at least one phosphate moiety. In another embodiment, the linker comprises at least one polyethylene glycol (PEG) moiety. In another embodiment, the linker comprises at least one triazole moiety.

In another embodiment, the linker comprises at least one moiety selected from: $C_1$-$C_{20}$ alkyl, $C_1$-$C_{20}$ alkylether, $C_1$-$C_{20}$ alkylamide, $C_1$-$C_{20}$ alkylphsophate, $C_1$-$C_{20}$ alkyl-NH, $C_1$-$C_{20}$ alkyl-0, $C_1$-$C_{20}$ alkyl-diamide, phosphate, $C_1$-$C_{20}$ alkylamine, NH, O, PEG, triazole, and NHC(O); wherein alkyl is optionally substituted, wherein substitutions include one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol and thioalkyl.

In another embodiment, the linker comprises NH, and $C_1$-$C_{20}$ alkyl moieties. In another embodiment, the linker comprises NH, and $C_1$-$C_{20}$ alkylether moieties. In another embodiment, the linker comprises NH, $C_1$-$C_{20}$ alkyl and phosphate moieties. In another embodiment, the linker comprises PEG, and phosphate moieties. In another embodiment, the linker comprises NH, $C_1$-$C_{20}$ alkylether and phosphate moieties. In another embodiment, the linker comprises PEG, phosphate, and $C_1$-$C_{20}$ alkyl moieties. In another embodiment, the linker comprises PEG, phosphate, O, and $C_1$-$C_{20}$ alkyl moieties. In another embodiment, the linker comprises phosphate, NH and $C_1$-$C_{20}$ alkyl moieties. In another embodiment, the linker comprises phosphate, NHC (O), PEG and $C_1$-$C_{20}$ alkyl moieties. In another embodiment, the linker comprises phosphate, PEG, NH and $C_1$-$C_{20}$ alkyl moieties. In another embodiment, the linker comprises phosphate, NHC(O), NH and $C_1$-$C_{20}$ alkyl moieties. In another embodiment, the linker comprises phosphate, NHC (O), PEG, triazole, $C_1$-$C_{20}$ alkyl and $C_1$-$C_{20}$ alkylether moieties. In another embodiment, the linker comprises phosphate, PEG, NH, triazole, and $C_1$-$C_{20}$ alkyl moieties. In another embodiment, the linker comprises phosphate, PEG, NH, NHC(O), and $C_1$-$C_{20}$ alkyl moieties. In another embodiment, the linker comprises phosphate, PEG, NH, triazole, $C_1$-$C_{20}$ alkyl and $C_1$-$C_{20}$ alkylether moieties. In another embodiment, the linker comprises phosphate, PEG, O, NHC(O), NH, and $C_1$-$C_{20}$ alkyl moieties.

In another embodiment, the linker consists of at least one moiety selected from: $C_1$-$C_{20}$ alkyl, $C_1$-$C_{20}$ alkylether, $C_1$-$C_{20}$ alkylamide, $C_1$-$C_{20}$ alkylphsophate, $C_1$-$C_{20}$ alkyl-NH, $C_1$-$C_{20}$ alkyl-0, $C_1$-$C_{20}$ alkyl-diamide, phosphate, $C_1$-$C_{20}$ alkylamine, NH, O, PEG, triazole, and NHC(O); wherein alkyl is optionally substituted, wherein substitutions include one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol and thioalkyl.

In another embodiment, the linker consists of NH and $C_1$-$C_{20}$ alkyl moieties. In another embodiment, the linker consists of NH and $C_1$-$C_{20}$ alkylether moieties. In another embodiment, the linker consists of NH, $C_1$-$C_{20}$ alkyl and phosphate moieties. In another embodiment, the linker consists of PEG and phosphate moieties. In another embodiment, the linker consists of NH, $C_1$-$C_{20}$ alkylether and phosphate moieties. In another embodiment, the linker consists of PEG, phosphate, and $C_1$-$C_{20}$ alkyl moieties. In another embodiment, the linker consists of PEG, phosphate, 0, and $C_1$-$C_{20}$ alkyl moieties. In another embodiment, the linker consists of phosphate, NH and $C_1$-$C_{20}$ alkyl moieties. In another embodiment, the linker consists of phosphate, NHC(O), PEG and $C_1$-$C_{20}$ alkyl moieties. In another embodiment, the linker consists of phosphate, PEG, NH and $C_1$-$C_{20}$ alkyl moieties. In another embodiment, the linker consists of phosphate, NHC(O), NH and $C_1$-$C_{20}$ alkyl moieties. In another embodiment, the linker consists of phosphate, NHC(O), PEG, triazole, $C_1$-$C_{20}$ alkyl and $C_1$-$C_{20}$ alkylether moieties. In another embodiment, the linker consists of phosphate, PEG, NH, triazole, and $C_1$-$C_{20}$ alkyl moieties. In another embodiment, the linker consists of phosphate, PEG, NH, NHC(O) and $C_1$-$C_{20}$ alkyl moieties. In another embodiment, the linker consists of phosphate, PEG, NH, triazole, $C_1$-$C_{20}$ alkyl and $C_1$-$C_{20}$ alkylether moieties. In another embodiment, the linker consists of phosphate, PEG, O, NHC(O), NH, and $C_1$-$C_{20}$ alkyl moieties.

In another embodiment, the linker is $C_1$-$C_{20}$ alkyl; $C_1$-$C_{20}$ alkylether, —C(O)NH-alkyl-; —NHC(O)-alkyl-; —C(O) NH-alkyl-C(O)NH—; —C(O)NH-alkyl-NHC(O)—; NH-alkyl-; NH-alkylether-; NH-alkylether-$PO_4$—, —$PO_4$-alkyl-NH—, NHC(O)-alkyl-NHC(O)—; —NHC(O)-alkyl-C(O)NH—; —($OCH_2CH_2$)$_n$—$PO_4$—($CH_2$)$_{0-10}$—; $PO_3$—[($OCH_2CH_2$)$_n$—$PO_3$]$_{1-3}$—O-alkyl, $PO_4$—[($CH_2CH_2O$)$_n$—$PO_3$]$_{1-3}$-alkyl-, [($CH_2CH_2O$)$_n$—$PO_3H$]$_{1-3}$, $PO_4H$—[($CH_2CH_2O$)$_n$—$PO_3H$]$_{1-3}$-alkyl-, [($CH_2CH_2O$)$_n$—$PO_3$]$_{1-3}$-alkyl-, NH-alkyl-$PO_4H$-alkyl, [($CH_2CH_2O$)$_n$—$PO_3$]$_3$-alkyl-NHC(O)-alkyl-, [$PO_3$—($OCH_2CH_2$)$_n$]$_3$—$PO_4$-alkyl-NHC (O)-alkyl-, —$PO_4$—[($OCH_2CH_2$)$_n$—$PO_4$]$_3$—, —$PO_4$—($OCH_2CH_2$)$_n$—$PO_4$—($CH_2$)$_{0-10}$—, —$PO_3$—($OCH_2CH_2$)$_n$—$PO_4$—($CH_2$)$_{0-10}$—, —[($CH_2CH_2O$)$_n$—$PO_3$]$_{1-3}$-alkyl-NH, —$PO_4$—[($CH_2CH_2O$)$_n$—$PO_3$]$_{1-3}$-alkyl-NH, —$PO_4$—($OCH_2CH_2$)$_n$—$PO_4$-alkyl-NHC(O)—; —C(O)NH-alkyl-$PO_4$—; —$PO_4$—CH—[alkyl-NHC(O)-alkyl-$PO_4$-alkyl-NHC(O)-alkyl-NH]$_2$—, alkyl-$PO_4$—CH-[alkyl-NHC(O)-alkyl-$PO_4$-alkyl-NHC(O)-alkyl-NH]$_2$—, —$PO_4$—CH-[alkyl-NHC(O)-alkyl-$PO_4$-alkyl-NHC(O)-alkyl-NHC(O)]$_2$—; —NHC(O)-alkyl-$PO_4$—; NH-alkyl- NH—, —O-alkyl-NH—, —NH-alkyl-O—; —[(CH$_2$CH$_2$O)$_n$—PO$_3$]$_{1-5}$-alkyl-NHC(O)-alkyl-NHC(O)-alkylether-triazole-(CH$_2$)$_{0-10}$—, —PO$_4$—[(CH$_2$CH$_2$O)$_n$—PO$_3$]$_{1-5}$-alkyl-NHC(O)-alkyl-NHC(O)-alkylether-triazole-(CH$_2$)$_{0-10}$—, —PO$_4$—[(OCH$_2$CH$_2$)$_n$—PO$_4$]$_{1-5}$-alkyl-NHC(O)-alkyl-NHC(O)-alkylether-triazole-(CH$_2$)$_{0-10}$—; (CH$_2$CH$_2$O)$_n$—PO$_3$-alkyl-NH-alkyl-triazole-(CH$_2$)$_{0-10}$—, —PO$_4$—(CH$_2$CH$_2$O)$_n$—PO$_3$-alkyl-NH-alkyl-triazole-(CH$_2$)$_{0-10}$—, —PO$_4$—(OCH$_2$CH$_2$)$_n$—PO$_4$-alkyl-amine-alkyl-triazole-(CH$_2$)$_{0-10}$—; —(OCH$_2$CH$_2$)$_n$—PO$_4$-alkyl-NHC(O); —PO$_4$—[(OCH$_2$CH$_2$)$_n$—PO$_4$]$_{1-5}$-alkyl-NHC(O)—; [(CH$_2$CH$_2$O)$_n$—PO$_3$]$_{1-5}$-alkyl[NHC(O)-alkyl-NH]-alkyl-PO$_4$-alkyl-PO$_4$-alkyl-NH—, —PO$_3$—[(OCH$_2$CH$_2$)$_n$—PO$_3$]$_{1-5}$—O-alkyl[NHC(O)-alkyl-NH]-alkyl-PO$_4$-alkyl-PO$_4$-alkyl-NH—, —PO$_4$—[(OCH$_2$CH$_2$)$_n$—PO$_4$]$_{1-5}$-alkyl[NHC(O)-alkyl-NHC(O)]-alkyl-PO$_4$-alkyl-PO$_4$-alkyl-NHC(O)—; —(OCH$_2$CH$_2$)$_n$—(CH$_2$)$_{0-10}$—, —(OCH$_2$CH$_2$)$_n$—(CH$_2$)$_{0-10}$—NHC(O)—; —PO$_4$—[(OCH$_2$CH$_2$)$_n$—PO$_4$]$_{1-3}$-alkyl-NHC(O); —PO$_4$—[(OCH$_2$CH$_2$)$_n$—PO$_4$]$_3$-alkyl-NHC(O)-alkyl-; —PO$_4$—[(OCH$_2$CH$_2$)$_n$—PO$_4$]$_2$-alkyl-NHC(O)-alkyl-; —PO$_4$—[(OCH$_2$CH$_2$)$_n$—PO$_4$]$_{1-3}$-alkyl-NHC(O)-alkyl-NHC(O)—; —PO$_4$—[(OCH$_2$CH$_2$)$_n$—PO$_4$]$_{1-3}$-alkyl- wherein n is an integer between 0 to 10, most preferably 6; —PO$_4$-alkyl-NHC(O)-alkyl-, —PO$_4$-alkyl-NHC(O)-alkyl-NHC(O)—, alkyl-NHC(O)—(CH$_2$)$_{0-10}$—PO$_4$-alkyl-NHC(O)-alkyl-NHC(O), wherein said alkyl is optionally substituted, wherein substitutions include one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol and thioalkyl; and wherein said alkyl is optionally interrupted by one or more heteroatoms selected from O, N, P, S or any combination thereof;

In another embodiment, the linker is NH-alkyl-; NH-alkylether-; —PO$_4$-alkyl-NH—, [(CH$_2$CH$_2$O)$_n$—PO$_3$H]$_{1-3}$, [(CH$_2$CH$_2$O)$_n$—PO$_3$]$_{1-3}$-alkyl-, [(CH$_2$CH$_2$O)$_n$—PO$_3$]$_3$-alkyl-NHC(O)-alkyl-, —[(CH$_2$CH$_2$O)$_n$—PO$_3$]$_{1-3}$-alkyl-NH, —PO$_4$—CH-[alkyl-NHC(O)-alkyl-PO$_4$-alkyl-NHC(O)-alkyl-NH]$_2$—, —[(CH$_2$CH$_2$O)$_n$—PO$_3$]$_{1-5}$-alkyl-NHC(O)-alkyl-NHC(O)-alkylether-triazole-(CH$_2$)$_{0-10}$—, (CH$_2$CH$_2$O)$_n$—PO$_3$-alkyl-NH-alkyl-triazole-(CH$_2$)$_{0-10}$—, or [(CH$_2$CH$_2$O)$_n$—PO$_3$]$_{1-5}$-alkyl[NHC(O)-alkyl-NH]-alkyl-PO$_4$-alkyl-PO$_4$-alkyl-NH—.

In another embodiment, X$^1$ of ODN derivative of formula IA, IB or IC is PO$_4$-alkyl-NH—, —[(CH$_2$CH$_2$O)$_n$—PO$_3$]$_{1-3}$-alkyl-NH, PO$_4$—CH—[alkyl-NHC(O)-alkyl-PO$_4$-alkyl-NHC(O)-alkyl-NH]$_2$, —[(CH$_2$CH$_2$O)$_n$—PO$_3$]$_{1-5}$-alkyl-NHC(O)-alkyl-NHC(O)-alkylether-triazole-(CH$_2$)$_{1-10}$—, (CH$_2$CH$_2$O)$_n$—PO$_3$-alkyl-NH-alkyl-triazole-(CH$_2$)$_{0-10}$—, or [(CH$_2$CH$_2$O)$_n$—PO$_3$]$_{1-5}$-alkyl[NHC(O)-alkyl-NH]-alkyl-PO$_4$-alkyl-PO$_4$-alkyl-NH—; wherein said alkyl is optionally substituted, wherein substitutions include one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol and thioalkyl.

In another embodiment, X$^{11}$ of ODN derivative of formula IIA, IIB or IIC is (CH$_2$CH$_2$O)$_n$—PO$_3$-alkyl-NH-alkyl-triazole-(CH$_2$)$_{0-10}$—, or [(CH$_2$CH$_2$O)$_n$—PO$_3$]$_{1-3}$-alkyl-; wherein said alkyl is optionally substituted, wherein substitutions include one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol and thioalkyl.

In another embodiment, X$^2$ of ODN derivative of formula IA, IB or IC is NH-alkyl or [(CH$_2$CH$_2$O)$_n$—PO$_3$H]$_{1-3}$, wherein said alkyl is optionally substituted, wherein substitutions include one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol and thioalkyl.

In another embodiment, X$^{2'}$ of ODN derivative of formula IIA, IIB or IIC is NH-alkylether, or [(CH$_2$CH$_2$O)$_n$—PO$_3$]$_{1-3}$-alkyl-, —[(CH$_2$CH$_2$O)$_n$—PO$_3$]$_3$-alkyl-NHC(O)-alkyl-; wherein said alkyl is optionally substituted, wherein substitutions include one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol and thioalkyl.

In some embodiments this invention is directed to a first oligodeoxyribose nucleotide (ODN) derivative comprising a first oligodeoxyribose nucleotide (ODN) sequence, a selective protein binder and a donor, acceptor or combination thereof. In another embodiment, said first ODN sequence and said selective protein binder are covalently bound; said first ODN sequence and said donor, acceptor or combination thereof, are covalently bound; said selective protein binder and said donor, acceptor or combination thereof are covalently bound; or any combination thereof. In another embodiment, the first oligodeoxyribose nucleotide (ODN) derivative is represented by the structure of formula IA. In another embodiment, the first oligodeoxyribose nucleotide (ODN) derivative is represented by the structure of formula IB. In another embodiment, the first oligodeoxyribose nucleotide (ODN) derivative is represented by the structure of formula IC. In another embodiment, the first oligodeoxyribose nucleotide (ODN) derivative is represented by the structure of formula IIIA. In another embodiment, the first oligodeoxyribose nucleotide (ODN) derivative is represented by the structure of formula IIIB In another embodiment, the first oligodeoxyribose nucleotide (ODN) derivative is represented by the structure of formula IIIC. In another embodiment, the first oligodeoxyribose nucleotide (ODN) derivative is represented by the structure of formula III. In another embodiment, the first oligodeoxyribose nucleotide (ODN) derivative is represented by the structure of formula ODN-58. In another embodiment, the first oligodeoxyribose nucleotide (ODN) derivative is represented by the structure of formula ODN-20. In another embodiment, the first oligodeoxyribose to nucleotide (ODN) derivative is represented by the structure of formula ODN-49. In another embodiment, the first oligodeoxyribose nucleotide (ODN) derivative is represented by the structure of formula ODN-51. In another embodiment, the first oligodeoxyribose nucleotide (ODN) derivative is represented by the structure of formula ODN-53. In another embodiment, the selective protein binder is marimastat, ethacrynic acid (EA), bis ethacrynic acid, Ni-nitrilotriacetic acid (NTA), bis-Ni-NTA, tris-Ni-NTA, PDGF-BB aptamer, heparin derivative, FGF aptamer, or estrogen. In another embodiment, the donor or acceptor is a fluorophore.

In some embodiments this invention is directed to a second oligodeoxyribose nucleotide (ODN) derivative comprising a second oligodeoxyribose nucleotide (ODN) sequence, a non-selective protein surface binder and a donor, acceptor or combination thereof. In another embodiment, said second ODN sequence and said non-selective protein surface binder are covalently bound; said second ODN sequence and said donor, acceptor or combination thereof, are covalently bound; said non-selective protein surface binder and said donor, acceptor or combination thereof are covalently bound; or any combination thereof. In another embodiment, the second oligodeoxyribose nucleotide (ODN) derivative is represented by the structure of formula IIA. In another embodiment, the second oligodeoxyribose nucleotide (ODN) derivative is represented by the structure of formula IIB. In another embodiment, the second oligodeoxyribose nucleotide (ODN) derivative is represented by the structure of formula IIC. In another embodiment, the second oligodeoxyribose nucleotide (ODN) derivative is represented by the structure of formula IVA. In another embodiment, the second oligodeoxyribose nucleotide (ODN) derivative is represented by the structure of formula IVB. In another embodiment, the second oligodeoxyribose nucleotide (ODN) derivative is represented by the structure of formula IVC. In another embodiment, the second oligodeoxyribose nucleotide (ODN) derivative is represented by the structure of formula IV. In another embodiment, the second oligodeoxyribose nucleotide (ODN) derivative is represented by the structure of formula V. In another embodiment, the second oligodeoxyribose nucleotide (ODN) derivative is represented by the structure of formula ODN-39. In another embodiment, the second oligodeoxyribose nucleotide (ODN) derivative is represented by the structure of formula ODN-56. In another embodiment, the second oligodeoxyribose nucleotide (ODN) derivative is represented by the structure of formula ODN-5. In another embodiment, the second oligodeoxyribose nucleotide (ODN) derivative is represented by the structure of formula ODN-6. In another embodiment, the second oligodeoxyribose nucleotide (ODN) derivative is represented by the structure of formula ODN-7. In another embodiment, the second oligodeoxyribose nucleotide (ODN) derivative is represented by the structure of formula ODN-8. In another embodiment, the second oligodeoxyribose nucleotide (ODN) derivative is represented by the structure of formula ODN-9. In another embodiment, the donor or acceptor is a fluorophore. In another embodiment, the non-selective protein surface binder comprises a peptide tripod, represented by the structure of formula A:

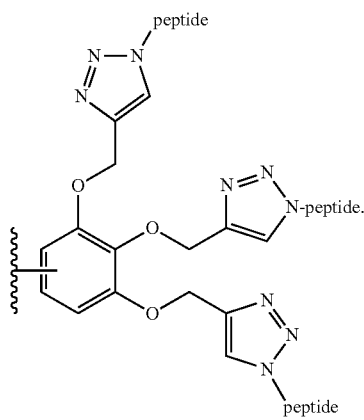

A

In some embodiments, this invention is directed to a complementary two oligodeoxyribose nucleotide (ODN) derivatives duplex and methods of use thereof, wherein said ODN derivatives include a first ODN derivative comprising at least one selective protein binder; and a second ODN derivative comprising at least one non-selective protein surface binder. In one embodiment, the first and second ODN derivatives are not covalently attached. In one embodiment, the first and second ODN derivatives are attached via hybridization of the two complementary sequences (first and second ODN sequences). In one embodiment, the first and second ODN derivatives are self-assembled in such that first and second ODN sequences hybridize and the donor and acceptor are in close vicinity such that conformational changes resulting from interactions with different protein and/or protein isoforms lead to different FRET efficiencies. In some embodiments, the first ODN derivative and second ODN derivative are water soluble.

In some embodiments, this invention is directed to an array of oligonucleotide derivative duplexes, each duplex comprises a complementary two oligodeoxyribose nucleotide (ODN) derivatives as described hereinabove, and methods of use thereof, wherein said duplex include a first ODN derivative comprising at least one selective protein binder and a donor or acceptor; and a second ODN derivative comprising at least one non-selective protein surface binder and a donor or acceptor, wherein if one ODN derivative comprises a donor, then the other one comprises an acceptor, and at least one of the donor and acceptor is a fluorophore.

In some embodiments, the two oligodeoxyribose nucleotide (ODN) derivatives of this invention consist of a first ODN derivative of formula IA, IB or IC; and a second ODN derivative of formula IIA, IIB or IIC. In some embodiments the two oligodeoxyribose nucleotide (ODN) derivatives are of formula IA and IIA. In some embodiments, the two oligodeoxyribose nucleotide (ODN) derivatives are of formula IB and IIB. In some embodiments, the two oligodeoxyribose nucleotide (ODN) derivatives are of formula IC and IIC. In some embodiments, the two oligodeoxyribose nucleotide (ODN) derivatives are of formula IA and IIB. In some embodiments, the two oligodeoxyribose nucleotide (ODN) derivatives are of formula IA and IIC. In some embodiments, the two oligodeoxyribose nucleotide (ODN) derivatives are of formula IB and IIA. In some embodiments, the two oligodeoxyribose nucleotide (ODN) derivatives are of formula IB and IIC. In some embodiments, the two oligodeoxyribose nucleotide (ODN) derivatives are of formula IC and IIA. In some embodiments, the two oligodeoxyribose nucleotide (ODN) derivatives are of formula IC and IIB.

In some embodiments, $X^1$, $X^2$, $X^{1'}$, $X^{2'}$ of formula IA, IB, IC, IIA, IIB, IIC, III, IV, V are independently a linker. In some embodiments, $X^1$, $X^2$, $X^{1'}$, $X^{2'}$ of formula IA, IB, IC, IIA, IIB, IIC, III, IV, V are independently a bond. In some embodiments $X^1$, $X^2$, $X^{1'}$, $X^{2'}$ of formula IA, IB, IC, IIA, IIB, IIC, III, IV, V are independently an alkyl. In some embodiments $X^1$, $X^2$, $X^{1'}$, $X^{2'}$ of formula IA, IB, IC, IIA, IIB, IIC, III, IV, V are independently an alkyl ether. In some embodiments $X^1$, $X^2$, $X^{1'}$, $X^{2'}$ of formula IA, IB, IC, IIA, IIB, IIC, III, IV, V are independently —C(O)NH-alkyl-. In some embodiments $X^1$, $X^2$, $X^{1'}$, $X^{2'}$ of formula IA, IB, IC, IIA, IIB, IIC, III, IV, V are independently —NHC(O)-alkyl-. In some embodiments $X^1$, $X^2$, $X^{1'}$, $X^{2'}$ of formula IA, IB, IC, IIA, IIB, IIC, III, IV, V are independently —C(O)NH-alkyl-C(O)NH—. In some embodiments $X^1$, $X^2$, $X^{1'}$, $X^{2'}$ of formula IA, IB, IC, IIA, IIB, IIC, III, IV, V are independently —C(O)NH-alkyl-NHC(O)—. In some embodiments $X^1$, $X^2$, $X^{1'}$, $X^{2'}$ of formula IA, IB, IC, IIA, IIB, IIC, III, IV, V are independently —NHC(O)-alkyl-NHC(O)—. In some embodiments $X^1$, $X^2$, $X^{1'}$, $X^{2'}$ of formula IA, IB, IC, IIA, IIB, IIC, III, IV, V are independently —NHC(O)-alkyl-C(O)NH—. In some embodiments $X^1$, $X^2$, $X^{1'}$, $X^{2'}$ of formula IA, IB, IC, IIA, IIB, IIC, III, IV, V are independently —(OCH$_2$CH$_2$)$_n$—PO$_4$—(CH$_2$)$_{0-10}$—, wherein n is an integer between 0 to 10. In some embodiments $X^1$, $X^2$, $X^{1'}$, $X^{2'}$ of formula IA, IB, IC, IIA, IIB, IIC, III, IV, V are independently —C(O)NH-alkyl-PO$_4$—. In some embodiments $X^1$, $X^2$, $X^{1'}$, $X^{2'}$ of formula IA, IB, IC, IIA, IIB, IIC, III, IV, V are independently —NHC(O)-alkyl-PO$_4$—. In some embodiments $X^1$, $X^2$, $X^{1'}$, $X^{2'}$ of formula IA, IB, IC, IIA, IIB, IIC, III, IV, V are independently —PO$_4$—[(OCH$_2$CH$_2$)$_n$—PO$_4$]$_{1-3}$-alkyl-. In some embodiments $X^1$, $X^2$, $X^{1'}$, $X^{2'}$ of formula IA, IB, IC, IIA, IIB, IIC, III, IV, V are independently —PO$_4$—(OCH$_2$CH$_2$)$_n$—PO$_4$-alkyl-. In some embodiments $X^1$, $X^2$, $X^{1'}$, $X^{2'}$ of formula IA, IB, IC, IIA, IIB, IIC, III, IV, V are independently —PO$_4$—[(OCH$_2$CH$_2$)$_n$—PO$_4$]$_2$-alkyl-. In some embodiments $X^1$, $X^2$, $X^{1'}$, $X^{2'}$ of formula IA, IB, IC, IIA, IIB, IIC, III, IV, V are independently —PO$_4$—[(OCH$_2$CH$_2$)$_n$—PO$_4$]$_3$-alkyl-. In some embodiments $X^1$, $X^2$, $X^{1'}$, $X^{2'}$ of formula IA, IB, IC, IIA, IIB, IIC, III, IV, V are independently —PO$_4$—[(OCH$_2$CH$_2$)$_n$—PO$_4$]$_{1-3}$-alkyl-NHC(O)-alkyl-NHC(O)—. In some embodiments $X^1$, $X^2$, $X^{1'}$, $X^{2'}$ of formula IA, IB, IC, IIA, IIB, IIC, III, IV, V are independently —PO$_4$—(OCH$_2$CH$_2$)$_n$—PO$_4$-alkyl-NHC(O)-alkyl-NHC(O)—. In some embodiments $X^1$, $X^2$, $X^{1'}$, $X^{2'}$ of formula IA, IB, IC, IIA, IIB, IIC, III, IV, V are independently —$PO_4$—[($OCH_2CH_2$)$_n$—$PO_4$]$_2$-alkyl-NHC(O)-alkyl-NHC(O)—. In some embodiments $X^1$, $X^2$, $X^{1'}$, $X^{2'}$ of formula IA, IB, IC, IIA, IIB, IIC, III, IV, V are independently —$PO_4$—[($OCH_2CH_2$)$_n$—$PO_4$]$_3$-alkyl-NHC(O)-alkyl-NHC(O)—. In some embodiment, n is an integer between 0 and 10. In some embodiments, n is 4. In some embodiments, n is 6. In some embodiments, n is 8. In some embodiments $X^1$, $X^2$, $X^{1'}$, $X^{2'}$ of formula IA, IB, IC, IIA, IIB, IIC, III, IV, V are independently —$PO_4$—[($OCH_2CH_2$)—]$_n$—$PO_4$]$_{1-3}$-alkyl-NHC(O). In some embodiments $X^1$, $X^2$, $X^{1'}$, $X^{2'}$ of formula IA, IB, IC, IIA, IIB, IIC, III, IV, V are independently —$PO_4$—($OCH_2CH_2$)$_n$—$PO_4$-alkyl-NHC(O). In some embodiments $X^1$, $X^2$, $X^{1'}$, $X^{2'}$ of formula IA, IB, IC, IIA, IIB, IIC, III, IV, V are independently —$PO_4$—[($OCH_2CH_2$)$_n$—$PO_4$]$_2$-alkyl-NHC(O). In some embodiments $X^1$, $X^2$, $X^{1'}$, $X^{2'}$ of formula IA, IB, IC, IIA, IIB, IIC, III, IV, V are independently —$PO_4$—[($OCH_2CH_2$)$_n$—$PO_4$]$_3$-alkyl-NHC(O). In some embodiments $X^1$, $X^2$, $X^{1'}$, $X^{2'}$ of formula IA, IB, IC, IIA, IIB, IIC, III, IV, V are independently —$PO_4$—[($OCH_2CH_2$)$_n$—$PO_4$]$_{1-5}$-alkyl[NHC(O)-alkyl-NHC(O)]-alkyl-$PO_4$-alkyl-$PO_4$-alkyl-NHC(O)—. In some embodiments $X^1$, $X^2$, $X^{1'}$, $X^{2'}$ of formula IA, IB, IC, IIA, IIB, IIC, III, IV, V are independently —$PO_4$—[($OCH_2CH_2$)$_n$—$PO_4$]$_2$-alkyl[NHC(O)-alkyl-NHC(O)]-alkyl-$PO_4$-alkyl-$PO_4$-alkyl-NHC(O)—. In some embodiments $X^1$, $X^2$, $X^{1'}$, $X^{2'}$ of formula IA, IB, IC, IIA, IIB, IIC, III, IV, V are independently —$PO_4$—[($OCH_2CH_2$)$_n$—$PO_4$]$_3$-alkyl[NHC(O)-alkyl-NHC(O)]-alkyl-$PO_4$-alkyl-$PO_4$-alkyl-NHC(O)—. In some embodiments $X^1$, $X^2$, $X^{1'}$, $X^{2'}$ of formula IA, IB, IC, IIA, IIB, IIC, III, IV, V are independently —$PO_4$—[($OCH_2CH_2$)$_n$—$PO_4$]$_{1-5}$-alkyl-NHC(O)-alkyl-NHC(O)-alkylether-triazole-($CH_2$)$_{0-10}$—. In some embodiments $X^1$, $X^2$, $X^{1'}$, $X^{2'}$ of formula IA, IB, IC, IIA, IIB, IIC, III, IV, V are independently —$PO_4$—[($OCH_2CH_2$)$_n$—$PO_4$]$_2$-alkyl-NHC(O)-alkyl-NHC(O)-alkylether-triazole-($CH_2$)$_{0-10}$—. In some embodiments $X^1$, $X^2$, $X^{1'}$, $X^{2'}$ of formula IA, IB, IC, IIA, IIB, IIC, III, IV, V are independently —$PO_4$—[($OCH_2CH_2$)$_n$—$PO_4$]$_3$-alkyl-NHC(O)-alkyl-NHC(O)-alkylether-triazole-($CH_2$)$_{0-10}$—. In some embodiments $X^1$, $X^2$, $X^{1'}$, $X^{2'}$ of formula IA, IB, IC, IIA, IIB, IIC, III, IV, V are independently —$PO_4$—CH-[alkyl-NHC(O)-alkyl-$PO_4$-alkyl-NHC(O)-alkyl-NHC(O)]$_2$—; In some embodiments $X^1$, $X^2$, $X^{1'}$, $X^{2'}$ of formula IA, IB, IC, IIA, IIB, IIC, III, IV, V are independently —$PO_4$—[($OCH_2CH_2$)$_n$—$PO_4$]$_3$—; In some embodiments $X^1$, $X^2$, $X^{1'}$, $X^{2'}$ of formula IA, IB, IC, IIA, IIB, IIC, III, IV, V are independently —$PO_4$—[($OCH_2CH_2$)$_n$—$PO_4$]$_3$—($CH_2$)$_{0-10}$—. In some embodiments $X^1$, $X^2$, $X^{1'}$, $X^{2'}$ of formula IA, IB, IC, IIA, IIB, IIC, III, IV, V are independently —$PO_4$—CH-[alkyl-NHC(O)-alkyl-$PO_4$-alkyl-NHC(O)-alkyl-NHC(O)]$_2$—. In some embodiments $X^1$, $X^2$, $X^{1'}$, $X^{2'}$ of formula IA, IB, IC, IIA, IIB, IIC, III, IV, V are independently —($OCH_2CH_2$)$_n$-triazole-($CH_2$)$_{0-10}$—. In some embodiments $X^1$, $X^2$, $X^{1'}$, $X^{2'}$ of formula IA, IB, IC, IIA, IIB, IIC, III, IV, V are independently —($OCH_2CH_2$)$_n$—$PO_4$-alkyl-NHC(O). In some embodiments $X^1$, $X^2$, $X^{1'}$, $X^{2'}$ of formula IA, IB, IC, IIA, IIB, IIC, III, IV, V are independently —($OCH_2CH_2$)$_n$—$PO_4$-alkyl[NHC(O)-alkyl-NHC(O)]-alkyl-$PO_4$-alkyl-$PO_4$-alkyl-NHC(O)—. In some embodiments $X^1$, $X^2$, $X^{1'}$, $X^{2'}$ of formula IA, IB, IC, IIA, IIB, IIC, III, IV, V are independently —($OCH_2CH_2$)$_n$—($CH_2$)$_{0-10}$—. In some embodiments $X^1$, $X^2$, $X^{1'}$, $X^{2'}$ of formula IA, IB, IC, IIA, IIB, IIC, III, IV, V are independently —($OCH_2CH_2$)—($CH_2$)$_{0-10}$—NHC(O)—. In some embodiments $X^1$, $X^{1'}$, $X^{2'}$ of formula IA, IB, IC, IIA, IIB, IIC, III, IV, V are independently —$PO_4$—[($OCH_2CH_2$)$_n$—$PO_4$]$_3$-alkyl-NHC(O). In some embodiments $X^1$, $X^2$, $X^{1'}$, $X^{2'}$ of formula IA, IB, IC, IIA, IIB, IIC, III, IV, V are independently —$PO_4$—[($OCH_2CH_2$)$_n$—$PO_4$]$_3$-alkyl-. In some embodiments $X^1$, $X^2$, $X^{1'}$, $X^{2'}$ of formula IA, IB, IC, IIA, IIB, IIC, III, IV, V are independently —$PO_4$-alkyl-CHC(O)-alkyl-. In some embodiments $X^1$, $X^2$, $X^{1'}$, $X^{2'}$ of formula IA, IB, IC, IIA, IIB, IIC, III, IV, V are independently —$PO_4$-alkyl-CHC(O)-alkyl-NHC(O)—. In some embodiments $X^1$, $X^2$, $X^{1'}$, $X^{2'}$ of formula IA, IB, IC, IIA, IIB, IIC, III, IV, V are independently alkyl-NHC(O)—($CH_2$)$_{0-10}$—$PO_4$-alkyl-NHC(O)-alkylNHC(O). In some embodiments $X^1$, $X^2$, $X^{1'}$, $X^{2'}$ of formula IA, IB, IC, IIA, IIB, IIC, III, IV, V are independently NH-alkyl. In some embodiments $X^1$, $X^2$, $X^{1'}$, $X^{2'}$ of formula IA, IB, IC, IIA, IIB, IIC, III, IV, V are independently NH-alkylether. In some embodiments $X^1$, $X^2$, $X^{1'}$, $X^{2'}$ of formula IA, IB, IC, IIA, IIB, IIC, III, IV, V are independently $PO_4$-alkyl-NH—. In some embodiments $X^1$, $X^2$, $X^{1'}$, $X^{2'}$ of formula IA, IB, IC, IIA, IIB, IIC, III, IV, V are independently [($CH_2CH_2O$)$_n$—$PO_3H$]$_{1-3}$, In some embodiments $X^1$, $X^2$, $X^{1'}$, $X^{2'}$ of formula IA, IB, IC, IIA, IIB, IIC, III, IV, V are independently [($CH_2CH_2O$)$_n$—$PO_3$]$_{1-3}$-alkyl-. In some embodiments $X^1$, $X^2$, $X^{1'}$, $X^{2'}$ of formula IA, IB, IC, IIA, IIB, IIC, III, IV, V are independently [($CH_2CH_2O$)$_n$—$PO_3$]$_3$-alkyl-NHC(O)-alkyl-. In some embodiments $X^1$, $X^2$, $X^{1'}$, $X^{2'}$ of formula IA, IB, IC, IIA, IIB, IIC, III, IV, V are independently [($CH_2CH_2O$)$_n$—$PO_3$]$_{1-3}$-alkyl-NH. In some embodiments $X^1$, $X^2$, $X^{1'}$, $X^{2'}$ of formula IA, IB, IC, IIA, IIB, IIC, III, IV, V are independently $PO_4$—CH-[alkyl-NHC(O)-alkyl-$PO_4$-alkyl-NHC(O)-alkyl-NH]$_2$—. In some embodiments $X^1$, $X^2$, $X^{1'}$, $X^{2'}$ of formula IA, IB, IC, IIA, IIB, IIC, III, IV, V are independently [($CH_2CH_2O$)$_n$—$PO_3$]$_{1-5}$-alkyl-NHC(O)-alkyl-NHC(O)-alkylether-triazole-($CH_2$)$_{0-10}$—. In some embodiments $X^1$, $X^2$, $X^{1'}$, $X^{2'}$ of formula IA, IB, IC, IIA, IIB, IIC, III, IV, V are independently ($CH_2CH_2O$)$_n$—$PO_3$-alkyl-NH-alkyl-triazole-($CH_2$)$_{0-10}$—. In some embodiments $X^1$, $X^2$, $X^{1'}$, $X^{2'}$ of formula IA, IB, IC, IIA, IIB, IIC, III, IV, V are independently [($CH_2CH_2O$)$_n$—$PO_3$]$_{1-5}$-alkyl[NHC(O)-alkyl-NH]-alkyl-$PO_4$-alkyl-$PO_4$-alkyl-NH—. In some embodiments $X^1$, $X^2$, $X^{1'}$, $X^{2'}$ of formula IA, IB, IC, IIA, IIB, IIC, III, IV, V are independently NH-alkylether-$PO_4$—. In some embodiments $X^1$, $X^2$, $X^{1'}$, $X^{2'}$ of formula IA, IB, IC, IIA, IIB, IIC, III, IV, V are independently $PO_3$—[($OCH_2CH_2$)$_n$—$PO_3$]$_{1-3}$—O-alkyl. In some embodiments $X^1$, $X^2$, $X^{1'}$, $X^{2'}$ of formula IA, IB, IC, IIA, IIB, IIC, III, IV, V are independently $PO_4$—[($CH_2CH_2O$)$_n$—$PO_3$]$_{1-3}$-alkyl-. In some embodiments $X^1$, $X^2$, $X^{1'}$, $X^{2'}$ of formula IA, IB, IC, IIA, IIB, IIC, III, IV, V are independently $PO_4H$—[($CH_2CH_2O$)$_n$—$PO_3H$]$_3$-alkyl-. In some embodiments $X^1$, $X^2$, $X^{1'}$, $X^{2'}$ of formula IA, IB, IC, IIA, IIB, IIC, III, IV, V are independently NH-alkyl-$PO_4H$-alkyl. In some embodiments $X^1$, $X^2$, $X^{1'}$, $X^{2'}$ of formula IA, IB, IC, IIA, IIB, IIC, III, IV, V are independently —[$PO_3$—($OCH_2CH_2$)$_n$]$_3$—$PO_4$-alkyl-NHC(O)-alkyl-. In some embodiments $X^1$, $X^2$, $X^{1'}$, $X^{2'}$ of formula IA, IB, IC, IIA, IIB, IIC, III, IV, V are independently —$PO_3$—($OCH_2CH_2$)$_n$—$PO_4$—($CH_2$)$_{0-10}$—. In some embodiments $X^1$, $X^2$, $X^{1'}$, $X^{2'}$ of formula IA, IB, IC, IIA, IIB, IIC, III, IV, V are independently —$PO_4$—[($CH_2CH_2O$)$_n$—$PO_3$]$_{1-3}$-alkyl-NH. In some embodiments $X^1$, $X^2$, $X^{1'}$, $X^{2'}$ of formula IA, IB, IC, IIA, IIB, IIC, III, IV, V are independently alkyl-$PO_4$—CH-[alkyl-NHC(O)-alkyl-$PO_4$-alkyl-NHC(O)-alkyl-NH]$_2$—. In some embodiments $X^1$, $X^2$, $X^{1'}$, $X^{2'}$ of formula IA, IB, IC, IIA, IIB, IIC, III, IV, V are independently —$PO_4$—[($CH_2CH_2O$)$_n$—$PO_3$]$_{1-5}$-alkyl-NHC(O)-alkyl-NHC(O)-alkylether-triazole-($CH_2$)$_{0-10}$—. In some embodiments $X^1$, $X^2$, $X^{1'}$, $X^{2'}$ of formula IA, IB, IC, IIA, IIB, IIC, III, IV, V are independently —$PO_4$—($CH_2CH_2O$)$_n$—$PO_3$-alkyl-NH-alkyl-triazole-($CH_2$)$_{0-10}$—. In some embodiments $X^1$, $X^2$, $X^{1'}$, $X^{2'}$ of formula IA, IB, IC, IIA, IIB, IIC, III, IV, V are independently —$PO_3$—[($OCH_2CH_2$)$_n$—$PO_3$]$_{1-5}$—O-alkyl[NHC(O)-alkyl-NH]-alkyl-$PO_4$-alkyl-$PO_4$-alkyl-NH—.

An "alkyl" or "alkylene" group refers, in one embodiment, to a saturated aliphatic hydrocarbon, including straight-chain and branched-chain. In one embodiment, the alkyl group has 1-20 carbons. In another embodiment, the alkyl has 1-12 carbons. In another embodiment, the alkyl group has 1-7 carbons. In another embodiment, the alkyl group has 1-5 carbons. In another embodiment, the alkyl group has 1-6 carbons. In another embodiment, the alkyl group has 1-4 carbons. The alkyl group may be unsubstituted or substituted by one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol and thioalkyl. In another embodiment, the alkyl is —(CH$_2$)$_6$—. In another embodiment, the alkyl is —(CH$_2$)$_2$—. In another embodiment, the alkyl is —(CH$_2$)$_3$—. In another embodiment, the alkyl is —CH$_2$—. In another embodiment, the alkyl is —CH$_2$—CH(CH$_2$—OH)—(CH$_2$)$_4$—. In another embodiment, the alkyl is —CH$_2$—CH(CH$_2$—OH)—.

An "alkyl ether" of this invention refers to a substituted or unsubstituted alkyl as defined above interrupted by one or more oxygen atoms. In another embodiment, alkyl ether refers to a PEG (poly ethylene glycol). In one embodiment, the alkylether has 1-6 carbon atoms. In another embodiment, the alkylether has 1-12 carbon atoms. In another embodiment, the alkylether has 1-20 carbon atoms. In another embodiment, the alkylether has 3 carbon atoms. In another embodiment, the alkylether has 4 carbon atoms. In another embodiment, the alkylether has 2-5 carbon atoms. In another embodiment, the alkylether has 2 carbon atoms. In another embodiment, the alkylether is —CH$_2$—CH$_2$—O—CH$_2$—. In another embodiment, the alkylether is —CH$_2$—CH$_2$CH$_2$—O—CH$_2$—CH(OH)CH$_2$—.

An "alkyl amine" of this invention refers to a substituted or unsubstituted alkyl as defined above, which has an amine moiety within the carbon atom chain. In another embodiment, alkyl amine refers to (CH$_2$)$_n$—NH—. In another embodiment, the amine moiety is at one end of the carbon chain. In another embodiment, the amine moiety is within the backbone of the carbon chain. In another embodiment, the alkyl amine is a substituted or unsubstituted linear or branched alkyl of 1-6 carbon atoms which has an amine moiety at one end. In another embodiment, the alkyl amine is a substituted or unsubstituted linear or branched alkyl of 1-12 carbon atoms which has an amine moiety at one end. In another embodiment, the alkyl amine is a substituted or unsubstituted linear or branched alkyl of 1-3 carbon atoms which has an amine moiety at one end.

An "alkyl amide" of this invention refers to a substituted or unsubstituted alkyl as defined above, which has an amide moiety at one end. In another embodiment, alkyl amide refers to (CH$_2$)$_n$—NHC(O). In another embodiment, alkyl amide refers to (CH$_2$)$_n$—C(O)NH wherein n is an integer between 1 and 10. In another embodiment, the alkyl amide is a substituted or unsubstituted linear or branched alkyl of 1-6 carbon atoms which has an amide moiety at one end. In another embodiment, the alkyl amide is a substituted or unsubstituted linear or branched alkyl of 1-12 carbon atoms which has an amide moiety at one end. In another embodiment, the alkyl amide is a substituted or unsubstituted linear or branched alkyl of 1-3 carbon atoms which has an amide moiety at one end. In another embodiment, the alkyl amide is —(CH$_2$)$_6$—NHC(O). In another embodiment, the alkyl amide is —(CH$_2$)$_2$—NHC(O). In another embodiment, the alkyl amide is —CH$_2$—NHC(O). In another embodiment, the alkyl amide is —CH$_2$—CH(CH$_2$—OH)—(CH$_2$)$_4$—NHC(O). In another embodiment, the alkyl amide is —CH$_2$—CH(CH$_2$—OH)—NHC(O).

An "alkyl di-amide" of this invention refers to a substituted or unsubstituted alkyl as defined above which is interrupted by two amide moieties. In one embodiment, alkyl di-amide refers to (CH$_2$)—NHC(O)—(CH$_2$)$_m$—NHC(O) wherein n is an integer between 1 and 10. In another embodiment, the alkyl di-amide is a substituted or unsubstituted linear or branched alkyl of 1-6 carbon atoms which has an amide moiety at one end of the carbon chain and another amide moiety inside the backbone of the chain. In another embodiment, the alkyl di-amide is a substituted or unsubstituted linear or branched alkyl of 2-12 carbon atoms which has two amide moieties within the carbon chain. In another embodiment, the alkyl di-amide is a substituted or unsubstituted linear or branched alkyl of 2-6 carbon atoms which has two amide moieties within the carbon chain. In another embodiment, the alkyl di-amide is a substituted or unsubstituted linear or branched alkyl of 1-20 carbon atoms which has two amide moieties within the carbon chain. In another embodiment, the alkyl di-amide is —CH$_2$—CH(CH$_2$OH)—NHC(O)—(CH$_2$)$_2$—NHC(O)—. In another embodiment, the alkyl di-amide is —NHC(O)—(CH$_2$)$_2$—NHC(O)—.

An "alkyl triazole" of this invention refers to a substituted or unsubstituted alkyl as defined above, which has a triazole moiety at one end. In one embodiment, alkyl triazole refers to (CH$_2$)$_n$-triazole wherein n is an integer between 1 and 10. In another embodiment n is 3. In another embodiment, the alkyl triazole is a substituted or unsubstituted linear or branched alkyl of 1-6 carbon atoms which has a triazole moiety at one end. In another embodiment, the alkyl triazole has 1-12 carbon atoms. In another embodiment, the alkyl triazole has 1-3 carbon atoms.

In some embodiments the first oligodeoxyribose nucleotide (ODN) derivatives of this invention and methods of use thereof, comprise at least one selective protein binder. In another embodiment, R$^1$ of formula IA, IB and IC is a selective protein binder as defined herein above.

In another embodiment, the selective protein binder, R$^1$, of formula I(A-C) comprise the following structure:

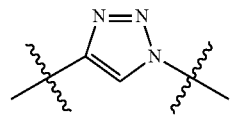 [SMILES: *c1cn(*)nn1]

In one embodiment the second oligodeoxyribose nucleotide (ODN) derivative of this invention and methods of use thereof comprise at least one non-selective protein surface binder as defined herein above. In another embodiment, R$^{1'}$ of formula IIA, IIB and IIC is a non-selective protein surface binder as defined herein above.

In another embodiment, the non-selective protein surface binder, R$^{1'}$ according to formula II(A-C), is represented by the structure of formula A:

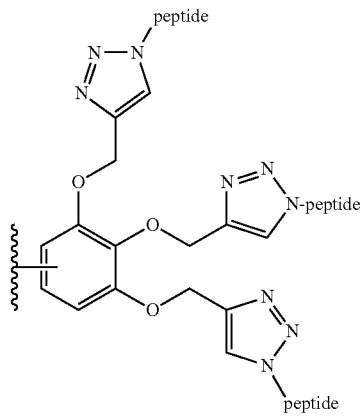

A wherein "peptide" is as defined herein above.

In another embodiment, the non-selective protein surface binder, R$^{1'}$, according to formulas II(A-C) comprise the following structure:

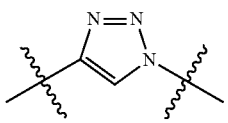 [SMILES: *c1cn(*)nn1]

In another embodiment, the peptides comprised in the non-selective binder $R^{1'}$ of formula II(A-C) comprise between 2 to 30 amino acid sequence. In another embodiment, the peptides comprise between 5 to 15 amino acid sequences. In another embodiment, the peptides comprise between 5 to 10 amino acid sequences. In another embodiment, the peptides further comprise linkers which link between the amino acid sequence of the peptide and the compound to which they are attached. In another embodiment, the peptides are attached to the N atoms of the compound through linkers. In another embodiment, the linker is a substituted or unsubstituted linear or branched alkyl chain of 1-50 carbon atoms, substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof. In another embodiment, the linker is a $C_1$-$C_6$ alkyl. In another embodiment, the linker is a propyl (i.e., —$CH_2$—$CH_2$—$CH_2$—). In another embodiment the peptides comprise the sequence as described in Table 1, Example 1. In another embodiment the peptides comprise the sequence as described in Table 3, Example 8. In another embodiment the peptides comprise the sequence as described in Table 5, Example 16. In another embodiment the peptide includes amino acid sequence interrupted by a donor or an acceptor, or substituted by a donor or an acceptor. In another embodiment, the donor or acceptor is covalently bonded to a lysine residue (K).

In some embodiments the first and second oligodeoxyribose nucleotide (ODN) derivatives of this invention and methods of use thereof, comprise a donor and an acceptor, wherein at least one of the donor or acceptor is a fluorophore. In one embodiment, if one of the oligodeoxyribose nucleotide (ODN) derivatives includes a donor, the other includes an acceptor. In one embodiment, Y of formula IA, IB, IC or Y' of formula IIA, IIB, IIC is a donor. In one embodiment, Y of formula IA, IB, IC or Y' of formula IIA, IIB, IIC is an acceptor. In one embodiment, Y of formula IA, IB and IC is an acceptor and Y' of formula IIA, IIB and IIC is a donor. In some embodiments, the donor or acceptor of this invention is fluorescein (6-FAM), FAM, cyanine dyes (e.g. Cy3, Cy5), nile red, rhodamine, dansyl, dabcyl, perylene, fluorenyl, coumarin, 7-methoxycoumarin (Mca) or derivative thereof.

In some embodiments, the donor of this invention is fluorescein (6-FAM, FAM) and the acceptor is dabcyl. In another embodiment, the donor is solvatochromic fluorophore. In another embodiment, the solvatochromic fluorophore is dansyl. In another embodiment, the donor is solvatochromic fluorophore dansyl and the acceptor is Cy3. In another embodiment, the donor is a fluorophore and the acceptor is a quencher. In another embodiment, the donor is Mca and the acceptor is dinitrophenol (Dnp).

In one embodiment the first ODN derivative includes a fluorophore. In one embodiment the second ODN derivative includes a fluorophore.

A "fluorophore" according to this invention refers to any fluorescent material or dye known in the art. In another embodiment, the fluorophore is fluorescein (6-FAM), FAM, cyanine dyes (e.g. Cy3, Cy5), sulfoindocyanine, nile red, rhodamine, dansyl, perylene, fluorenyl, coumarin, 7-methoxycoumarin (Mca), dabcyl or derivative thereof.

In some embodiments, the fluorophore of this invention is a fluorescent dye. In another embodiment, the fluorescent dye is substituted or unsubstituted anthracene; substituted or unsubstituted nile red; substituted or unsubstituted dansyl; substituted or unsubstituted fluorenyl; substituted or unsubstituted naphthalene; substituted or unsubstituted tetracene; substituted or unsubstituted perylene; substituted or unsubstituted pyrene substituted or unsubstituted fluorescein; substituted or unsubstituted rhodamine; substituted or unsubstituted cyanine, substituted or unsubstituted coumarin; or any other fluorescent dye known in the art and/or disclosed in http://www.fluorophores.org which is incorporated herein by reference. In another embodiment, the fluorescent dye of this invention is anthracene, naphthalene, fluorenyl, dansyl, nile red, fluorescein, rhodamine, perylene, cyanine, Cy3, Cy5, coumarin, derivative thereof, or combination thereof. In another embodiment, the fluorescent dye of this invention is substituted by one to three substituents. In another embodiment the fluorescent dye is substituted by alkyl, alkenyl, haloalkyl, aryl, O-aryl, —$(CH_2)$n-aryl, cycloalkyl, O-cycloalkyl, $CF_3$, F, I, Br, Cl, $NO_2$, CN, $N(Z)_2$, COOH, CO—Z, NHCOZ, CONHZ, $(CH_2)_n NH_2$, $(CH_2)_n NH$—Z, S—Z, SH, O—Z, $(CH_2)_n OH$, $(CH_2)_n COOH$, or OH; wherein Z is H, alkyl, haloalkyl, dihaloalkyl, trihaloalkyl, aryl, phenyl or halogen and n is between 0 and 8. In another embodiment n is between 1 and 6.

In some embodiments, this invention provides a first oligodeoxyribose nucleotide, (ODN) derivative represented by formula IA: ODN1-$X^2$—Y—$X^1$—$(R^1)_k$. In one embodiment, the first ODN derivative of formula IA is represented by the structure of formula III:

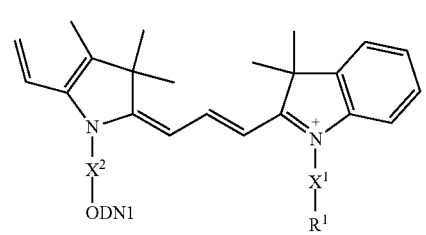

wherein ODN1, $X^1$, $X^2$ and $R^1$ are as defined for formula IA to IC.

In some embodiments, this invention provides a first oligodeoxyribose nucleotide, (ODN) derivative represented by formula IA: ODN1-$X^2$—Y—$X^1$—$(R^1)_k$. In one embodiment, the first ODN derivative of formula IA is represented by the structure of formula ODN-58:

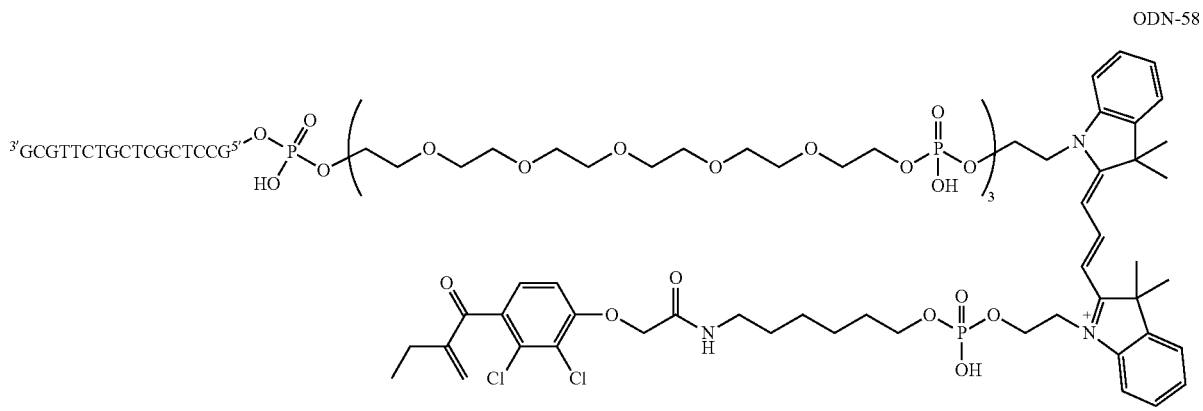

ODN-58 wherein $X^2$ of formula IA is $[(CH_2CH_2O)_n—PO_3H]_{1-3}$, n is 6, Y is Cy3, $X^1$ is $PO_4$-alkyl-NH, $R^1$ is EA and k is 1.

In one embodiment, the first ODN derivative of formula IA is represented by the structure of formula ODN-20:

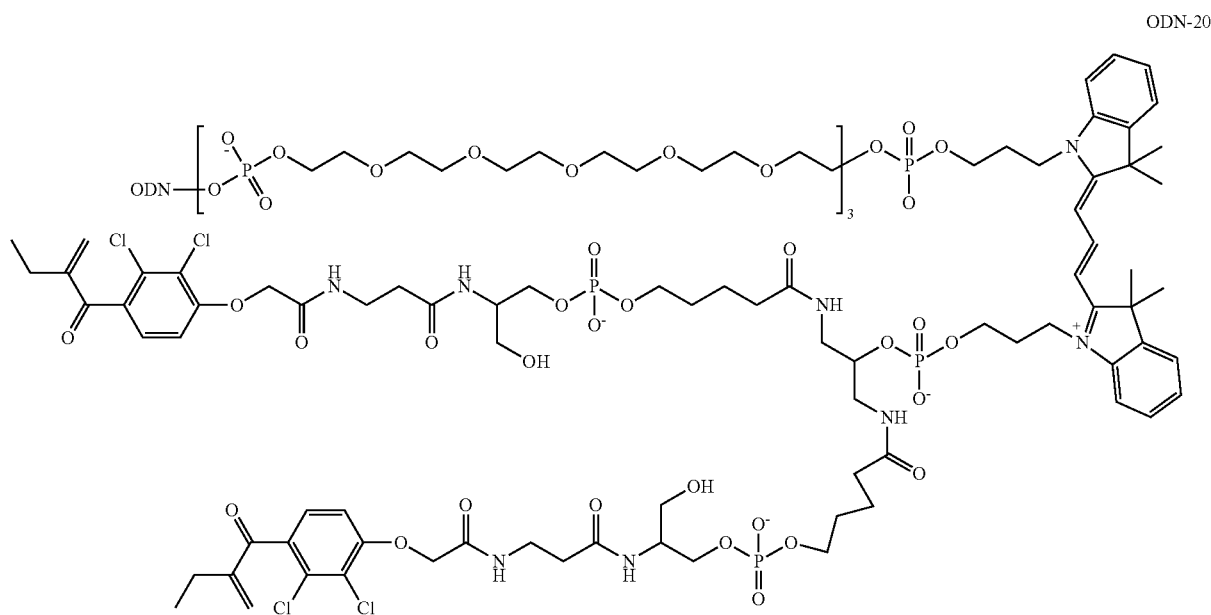

ODN-20 wherein $X^2$ of formula IA is $[(CH_2CH_2O)_n—PO_3H]_{1-3}$, n is 6, Y is Cy3, $X^1$ is $PO_4$—CH-[alkyl-NHC(O)-alkyl-$PO_4$-alkyl-NHC(O)-alkyl-NH]$_2$—, $R^1$ is EA and k is 2.

In some embodiments, this invention provides a first oligodeoxyribose nucleotide (ODN) derivative represented by formula IB: Y—$X^2$—ODN1-$X^1$—$(R^1)_k$.

In one embodiment, the first ODN derivative of formula IB is represented by the structure of formula ODN-49:

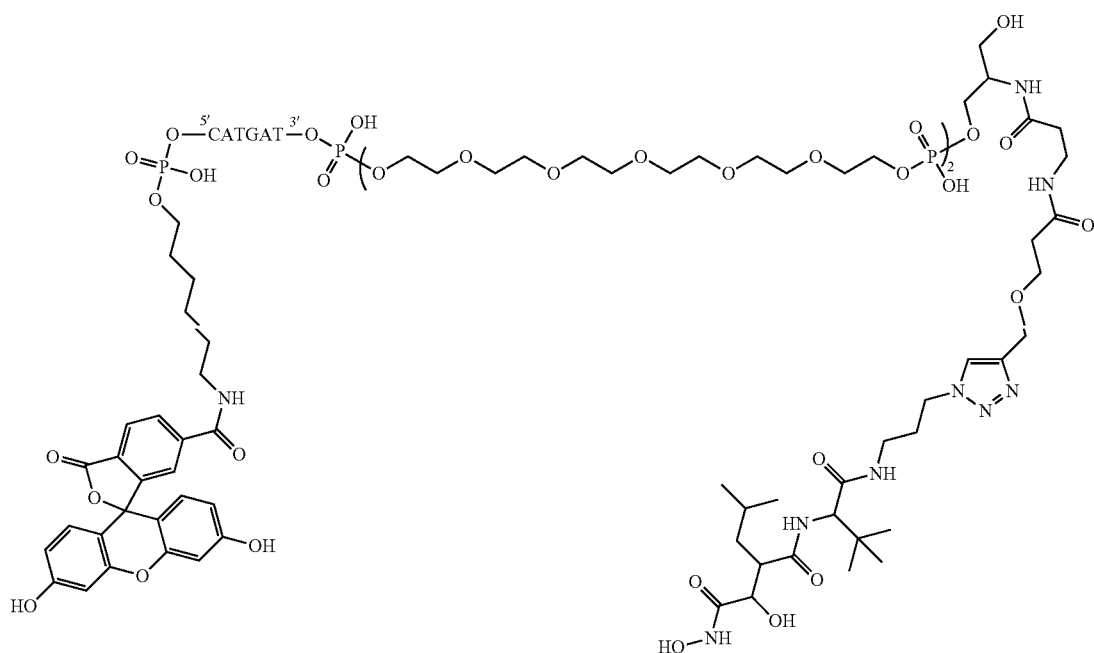

wherein Y of formula IB is a FAM, $X^2$ is NH-alkyl, $X^1$ is —[(CH$_2$CH$_2$O)$_n$—PO$_3$]$_{1-5}$-alkyl-NHC(O)-alkyl-NHC(O)-alkylether-triazole-(CH$_2$)$_{0-10}$—, $R^1$ is marimastat and k is 1.

In one embodiments, the first ODN derivative of formula IB is represented by the structure of formula ODN-51:

wherein Y of formula IB is FAM, $X^2$ is NH-alkyl, $X^1$ is —[(CH$_2$CH$_2$O)$_n$—PO$_3$]$_{1-3}$-alkyl-NH, $R^1$ is EA and k is 1.

In one embodiments, the first ODN derivative of formula IB is represented by the structure of formula ODN-53:

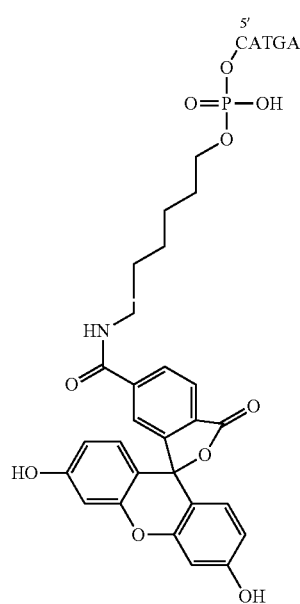
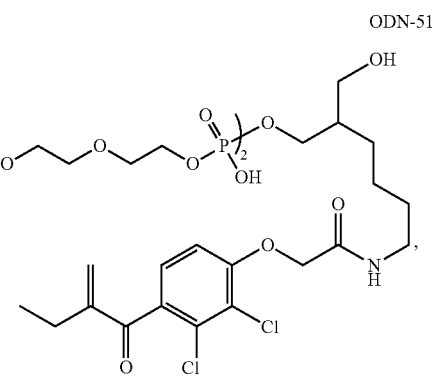

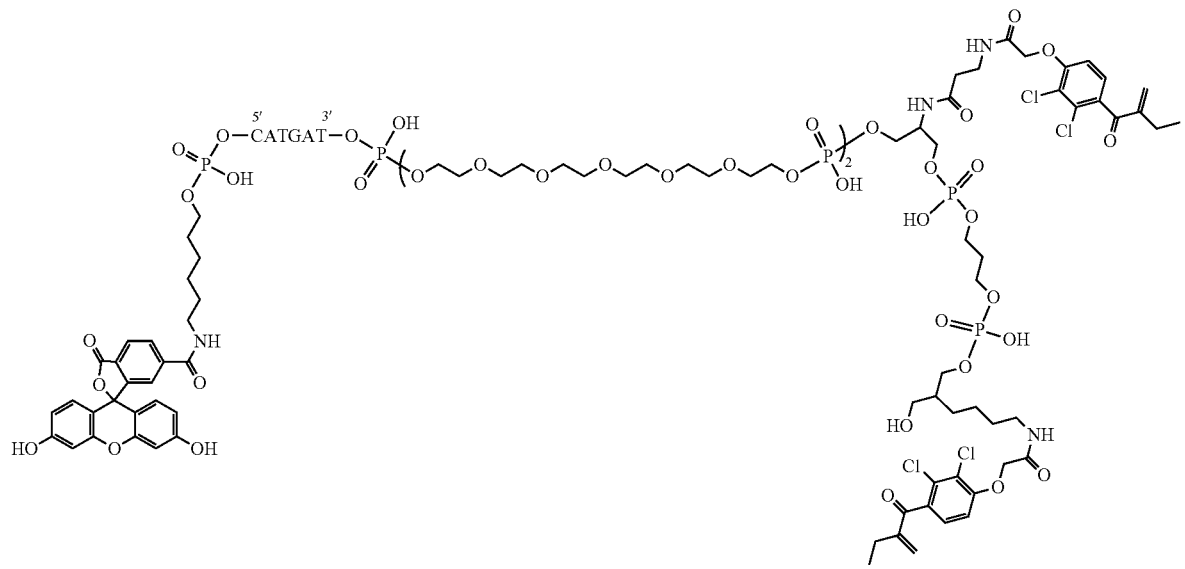

ODN-53 wherein Y of formula IB is FAM, $X^2$ is NH-alkyl, $X^1$ is $[(CH_2CH_2O)_n—PO_3]_{1-5}$-alkyl[NHC(O)-alkyl-NH]-alkyl-$PO_4$-alkyl-$PO_4$-alkyl-NH, n is 6, $R^1$ is EA and k is 2.

In one embodiment, the first ODN derivative of formula IB is represented by the following structure:

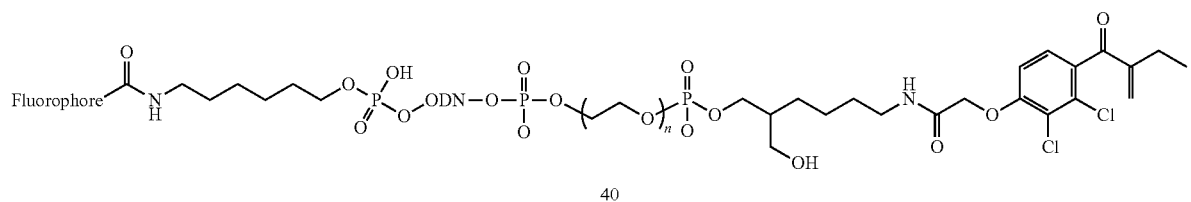

wherein Y of formula IB is a fluorophore, $X^2$ is NH-alkyl, $X^1$ is —$[(CH_2CH_2O)_n—PO_3]_{1-3}$-alkyl-NH, n is 6, k is 1 and $R^1$ is EA.

In some embodiments, this invention provides a second oligodeoxyribose nucleotide (ODN) derivative represented by formula IIA: ODN2-$X^{2\prime}$—Y'—$X^{1\prime}$—$R^{1\prime}$. In one embodiment, the second ODN derivative of formula IIA is represented by the structure of formula IV:

IV

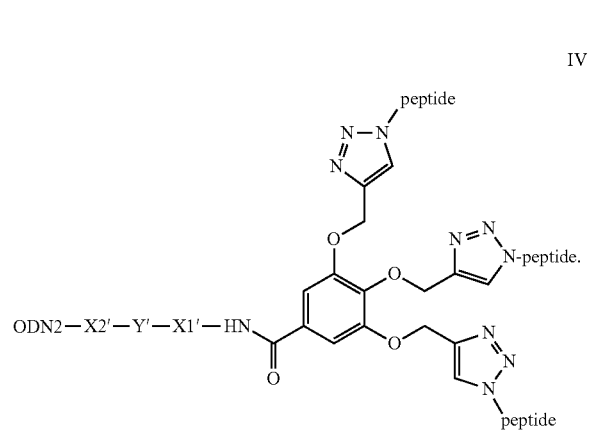

In one embodiment, $R^{1\prime}$ of formulas II(A-C) is represented by the following structure:

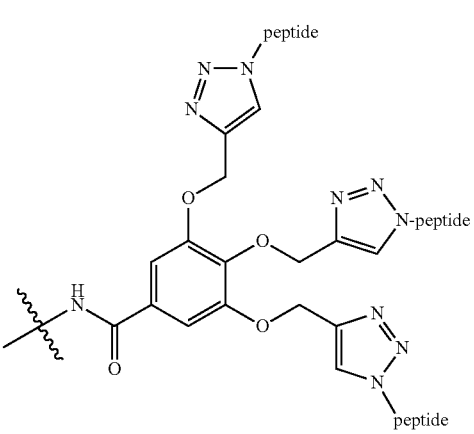

In some embodiments, this invention provides a second oligodeoxyribose nucleotide (ODN) derivative represented by formula IIB: Y'—$X^{2\prime}$-ODN2-$X^{1\prime}$—$R^{1\prime}$ (IIB). In one embodiment, the second ODN derivative of formula IIB is represented by the structure of formula ODN-39:

35
36
ODN-39
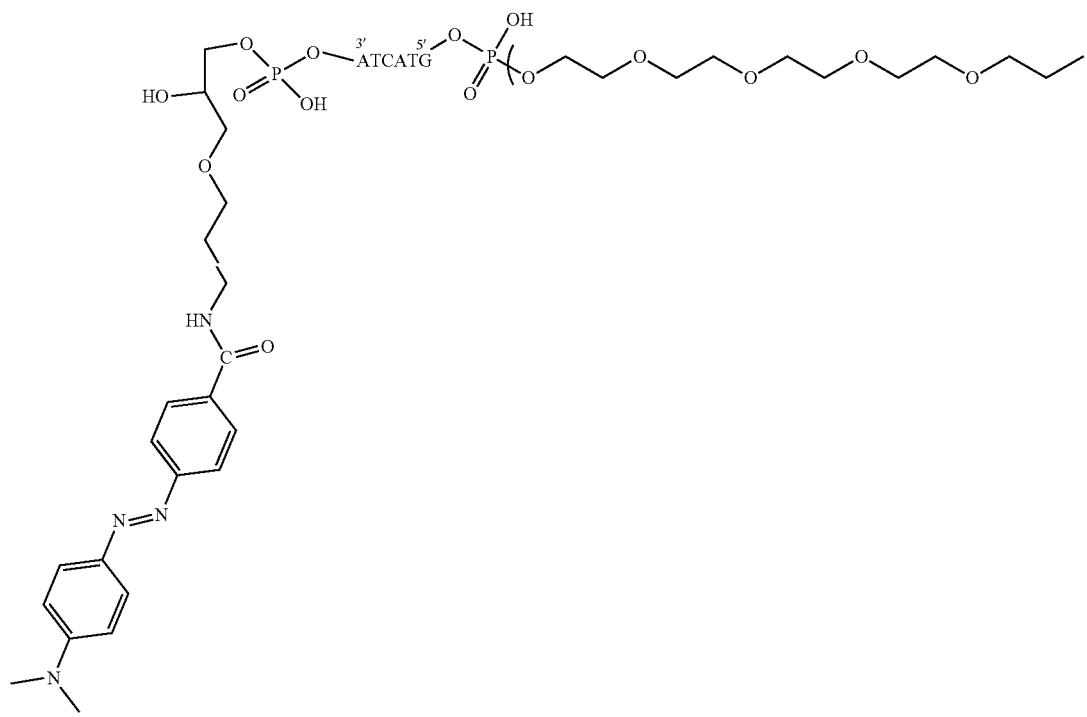
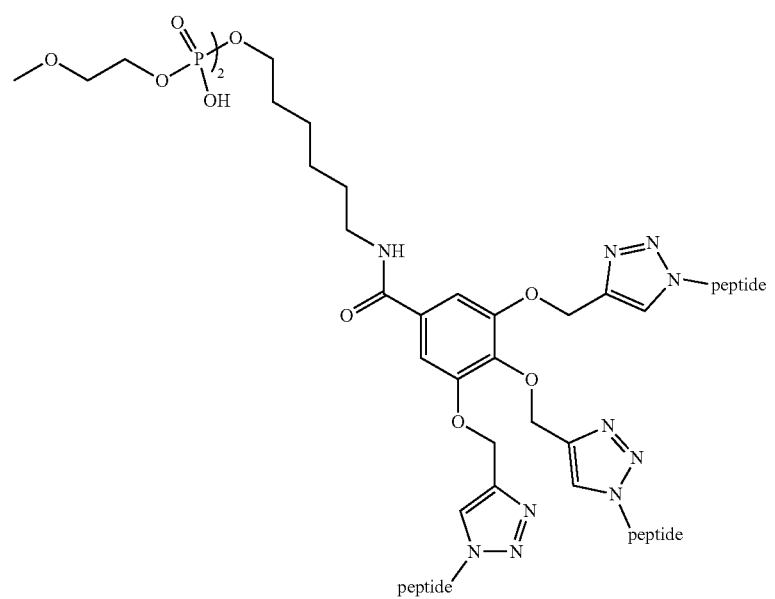

wherein Y' of formula IIB is Dabcyl, $X^{2'}$ is NH-alkylether, $X^{1'}$ is $[(CH_2CH_2O)_n—PO_3]_{1-3}$-alkyl, n is 6, and $R^{1'}$ is:

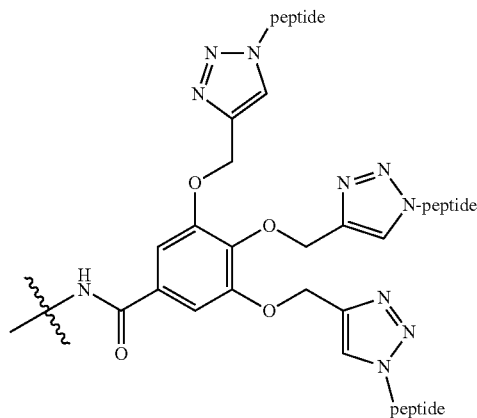

wherein "peptide" is as defined herein above.

In one embodiment, the second ODN derivative of formula IIB is represented by the following structure:

wherein Y' of formula IIB is Dabcyl, $X^{2'}$ is NH-alkylether, $X^{1'}$ is $[(CH_2CH_2O)_n—PO_3]$-alkyl wherein n is an integer between 0 to 10 and $R^{1'}$ is:

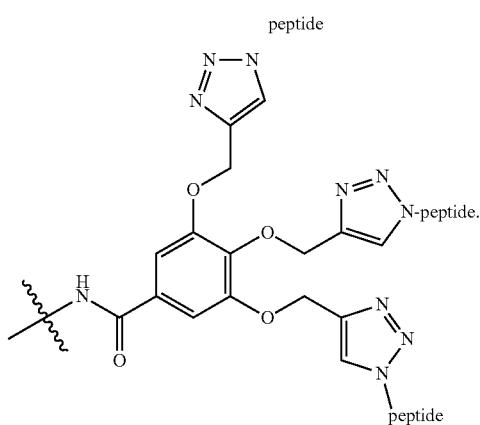

wherein "peptide" is as defined herein above.

In one embodiment, the second ODN derivative of formula IIB is represented by the following structure:

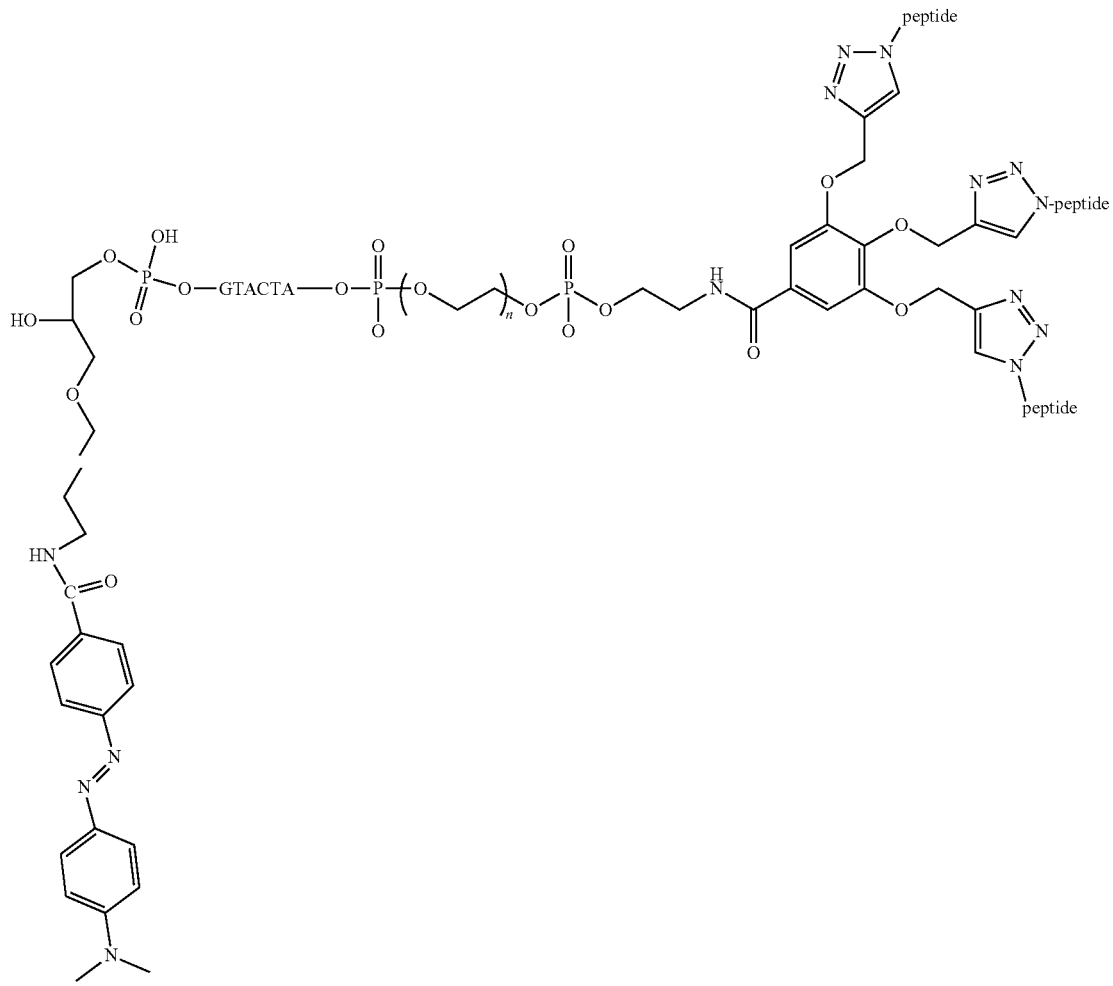

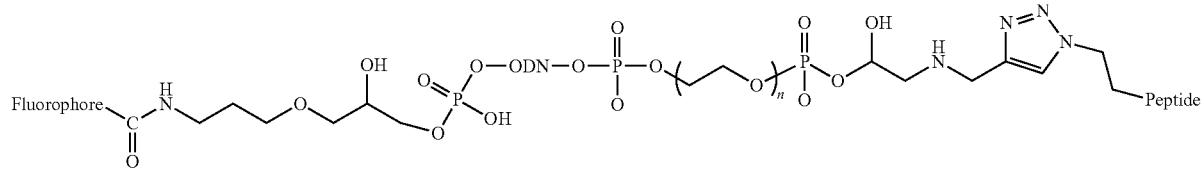

wherein Y' of formula IIB is a fluorophore, $X^{2'}$ is NH-alkylether, $X^{1'}$ is $(CH_2CH_2O)_n$—$PO_3$-alkyl-NH-alkyl-triazole-$(CH_2)_{0-10}$, and $R^{1'}$ is a peptide as defined herein above.

In some embodiments, this invention provides a second oligodeoxyribose nucleotide (ODN) derivative represented by formula IIC: ODN2-$X^{2'}$—$R^{1'}$—$(X^{1'}$—Y'$)_{k'}$. In one embodiment, the second ODN derivative of formula IIC is represented by the structure of formula V:

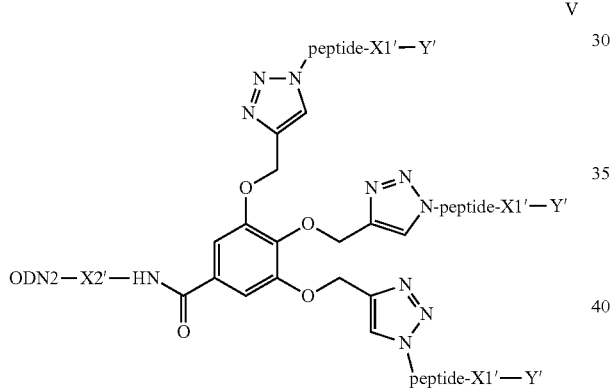

V wherein "peptide" is as defined herein above.

In one embodiment the oligodeoxyribose nucleotide (ODN) derivatives of IIC is represented by the structure of formula:

ODN-56

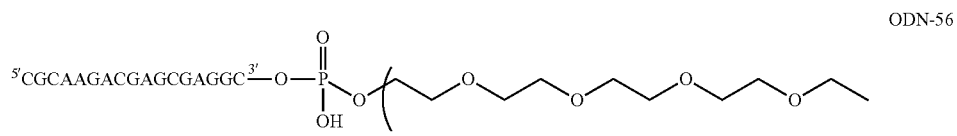

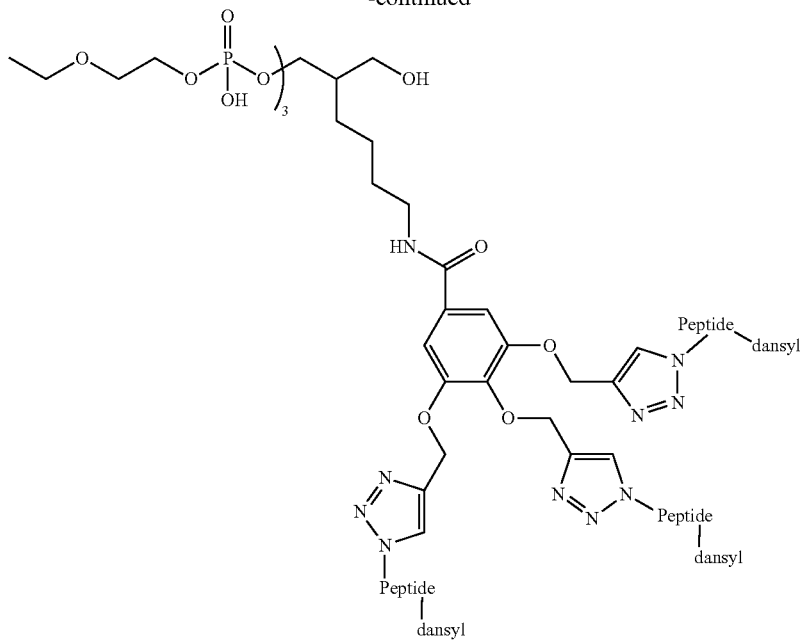
wherein $X^{2'}$ of formula IIC is $[(CH_2CH_2O)_n—PO_3]_{1-3}$-alkyl, n is 6, $R^{1'}$ is represented by the following formula:
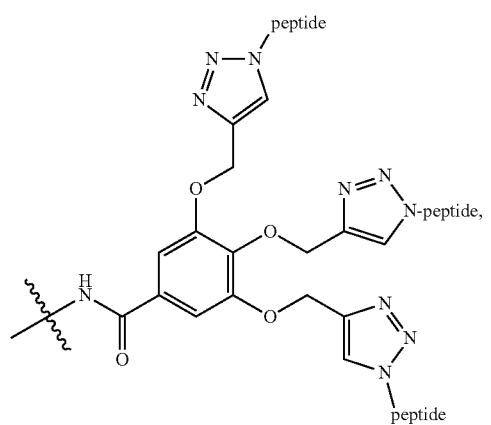
Y' is dansyl and k' is 3; and
wherein "peptide" is as defined herein above.
In one embodiment the oligodeoxyribose nucleotide (ODN) derivatives of IIC is represented by the structure of formula:

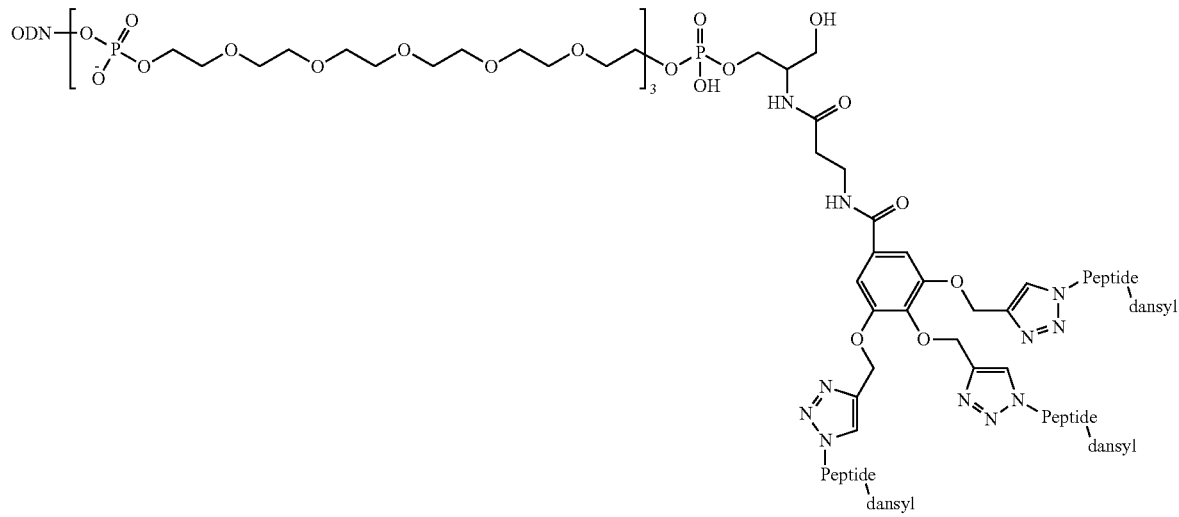

ODN-5 to 9 wherein $X^{2'}$ of formula IIC is $[(CH_2CH_2O)_n—PO_3]_3$-alkyl-NHC(O)-alkyl, n is 6, $R^{1'}$ is represented by the following formula:

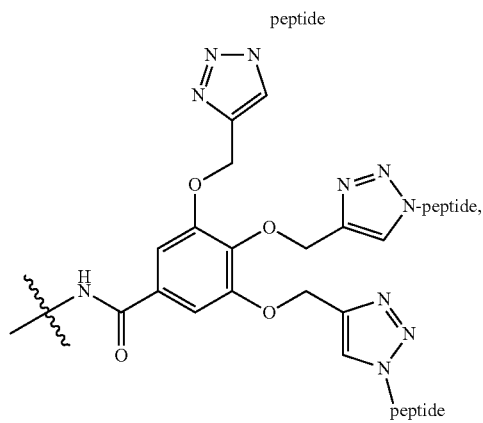

Y' is dansyl and k' is 3;
wherein "peptide" is as defined herein above.

In some embodiments, this invention is directed to complementary two oligodeoxyribose nucleotide (ODN) derivatives consisting of a first ODN and a second ODN derivative, wherein said first ODN derivative is represented by the structure of formula IIIA, IIIB or IIIC:

ODN1-[(PEG)$_m$-(P)$_n$]$_v$—X$^2$—Y—(P)$_q$-(Split)[X$^1$—R$^1$]$_t$  (IIIA);

Y—X$^2$—ODN1-[(PEG)$_m$-(P)$_n$]$_v$-(Split)[X$^1$—R$^1$]$_t$  (IIIB);

ODN1-[(PEG)$_m$-(P)$_n$]$_v$—X$^2$-(Split)[R$^1$—X$^1$—Y]$_t$  (IIIC);

and said second ODN derivative is represented by the structure of formula IVA, IVB or IVC:

ODN2-[(PEG)$_{m'}$—(P)$_{n'}$]$_{v'}$—X$^{2'}$—Y'—(P)$_{q'}$—X$^{1'}$-(Q)(R$^{1'}$)$_k$  (IVA);

Y'—X$^{2'}$-ODN2-[(PEG)$_{m'}$—(P)$_{n'}$]$_{v'}$—X$^{1'}$-(Q)(R$^{1'}$)$_k$  (IVB);

ODN2-[(PEG)$_{m'}$—(P)$_{n'}$]$_{v'}$—X$^{2'}$-(Q)[R$^{1'}$—X$^{1'}$—Y']$_k$  (IVC);

wherein
ODN1 is a first oligodeoxyribose nucleotide sequence and ODN2 is a second oligodeoxyribose nucleotide sequence, wherein said second sequence is complementary to said first sequence;
$X^1$, $X^{1'}$, $X^2$, and $X^{2'}$ are each independently a linker or a bond;
each P is independently $PO_3$, $PO_2OH$, $PO(OH)_2$, $PO_4$, $PO_3OH$ or $PO_2(OH)_2$;
n, n', q and q' are each 0 or 1;
PEG is $OCH_2CH_2$;
m and m' are each an integer between 0 and 10, preferentially 6;
v and v' are each an integer between 1 and 10, preferentially 0, 1, 2, and 3;
Split is C, CH, $CH_2$—C, $CH_2$—CH or absent;
t is 1, 2 or 3; wherein if Split is C or $CH_2$—C then t is 3; if Split is CH or $CH_2$—CH then t is 2 and if Split is absent than t is 1;
Q is either absent, alkyl triazole or represented by the structure of formula B:

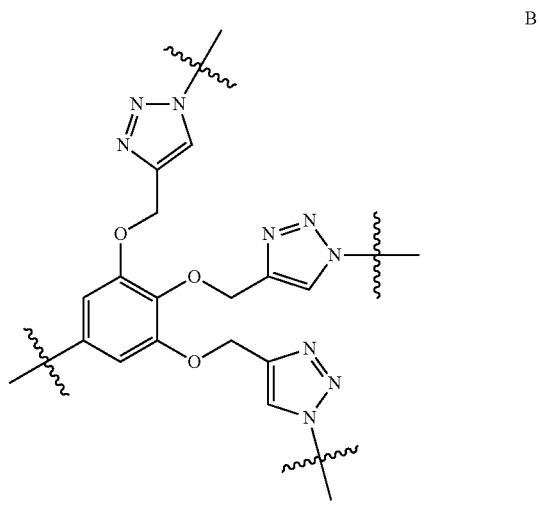 [SMILES: *c1cc(OCc2cn(*)nn2)c(OCc2cn(*)nn2)c(OCc2cn(*)nn2)c1]

B k is either 1 or 3; wherein if Q is B then k is 3, otherwise k is 1;

Y and Y' is a donor or acceptor, wherein at least one of said donor or acceptor is a fluorophore, wherein if Y is a donor the Y' is an acceptor and vice versa;

$R^1$ is a selective protein binder; and $R^{1'}$ is a peptide as defined herein above;

wherein, if t is 2 or 3, then each of $X^1$, $X^{1'}$, $R^1$, $R^{1'}$, Y, Y', Q and k can be same or different.

In one embodiment, $X^1$, $X^{1'}$, $X^2$, and $X^{2'}$ are each independently a bond. In another embodiment, $X^1$, $X^{1'}$, $X^2$, and $X^{2'}$ are each independently a linker.

In another embodiment, the linker is a hydrophilic linker. In another embodiment, the linker is flexible linker.

In another embodiment, the linker comprises at least one $C_1$-$C_{20}$ alkyl. In another embodiment, the linker comprises at least one $C_1$-$C_{20}$ alkylether-NH. In another embodiment, the linker comprises at least one $C_1$-$C_{20}$ alkyl-NH. In another embodiment, the linker comprises at least one $C_1$-$C_{20}$ alkylamide. In another embodiment, the linker comprises at least one $C_1$-$C_{20}$ alkyl-diamide. In another embodiment, the linker comprises at least one $C_1$-$C_{20}$ alkyl ether. In another embodiment, the linker comprises at least one phosphate moiety. In another embodiment, the linker comprises at least one triazole moiety.

In another embodiment, the linker comprises at least one moiety selected from: $C_1$-$C_{20}$ alkyl, $C_1$-$C_{20}$ alkyl-NH, $C_1$-$C_{20}$ alkylether-NH, $C_1$-$C_{20}$ alkylether, $C_1$-$C_{20}$ alkylamide, $C_1$-$C_{20}$ alkyl-diamide, $C_1$-$C_{20}$ alkyl-O, $C_1$-$C_{20}$ alkylamine, phosphate, NH, O, triazole, and NHC(O); wherein alkyl is optionally substituted, wherein substitutions include one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol and thioalkyl.

In another embodiment, the linker comprises $C_1$-$C_{20}$ alkyl-NH. In another embodiment, the linker comprises $C_1$-$C_{20}$ alkyl-amide. In another embodiment, the linker comprises $C_1$-$C_{20}$ alkylether-NH. In another embodiment, the linker comprises $C_1$-$C_{20}$ alkyl-diamide. In another embodiment, the linker comprises $C_1$-$C_{20}$ alkyl-NH. In another embodiment, the linker comprises phosphate, $C_1$-$C_{20}$ alkylamide, and $C_1$-$C_{20}$ alkyl-NH moieties. In another embodiment, the linker comprises phosphate, $C_1$-$C_{20}$ alkyl-NH and $C_1$-$C_{20}$ alkyl moieties. In another embodiment, the linker comprises $C_1$-$C_{20}$ alkylamide, $C_1$-$C_{20}$ alkyl-NH, $C_1$-$C_{20}$ alkyl, and phosphate moieties. In another embodiment, the linker comprises NHC(O), and $C_1$-$C_{20}$ alkyl-NH moieties. In another embodiment, the linker comprises phosphate, $C_1$-$C_{20}$ alkyl, phosphate, and $C_1$-$C_{20}$ alkyl-NH moieties. In another embodiment, the linker comprises $C_1$-$C_{20}$ alkyl, $C_1$-$C_{20}$ alkyl-NH and triazole moieties. In another embodiment, the linker comprises $C_1$-$C_{20}$ alkyl-diamide, $C_1$-$C_{20}$ alkylether, $C_1$-$C_{20}$ alkyl, and triazole moieties.

In another embodiment, the linker consist of at least one moiety selected from: $C_1$-$C_{20}$ alkyl, $C_1$-$C_{20}$ alkyl-NH, $C_1$-$C_{20}$ alkylether-NH, $C_1$-$C_{20}$ alkylether, $C_1$-$C_{20}$ alkylamide, $C_1$-$C_{20}$ alkyl-diamide, $C_1$-$C_{20}$ alkyl-O, $C_1$-$C_{20}$ alkylamine, phosphate, NH, O, triazole, and NHC(O); wherein alkyl is optionally substituted, wherein substitutions include one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol and thioalkyl.

In another embodiment, the linker consists of $C_1$-$C_{20}$ alkyl-NH. In another embodiment, the linker consists of $C_1$-$C_{20}$ alkyl-amide. In another embodiment, the linker consists of $C_1$-$C_{20}$ alkylether-NH. In another embodiment, the linker consists of $C_1$-$C_{20}$ alkyl-diamide. In another embodiment, the linker consists of $C_1$-$C_{20}$ alkyl-NH. In another embodiment, the linker consists of phosphate, $C_1$-$C_{20}$ alkylamide, and $C_1$-$C_{20}$ alkyl-NH moieties. In another embodiment, the linker consists of phosphate, $C_1$-$C_{20}$ alkyl-NH and $C_1$-$C_{20}$ alkyl moieties. In another embodiment, the linker consists of $C_1$-$C_{20}$ alkylamide, $C_1$-$C_{20}$ alkyl-NH, $C_1$-$C_{20}$ alkyl, and phosphate moieties. In another embodiment, the linker consists of NHC(O), and $C_1$-$C_{20}$ alkyl-NH moieties. In another embodiment, the linker consists of phosphate, $C_1$-$C_{20}$ alkyl, phosphate, and $C_1$-$C_{20}$ alkyl-NH moieties. In another embodiment, the linker consists of $C_1$-$C_{20}$ alkyl, $C_1$-$C_{20}$ alkyl-NH and triazole moieties. In another embodiment, the linker consists of $C_1$-$C_{20}$ alkyl-diamide, $C_1$-$C_{20}$ alkylether, $C_1$-$C_{20}$ alkyl, and triazole moieties.

In another embodiment, each of said linkers is independently a substituted or unsubstituted $C_1$-$C_{20}$ alkyl-NHC(O)-alkyl-NHC(O); a substituted or unsubstituted $C_1$-$C_{20}$ alkyl-NHC(O)-alkyl-phosphate-alkyl-NHC(O)-alkyl-NH; a substituted or unsubstituted $C_1$-$C_{20}$-alkyl-NHC(O); a substituted or unsubstituted $C_1$-$C_{20}$ alkyl-NH; a substituted or unsubstituted $C_1$-$C_{20}$ alkyl-NHC(O)-alkyl-NHC(O)-alkylether-alkyl-triazole; a substituted or unsubstituted $C_1$-$C_{20}$ NHC(O)-alkyl-NH— and $C_1$-$C_{20}$ alkyl-phosphate-alkyl-phosphate-alkyl-NH; a substituted or unsubstituted $C_1$-$C_{20}$ alkyl-NH-alkyl-triazole; a substituted or unsubstituted $C_1$-$C_{20}$ alkylether-NH; a substituted or unsubstituted $C_1$-$C_{20}$ alkyl; a substituted or unsubstituted $C_1$-$C_{20}$ alkyl-NH; a substituted or unsubstituted $C_1$-$C_{20}$ NHC(O)-alkyl-NH; substituted or unsubstituted $C_1$-$C_{20}$ alkyl ether, substituted or unsubstituted $C_1$-$C_{20}$ alkyl ether-alkyl-phosphate, substituted or unsubstituted $C_1$-$C_{20}$ alkyl di-amide-alkylether, substituted or unsubstituted $C_1$-$C_{20}$ alkyl di-amide-alkylether-triazole-alkyl, substituted or unsubstituted $C_1$-$C_{20}$ alkyl amide, substituted or unsubstituted $C_1$-$C_{20}$ alkyl di-amide, substituted or unsubstituted $C_1$-$C_{20}$ alkyl triazole, substituted or unsubstituted $C_1$-$C_{20}$ alkyl-NH-alkyl-triazole substituted or unsubstituted $C_1$-$C_{20}$ alkyl-phosphate-alkyl-phosphate-alkylamide-, substituted or unsubstituted $C_1$-$C_{20}$ alkyl-phosphate-alkyl-phosphate-alkyl-NH—, substituted or unsubstituted alkylamide-alkyl-phosphate-alkylamide-alkylamide-, substituted or unsubstituted $C_1$-$C_{20}$ alkylamide-alkyl-phosphate-alkylamide-alkyl-NH—, substituted or unsubstituted alkylamine-alkyltriazole; wherein said substitutions are selected from hydroxyl, methylene-hydroxyl, halogen, CN, $NO_2$, linear or branched $C_1$-$C_6$ alkyl, linear or branched $C_1$-$C_6$ alkoxy, linear or branched $C_1$-$C_6$ haloalkyl, or any combination thereof.

In some embodiments, this invention provides a first oligodeoxyribose nucleotide (ODN) derivative represented by formula IIIA: ODN1-[(PEG)$_m$-(P)$_n$]$_v$—$X^2$—Y—(P)$_q$-(Split)[$X^1$—$R^1$]$_t$. In one embodiments, the first ODN derivative of formula IIIA is represented by the structure of formula ODN-58:

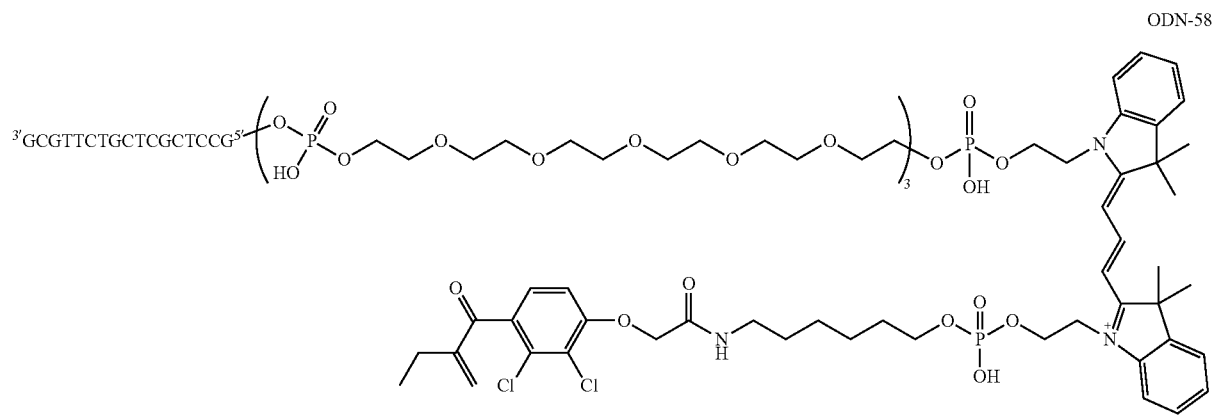

ODN-58 wherein n of formula IIIA is 1, m is 6, v is 3, $X^2$ is a bond, Y is Cy3, q is 1, Split is absent, $X^1$ is $C_1$-$C_{20}$ alkyl-NH, $R^1$ is EA and t is 1.

In another embodiment, the ODN derivative of formula IIIA is represented by the structure of formula ODN-20:

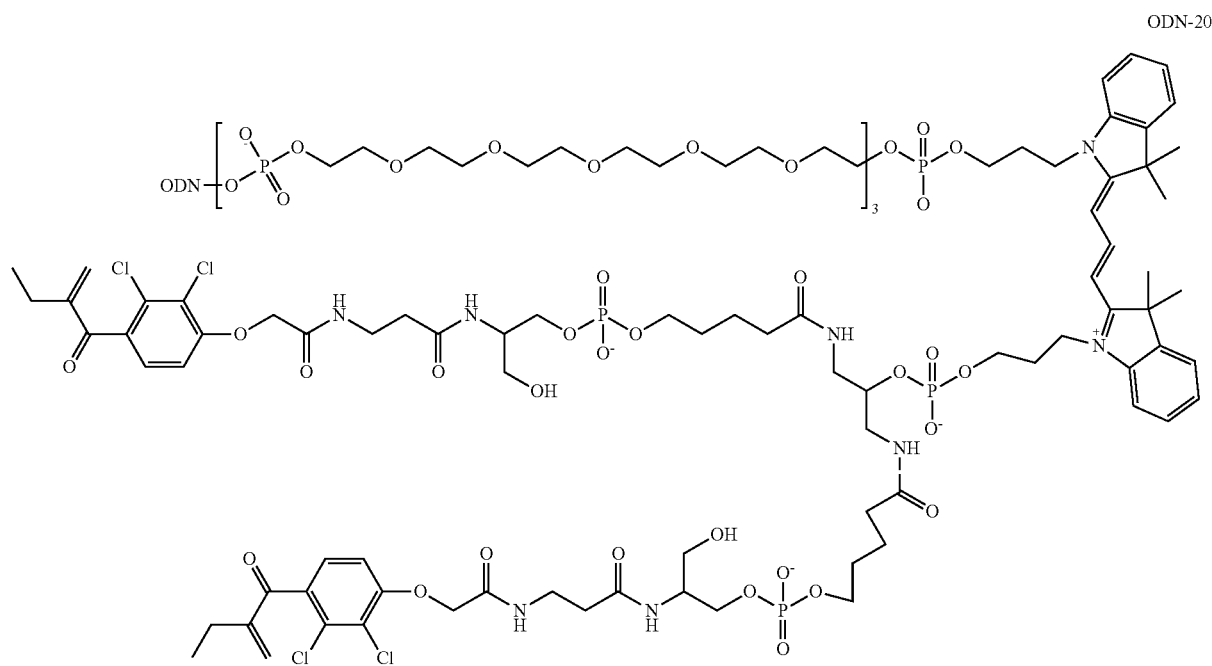

ODN-20 wherein n of formula IIIA is 1, m, 6 is v is 3, $X^2$ is a bond, Y is Cy3, q is 1, Split is CH, $X^1$ is substituted or unsubstituted $C_1$-$C_{20}$ alkylamide-alkyl-phosphate-alkylamide-alkyl-NH—, $R^1$ is EA and t is 2.

In some embodiments, this invention provides a first oligodeoxyribose nucleotide (ODN) derivative represented by formula IIIB: Y—$X^2$—ODN1-[(PEG)$_m$-(P)$_n$]$_v$-(Split)[$X^1$—$R^1$]$_t$. In one embodiments, the ODN derivative of formula IIIB is represented by the structure of formula ODN-51:

ODN-51
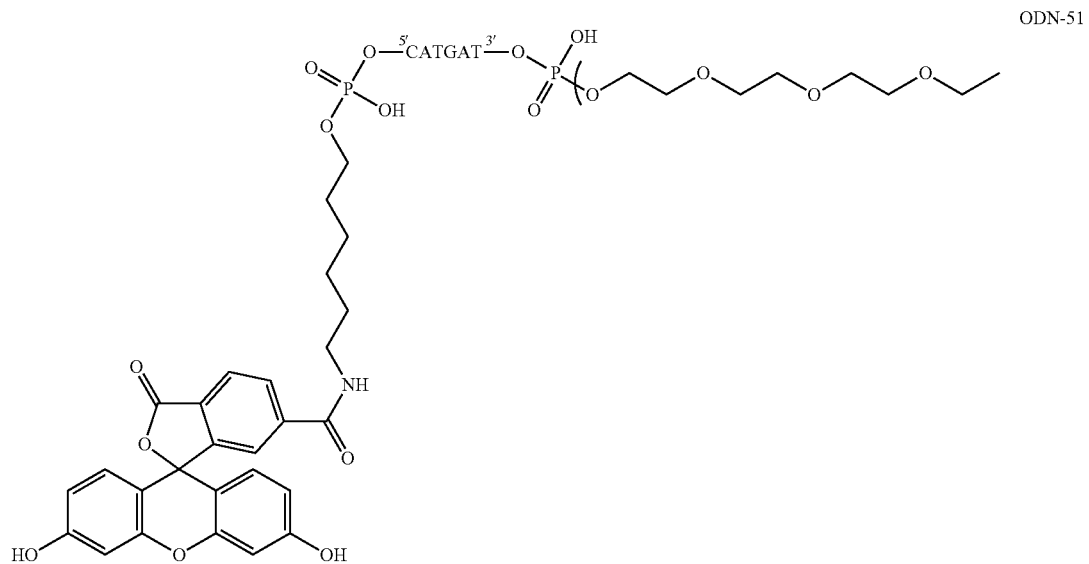
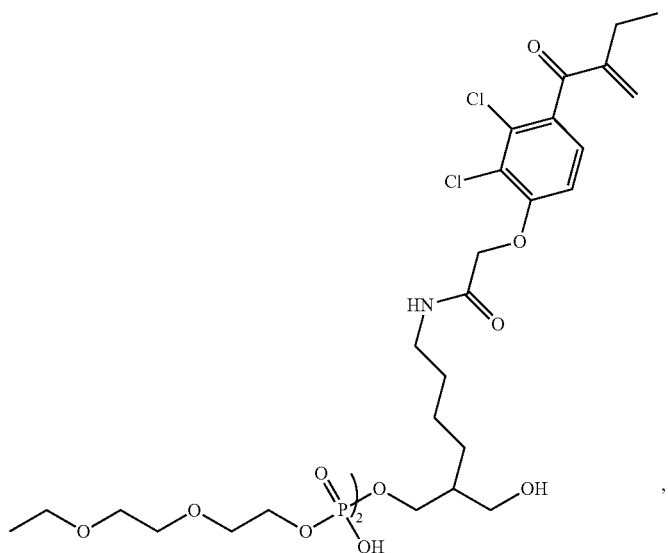
wherein Y of formula IIIB is FAM, $X^2$ is $C_1$-$C_{20}$ alkyl-NH, n is 1, m is 6, v is 2, Split is absent, $X^1$ is $C_1$-$C_{20}$ alkyl-NH, and $R^1$ is EA;
In one embodiments, the ODN derivative of formula IIIB is represented by the structure of formula ODN-53:

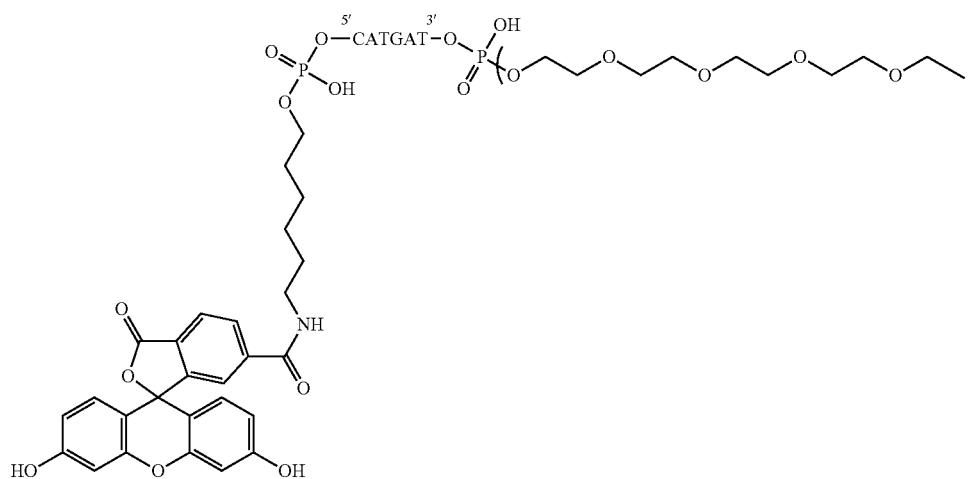
ODN-53
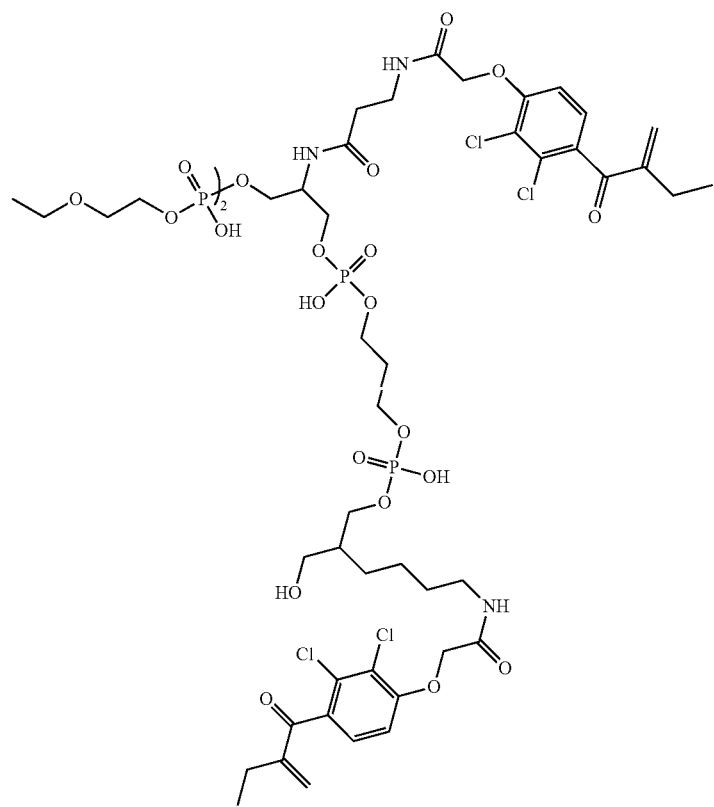
wherein Y of formula IIIB is FAM, $X^2$ is $C_1$-$C_{20}$ alkyl-NH, n is 1, m is 6, v is 2, Split is $CH_2CH$, t is 2, and each $X^1$ is independently $C_1$-$C_{20}$ NHC(O)-alkyl-NH or $C_1$-$C_{20}$ alkyl-phosphate-alkyl-phosphate-alkyl-NH, and $R^1$ are both EA.
In one embodiment, the first ODN derivative of formula IIIB is represented by the following structure:

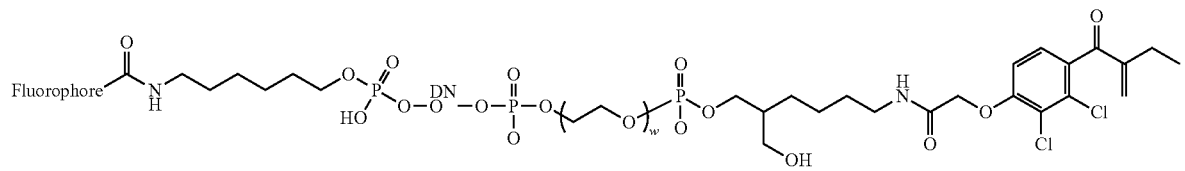

wherein Y of formula IIIB is a fluorophore, $X^2$ is $C_1$-$C_{20}$ alkyl-NH, n is 1, m is w, v is 1, Split is absent, $X^1$ is $C_1$-$C_{20}$ alkyl-NH, $R^1$ is EA and t is 1.

In one embodiment, the first ODN derivative of formula IIIB is represented by the following structure:

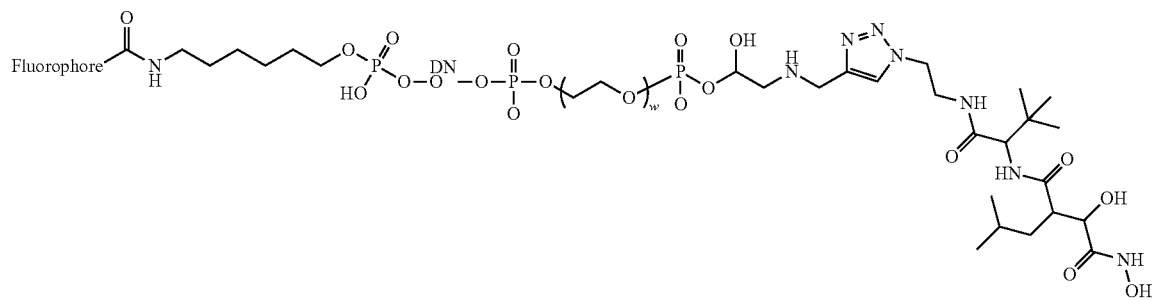

wherein Y of formula IIIB is fluorophore, $X^2$ is $C_1$-$C_{20}$ alkyl-NH, n is 1, m is w, v is 1, Split is absent, $X^1$ is $C_1$-$C_{20}$ alkyl-NH-alkyl-triazole, $R^1$ is a Mariamstat and t is 1.

In one embodiments, the first ODN derivative of formula IIIB is represented by the structure of formula ODN-49:

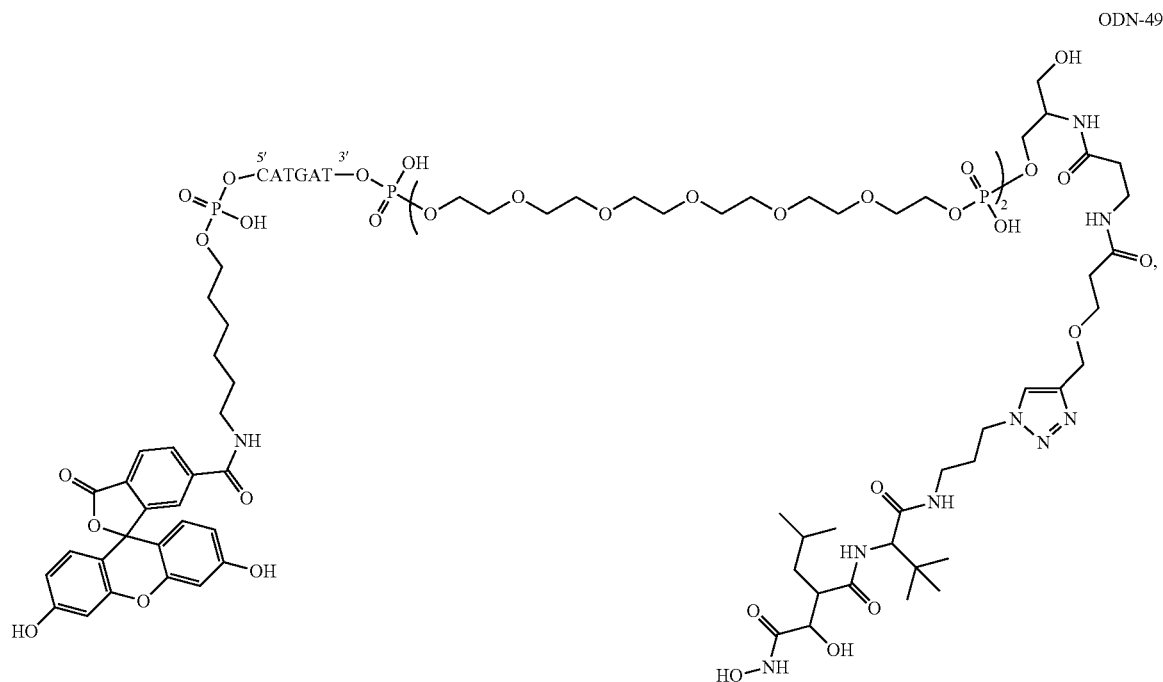

ODN-49 wherein Y of formula IIIB is a FAM, $X^2$ is $C_1$-$C_{20}$ alkyl-NH, n is 1, m is 6, v is 2, Split is absent, $X^1$ is $C_1$-$C_{20}$ alkyl di-amide-alkylether-triazole-alkyl, $R^1$ is Marimastat and t is 1.

In some embodiments, this invention provides a second oligodeoxyribose nucleotide (ODN) derivative represented by formula IVB: Y'—$X^{2'}$-ODN2-[(PEG)$_{m'}$—(P)$_{n'}$]$_{v'}$—$X^{1'}$-(Q)($R^{1'}$)$_k$. In one embodiment, the second ODN derivative of formula IVB is represented by the structure of formula ODN-39:

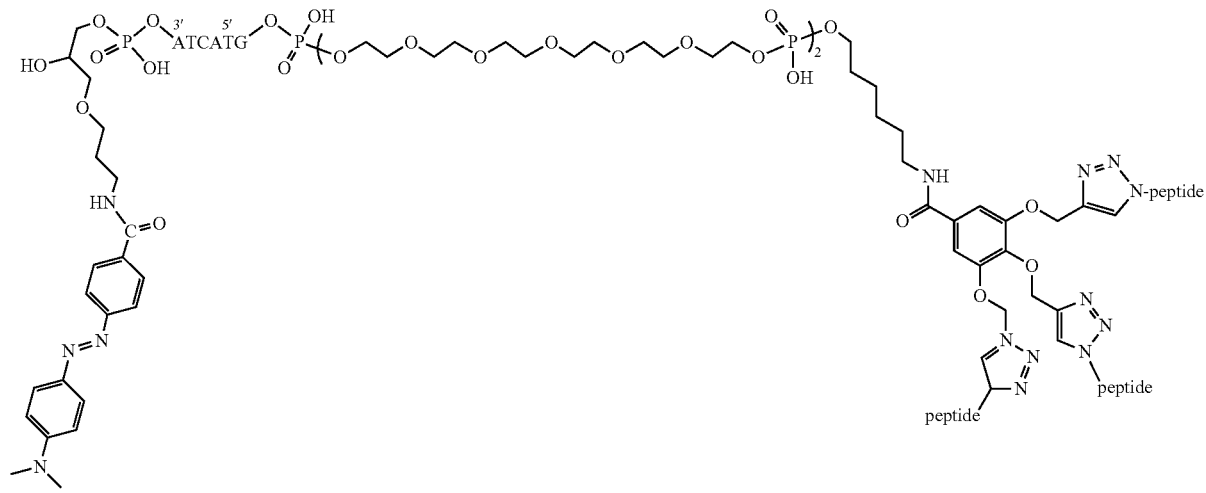

ODN-39 wherein Y' of formula IVB is dabcyl, $X^{2'}$ is $C_1$-$C_{20}$ alkylether-NH, n' is 1, m' is 6, v' is 2, $X^{1'}$ is $C_1$-$C_{20}$ alkyl amide, Q is represented by formula B as described hereinabove, $R^{1'}$ is a peptide as defined herein above and k is 3.

In one embodiment, the second ODN derivative of formula IVB is represented by the following structure:

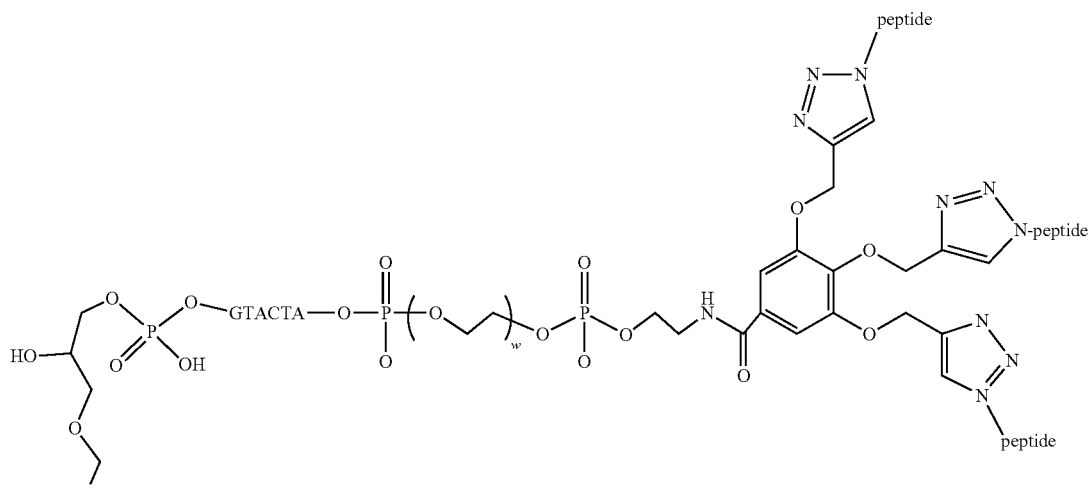

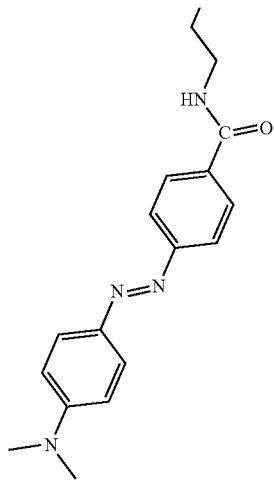

wherein Y' of formula IVB is dabcyl, $X^{2'}$ is $C_1$-$C_{20}$ alkylether-NH, n' is 1, m' is w, v' is 1, $X^{1'}$ is $C_1$-$C_{20}$ alkyl amide, Q is represented by formula B as described hereinabove, $R^{1'}$ is a peptide as defined herein above and k is 3.

In some embodiments, this invention provides a second oligodeoxyribose nucleotide (ODN) derivative represented by formula IVC: ODN2-[(PEG)$_{m'}$—(P)$_{n'}$]$_{v'}$—$X^{2'}$-(Q)[$R^{1'}$—$X^{1'}$—Y']$_k$.

In one embodiment the oligodeoxyribose nucleotide (ODN) derivatives of IVC is represented by the structure of formula ODN-56:

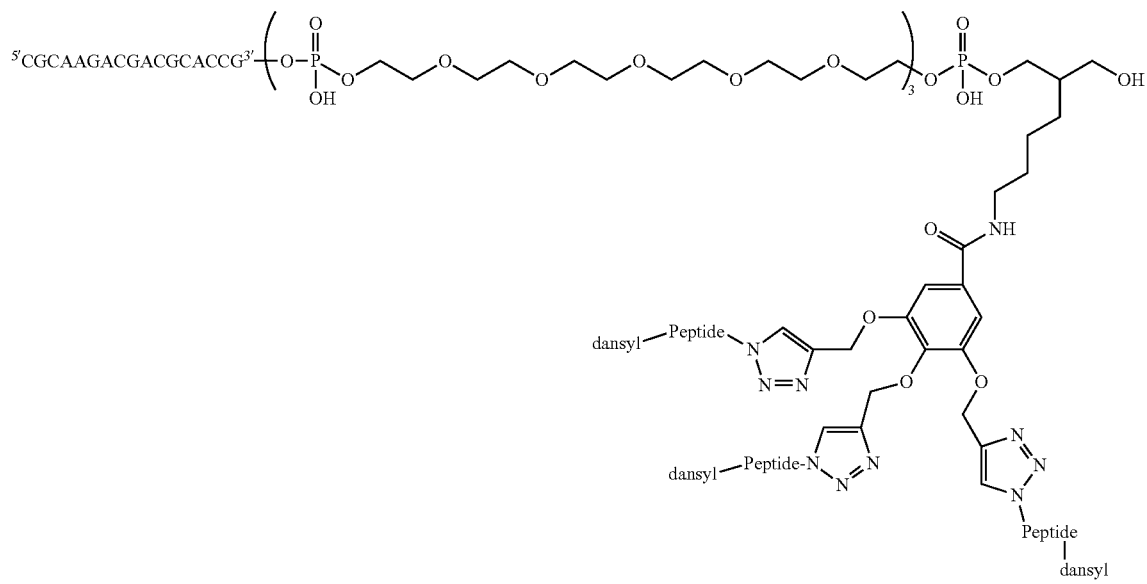

ODN-56 wherein n' of formula IVC is 1, m' is 6, v' is 3, $X^{2'}$ is $C_1$-$C_{20}$ alkyl amide, Q is represented by formula B as described hereinabove, $R^{1'}$ is a peptide as defined herein above, Y' is dansyl and k is 3.

In one embodiment the oligodeoxyribose nucleotide (ODN) derivatives of IVC is represented by the structure of formulas ODNs-5-9:

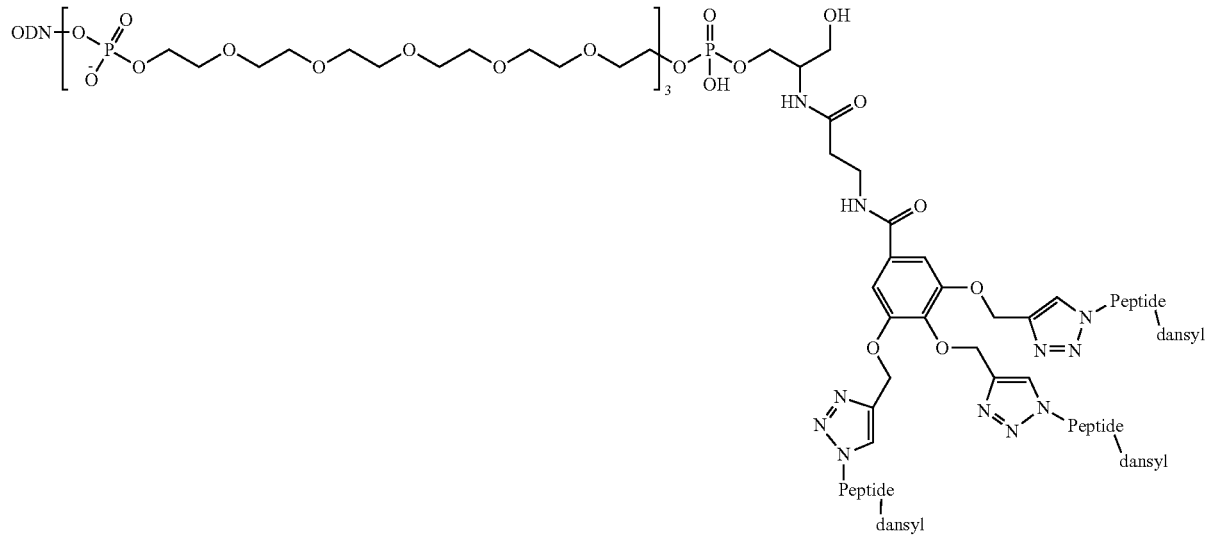

ONDs-5-9 wherein n' of formula IVC is 1, m' is 6, v' is 3, $X^{2'}$ is substituted $C_1$-$C_{20}$ alkyl di-amide, Q is represented by formula B as described hereinabove, $R^{1'}$ is a peptide as defined herein above, Y' is dansyl and k is 3.

In one embodiment, ODN1 and ODN2 can be any oligodeoxyribose nucleotide known to the skilled in the art, which are complementary to each other. In some embodiments, ODN1, ODN2 and/or ODN of formulas I(A-C), II(A-C), III(A-C), IV(A-C) and of formulas ODN-58, ODN-20, ODNs-5-9 is 5'-CGCAAGACGAGCGAGGC-3' (Seq. ID. 2). In some embodiments, ODN1, ODN2 and/or ODN of formulas I(A-C), II(A-C), III(A-C), IV(A-C) and of formulas ODN-58, ODN-20, ODNs-5-9 is 5'-GC-CTCGCTCGTCTTGCG-3' (Seq ID. 3). In one embodiment, ODN1 of formulas I(A-C) and/or III(A-C) is 5'-GC-CTCGCTCGTCTTGCG-3' (Seq ID. 3). In another embodiment, ODN2 of formulas II(A-C) and/or IV(A-C) is 5'-CG-CAAGACGAGCGAGGC-3' (Seq ID. 2). In another embodiment, ODN1 of formulas I(A-C) and/or III(A-C) is 5'-TAGTAC-3' (Seq ID 1). In another embodiment, ODN2 of formulas II(A-C) and/or IV(A-C) is 5'-GTACTA-3' (Seq ID 4). In another embodiment, ODN2 of formulas II(A-C) and/or IV(A-C) has between 3 and 8 oligodeoxyribose nucleotides. In another embodiment, ODN1 of formulas I(A-C) and/or III(A-C) has between 3 and 8 oligodeoxyribose nucleotides. In another embodiment, ODN2 of formulas II(A-C) and/or IV(A-C) has 6 oligodeoxyribose nucleotides. In another embodiment, ODN1 of formulas I(A-C) and/or III(A-C) has 6 oligodeoxyribose nucleotides. In another embodiment, ODN2 of formulas II(A-C) and/or IV(A-C) has between 10 and 20 oligodeoxyribose nucleotides. In another embodiment, ODN1 of formulas I(A-C) and/or III(A-C) has between 10 and 20 oligodeoxyribose nucleotides. In another embodiment, ODN2 of formulas IIIA-C) and/or IV(A-C) has 17 oligodeoxyribose nucleotides. In another embodiment, ODN1 of formulas I(A-C) and/or III(A-C) has 17 oligodeoxyribose nucleotides.

In some embodiments, the two oligodeoxyribose nucleotide (ODN) derivatives of this invention consist of a first ODN derivative of formula IIIA, IIIB or IIIC; and a second ODN derivative of formula IVA, IVB or IVC. In some embodiments the two oligodeoxyribose nucleotide (ODN) derivatives are of formula IIIA and IVA. In some embodiments, the two oligodeoxyribose nucleotide (ODN) derivatives are of formula IIIB and IVB. In some embodiments, the two oligodeoxyribose nucleotide (ODN) derivatives are of formula IIIC and IVC. In some embodiments, the two oligodeoxyribose nucleotide (ODN) derivatives are of formula IIIA and IVB. In some embodiments, the two oligodeoxyribose nucleotide (ODN) derivatives are of formula IIIA and IVC. In some embodiments, the two oligodeoxyribose nucleotide (ODN) derivatives are of formula IIIB and IVA. In some embodiments, the two oligodeoxyribose nucleotide (ODN) derivatives are of formula IIIB and IVC. In some embodiments, the two oligodeoxyribose nucleotide (ODN) derivatives are of formula IIIC and IVA. In some embodiments, the two oligodeoxyribose nucleotide (ODN) derivatives are of formula IIIC and IVB.

In some embodiments, $X^1$, $X^2$, $X^{1'}$, $X^{2'}$ of formula IIIA, IIIB, IIIC, IVA, IVB, IVC, are independently a bond. In some embodiments, $X^1$, $X^2$, $X^{1'}$, $X^{2'}$ of formula IIIA, IIIB, IIIC, IVA, IVB, IVC, are independently a linker. In some embodiments $X^1$, $X^2$, $X^{1'}$, $X^{2'}$ of formula IIIA, IIIB, IIIC, IVA, IVB, IVC, are independently a substituted or unsubstituted $C_1$-$C_{20}$ alkyl. In some embodiments $X^1$, $X^2$, $X^{1'}$, $X^{2'}$ of formula IIIA, IIIB, IIIC, IVA, IVB, IVC, are independently a substituted or unsubstituted $C_1$-$C_{20}$ alkyl-NH. In some embodiments $X^1$, $X^2$, $X^{1'}$, $X^{2'}$ of formula IIIA, IIIB, IIIC, IVA, IVB, IVC, are independently a substituted or unsubstituted $C_1$-$C_{20}$ NHC(O)-alkyl-NH. In some embodiments $X^1$, $X^2$, $X^{1'}$, $X^{2'}$ of formula IIIA, IIIB, IIIC, IVA, IVB, IVC, are independently substituted or unsubstituted $C_1$-$C_{20}$ alkyl ether. In some embodiments $X^1$, $X^2$, $X^{1'}$, $X^{2'}$ of formula IIIA, IIIB, IIIC, IVA, IVB, IVC, are independently substituted or unsubstituted $C_1$-$C_{20}$ alkyl ether-alkylphosphate. In some embodiments $X^1$, $X^2$, $X^{1'}$, $X^{2'}$ of formula IIIA, IIIB, IIIC, IVA, IVB, IVC, are independently $C_1$-$C_{20}$ alkyl di-amide-di-amide-alkylether-triazole-alkyl. In some embodiments $X^1$, $X^2$, $X^{1'}$, $X^{2'}$ of formula IIIA, IIIB, IIIC, IVA, IVB, IVC, are independently substituted or unsubstituted $C_1$-$C_{20}$ alkyl di-amide. In some embodiments $X^1$, $X^2$, $X^{1'}$, $X^{2'}$ of formula IIIA, IIIB, IIIC, IVA, IVB, IVC, are independently substituted or unsubstituted $C_1$-$C_{20}$ alkyl-phosphate-alkyl-phosphate-alkyl-NH—. In some embodiments $X^1$, $X^2$, $X^{1'}$, $X^{2'}$ of formula IIIA, IIIB, IIIC, IVA, IVB, IVC, are independently substituted or unsubstituted $C_1$-$C_{20}$ alkylamide-alkyl-phosphate-alkylamide-alkyl-NH—. In some embodiments $X^1$, $X^2$, $X^{1'}$, $X^{2'}$ of formula IIIA, IIIB, IIIC, IVA, IVB, IVC, are independently an alkyl ether. In some embodiments $X^1$, $X^2$, $X^{1'}$, $X^{2'}$ of formula IIIA, IIIB, IIIC, IVA, IVB, IVC are independently alkylamide. In some embodiments $X^1$, $X^2$, $X^{1'}$, $X^{2'}$ of formula IIIA, IIIB, IIIC, IVA, IVB, IVC are independently alkyl di-amide. In some embodiments $X^1$, $X^2$, $X^{1'}$, $X^{2'}$ of formula IIIA, IIIB, IIIC, IVA, IVB, IVC are independently alkyl triazole. In some embodiments $X^1$, $X^2$, $X^{1'}$, $X^{2'}$ of formula IIIA, IIIB, IIIC, IVA, IVB, IVC are independently alkyl-phosphate-alkyl-phosphate-alkylamide-. In some embodiments $X^1$, $X^2$, $X^{1'}$, $X^{2'}$ of formula IIIA, IIIB, IIIC, IVA, IVB, IVC are independently alkyl-amide-alkyl-phosphate-alkylamide-alkyl-amide-. In some embodiments $X^1$, $X^2$, $X^{1'}$, $X^{2'}$ of formula IIIA, IIIB, IIIC, IVA, IVB, IVC are independently alkyl di-amide-alkylether-triazole-alkyl. In some embodiments $X^1$, $X^2$, $X^{1'}$, $X^{2'}$ of formula IIIA, IIIB, IIIC, IVA, IVB, IVC are independently alkyl di-amide-alkylether.

In some embodiments each P of formula IIIA, IIIB, IIIC, IVA, IVB, IVC is independently $PO_3$, $PO_2OH$, $PO(OH)_2$, $PO_4$, $PO_3OH$ or $PO_2(OH)_2$. In some embodiments, P is $PO_3$. In some embodiments, P is $PO_2OH$. In some embodiments, P is $PO(OH)_2$. In some embodiments, P is $PO_4$. In some embodiments, P is $PO_3OH$. In some embodiments, P is $PO_2(OH)_2$.

In some embodiments, n of formula IIIA, IIIB, IIIC is 1. In some embodiments, n of formula IIIA, IIIB, IIIC is 0.

In some embodiments, n' of formula IVA, IVB, IVC is 1. In some embodiments n' of formula IVA, IVB, IVC is 0.

In some embodiments q of formula IIIA is 1. In some embodiments q of formula IIIA is 0.

In some embodiments q' of formula IVA is 1. In some embodiments q' of formula IVA is 0.

In some embodiments, m of formula IIIA, IIIB, IIIC is 6. In some embodiments m of formula IIIA, IIIB, IIIC is 0. In some embodiments m of formula IIIA, IIIB, IIIC is 2. In some embodiments m of formula IIIA, IIIB, IIIC is 3. In some embodiments m of formula IIIA, IIIB, IIIC is 4. In some embodiments m of formula IIIA, IIIB, IIIC is 5. In some embodiments m of formula IIIA, IIIB, IIIC is 7. In some embodiments m of formula IIIA, IIIB, IIIC is 8. In some embodiments m of formula IIIA, IIIB, IIIC is 9. In some embodiments m of formula IIIA, IIIB, IIIC is 10.

In some embodiments m' of formula IVA, IVB, IVC is 6. In some embodiments m' of formula IVA, IVB, IVC is 0. In some embodiments m' of formula IVA, IVB, IVC is 2. In some embodiments m' of formula IVA, IVB, IVC is 3. In some embodiments m' of formula IVA, IVB, IVC is 4. In some embodiments m' of formula IVA, IVB, IVC is 5. In some embodiments m' of formula IVA, IVB, IVC is 7. In some embodiments m' of formula IVA, IVB, IVC is 8. In some embodiments m' of formula IVA, IVB, IVC is 9. In some embodiments m' of formula IVA, IVB, IVC is 10.

In some embodiments, v of formula IIIA, IIIB, IIIC is an integer between 1 and 10. In some embodiments, v is 0. In some embodiments, v of formula IIIA, IIIB, IIIC is 1. In some embodiments, v of formula IIIA, IIIB, IIIC is 2. In some embodiments, v of formula IIIA, IIIB, IIIC is 3.

In some embodiments v' of formula IVA, IVB, IVC is an integer between 1 and 10. In some embodiments v' is 0. In some embodiments v' of formula IVA, IVB, IVC is 1. In some embodiments v' of formula IVA, IVB, IVC is 2. In some embodiments v' of formula IVA, IVB, IVC is 3.

In some embodiments Split of formula IIIA, IIIB, IIIC is absent. In some embodiments Split of formula IIIA, IIIB, IIIC is C. In some embodiments Split of formula IIIA, IIIB, IIIC is CH. In some embodiments Split of formula IIIA, IIIB, IIIC is $CH_2$—C. In some embodiments Split of formula IIIA, IIIB, IIIC is $CH_2$—CH.

In some embodiments Q of formula IVA, IVB and/or IVC is absent. In some embodiments Q of formula IVA, IVB and/or IVC is alkyl triazole. In some embodiments Q of formula IVA, IVB and/or IVC is represented by the structure of formula B:

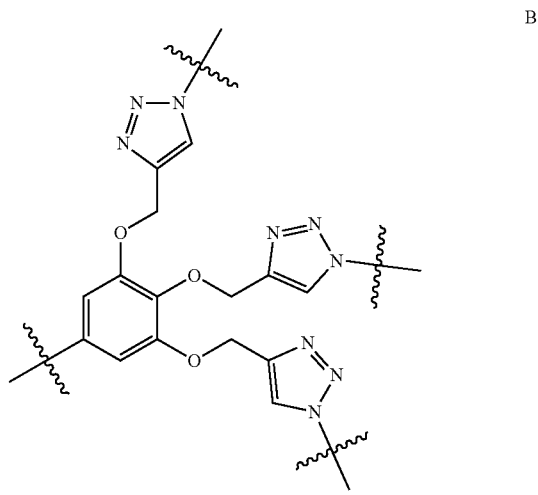 [SMILES: *c1cc(OCc2cn(*)nn2)c(OCc2cn(*)nn2)c(OCc2cn(*)nn2)c1]

B

In some embodiments t of formula IIIA, IIIB and/or IIIC is 1. In some embodiments t is 2. In some embodiments t is 3.

In some embodiments k of formula IVA, IVB and/or IVC is 1. In some embodiments k of formula IVA, IVB and/or IVC is 3.

In some embodiments the first oligodeoxyribose nucleotide (ODN) derivatives of this invention and methods of use thereof, comprise at least one selective protein binder. In another embodiment, $R^1$ of formula IIIA, IIIB and IIIC is a selective protein binder as defined herein above.

In one embodiment the second oligodeoxyribose nucleotide (ODN) derivative of this invention and methods of use thereof comprise at least one non-selective protein surface binder. In another embodiment, $(Q)(R^{1'})_k$ of formula IVA, IVB and/or $(Q)[R^{1'}—X^{1'}—Y']_k$ of formula IVC is a non-selective protein surface binder. In another embodiment, the non-selective protein surface binder is a peptide derivative. In another embodiment, the non-selective protein surface binder is a tripodal peptides having a surface of 750-1500 $Å^2$.

In another embodiment, $R^{1'}$ of formula IVA, IVB and IVC is a peptide. In another embodiment, the peptide comprises a sequence of between 2 to 30 amino acids. In another embodiment, the peptide comprises a sequence of between 5 to 15 amino acids. In another embodiment, the peptide comprises a sequence of between 5 to 10 amino acids. In another embodiment, the peptides further comprise linkers which link between the amino acid sequence of the peptide and the compound to which they are attached. In another embodiment, the peptides are attached to the N atoms of the compound through linkers. In another embodiment, the linker is a substituted or unsubstituted linear or branched alkyl chain of 1-50 carbon atoms, substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof. In another embodiment, the linker is a $C_1$-$C_6$ alkyl. In another embodiment, the linker is a propyl (i.e., —$CH_2$—$CH_2$—$CH_2$—). In another embodiment the peptides comprises the sequence as described in Table 3, Example 8. In another embodiment the peptides comprises the sequence as described in Table 1, Example 1. In another embodiment the peptides comprises the sequence as described in Table 5, Example 16. In another embodiment the peptide comprises amino acid sequence interrupted by a donor or an acceptor, or substituted by a donor or an acceptor. In another embodiment, the donor or acceptor is covalently bonded to a lysine residue (K).

A non-selective protein surface binder is referred to a compound or moiety that comprises a functionalized amino acid sequence or peptide groups that react non-specifically, with complementary protein surfaces based on their size, topology and electrostatic potential, as defined herein above. In one embodiment the non-selective protein surface binder is a tripodal protein surface binder, represented by formula (A) as described herein above.

In some embodiments the first and second oligodeoxyribose nucleotide (ODN) derivatives of this invention and methods of use thereof, comprise a donor and an acceptor, wherein at least one of the donor or acceptor is a fluorophore as defined herein above. In one embodiment, if one of the oligodeoxyribose nucleotide (ODN) derivatives includes a donor, the other includes an acceptor. In one embodiment, Y of formula IIIA, IIIB, IIIC, or Y' of formula IVA, IVB, IVC is a donor. In one embodiment, Y of formula IIIA, IIIB, IIIC or Y' of formula IVA, IVB, IVC is an acceptor. In one embodiment, Y of formula IIIA, IIIB, IIIC is an acceptor and Y' of formula IVA, IVB, IVC is a donor. In one embodiment the first ODN derivative includes a fluorophore. In one embodiment the second ODN derivative includes a fluorophore. In some embodiment, the fluorophore of this invention is any fluorescent material or dye known in the art. In another embodiment, the fluorophore is fluorescein (6-FAM), FAM, cyanine dyes (e.g. Cy3, Cy5), sulfoindocyanine, nile red, rhodamine, dansyl, perylene, fluorenyl, coumarin, dabcyl or derivative thereof.

In some embodiment, the donor or acceptor of this invention is fluorescein (6-FAM), FAM, cyanine dyes (e.g. Cy3, Cy5), nile red, rhodamine, dansyl, dabcyl, perylene, fluorenyl, coumarin, 7-methoxycoumarin (Mca) or derivative thereof.

In some embodiments, the donor of this invention is fluorescein (6-FAM, FAM) and the acceptor is dabcyl. In another embodiment, the donor is solvatochromic fluorophore. In another embodiment, the solvatochromic fluorophore is dansyl. In another embodiment, the donor is solvatochromic dansyl and the acceptor is Cy3. In another embodiment, the donor is Mca and the acceptor is dinitrophenol (Dnp).

In some embodiment, the fluorophore of this invention is a fluorescent dye as defined herein above.

This invention is also directed to a compound, which comprises the non-selective protein surface binder represented by the structure of formula A:

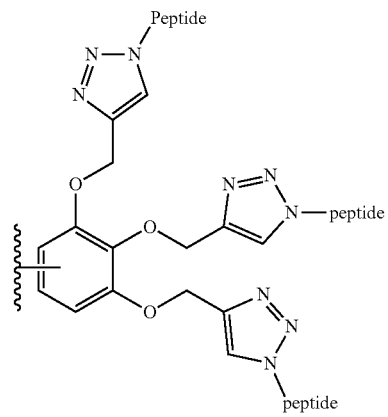

wherein "peptide" is as defined herein above.

In another embodiment, the compound is a protein sensor. In another embodiment, the compound further comprises a protein selective binder.

This invention is also directed to the reagents and precursors that are used for the preparation of the first and second ODN derivatives of formulas I(A-C), II(A-C), III(A-C) and/or IV(A-C). In some embodiments, the precursor for the first or the second ODN derivative of formulas I(A-C), II(A-C), III(A-C) and/or IV(A-C) is represented by the following formulas:

```
ODN-10:  5'-YZWXXXGCCTCGCTCGTCTTGCG-3'

ODN-3:   5'-CGCAAGACGAGCGAGGCXXXY-3'
``` wherein each X, Y, Z and W are represented by the following fragments:

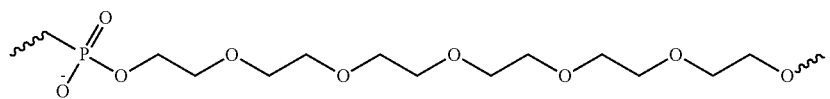

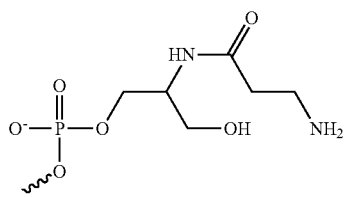

-continued

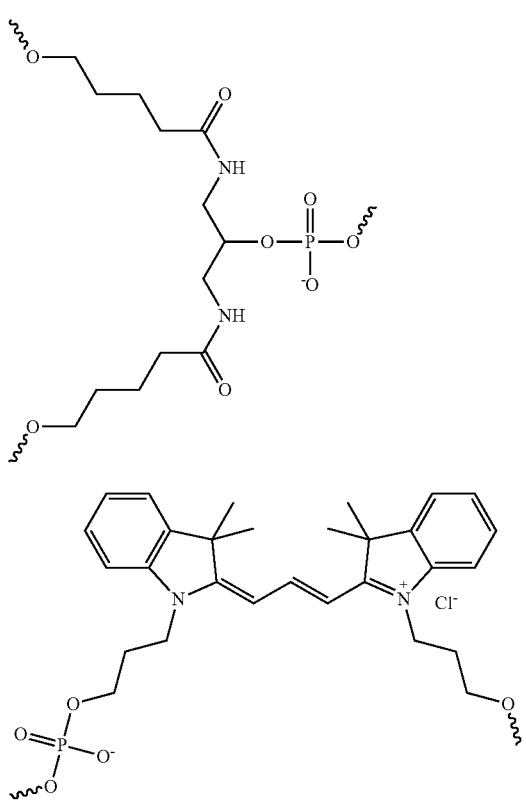

Z

W wherein each end etheral O atom of a fragment (X, Z or W) represent a phosphate O atom of the fragment attached to it.

In some embodiments, the precursor for the non-selective tripodal protein surface binder of the second ODN derivative of formulas IIIA-C), and/or IV(A-C) is represented by the following formulas:

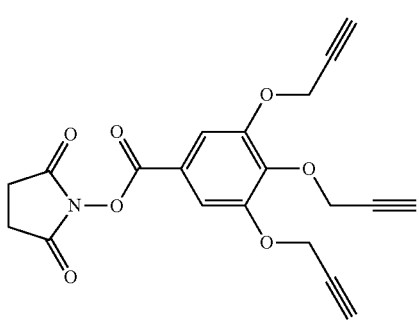 [SMILES: C#CCOc1cc(C(=O)ON2C(=O)CCC2=O)cc(OCC#C)c1OCC#C]

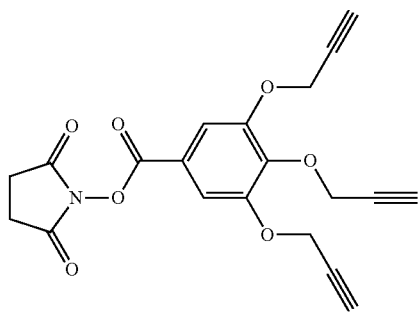 [SMILES: C#CCOc1cc(C(=O)ON2C(=O)CCC2=O)cc(OCC#C)c1OCC#C]

In another embodiment, said precursor is first conjugated to an amino derivatized compound (e.g. ODN derivative) followed by its conjugation to an azido-modified peptide (i.e. $N_3$-peptide) using the copper-catalyzed Huisgen 1,3-dipolar cycloaddition (the "click reaction"), thereby resulting in the formation of a non-selective synthetic protein receptor according to this invention.

In one embodiment, this invention provides a method for the preparation of a compound comprising a non-selective tripodal protein surface binder, said method comprises the following steps:
 a. conjugation of a compound represented by the following formulas:

to an amino derivatized compound; and
 b. conjugation of the product resulting from step a to an azido-modified peptide using the copper-catalyzed Huisgen 1,3-dipolar cycloaddition (the "click reaction"),
 thereby resulting in the formation of a compound comprising a non-selective tripodal protein surface binder.

In another embodiment, the amino derivatized compound is an oligodeoxyribose nucleotide sequence derivative. In another embodiment, the amino derivatized compound is a peptide nucleic acid oligomer derivative. In another embodiment, the amino derivatized compound is an alkyl amino compound. In another embodiment, the amino derivatized compound is any compound with an amino moiety.

In one embodiment, this invention provides a method for the preparation of a protein biosensor which comprises a non-selective tripodal protein surface binder, said method comprises the following steps:
 a. conjugation of a compound represented by the following formulas:

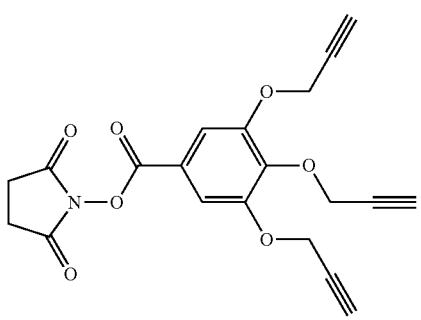 [SMILES: C#CCOc1cc(C(=O)ON2C(=O)CCC2=O)cc(OCC#C)c1OCC#C]

to an amino derivatized compound; and b. conjugation of the product resulting from step a to an azido-modified peptide using the copper-catalyzed Huisgen 1,3-dipolar cycloaddition (the "click reaction"), thereby resulting in the formation of a protein biosensor which comprises a non-selective tripodal protein surface binder.

In another embodiment, the amino derivatized compound is an oligodeoxyribose nucleotide (ODN) sequence derivative. In another embodiment, the amino derivatized compound is a peptide nucleic acid (PNA) oligomer derivative. In another embodiment, the amino derivatized compound is an alkyl amino compound. In another embodiment, the amino derivatized compound is any compound with an amino moiety.

In one embodiment, this invention provides a method of differentiating between proteins and protein isoforms in a biological medium comprising:

(i) incubating an array of oligodeoxyribose nucleotide (ODN) derivatives with a biological medium comprising said proteins and/or protein isoforms;

wherein each of said duplexes consists of a first ODN derivative comprising an a first ODN sequence, at least one selective protein binder and a donor or acceptor; and a second ODN derivative comprising a second ODN sequence, which is complementary to the first ODN sequence, at least one non-selective protein surface binder and a donor or acceptor, wherein if one of said ODN derivatives comprises a donor than the other one comprises an acceptor, and wherein at least one of said donor or said acceptor is a fluorophore;

wherein the duplexes differ from each other in their non-selective binders;

wherein binding said protein and/or protein isoforms with each of said duplexes results in a conformational change of said duplex and thereby provide a unique optical signature for each duplex; and (ii) measuring said optical signature obtained by said binding of step (i);

thereby, differentiating between proteins and/or protein isoforms in said biological medium.

In one embodiment, this invention provides a method of diagnosing a disease or disorder in a subject, wherein said diagnosis comprises detection of a protein biomarker; said method comprises:

(i) collecting a biological sample from a subject;

(ii) optionally isolating components from said biological sample;

(iii) incubating an array of complementary oligodeoxyribose nucleotide (ODN) derivatives duplexes with said biological sample;

wherein each of said duplexes consists of a first ODN derivative comprising a first ODN sequence, at least one selective protein binder and a donor or acceptor; and a second ODN derivative comprising a second ODN sequence, which is complementary to the first ODN sequence, at least one non-selective protein surface binder and a donor or acceptor, wherein if one of said ODN derivatives comprises a donor than the other one comprises an acceptor, and wherein at least one of said donor or said acceptor is a fluorophore;

wherein the duplexes differ from each other in their non-selective binders;

wherein binding of said protein biomarker with each of said duplexes results in a conformational change of said duplex and thereby to a unique optical signature for each duplex;

(iv) measuring said optical signature obtained by said binding of step (iii); and (v) identifying said protein biomarker in said sample based on the measurement of a unique optical signature, which characterizes the specific protein biomarker; or measuring a change in a concentration of a protein biomarker in said sample compared to normative values, wherein said protein biomarker is characteristic of a disease or disorder;

thereby, diagnosing a disease or disorder in a subject.

In one embodiment, the protein biomarker is MMP-1. In another embodiment, the protein biomarker is MMP-2. In another embodiment, the protein biomarker is MMP-7. In another embodiment, the protein biomarker is MMP-9. In another embodiment, the protein biomarker is GST α (A). In another embodiment, the protein biomarker is GST μ (M). In another embodiment, the protein biomarker is GST 7π (P). In another embodiment, the protein biomarker is GST-A. In another embodiment, the protein biomarker is GST-A1. In another embodiment, the protein biomarker is GST-A2. In another embodiment, the protein biomarker is GST-P. In another embodiment, the protein biomarker is GST-M1. In another embodiment, the protein biomarker is GST-P. In another embodiment, the protein biomarker is any combination of MMP-1, MMP-2, MMP-7, MMP-9 biomarkers. In another embodiment, the protein biomarker is any combination of GST α (A), GST μ (M), GST π (P), GST-A, GST-A1, GST-A2, GST-P, GST-M1 biomarkers.

In one embodiment, the disease is cancer. In another embodiment, the disease is breast cancer, lung cancer, colorectal cancer, pancreas cancer, bladder cancer, ovarian cancer, prostate cancer, brain cancer, clear cell renal cell carcinoma, gastric cancer or any combination thereof.

In another embodiment, the disorder is renal tubular injury. In another embodiment, the disorder is graft failure or regeneration following living donor liver transplantation.

In one embodiment, this invention is directed to a method of creating libraries of tripodal protein surface binders, said method comprises the conjugation of compound 7:

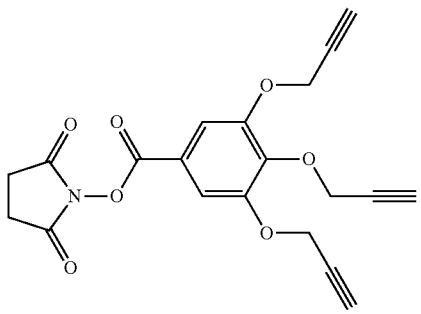 [SMILES: C#CCOc1cc(C(=O)ON2C(=O)CCC2=O)cc(OCC#C)c1OCC#C]

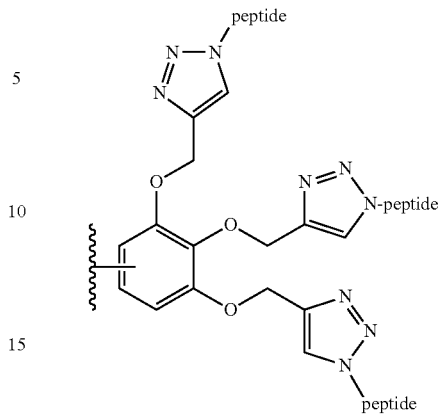

wherein "peptide" is as defined herein above.

In another embodiment, each synthetic receptor further comprises a selective protein binder. In another embodiment, each synthetic receptor further comprises a donor and an acceptor, wherein at least one of the donor or acceptor is a fluorophore. In another embodiment, each donor or acceptor is attached to or in close proximity to one of the selective and non-selective binders of said synthetic receptor. In another embodiment, each synthetic receptor comprises different peptides.

In one embodiment, this invention is directed to a protein sensor, said sensor comprises an array of synthetic receptors, wherein each synthetic receptor comprises a selective protein binder, a non-selective protein surface binder, a donor and an acceptor, wherein each donor or acceptor is attached to or in close proximity to one of the selective and non-selective binders, wherein at least one of the donor or acceptor is a fluorophore. In another embodiment, the non-selective protein surface binder comprises a peptide tripod, represented by the structure of formula A:

to an amino derivatized compound followed by a conjugation of an azido-modified peptide using the copper-catalyzed Huisgen 1,3-dipolar cycloaddition (the "click reaction"). In another embodiment, the amino derivatized compound is an amino ODN derivative. In another embodiment, the amino derivatized compound is an amino PNA derivative. In another embodiment, the amino derivatized compound is an amino alkyl derivative.

In one embodiment, this invention is directed to a protein sensor, said sensor comprises a tripodal protein surface binder represented by the structure of formula A:

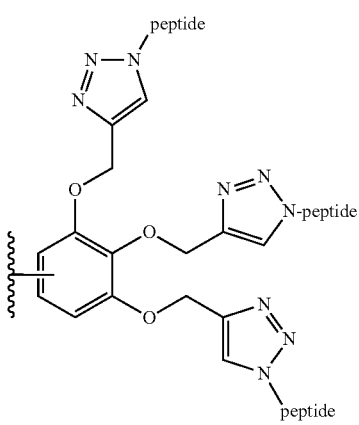

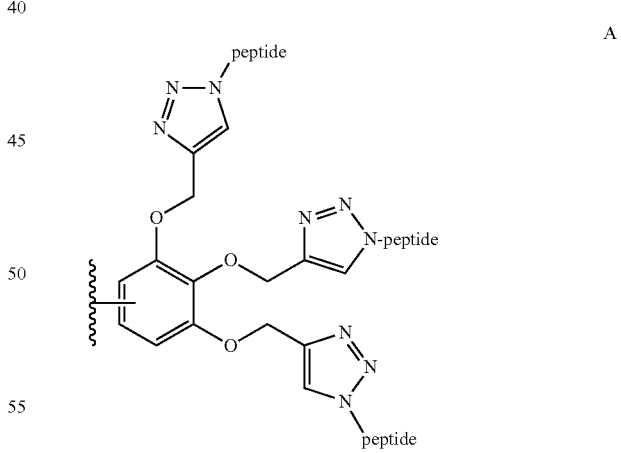

wherein "peptide" is as defined herein above.

In another embodiment, the protein sensor further comprises a selective protein binder. In another embodiment, the protein sensor further comprises a donor and an acceptor, wherein at least one of the donor or acceptor is a fluorophore. In another embodiment, each donor or acceptor is attached to or in close proximity to one of the selective and non-selective binders of said sensor.

In one embodiment, this invention is directed to a protein sensor, said sensor comprises an array of synthetic receptors, wherein each synthetic receptor comprises a non-selective tripodal protein surface binder represented by the structure of formula A:

In one embodiment, this invention is directed to a protein sensor wherein said sensor comprises an array of synthetic receptors, wherein each synthetic receptor comprises an oligodeoxyribose nucleotide (ODN) derivatives duplex of this invention.

In one embodiment, this invention is directed to a protein sensor, said sensor consists of an array of complementary oligodeoxyribose nucleotide (ODN) derivatives duplexes, each duplex of such array consists of a first ODN derivative comprising a first ODN sequence and at least one selective protein binder; and a second ODN derivative comprising a second ODN sequence, which is complementary to the first ODN sequence, and at least one non-selective protein surface binder; wherein each of the ODN derivatives independently further comprises a donor, an acceptor or combination thereof, wherein at least one of the donor or acceptor is a fluorophore. In another embodiment, the non-selective protein surface binder comprises a peptide tripod, represented by the structure of formula A:

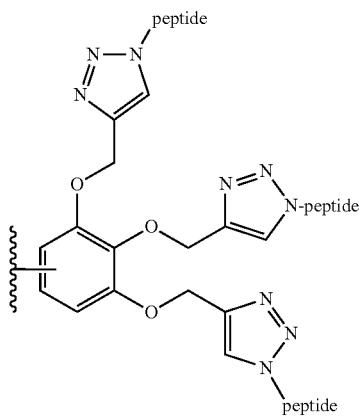

A wherein "peptide" is as defined herein above.

In another embodiment, the duplexes of the array are different from each other in the peptide sequence that is comprised in their non-selective protein surface binder.

In one embodiment, this invention is directed to a cross reactive protein sensor array, said sensor array consists of an array of complementary oligodeoxyribose nucleotide (ODN) derivatives duplexes, each duplex of such array consists of a first ODN derivative comprising a first ODN sequence and at least one selective protein binder; and a second ODN derivative comprising a second ODN sequence, which is complementary to the first ODN sequence, and at least one non-selective protein surface binder; wherein each of the ODN derivatives independently further comprises a donor, an acceptor or combination thereof, wherein at least one of the donor or acceptor is a fluorophore, and wherein if one ODN derivative comprises a donor then the other ODN derivative comprises an acceptor. In another embodiment, the non-selective protein surface binder comprises a peptide tripod, represented by the structure of formula A:

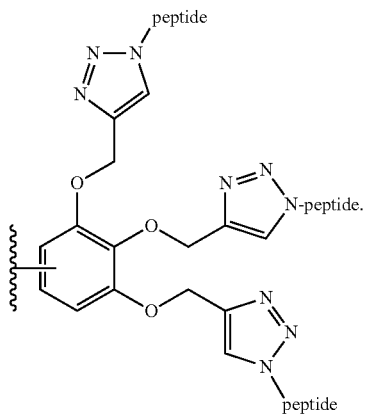

A

In another embodiment, the duplexes of the array are different from each other in the peptide sequence that is comprised in their non-selective protein surface binder.

In one embodiment, this invention provides a cross reactive sensor array for discriminating between closely related proteins in a biological medium, said sensor array comprises an array of synthetic receptors, wherein each of said synthetic receptors comprises complementary two oligodeoxyribose nucleotide (ODN) derivatives (i.e. an ODN duplex), wherein said two ODN derivatives consist of a first ODN derivative which comprises a first ODN sequence and at least one selective protein binder; and a second ODN derivative comprising a second ODN sequence, which is complementary to the first ODN sequence, at least one non-selective protein surface binder and a donor or acceptor, wherein if one ODN derivative comprises a donor, the other one comprises an acceptor, and wherein at least one of said donor or said acceptor is a fluorophore, and wherein said synthetic receptors differ from each other in their non-selective protein surface binder. In another embodiment, the non-selective protein surface binder comprises a peptide tripod, represented by the structure of formula A:

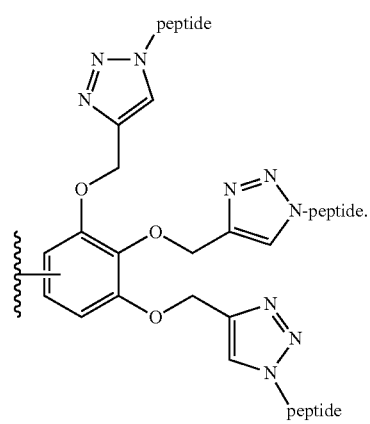

A

In one embodiment, this invention provides an array of synthetic receptors that can discriminate between closely related proteins in a biological medium, wherein each of said synthetic receptors comprises oligodeoxyribose nucleotide (ODN) derivatives duplex, wherein each of said ODN derivatives duplexes consists of a first ODN derivative which comprises a first ODN sequence and at least one selective protein binder; and a second ODN derivative comprising a second ODN sequence, which is complementary to the first ODN sequence, at least one non-selective protein surface binder and a donor or acceptor, wherein if one ODN derivative comprises a donor the other one comprises an acceptor, and wherein at least one of said donor or said acceptor is a fluorophore, and wherein said synthetic receptors differ from each other in their non-selective protein surface binder. In another embodiment, the closely related proteins are protein isoforms.

A "protein isoform" refers to several different forms of the same protein, with slightly different amino acid sequences, but with similar activity. Different forms of a protein may be produced from related genes or may arise from the same gene by alternate splicing.

In one embodiment, this invention is directed to a protein sensor as described hereinabove. In another embodiment, the proteins are enzymes. In another embodiment, the enzymes are isozymes. In another embodiment, the proteins are matrix metalloproteases (MMPs) protein and its isoforms. In another embodiment, the proteins are glutathione S-Transferase (GSTs) protein and its isoforms. In another embodiment, the proteins are platelet derived growth factors. In another embodiment, the proteins are Histidine-tag proteins. In another embodiment, the proteins are estrogen receptor (ERα or ERβ). In another embodiment, the proteins are fibroblast growth factor (FGF). In another embodiment, the proteins are glycoforms of the gp120 protein.

An "ODN derivative duplex" refers to two complementary ODN derivatives which are hybridized. In another embodiment, an "ODN derivative duplex" refers to two complementary oligomeric peptide nucleic acid (PNA) derivatives which are hybridized.

In one embodiment, the first ODN derivative of the duplexes according to this invention, as described hereinabove is represented by the structure of formula IA, IB, IC, IIIA, IIIB, IIIC, III, ODN-20, ODN-58, ODN-49, ODN-51, or ODN-53.

In one embodiment, the second ODN derivative of the duplexes according to this invention, as described hereinabove is represented by the structure of formula IIA, IIB, IIC, IVA, IVB, IVC, IV, V, ODN-39, ODN-56, ODN-5, ODN-6, ODN-7, ODN-8, or ODN-9. In another embodiment, ODNs-5-9 are five ODN derivatives which differ from each other in their non-selective protein surface binder. In another embodiment each of the non-selective protein surface binders comprises three identical peptides. In another embodiment each of the non-selective protein surface binders comprises three different peptides. In another embodiment, ODNs-5-9 are five ODN derivatives which differ from each other in their non-selective protein surface binder peptide sequences.

An "array" is referred herein as between 3 to 10 ODN duplexes of this invention. Generating an array of ODN duplexes, which differ solely in their protein surface binding domain (i.e possess different amino-acid sequence; different peptides), will afford an analytical device in which all of the receptors bind preferentially to a particular protein family.

In one embodiment, the array according to this invention as described hereinabove consists of between 3 and 10 synthetic receptors. In another embodiment, the array consists of between 3 and 6 synthetic receptors. In another embodiment, the array consists of between 2 and 7 synthetic receptors. In another embodiment, the array consists of 4 synthetic receptors. In one embodiment, the array consists of 5 synthetic receptors. In another embodiment, the array consists of 6 synthetic receptors.

In one embodiment, each of said non-selective protein surface binders according to this invention as described hereinabove comprises at least one peptide, wherein said at least one peptide is different for each synthetic receptor in said array. In another embodiment, each of said non-selective protein surface binders comprises three identical peptides, wherein said peptides are different for each synthetic receptor in said array. In another embodiment, the non-selective protein surface binder comprises a peptide tripod, represented by the structure of formula A:

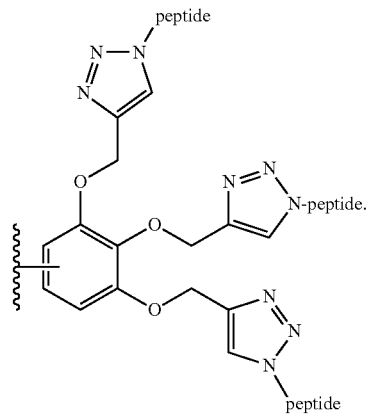

In some embodiments the methods of this invention are directed to a) differentiating between proteins and protein isoforms; b) identifying proteins and protein isoforms; c) detecting proteins and protein isoforms; or d) diagnosing a disease or disorder, using the ODN derivatives of this invention, ODN derivatives duplexes of this invention and/or arrays of ODN derivatives duplexes of this invention. In one embodiment the protein is matrix metalloproteases (MMPs) protein and its isoforms. In another embodiment, the protein is glutathione S-Transferase (GSTs) protein and its isoforms. In another embodiment, the protein is a platelet derived growth factor. In another embodiment, the protein is Histidine-tag proteins. In another embodiment, the protein is a fibroblast growth factor, Estrogen receptor (ERα or ERβ), or glycoform of the pg120 protein.

A "protein isoform" refers to several different forms of the same protein, with slightly different amino acid sequences, but with similar activity. Different forms of a protein may be produced from related genes or may arise from the same gene by alternate splicing.

Figure 11A:
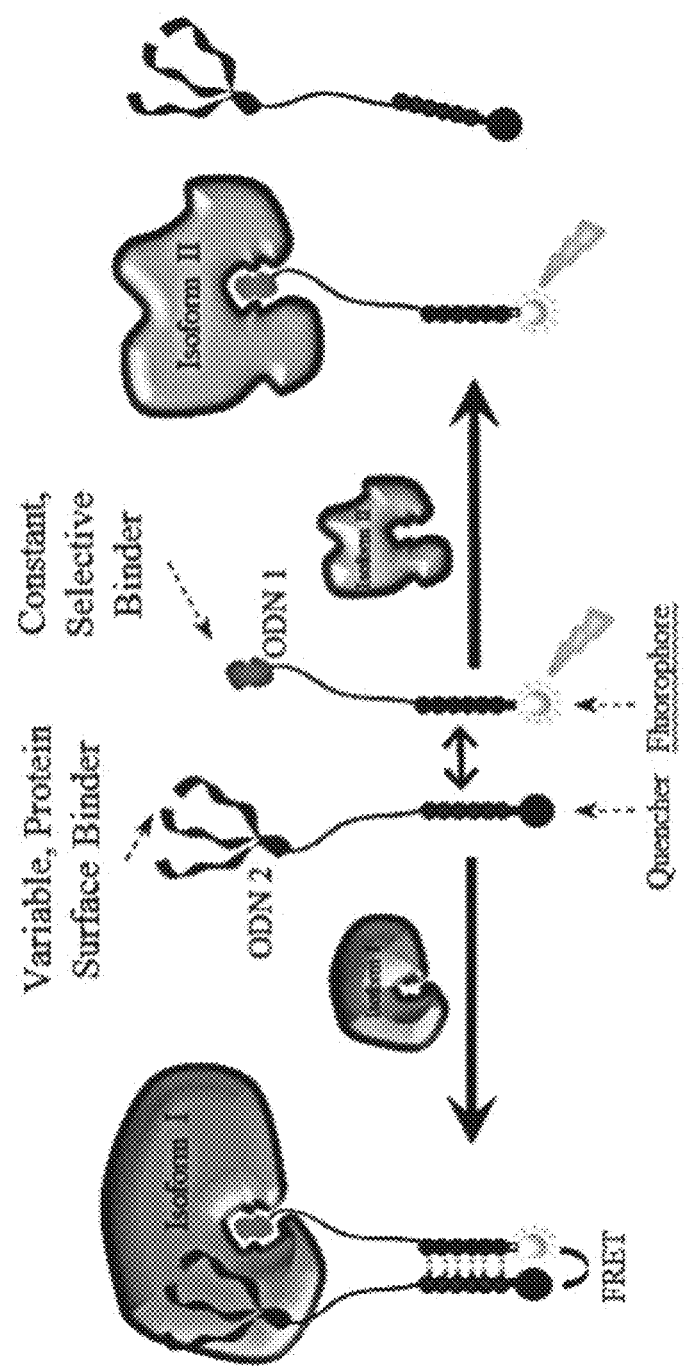
FIG. 11A-11B depicts schematic illustrations of protein binders with dual binding modes: selective and non-selective.
Figure 11B:
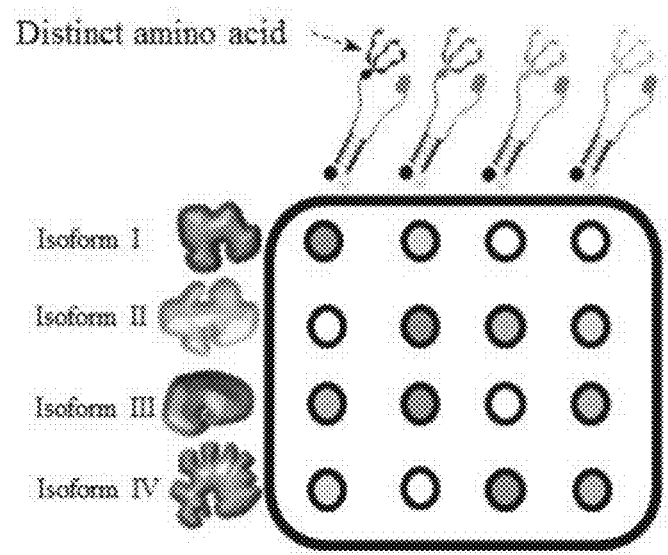
Figure 12A:
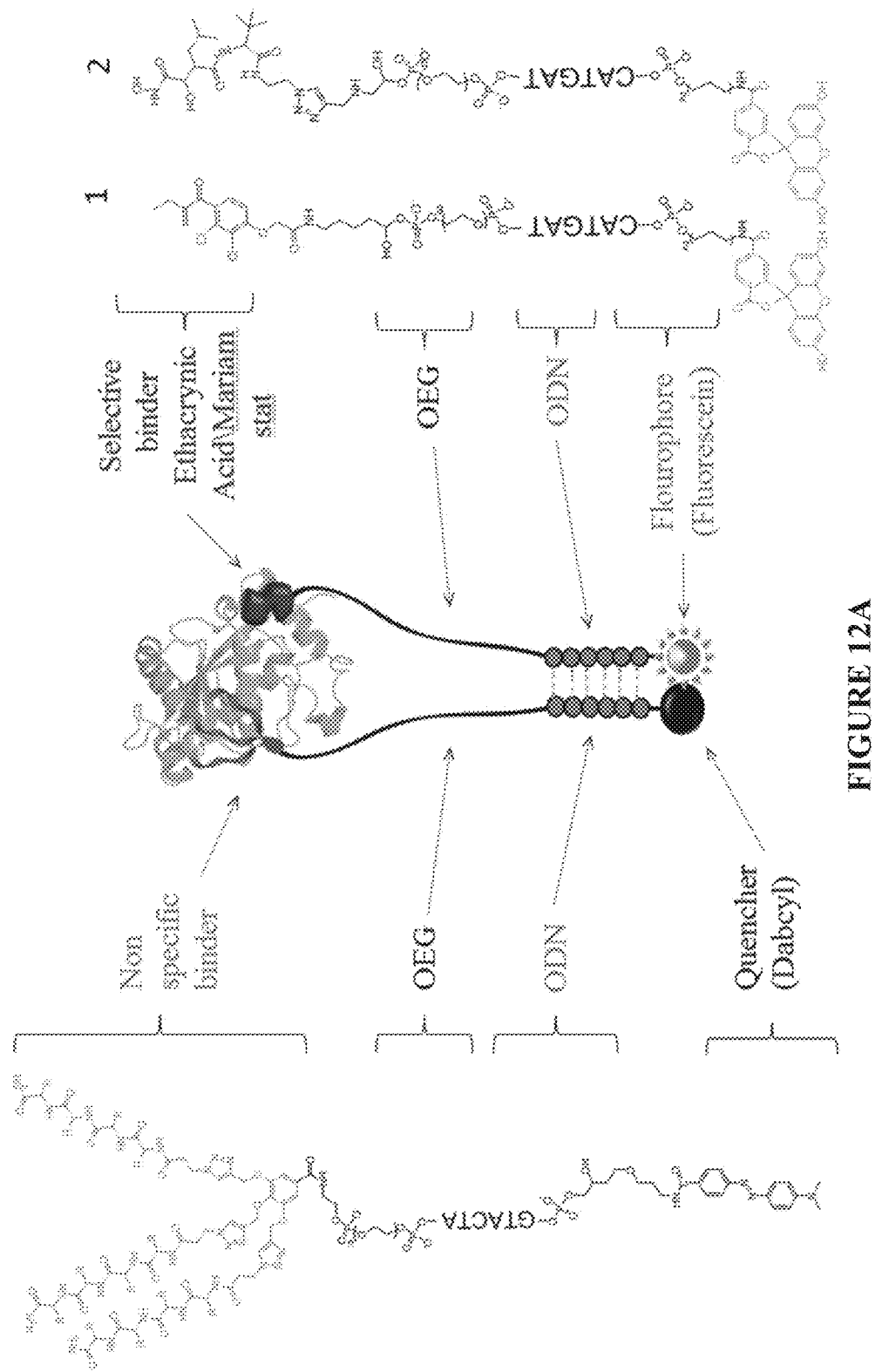
FIG. 12A-12B depicts schematic differential molecular beacons with dual binding modes: selective and non-selective. The variable, non-selective strand (left) is modified with a quencher (e.g. dabcyl) and a tripodal peptide binder, whereas the selective binding strand (right) is appended with a fluorophore (e.g. 6-FAM) (FIG. 12A) or Cys 3 (FIG. 12B) and a broad spectrum inhibitor of MMPs (Comp. 1) or GSTs (e.g. 'marimastat' or ethacrynic acid) (Comp. 2 and FIG. 12B).
Figure 12B:
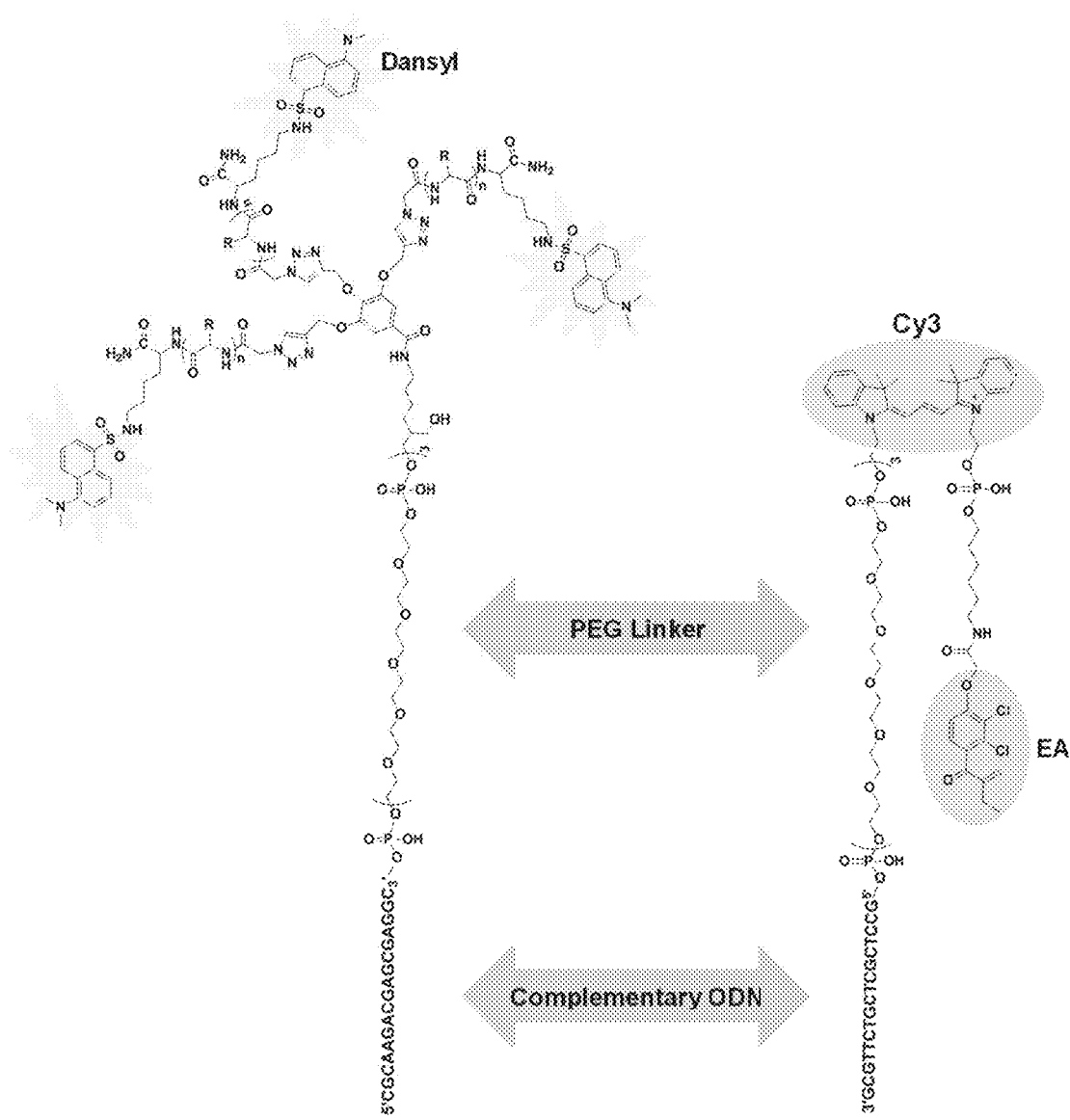

In some embodiments, the methods of this invention are directed to a) differentiating between proteins and protein isoforms; b) identifying proteins and protein isoforms; c) detecting proteins and protein isoforms; or d) diagnosing a disease, comprising measuring an optical signature obtained by contacting ODN derivatives, ODN derivatives duplexes and/or arrays of ODN derivatives duplexes of this invention and a protein. In one embodiment, the unique optical signature of an array of ODN duplexess of this invention (FIG. 11A-11B) provides an optical/fluorescent pattern which is characteristic to a protein or to a protein isoform. In another embodiment, the fluorescence pattern is obtained following irradiation of the donor of the ODN derivatives of this invention at a wavelength that causes the excitation of said donor. In another embodiment, the fluorescence pattern indicates that the protein is present in the analyzed biological sample.

In some embodiments, a fluorescent pattern is obtained from an array of ODN duplexes of this invention. The fluorescent pattern obtained from this invention is used to identify, detect, differentiate a protein of this invention, or diagnose a disease or disorder which is characterize by the presence of the protein.

Binding of different proteins to the synthetic receptors of the invention, affects differently the distance and the orientation of the photoluminescent species which are incorporated into the receptor structure (i.e. donor and acceptor), as well as induces conformational changes in the receptor-protein complex that would result in different optical signature for each protein tested. In another embodiment binding of different proteins affects differently the emission of each fluorescent dye, as well as induces conformational changes that would result in different fluorescence resonance energy transfer (FRET) processes between them. The combination of these effects provides a vast number of unique optical signatures.

In another embodiment, the methods of this invention comprise an optional isolation of components from a biological sample. In another embodiment, "isolating components" refers to isolating cells having proteins; isolating sugars, desalination, isolating glycans, phosphates (non-limiting examples include ATP, ADP, AMP, GMP), isolating phospholipids, isolating glycoprotein, a glycolipid or a proteoglycan from the biological sample.

In one embodiment, the method of this invention is directed to a method of diagnosing a disease or disorder in a subject. In another embodiment, the disease or disorder is characterized by different expression of various proteins and protein isoforms than their normative expression level. Non limited examples of a diseases are cancers (colorectal, prostate, breast, lung, gastric, pancreas, bladder, ovarian, or brain), hepatitis c, phenylketonuria, Alzheimer, type II diabetes, familial hypercholesterolemia. In another embodiment, the method of this invention is directed to identifying a renal tubular injury (using GST proteins as biomarkers). In another embodiment, the method of this invention is directed to monitoring graft failure or regenerations following living donor liver transplantation (using GST proteins as biomarkers).

In one embodiment, the methods of this invention include a step of measuring the optical signature of the contacting/binding of the ODNs of this invention and a protein. In another embodiment, the unique optical signature of an array of hybridized ODNs provides a fluorescence pattern (FIG. 11A-11B) characteristic of a protein isoform; and said fluorescence pattern is obtained following irradiation of the donor species at a wavelength that causes the excitation of the donor species. In another embodiment, the fluorescence pattern indicates the presence of at least one protein in a biological medium.

In some embodiments, the methods are directed to a) differentiating between proteins and protein isoforms; b) identifying proteins and protein isoforms; c) detecting proteins and protein isoforms; or d) diagnosing a disease, in a biological medium or biofluids. In one embodiment, the biological medium is serum, blood, plasma, urine, saliva, a tissue, a peritoneal, stool, mucus, tears, sweat, a biopsy, sperm or a cerebrospinal fluid sample.

In some embodiments, the methods are directed to diagnosing a disease by identifying or detecting a protein biomarker. In one embodiment, a protein biomarker is a matrix metalloproteases (MMPs) protein, wherein said MMP is a biomarker for cancer. In another embodiment, the MMP comprises for example the following isoforms: MMP-1, MMP-2, MMP-7 or MMP-9. In another embodiment, the MMP-1 is a biomarker for breast, lung and colorectal cancer. In another embodiment, MMP-2 is a biomarker for pancreas, bladder, colorectal, ovarian, prostate, brain, pancreas, lung and colorectal cancer. In another embodiment, MMP-7 is a biomarker for pancreas, lung and colorectal cancer. In another embodiment, MMP-9 is a biomarker for breast, pancreas, bladder, lung, colorectal, ovarian, prostate and brain cancer.

In some embodiments, the methods are directed to diagnosing a disease by identifying or detecting a protein biomarker. In one embodiment, a protein biomarker is a glutathione S-Transferase (GSTs), wherein said GST is a biomarker for cancer. In another embodiment the GST comprises for example the following isoforms: GSTA1, GSTA2, GSTM1 and GSTP1. In another embodiment, GST A1 is a biomarker for breast, lung, prostate and colorectal cancer. In another embodiment GST A2 is a biomarker for prostate and lung cancer. In another embodiment GST M1 is a biomarker for prostate and breast cancer. In another embodiment GST P1 is a biomarker for breast, lung and gastric cancer.

In some embodiments, the methods of this invention are directed to differentiating Fibroblast Growth Factors (FGFs) proteins. Characterization of FGFs that bind to an octasaccharide library of heparin/heparan sulfate revealed that positions 2-O-sulfate (A) and 6-0 sulfate (B), together or separated are essential for binding and that protein recognition involves sequences containing variable degrees of 6-O-sulfation of the A-B disaccharide unit. In another embodiment, 12-sulfated-octasaccharide heparin is a selective protein binder for FGF.

In some embodiments, the methods of this invention are directed to differentiating and characterizing ER biomarkers. In another embodiment, the methods of this invention are directed to differentiating and characterizing ERα and ERβ biomarkers.

In some embodiments, the methods of this invention are directed to differentiating glycoforms of the gp120 protein. Distinguishing between different strains of the immunodeficiency virus type 1 (HIV-1) by targeting its surface envelope protein gp120. This is a particularly important target because its changing glycosylation patterns enable the virus to evade immune responses. Existing approaches for differentiating between HIV envelop protein require expression of high concentrations of viral proteins and extensive efforts using mass spectrometry. The methods of this invention provide a high-throughput method to assess general glycosylation and therefore assist in classifying strains exhibiting distinct pathogenicities. Differentiation of gp120 glycoforms will be achieved by using B40 aptamer, which binds gp120 independently of N-linked glycosylation.

Various concentrations of biomarkers may be detected and measured by the methods described herein. Biomarkers at concentrations of between about 1-5 mM, 1-100 μM, 50-100 mg/mL, 50-500 nM or less than, e.g., 100 milligrams/milliliter (mg/ml), 10 mg/ml, 1 mg/ml, 100 micrograms/milliliter (μg/ml), 10 μg/ml, 1 μg/ml, 100 nanograms/milliliter (ng/ml), 10 ng/ml, 1 ng/ml, may be detected in the biological sample, and the concentration may be measured.

In one embodiment, the method of this invention is directed to a method of diagnosing a disease in a subject by measuring a change in a concentration of a protein biomarker compared to its normative values, wherein said change is characteristic of a disease or a disorder.

The term "normative value" refers to the control, i.e. a concentration range of the tested protein biomarker found in a normal healthy subject.

In one embodiment, the method of this invention is directed to a method of diagnosing a disease in a subject. In another embodiment, a subject refers to a mammal, a human, a female or a male.

The terms "comprises" and variations thereof do not have a limiting meaning where these terms appear in the description and claims.

Unless otherwise specified, "a" "an," "the," and "at least one" are used interchangeably and mean one or more than one.

The following examples are presented in order to more fully illustrate the preferred embodiments of the invention. They should in no way be construed, however, as limiting the broad scope of the invention.

EXAMPLES

Materials and Methods

All solvents and reagents were obtained from commercial suppliers and used without further purification.

The $^1$H NMR spectra were recorded either on a Bruker Avance 300 MHz NMR spectrometer. Or on a Bruker DPX-300 MHz spectrometer. Chemical shifts are reported in ppm on the δ scale down field from TMS as the internal standard. The following abbreviations were used to describe the peaks: s—singlet, d—doublet, dd—double doublet, t—triplet, q—quartet, quin—quintet, m—multiplet, and b—broad. Electrospray mass spectrometry (ES-MS) was performed with a Micromass Platform LCZ-4000 instrument at the Weizmann Institute of Science mass spectrometry facility. Matrix assisted laser desorption ionization time-of-flight (MALDI-TOF) mass spectrometry was performed on an AB SCIEX 5800 System, equipped with an Nd: YAG (355 nm) laser with a 1 KHz pulse (Applied Biosystems), at the Weizmann Institute of Science mass spectrometry facility.

The UV-Vis spectra were measured on a Varian Cary UV-Visible spectrophotometer, and emission spectra were recorded on a Varian Cary Eclipse fluorescence spectrophotometer with excitation and emission slit widths of 20 nm.

Peptides were synthetized on Aan automated peptide synthesizer (Advanced ChemTech, Apex 396). Analytical reversed-phase high-performance liquid chromatography (RP-HPLC) analysis of peptides was performed on a Waters liquid chromatography system equipped with a 2487 dual wavelength UV detector, 600 gradient pump and a 717 plus Autosampler.

The peptides were purified by RP-HPLC using a ThermoSeparation instrument (P200 pump, UV 100 detector) and a pre-packed Vydac $C_{18}$ column. Standard RP-HPLC conditions were as follows: mobile phase A=0.1% TFA in $H_2O$; mobile phase B: 0.1% TFA in 25:75, $H_2O:CH_3CN$. Fluorescence and enzymatic assays were measured using a BioTek synergy H4 hybrid multiwell plate reader in black flat-bottom polystyrene NBS 384 well microplates (Corning).

Modified oligonucleotides were synthesized by the W. M. Keck Foundation Biotechnology at Yale University, using standard automated solid phase synthesis. Concentrations of the oligonucleotides were based on their respective electronic absorption at 260 nm and their molar extinction coefficients were obtained by nearest neighbor calculations. The oligonucleotide purification was carried out on a Waters 2695 separation module HPLC system with a 2994 photodiode array detector using either a Waters XBridge™ OST C18 column (2.5 μM, 4.6×50 mm) or a XBridge™ OST C18 column (2.5 μM, 10 mm×50 mm) Purifications and analyses were achieved using the following eluents: mobile phase A=5:5:90 $TEAA:CH_3CN:H_2O$, mobile phase B=5:65:30 TEAA: $CH_3CN:H_2O$. Different gradients were used and details are given, when necessary. Oligonucleotide samples were desalted using illustra MicroSpin G-25 Columns (GE Healthcare) according to the manufacturer's instructions. Recombinant human MMP isoforms 1, 2, 7, and 9 were purchased from ProSpec-Tany TechnoGene Ltd. Human GST isoforms A1-1, A2-2, M1-1, and P1-1 were purchased from Oxford Biomedical Research. All protein concentrations were given by the manufacturers which is determined the Bradford protein assay.

Activated MMPs were dialyzed using a Slide-A-Lyzer MINI Dialysis Device, 10K MWCO, 0.1 mL (Thermo Scientific). Urine samples was collected from a healthy man and immediately divided into 1.5-mL aliquots and frozen at −80° C. Urine samples were desalted and concentrated using Amicon Ultra 2 mL10K MWCO. Oligonucleotide samples were desalted using illustra MicroSpin G-25 Columns (GE Healthcare) according to the manufacturer's instructions. Concentrations of the oligonucleotides were quantified based on their respective electronic absorption at 260 nm and the molar extinction coefficient for the oligonucleotide at this wavelength. The extinction coefficient of 6-FAM and Dabcyl dyes at 260 nm are 20,900 $M^{-1}cm^{-1}$ and 29,100 $M^{-1}cm^{-1}$, respectively. Extinction coefficient of Cy3 dye at 260 nm is 4,930 $M^{-1}cm^{-1}$. Absorbance spectra were recorded on a Varian Cary UV-visible spectrophotometer. FRET measurements were performed on a Varian Cary fluorimeter using quartz cuvettes. Fluorescence polarization and enzymatic assays were measured using a BioTek synergy H4 hybrid multiwell plate reader in black flat-bottom polystyrene NBS 384 well microplates (corning). Concentration measurements were performed on a Varian Cary fluorimeter using quartz cuvettes.

Recombinant human GST isoforms A1-1, A2-2, M1-1, and P1-1 were purchased from Oxford Biomedical Research. Transferrin, apolipoprotein-A1 (APOA1), Fibroblast growth factor 21 (FGF-21), and leptin were purchased from ProSpec-Tany TechnoGene Ltd. (Ness Ziona, Israel). Immunoglobulin G (IgG) and $\alpha_1$-acid-glycoprotein were purchased from Sigma-Aldrich. Haptoglobin mixed type and thyroglobulin were obtained from Merck Millipore. 3-azidopropionie acid, Fmoc-Lys(Dansyl)-OH and compound 8 were synthesiszed according to published procedures, respectively (Grandjean, C.; Boutonnier, A.; Guerreiro, C.; Fournier, J. M.; Mulard, L. A., *J. Org. Chem.* 2005, 70, 7123; Dantas de Araújo, A.; Palomo, J. M.; Cramer, J.; Seitz, O.; Alexandrov, K.; Waldmann, H., *Chem. Eur. J.* 2006, 12, 6095; Camponovo, J.; Ruiz, J.; Cloutet, E.; Astruc, D. *Chem. Eur. J.* 2009, 15, 2990).

The oligonucleotides purification was carried out on a Waters 2695 separation module HPLC system with 2994 photodiode array detector using either Waters XBridge™ OST C18 column (2.5 μM, 4.6 mm×50 mm) or XBridge™ OST C18 column (2.5 μM, 10 mm×50 mm) Oligonucleotide samples were desalted using illustra MicroSpin G-25 Columns (GE Healthcare) according to manufacturer's instructions. Concentrations of the oligonucleotides were quantified based on their respective electronic absorption at 260 nm and the molar extinction coefficient of the oligonucleotide at this wavelength. Extinction coefficient of Cy3 dye at 260 nm is 4930 $M^{-1}cm^{-1}$. Absorbance spectra were recorded on a Varian Cary UV-visible spectrophotometer. FRET measurements were performed on a Varian Cary fluorimeter using quartz cuvettes. Enzymatic assays were carried out using a BioTek synergy H4 hybrid multiwell plate reader in clear flat-bottom polystyrene 384 well microplates, (corning). Differentiation assays were carried out using a BioTek synergy H4 hybrid multiwell plate reader in c and black flat-bottom polystyrene NBS 384 well microplates (corning).

ODNs Sequences:

ODN-10 and ODN-3 were obtained from Keck Foundation Biotechnology at Yale University.

```
ODN-10:  5'-YZWXXXGCCTCGCTCGTCTTGCG-3'

ODN-3:   5'-CGCAAGACGAGCGAGGCXXXY-3'
```

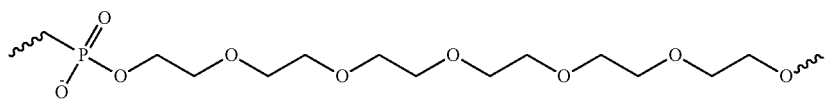 X

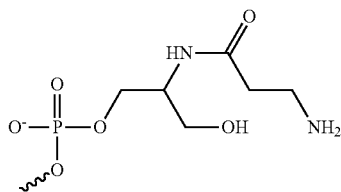 Y

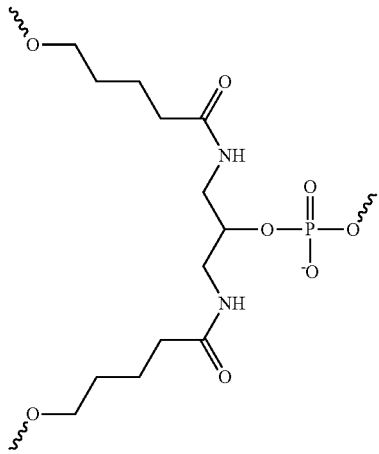 Z

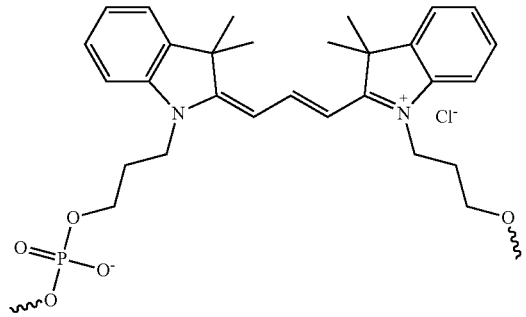 W

Example 1

Cross-Reactive Sensor Array Discriminates Among Different GST Biomarkers in Biological Mixtures The sensing strategy according to this invention relies on using receptors with dual function mode; specific and non-specific. On the one hand, these receptors bind particular protein groups with high affinity and selectivity. On the other hand, they possess a nonspecific binding domain that respond differently to closely related isoforms, therefore generating unique signal pattern for each isoform. The receptors consist of two complementary oligonucleotides (ODNs). One strand is linked to ethacrynic acid (EA), a broad-spectrum inhibitor of GSTs, and the complementary strand is modified with a tripodal peptide scaffold that functions as non-selective protein surface binder. The specific strand which is maintained in all the receptors' structures allows selective binding of the receptors to the GST protein family. The peptide sequences were varied to achieve a series of non-selective protein surface receptors. The tripodal peptide motif interacted with GST surface by means of hydrogen bonding, electrostatic interaction or hydrophobic interaction, allowing the system to respond distinctively to each GST isoform. In addition, a fluorescent donor and an acceptor were also incorporated in the proximity of both selective and non-selective binders. The peptides were labeled with solvatochromic fluorophore (dansyl) whose emission spectrum overlaps the excitation spectrum of Cy3 in the proximity of EA molecule. Binding to different GSTs affected both the distance and the orientation between these fluorophores and thus the fluorescence resonance energy transfer (FRET) efficiency was altered (FIG. 1A-1D).

TABLE 1

Sequences of peptide used for generation of a library of receptors

| Receptor | ODN-Peptide Conjugate | Peptide Sequence | |
|---|---|---|---|
| 1 | ODN-5 | $N_3$—$(CH_2)_3$-K(dansyl)-F-D-S-E-F-D-S-E | (Seq. ID. 5) |
| 2 | ODN-6 | $N_3$—$(CH_2)_3$-K(dansyl)-S-T-G-V-S-T-G-V | (Seq. ID. 6) |
| 3 | ODN-7 | $N_3$—$(CH_2)_3$-Y-G-E-G-E-F-N-K(dansyl) | (Seq. ID. 7) |
| 4 | ODN-8 | $N_3$—$(CH_2)_3$-K(dansyl)-G-P-L-A-S-E-S-T | (Seq. ID. 8) |
| 5 | ODN-9 | $N_3$—$(CH_2)_3$-K(dansyl)-G-R-V-G-A-V-S-G | (Seq. ID. 9) |

Figure 2A:
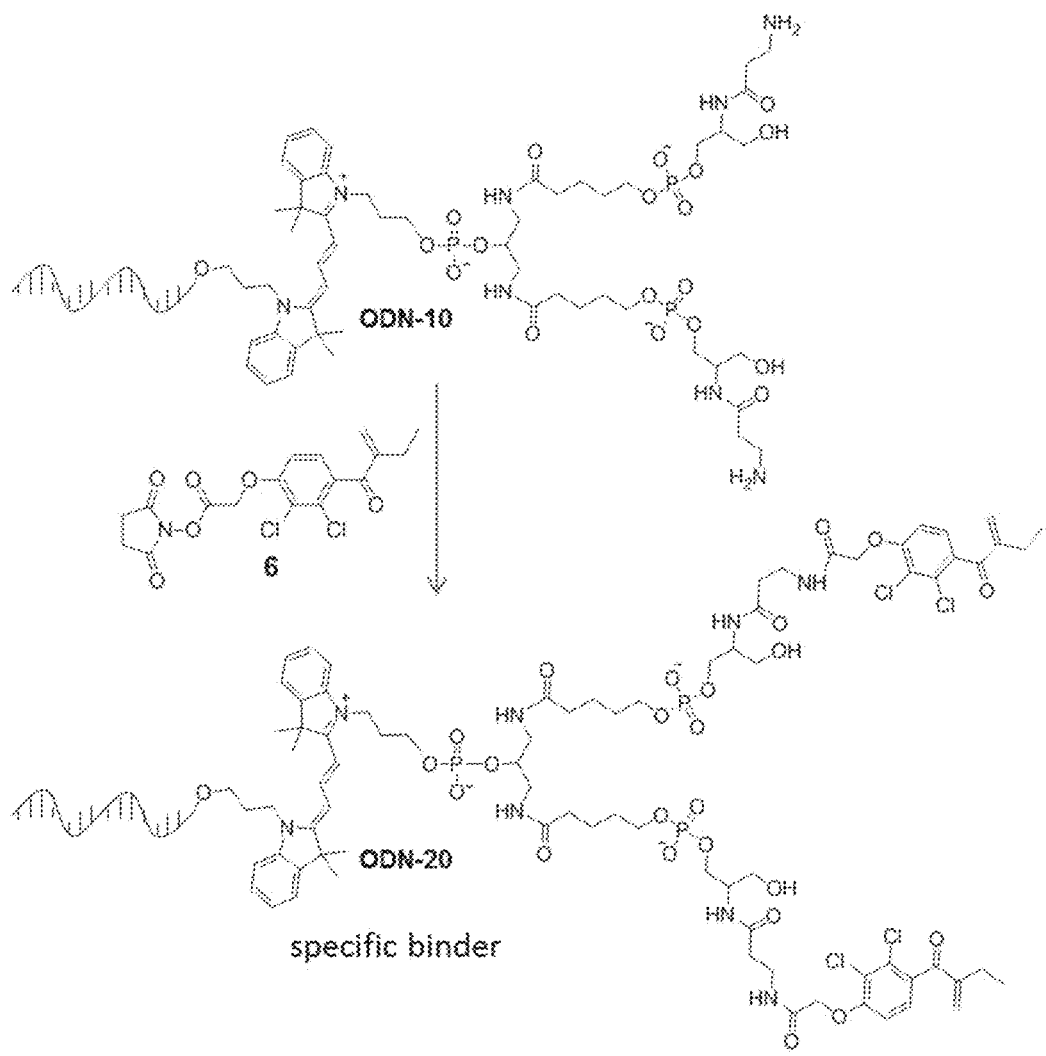
FIG. 2A-2C depicts Synthetic steps for preparing the (FIG. 2A) selective and (FIG. 2B) non-selective ODN strands.
Figure 2B:
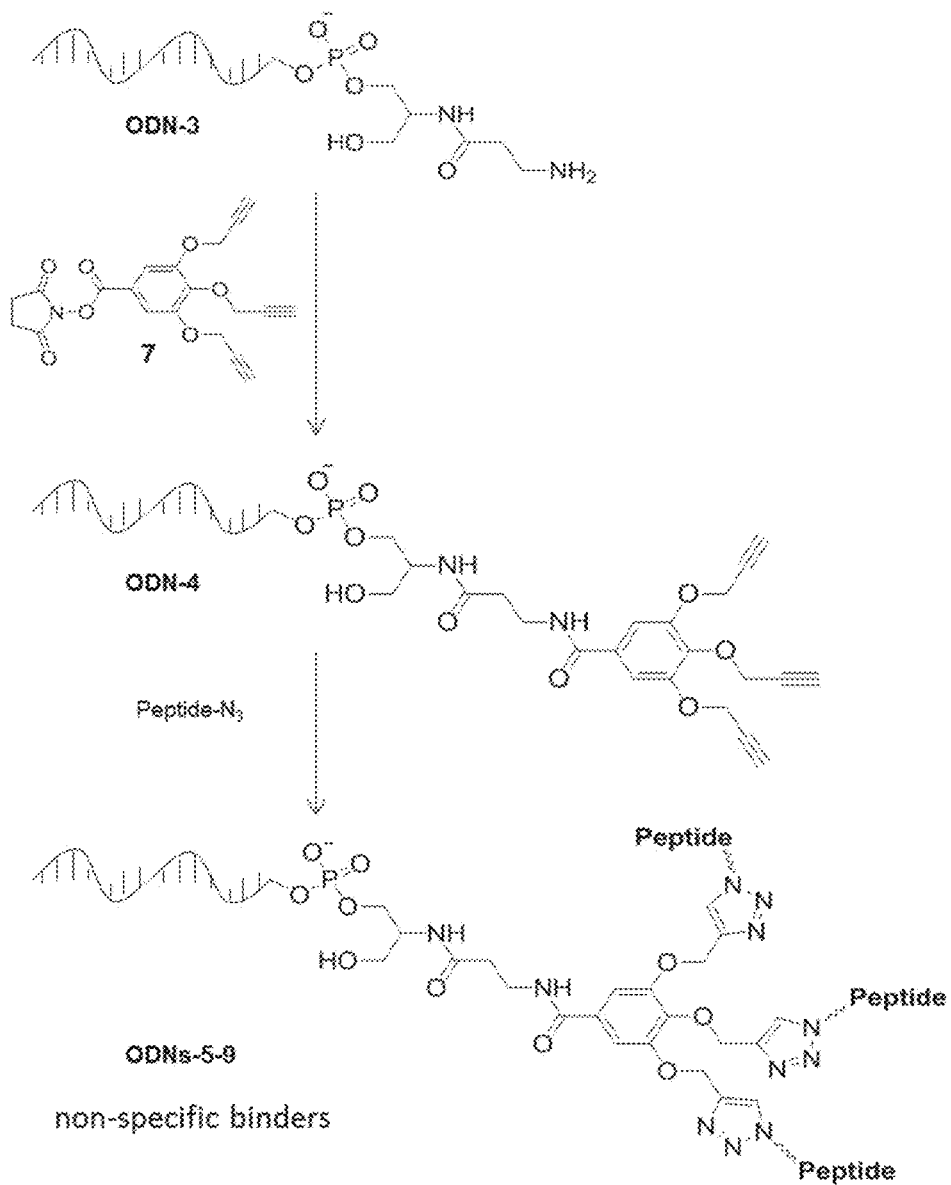
Figure 2C:
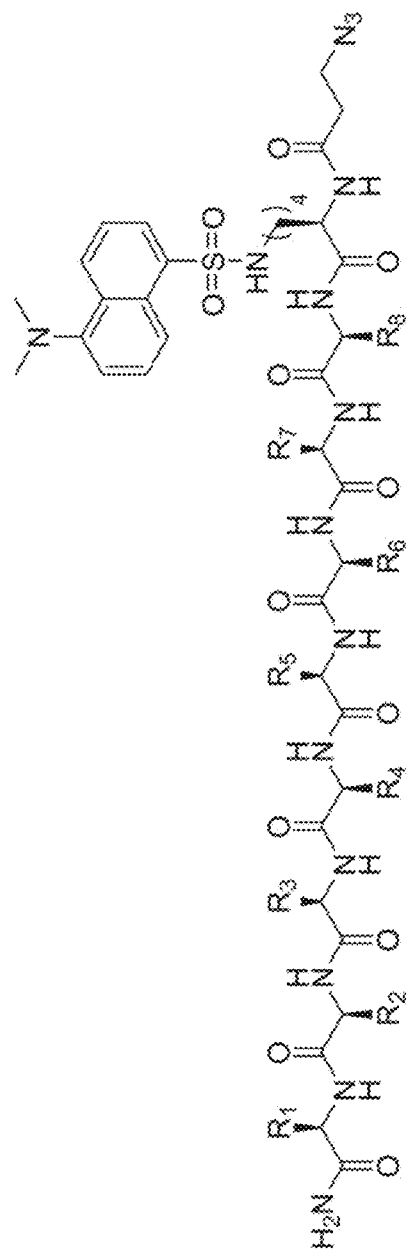

Based on these principles, a DNA-based receptors library with selectivity towards glutathione S-transferases (GSTs) was generated (FIG. 2A-2C). The GST isoforms A1-1, A2-2, P1-1 and M1-1 having different isoelectric point were selected as sensing targets (Table 2).

TABLE 2

Isoelectric point (pI) of the GST isozymes.

| GST Isoform | Isoelectric Point (pI) |
|---|---|
| GST-A1-1 | 8.9 |
| GST-A2-2 | 8.5 |
| GST-M1-1 | 6.2 |
| GST-P1-1 | 5.4 |

GSTs were selected as the target proteins for this study because comparative analysis of GST isozymes in biofluids revealed a clear correlation between their expression profiles and disease states. In addition, a broad spectrum inhibitor (i.e., ethacrynic acid, EA) for this class of enzymes is known and could be used to generate a GST-specific binding strand (FIG. 2A).

Figure 3:
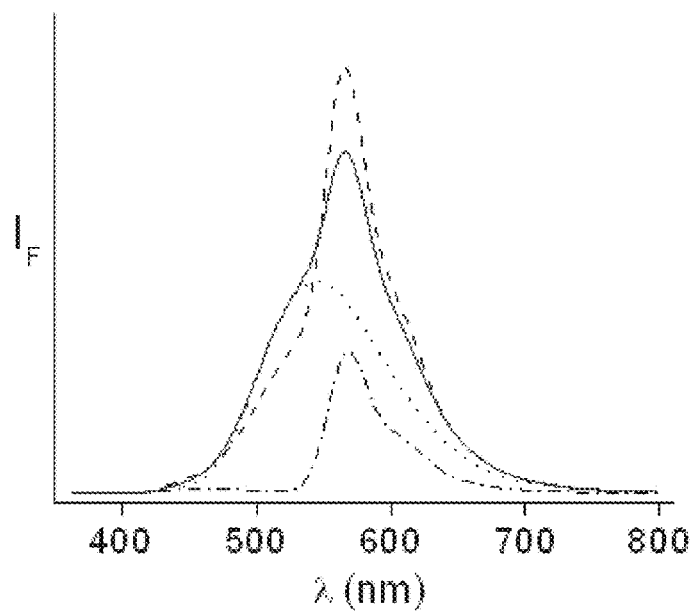
FIG. 3 depicts the fluorescence emission spectra of (dash dotted line) Cy3-labeled ODN-20, (solid line) immediately after addition of ODN-7, and (dashed line) after incubation with ODN-7 for 30 min; and fluorescence emission spectra of (dotted line) dansyl-labeled ODN-7. The experiments were carried out using 1 µM concentration of ODN-20 and ODN-7 in PBS buffer (15 mM, pH=7.4). Excitation wavelength: 325 nm.
Figure 4A:
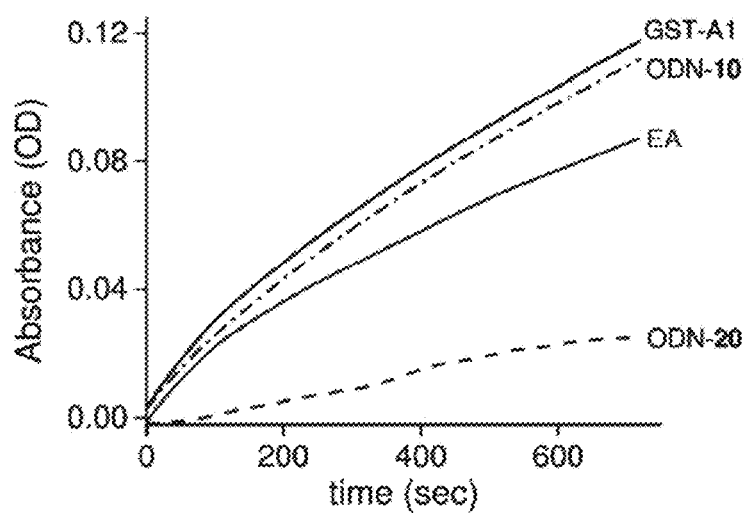
FIG. 4A-4D depicts the inhibition of (FIG. 4A) GST-A1, (FIG. 4B) GST-M1, (FIG. 4C) GST-A2, and (FIG. 4D) GST-P1 activity in the presence of (dash dotted line) ODN-10 (500 nM), (dashed line) ODN-20 (500 nM), and (solid gray line) EA (1 µM). Black solid lines represent the enzyme activity without inhibitor. ODN-10 and EA were used as control. Formation of CDNB-GSH conjugate was monitored by following the absorbance at λ=340 nm. The experiments were performed at room temperature and using GST (20 nM), GSH (0.25 mM), CDNB (0.5 mM) in PBS buffer (10 mM, pH=6.5).
Figure 4B:
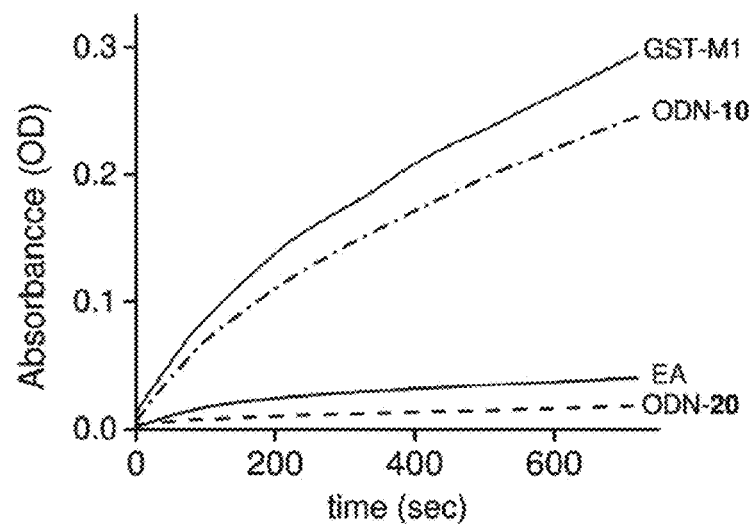
Figure 4C:
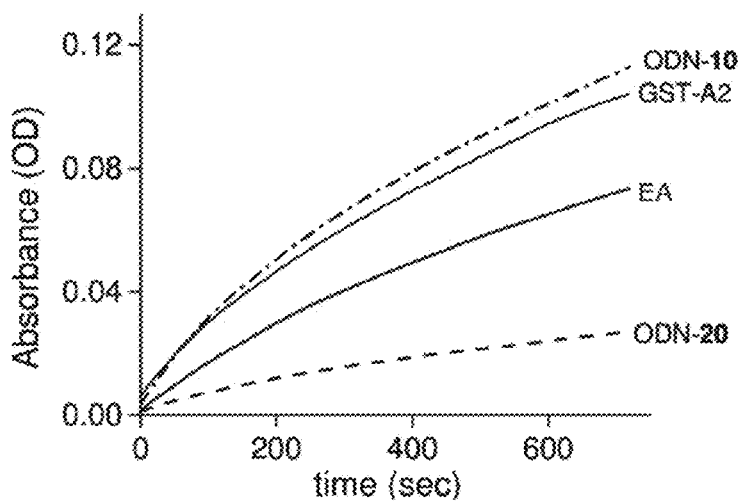
Figure 4D:
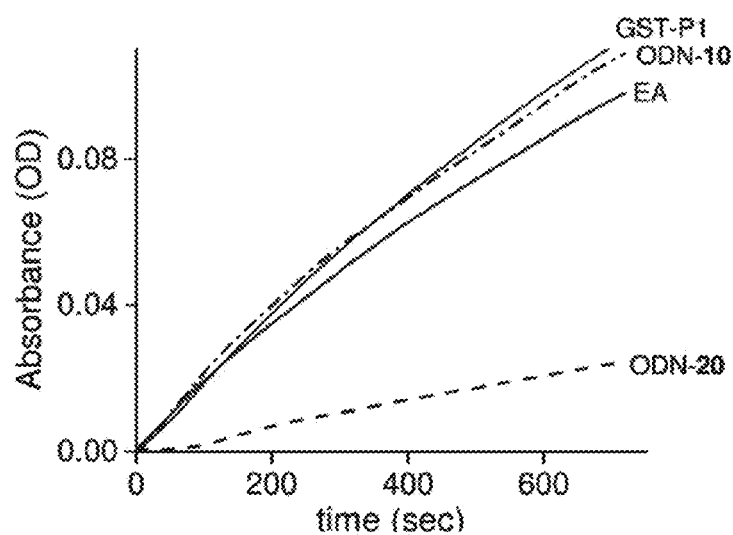

Five ODN sets composed of diverse peptide sequences as sensing elements were prepared (FIG. 2A-2C and Table 1). The bivalent analogs of EA have been shown to exhibit significantly greater affinity for GST enzymes. Therefore, EA was covalently coupled to a bis-amino-modified oligonucleotide (ODN-10) to afford the specific strand (ODN-20) (FIG. 2A). A library of non-specific strands (ODNs-5-9, FIG. 2B) was prepared by coupling of compound 7 (synthesis described below) to an amino-modified oligonucleotide (ODN-3) and subsequent click reaction with azide-functionalized peptides (Table 1). The equimolar ratio of complementary oligonucleotide strands were then heated to 95° C. for 5 min and slowly cooled to room temperature to form receptors 1-5. Upon hybridization, an efficient FRET process between the acceptor Cy3 and donor dansyl moieties was observed reflecting the close proximity of two fluorophores (FIG. 3).

In the first step, enzymatic assays were performed to confirm broad spectrum inhibition by ODN-20 (FIG. 2A), namely, that the specific GST binder can bind and inhibit the activity of different GST isozymes. These assays, which were conducted according to a previously reported procedure (Habig, W. H.; Pabst, M. J.; Jakoby, W. B. *J. Bio. Chem.* 1974, 249, 7130) were also used to evaluate the affinity of the system toward GSTs (see below). As shown in FIG. 4A-4D, the enzymatic activity of GST-A1, GST-M1, GST-A2, and GST-P1, (which catalyzes the conjugation of glutathione (GSH) to 1-chloro-2,4-dinitrobenzene (CDNB)) was followed in the absence and in the presence of ODN-20 (500 nM), a commercial inhibitor (EA, 1 µM), and a control strand, ODN-10, which lacks EA groups (500 nM) by monitoring the change in the absorbance at 340 nm. The much stronger inhibition of these isozymes by ODN-20 indicates that a broad spectrum GST binder with nanomolar affinities toward the four different isozymes was obtained.

Figure 26:
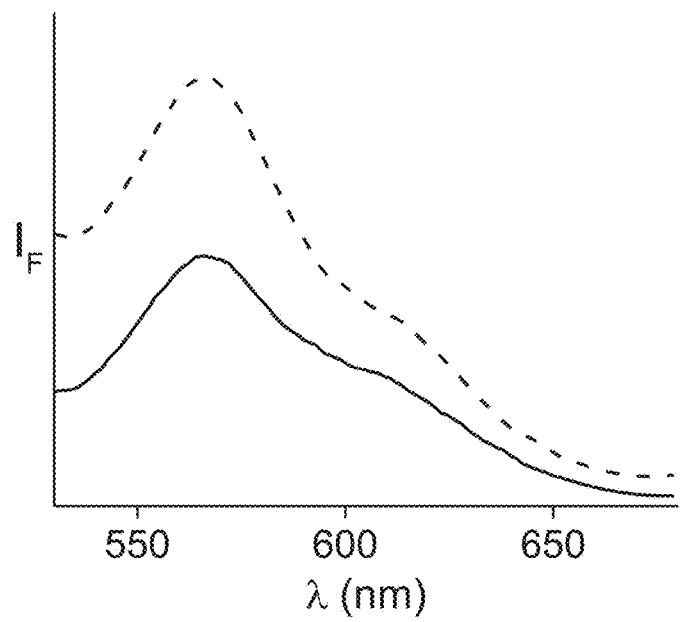
FIG. 26 depicts a representative fluorescence emission spectra of 20 nM ODN-5 (solid line) before and (dashed line) after addition of 150 nM GST-A1.

A set of DNA duplex-based GST receptors (FIG. 1B, duplexes 1-5) consisting of a selective (ODN-20) and non-selective binding strands (ODNs-5-9) was then generated by heating equimolar ratio of ODN-20 and complementary ODNs-5-9 to 95° C. for 5 min and slowly cooling to room temperature. The formation of these duplexes was confirmed by gel electrophoresis as well as by observing FRET processes between the donors (i.e., dansyl groups) and the Cy3 acceptor (FIG. 3). The emission of Cy3 was further enhanced when the different duplexes were incubated distinct GST isozymes (150 nM) (FIG. 26), indicating the ability of the DNA-based fluorescent receptors to signal the receptor-GST interactions.

Figure 7A:
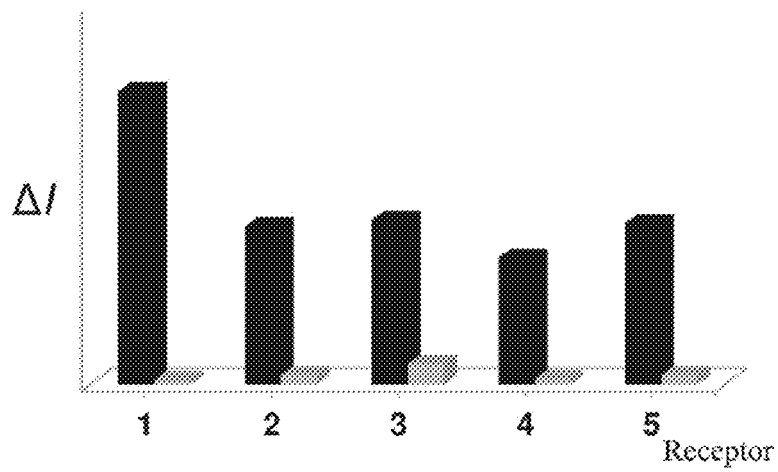
FIG. 7A-7B depict (FIG. 7A) Change in the intensities (ΔI) of (■) receptors 1-5, and (□) the corresponding control duplexes lacking EA moiety upon addition of GST-P1. The experiments were carried out using 20 nM of each duplex and 150 nM of each GST isozyme.
Figure 7B:
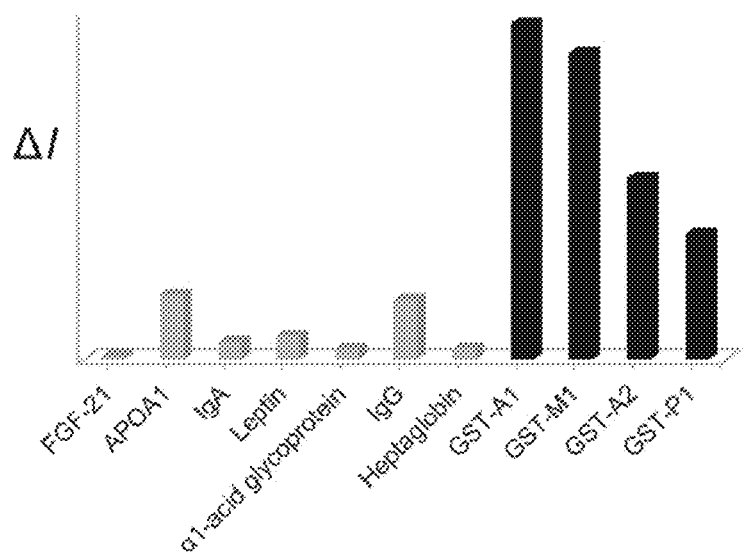
Figure 8:
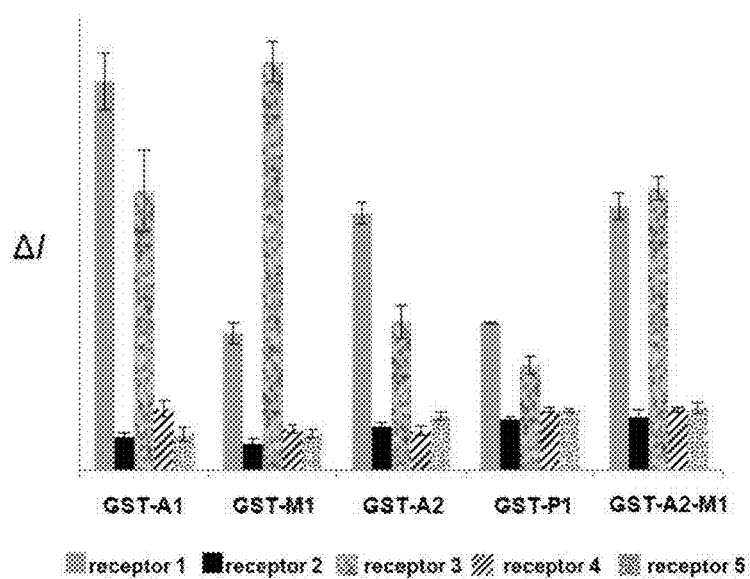
FIG. 8 depicts the change in the fluorescence intensities (ΔI) for four GST isoforms and combination of GST-A2 and GST-M1 in urine using receptors 1-5. The experiments were carried out using 50 nM of each receptor and 500 nM of each GST isozyme. For the mixture of GST isozymes, concentration of GST-M1 and GST-A2 were 250 nM each.

The most important principle underlying the design of this sensory system is that binding cooperatively between the selective and non-selective binders would transform relatively weak tripodal peptide-GST interactions into much stronger ones. To confirm the manifestation of the "chelate effect", which should endow the modified duplexes with selectivity toward GSTs (FIG. 1B), two experiments were performed (FIG. 7A-7B). In the first, the different receptors (1-5) were incubated with different GSTs (150 nM) and their fluorescence response was compared to that of duplexes, which lack a GST inhibitor (FIG. 7A). In the second experiment, the different receptors were treated with common serum proteins or protein biomarkers, such as transferrin, mixed-type haptoglobin, al-acid glycoprotein, immunoglobulin G (IgG), leptin, thyroglobulin, apolipoprotein A1 (APOA1), and fibroblast growth factor-21 (FGF-21) (FIG. 7B). Remarkably, while duplexes 1-5 exhibited strong response to nanomolar concentrations of GSTs (150 nM), only a small or negligible effect on Cy3 emission was observed for the control duplexes (FIG. 7A) Similarly, the emission intensity was only slightly changed upon incubating the receptors with excess (0.5-1 nM) of other proteins (FIG. 7B). Taken together, these results show that the fluorescence response in this system mainly originates from the interaction of the receptors with GSTs.

The realization of targeted protein surface sensors such as 1-5, might open the way for developing a cross-reactive sensor array that can discriminate among different GST biomarkers in biological mixtures. For example, the presence of GST-A in urine or in blood plasma is an early biomarker for hepatocellular damage, whereas elevated serum levels of GST-P has been proposed as a tool for monitoring cancer patients during the course of treatment. It has also been demonstrated that tracking both GST-A and GST-P in urine could provide information on the site of renal tubular injury, and that detecting these isozymes in plasma can help predict and monitor graft failure or regeneration following living donor liver transplantation.

Figure 5A:
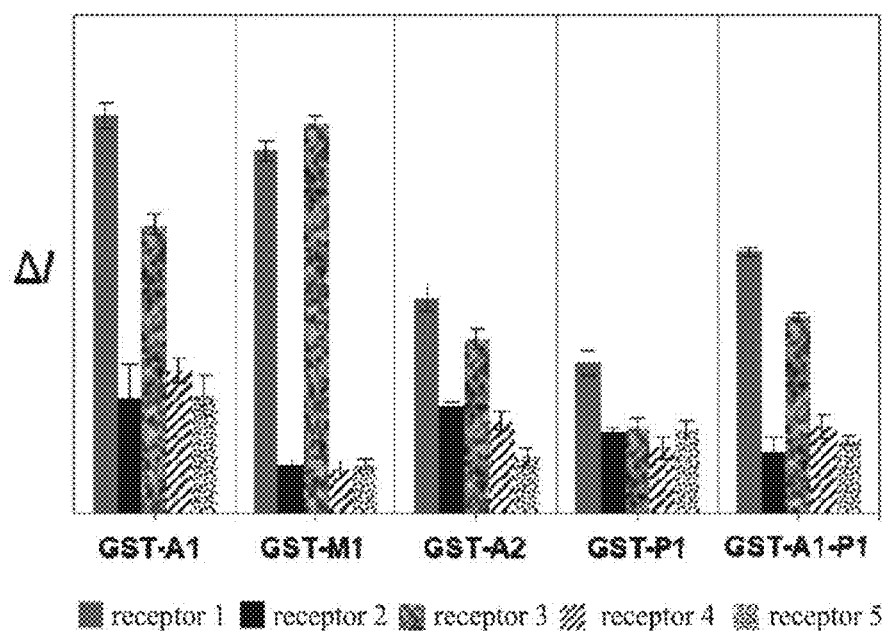
FIG. 5A-5B depicts (FIG. 5A) Change in the fluorescence intensities (ΔI) for four GST isoforms and combination of GST-A1 and GST-P1 in PBS buffer (3.5 mM, pH=6.5) using receptors 1-5.
Figure 9:
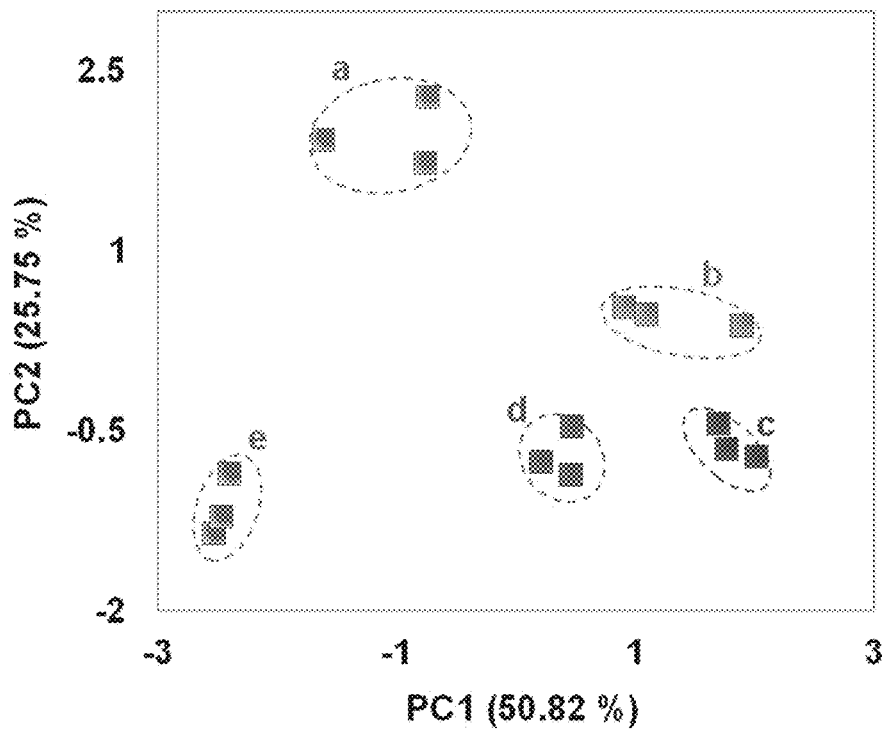
FIG. 9 depicts PCA mapping of the GST isozymes in urine. (a) GST-A1, (b) GST-A2-GST-M1, (c) GST-P1, (d) GST-A2, and (e) GST-M1.
Figure 10:
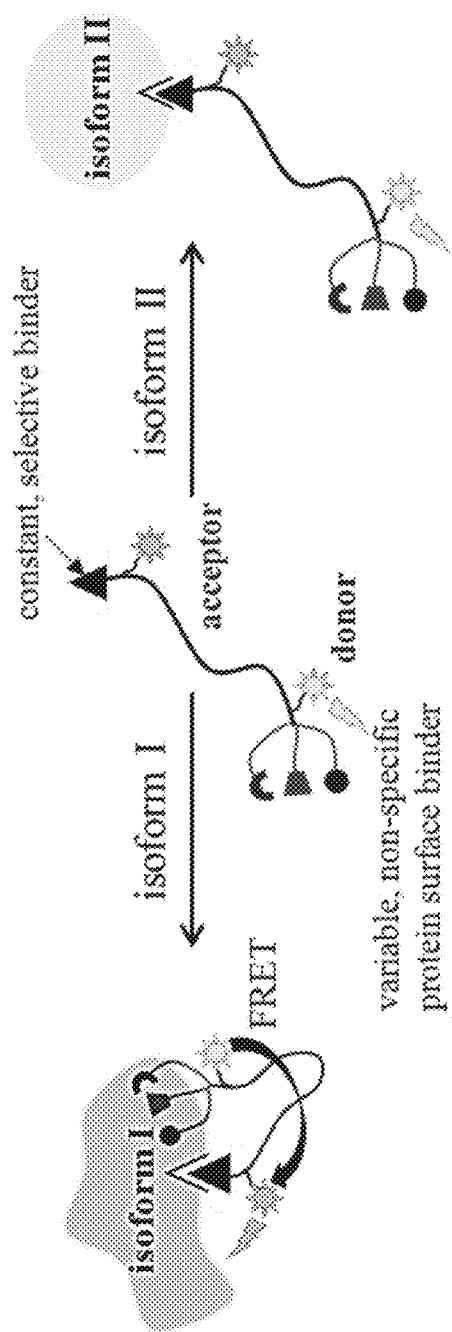
FIG. 10 depicts a general concept of synthetic protein receptors with dual interaction modes: selective and non-selective. A selective binder (black triangle) labeled with a fluorescent acceptor provides the molecule with high affinity and selectivity toward a particular protein class. The branched, non-selective protein surface binder appended with a fluorescent donor varies between the different receptors. The position of the donor and acceptor can interchange. Binding to different proteins is expected to induce different conformations, leading to distinct FRET efficiencies (isoform I vs. II).

To demonstrate the potential use of such systems in medical diagnosis a sensor array prototype, consisting if duplexes 1-5, was prepared and its ability to discriminate among different GSTs and their combinations was tested in the absence and in the presence of other proteins (FIG. 5B and FIG. 6), as well as within human urine (FIG. 9). In a typical experiment, receptors 1-5 (20 nM) in PBS buffer (3.5 mM, pH 6.5) were loaded onto a 384-well plate and the changes in the Cy3 emission intensities were recorded for four replicates using excitation and emission filters of 325/15 and 620/40 nm, respectively. As shown in FIG. 5A, the addition of different GST isozymes (150 nM) resulted in various fluorescence profiles for GST-A1, GST-A2, GST-A2, GST-M1 as well as for combination of GST-M1 and GST-P1. Analysing the patterns using principal component analysis (PCA) (FIG. 5B, squares) resulted in markedly distinct clusters, which indicates that the system can discriminate among closely related GST isozymes.

Figure 5B:
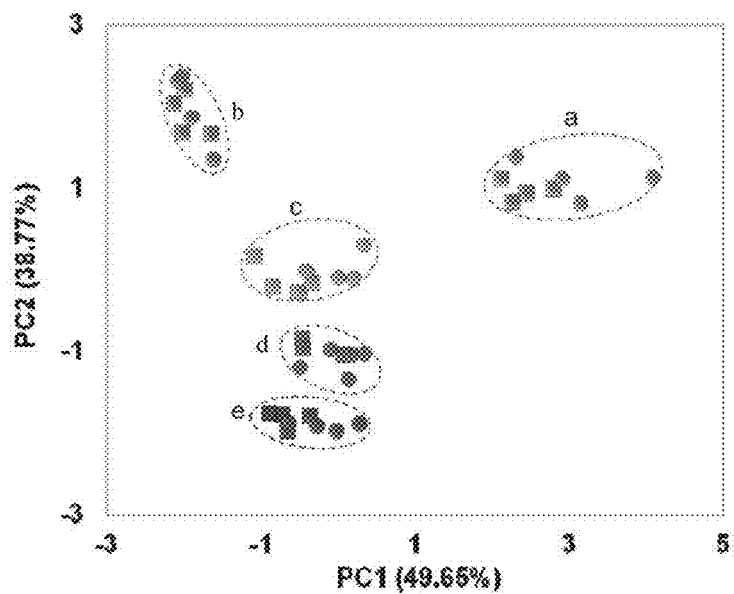
Figure 6:
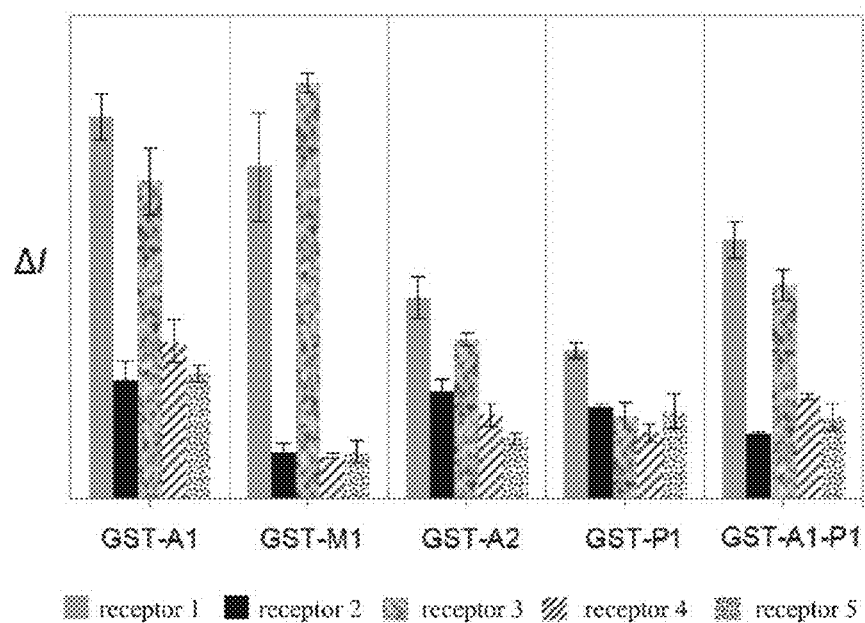
FIG. 6 depicts the change in the fluorescence intensities (ΔI) for four GST isoforms and combination of GST-A1 and GST-P1 in (a spiked protein solution (total concentration of 1.05 μM) using receptors 1-5. The spiked protein solution contained transferrin (150 nM), haptoglobin mixed type (150 nM), IgG (150 nM), α₁-acid-glycoprotein (150 nM), APOA1 (150 nM), leptin (100 nM), FGF-21 (100 nM), thyroglobulin (100 nM). The experiments in were carried out using 26 nM of each receptor and 300 nM of GST isozymes.

In the next step, a mixture of eight highly abundant serum proteins and biomarkers was spiked into the buffer solution (with a total concentration of 1.05 nM) and fluorescence patterns were recorded under similar conditions (FIG. 5B and FIG. 6). The protein mixture constituted of common serum proteins and protein biomarkers, namely, transferrin, mixed-type haptoglobin, α1-acid glycoprotein, immunoglobulin G (IgG), leptin, thyroglobulin, apolipoprotein A1 (APOA1), and fibroblast growth factor-21 (FGF-21). In this medium, slightly higher concentration of GST (300 nM) was required to obtain sufficient fluorescence response, which might be due to some non-specific interactions with other proteins. Remarkably, the generated fluorescent patterns in the presence and in the absence of the protein mixture were very similar (FIGS. 5B and 6), which confirm the viability of our approach (FIG. 1A-1D). The feasibility of distinguishing among different GSTs in human urine (FIG. 9) further support the potential of such systems to identify small populations of disease biomarkers in complex medium such as human physiological fluids.

The detection and identification of proteins in complex medium such as human physiological fluids remains a major challenge in biomarkers discovery and validation. After successful GST differentiation in mixture of other proteins, the performance of the sensor array was investigated in human urine. Urine samples were desalted (see below for details) to minimize the fluorescence background signal of the matrix. Then, the receptors 1-5 (40 nM) were dissolved in desalted urine samples and Cy3 emission intensities of the receptors were recorded before and after addition of the GST isozymes (500 nM). The fluorescent intensity changes of the receptors were recorded for each GST isozyme which resulted in a characteristic fluorescence pattern for each isozyme PCA analysis of the data revealed well separated clusters corresponding to different forms of the GST enzymes (FIG. 9).

In summary, a general methodology for endowing optical cross-reactive sensor arrays with selectivity toward particular protein groups was demonstrated. The fundamental principle underlying this approach is the feasibility of realizing signaling protein receptors with two distinct binding motifs: selective and non-selective. The first enables the receptors to bind particular protein groups with high affinity and selectivity, while the second allows them to differentiate between closely related isoforms. The use of DNA-duplexes for scaffolding the receptors not only provides the system with inherent water solubility—it also facilitates device integration and modification. This should allow one to "program" such devices to identify various other classes of protein biomarkers simply by modifying the selective binding strand.

Example 2

Synthesis of Various ODN-Peptide Conjugates
(FIG. 2A-2C)

Synthesis of Compound 6 (FIG. 2A)

Ethacrynic acid (0.9 g, 3 mmol) was suspended in dry DCM, then N-hydroxysuccinimide (0.42 g, 3.6 mmol) and DIC (465 μl, 3 mmol) were added to the solution. The reaction mixture was stirred overnight. The organic layer was washed with HCl (0.1 N) and brine. The organic phase was dried over anhydrous sodium sulfate and the solvent was removed under vacuum. The product was purified by combiflash using silica gel column chromatography (eluent: 2% MeOH in DCM). Yield: 36%. $^1$H NMR (CDCl$_3$, 300 MHz): δ 2.49 (t, J=3.0 Hz, 1H); 2.57 (t, J=3.0 Hz, 2H); 2.93 (s, 4H); 4.83 (d, J=2.0 Hz, 4H); 4.89 (d, J=3.0 Hz, 2H); 7.57 (s, 2H). MS (ESI): calcd for [M]$^+$400.21. found 400.16.

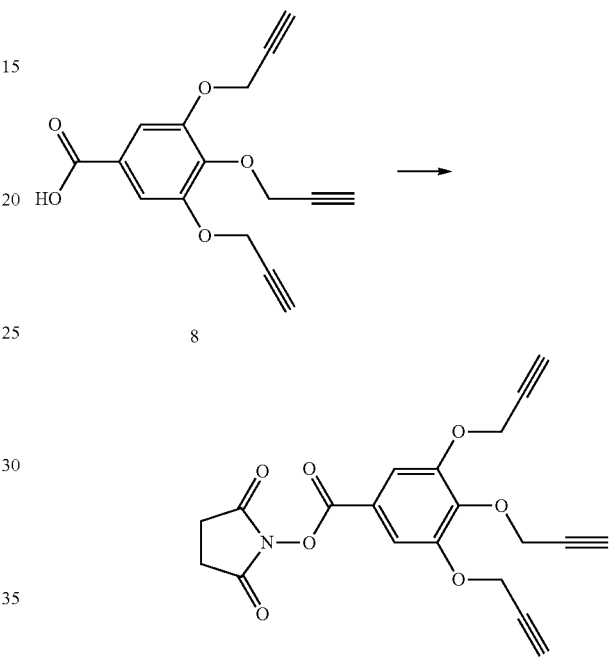

Synthesis of Compound 7

Compound 8 (1.5 g, 5.28 mmol) was suspended in dry DCM, then N-hydroxysuccinimide (0.06 g, 5.28 mmol) and DIC (818 μl, 5.28 mmol) were added to the solution and the mixture was stirred overnight. The organic layer was washed with HCl (0.1 N) and brine, dried over anhydrous sodium sulfate. The solvent was removed under reduced pressure and the product was purified by combiflash using silica gel column chromatography (eluent: 1.5% MeOH in DCM). Yield: 75%. $^1$H NMR (CDCl$_3$, 300 MHz): δ 2.49 (t, J=3.0 Hz, 1H); 2.57 (t, J=3.0 Hz, 2H); 2.93 (s, 4H); 4.83 (d, J=2.0 Hz, 4H); 4.89 (d, J=3.0 Hz, 2H); 7.57 (s, 2H). MS (ESI): calcd for [M+Na]$^+$404.33. found 404.04; calcd for [2M+Na]+785.66. found 785.17.

Synthesis of Selective ODN-20-Peptide Conjugate

Synthesis of ODN-20. The amino-modified ODN-10 (370 nmol) was dissolved in 175 μl MQ water and Na$_2$CO$_3$/NaHCO$_3$ buffer (80 μl, 1M, pH=8.75) was added to maintain basic condition of the reaction. The NHS-ester of ethacrynic acid (compound 6, 74 μmol in 120 μL DMSO) was added in two equal portion and the reaction was mixed overnight. The sediment was removed by centrifugation and the sample was lyophilized. The oligonucleotide was re-suspended in 300

μL MQ water and then was filtrated through MicroSpin G-25 columns (GE Healthcare) according to the manufacturer's protocol. The oligonucleotide was afterward purified using RE-HPLC. MALDI-TOF MS (m/z): calcd. 8040.64. found 8038.

Synthesis of Non Selective ODNs-5-9-Peptide Conjugates

Synthesis of ODN-4

The amino-modified oligonucleotide ODN-3 (385 nmol) was dissolved in 150 μl MQ water and 150 μl of $Na_2CO_3$/$NaHCO_3$ buffer (1 M, pH=8.75, 150 μL) was added to maintain basic condition of the reaction. Then the NHS ester 7 (38.5 μmol in 120 μL DMSO) was added in two portions with time interval of 4 hours. The coupling reaction was performed overnight at room temperature. The sediment was removed by centrifugation, and the reaction mixture was filtrated through MicroSpin G-25 columns (GE Healthcare) according to the manufacturer's protocol. The product was further purified by RE-HPLC. MALDI-TOF MS (m/z): calcd. 6777.70. found 6768.77.

General Procedure for Peptide Synthesis.

The peptides were synthesized on Rink amide resin using an automated synthesizer (Advanced ChemTech, Apex 396). Coupling reactions were run on a 0.1-mmol scale using standard Fmoc protocol. The coupling was carried out using six-fold excess of each amino acid (coupling for 2×45 min), PyBOP/DIEA as coupling reagents and 25% piperdine in NMP for Fmoc deprotection. Fmoc-Lys(Dansyl)-OH (2 equiv.) and azidopropionic acid (2 equiv.) were coupled to the peptide chain manually. The peptides were cleaved from resin by TFA/$H_2O$/triisopropylsilane (95:2.5:2.5) for 2 h. The peptides were purified using preparative RP-HPLC on a $C_{18}$ column and characterized by electrospray mass spectrometry.

P1: ESI-MS (m/z): calcd. 1430.5. found 1432.73.
P2: ESI-MS (m/z): calcd. 1164.29. found 1164.75.
P3: ESI-MS (m/z): calcd. 1272.34. found 1271.04.
P4: ESI-MS (m/z): calcd. 1218.34. found 1217.78.
P5: ESI-MS (m/z): calcd. 1159.32. found 1158.77.

General Procedure for the Synthesis of ODN-Peptide Conjugates (ODN5-5-9)

ODN-4 (60 nmol) was dissolved in fresh MQ water (50 μL). TEAA buffer (20 μL, 2 M pH 7), corresponding azide functionalized peptide (720 nmol in 85 μL DMSO) and ascorbic acid (20 μL of a 15 mM freshly prepared stock solution) were subsequently added. Then, the solution was degassed by argon for a few minutes and $CuSO_4$/TBTA complex (30 μL, of a 10 mM stock solution) was added. The resulting mixture was tightly closed and stirred overnight. The ODN-peptide conjugates were afterward purified using RE-HPLC.

ODN-5: MALDI-TOF MS (m/z): calcd. 11072. found 11058.
ODN-6: MALDI-TOF MS (m/z): calcd. 10270. found 10256.
ODN-7: MALDI-TOF MS (m/z): calcd. 10594. found 10578.
ODN-8: MALDI-TOF MS (m/z): calcd. 10432. found 10438.
ODN-9: MALDI-TOF MS (m/z): calcd. 10255. found 10266.

Example 3

GST Kinetic Measurements

The GST activity was measured spectrophotometrically at 25° C. using variable concentrations of chloro-2,4-dinitrobenzene (CDNB) and GSH (1 mM) as substrates, in phosphate buffer (10 mM, pH 6.5). In a typical experiment, GST and ODN-20 (variable concentrations) were incubated for 10 min and then GSH and CDNB was subsequently added. The GST concentration was 20 nM. The GSH concentration (1 mM) was kept constant and the concentration of CDNB was varied from 0.1 mM to 0.8 mM. Formation of S-(2,4-dinitrophenyl)-glutathione was monitored using a plate reader at λ=340 nm. The data were fitted to Michaelis-Menten equation using Sigmaplot version 12.0 statistical software (Systat) to determine the $K_i$ values for competitive inhibition.

Example 4

Hybridization of Complementary DNA Strands

Equimolar concentration (2 μM) of complementary single-strands in phosphate buffer (15 mM, Ph=7.4) was heated to 95° C. and slowly cooled to room temperature for 30 min to ensure formation of equilibrium structures.

Example 5

Fluorescence Resonance Energy Transfer Measurements

Equimolar concentrations of each of the complementary DNA strands in 15 mM phosphate buffer, pH 7.4 were incubated at 95° C. for 5 mM and then slowly cooled to room temperature. FRET experiments were carried out with single- or double-stranded DNA (1.5 μM, 60 μL) in phosphate buffer (15 mM, pH 7.4). Fluorescence emission spectra were recorded using) $\lambda_{ex}$=325 nm and excitation and emission slit widths of 20 nm in quartz cuvettes.

Example 6

GST Sensing in Buffer Solution and in Presence of Protein Mixture

The receptors in phosphate buffer (3.5 mM, pH=6.5) were dispensed into 384-well microplates and then fluorescence intensity were recorded using excitation and emission filters of at 360/40 and 620/40, respectively, along with a 50% cut-off mirror. Then, GST isoforms (0.6 μL) were added to each well and the fluorescence intensity values were recorded again. The difference between two reads before and after addition of GST isoforms was treated as the fluorescence response. The protein mixture (total concentration of 1.05 μM) used in the experiments contained the following proteins: transferrin (150 nM) haptoglobin mixed type (150 nM), IgG (150 nM), $α_1$-acid-glycoprotein (150 nM), APOA1 (150 nM), leptin (100 nM), FGF-21 (100 nM), and thyroglobulin (100 nM). The final concentration of the receptors and GST isoforms in buffer solution were 20 nM and 150 nM, respectively. The final concentration of the receptors and GST isoforms in buffer solution containing protein mixture were 26 nM and 300 nM, respectively. Fluorescence values for GST-P1 and combination of GST-A1 and GST-P1 were recorded after 45 min incubation. For other GST isoforms, the fluorescence values were recorded immediately after incubation. Fluorescence data carried out in four replicates and the data was subjected to principal component analysis (PCA) using XLSTAT (version 2013.1.01).

Example 7

GST Sensing in Urine Samples

Human urine sample was desalted and concentrated using ProteoSpin™ urine protein concentration kit from Norgen BioTek Corp. according to manufacturer's protocol. The concentrated and salt-free human urine samples were then diluted to the initial volume of urine in phosphate buffer (3.5 mM, pH=6.5). The receptors in urinary samples (50 nM) were dispensed into 384-well microplates and then fluorescence intensity were recorded using excitation and emission filters of 360/40 and 620/40, respectively, along with a 50% cut-off mirror. Then GST isoforms (500 nM, 0.6 µL) were added to each well and the fluorescence intensity values were recorded again. Fluorescence values for GST-P1 and combination was recorded after 45 min incubation. Fluorescence data for other GST isoforms was recorded immediately after incubation. The difference between two reads before and after addition of GST isoforms was treated as the fluorescence response. This process was measured in triplicates and the data was subjected to principal component analysis (PCA) using XLSTAT (version 2013.1.01).

Example 8

Figure 13A:
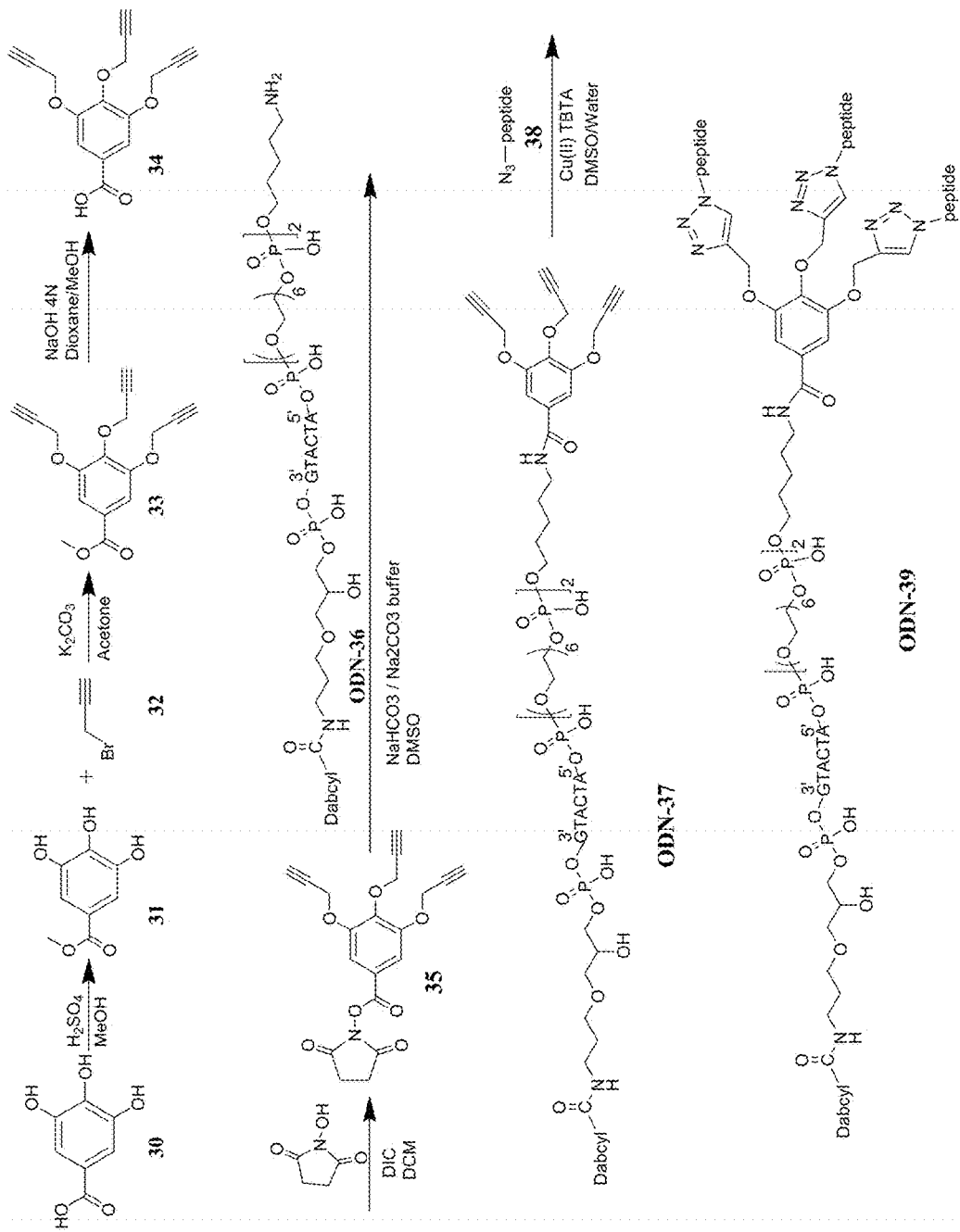
FIG. 13A-13D depicts a synthetic scheme of the molecular beacons of this invention.

Synthesis of Non Selective ODN-39-Peptide Conjugates (FIG. 13A)

Methyl 3,4,5 Trihydroxy Benzoate (31)

To a stirred solution of Gallic acid (30, 6 g, 35 mmol) in Methanol (100 mL), $H_2SO_4$ (4 mL, 74 mmoles) was added and the solution was refluxed at 80° C. for 12 hours. The reaction was monitored by thin layer chromatography (TLC) (EtOAc: Hexane, 80:20). The reaction mixture was evaporated to the crude solid. After extraction with EtOAc the solution was washed once by saturated $NaHCO_3$, once by distilled water, and dried with $MgSO_4$. Finally, the solvents were evaporated under reduced pressure to yield a substance resembling white powder. Yield: 5.76 g, 96%. $^1$H-NMR (300 MHz, in MeOD) δ 7.05 (s, 2H); 4.90 (s, 3H); 3.83 (s, 3H).

3,4,5 tris(proparyloxy)benzoate (33)

A mixture of Methyl 3,4,5 trihydroxy benzoate (31, 4.14 g, 22.5 mmol) and propargyl bromide (32) 80% in toluene (8.7 mL, 78.75 mmol) was stirred for 10 minutes in 50 mL of degassed acetone. $K_2CO_3$ (21.05 g, 150 mmol) was added. The reaction mixture was stirred under reflux overnight and monitored by TLC (Hexane: EtOAc, 1:1; colored by potassium permanganate). After redissolving in DCM, $MgSO_4$ was added to the stirred reaction mixture and filtered after 10 minutes. The solvents were removed under reduced pressure to produce yellow oil. Yield: 3.02 g, 73%. $^1$H-NMR (300 MHz, in $CDCl_3$), δ 7.47 (s, 2H,); 4.8 (s, 6H); 3.93 (s, 3H). ES-MS (m/z): calcd. 298.08. found 299.02 (M+H).

3,4,5-tris(prop-2-yn-1-yloxy)benzoic acid (34)

3,4,5 tris(proparyloxy)benzoate (33, 4.2 g, 14 mmol) was dissolved in dioxane/Methanol/4N NaOH: 130 mL/50 mL/25 mL. The obtained reaction mixture was stirred for 5 hours at room temperature. Then the reaction mixture was acidified by 1N HCl (pH 1-2) and the solvents were removed under reduced pressure. The residue was redissolved in EtOAc (100 mL) and the organic phase was washed with 1N $KHSO_4$ (13.6 g in 100 mL water) 3 times, and brine 3 times as well, dried and evaporated under vacuum. Yield: 3.85 g, 91%. $^1$H-NMR (300 MHz, in $CDCl_3$), δ 7.77 (m, 2H); 7.59 (m, 1H); 7.51 (s, 1H); 4.85 (d, J=3 Hz, 4H); 4.80 (d, J=3 Hz, 2H); 3.02 (s, 2H); 2.88 (s, H). ES-MS (m/z): calcd. 284.07. found 285 (M+H).

2,5-dioxopyrrolidin-1-yl 3,4,5-tris(prop-2-yn-1-yloxy)benzoate (35)

3,4,5-tris(prop-2-yn-1-yloxy)benzoic acid (34, 0.5 g, 1.7 mmol), N-hydroxysuccinimide (NHS, 202.4 mg, 1.7 mmol), and DIC (270 µl, 1.7 mmol) were mixed in 8 mL DCM. DMF (2 mL) was added to obtain a clear solution. The solution was left overnight at room temperature and monitored by TLC (DCM:MeOH, 98:2). The mixture was extracted with HCl (0.1N), followed by drying with $MgSO_4$ and evaporation; then the product was purified by Combiflash using silica gel column chromatography (eluent: 1% MeOH in DCM). Yield: 80%. $^1$H NMR ($CDCl_3$, 300 MHz): δ 2.49 (t, J=3.0 Hz, 1H); 2.57 (t, J=3.0 Hz, 2H); 2.93 (s, 4H); 4.83 (d, J=2.0 Hz, 4H); 4.89 (d, J=3.0 Hz, 2H); 7.57 (s, 2H). ES-MS (m/z): calcd. 400.21. found 400.16, 422.10 (M+Na), 823.14 (2M+Na).

Synthesis of ODN-37

2,5-dioxopyrrolidin-1-yl 3,4,5-tris(prop-2-yn-1-yloxy) benzoate (35, 20 mg, 52.5 µmol) was dissolved in 200 µL DMSO Amine-terminated Dabcyl tagged oligo (ODN-36, 350 nmol in 100 µL) [ODN-36 was prepared by automated DNA synthesizer using the suitable phosphoamidite] was added to 100 µL $NaHCO_3/Na_2CO_3$ buffer (pH 8.75). The DMSO and Buffer solutions were mixed and white precipitate was formed. The reaction was mixed overnight at room temperature. The sediment was removed by centrifugation and then 1 mL milli-Q water was added and the sample was lyophilized. The DNA was re-suspended in 300 µl milli-Q water and desalted using MicroSpin G-25 columns according to the manufacturer's instructions (GE Healthcare). The HPLC analysis of the product showed minor traces of ODN-8 (~10% peak area) and the product with a major peak (90% peak area). Yield: 70%. MALDI-TOF MS (m/z): calcd. 6074. found: 6074.

Synthesis of ODN-39-Peptide

A solution of alkyne-modified oligonucleotide (ODN-37, 100 nmol) in 100 µl milli-Q water and a solution of ascorbic acid in milli-Q water (80 µL, 5 mM) were mixed and buffered with Triethylammonium acetate (TEAA) (20 nt, pH 7.0) to maintain a neutral pH. After addition of the azide functionalized peptide (15 equiv. in 15 µl DMSO-according to Table 3 below), the solution was degassed by argon bubbling for 1 min. Then a solution of $CuSO_4$/tris-(Benzyltriazolylmethyl)amine (TBTA) (10 mM, 40 µL) was added. The reaction was stirred for 2-12 h at 25° C. The ODN-peptide conjugates were purified using HPLC, eluted at 60%-70% B, depending on the peptide sequence.

TABLE 3

Peptide sequences used for preparing different oligonucleotide - peptide conjugate

| ODN | Sequence | Seq. ID. | Molecular Weight | Peptide DNA conjugate-Calculated Mw | Peptide DNA conjugate-Measured Mw (Maldi) |
|---|---|---|---|---|---|
| ODN-39-P1 | TSPVG | Seq. ID. 10 | 555.58 | 5743 | 5743 |
| ODN-39-P2 | KIRQK | Seq. ID. 11 | 767.92 | 6380 | 6380 |
| ODN-39-P3 | KKRQKF | Seq. ID. 12 | 930.11 | 6866 | 6868 |
| ODN-39-P4 | EGDFN | Seq. ID. 13 | 676.64 | 6106 | 6098 |
| ODN-39-P5 | LYATQGD | Seq. ID. 14 | 862.89 | 6665 | 6668 |
| ODN-391-P6 | ISYVEGT | Seq. ID. 15 | 863.91 | 6668 | 6673 |
| ODN-39-P7 | LYTAVSLG | Seq. ID. 16 | 919.04 | 6861 | 6868 |
| ODN-39-P8 | PGGSTPVSSANM | Seq. ID. 17 | 1200.28 | 7677 | 7680 |
| ODN-39-P9 | AIPVSREEK | Seq. ID. 18 | 1124.25 | 7449 | 7454 |

ODN-39-P1: yield: 71%. MALDI-TOF MS (m/z): calcd. 5743. found 5743.

ODN-39-P2: yield: 35%. MALDI-TOF MS (m/z): calcd. 6380. found 6380.

ODN-39-P3: yield: 25%. MALDI-TOF MS (m/z): calcd. 6866. found 6868.

ODN-39-P4: yield: 55%. MALDI-TOF MS (m/z): calcd. 6106.6. found 6108.

ODN-39-P5: yield: 60%. MALDI-TOF MS (m/z): calcd. 6665. found 6668.

ODN-39-P6: yield: 42%. MALDI-TOF MS (m/z): calcd. 6668. found 6671.

ODN-39-P7: yield: 30%. MALDI-TOF MS (m/z): calcd. 6861. found 6868.

ODN-38-P8: yield: 22%. MALDI-TOF MS (m/z): calcd. 7677. found 7680.

ODN-39-P9: yield: 30%. MALDI-TOF MS (m/z): calcd. 7449. found 7454.

Example 9

Figure 13B:
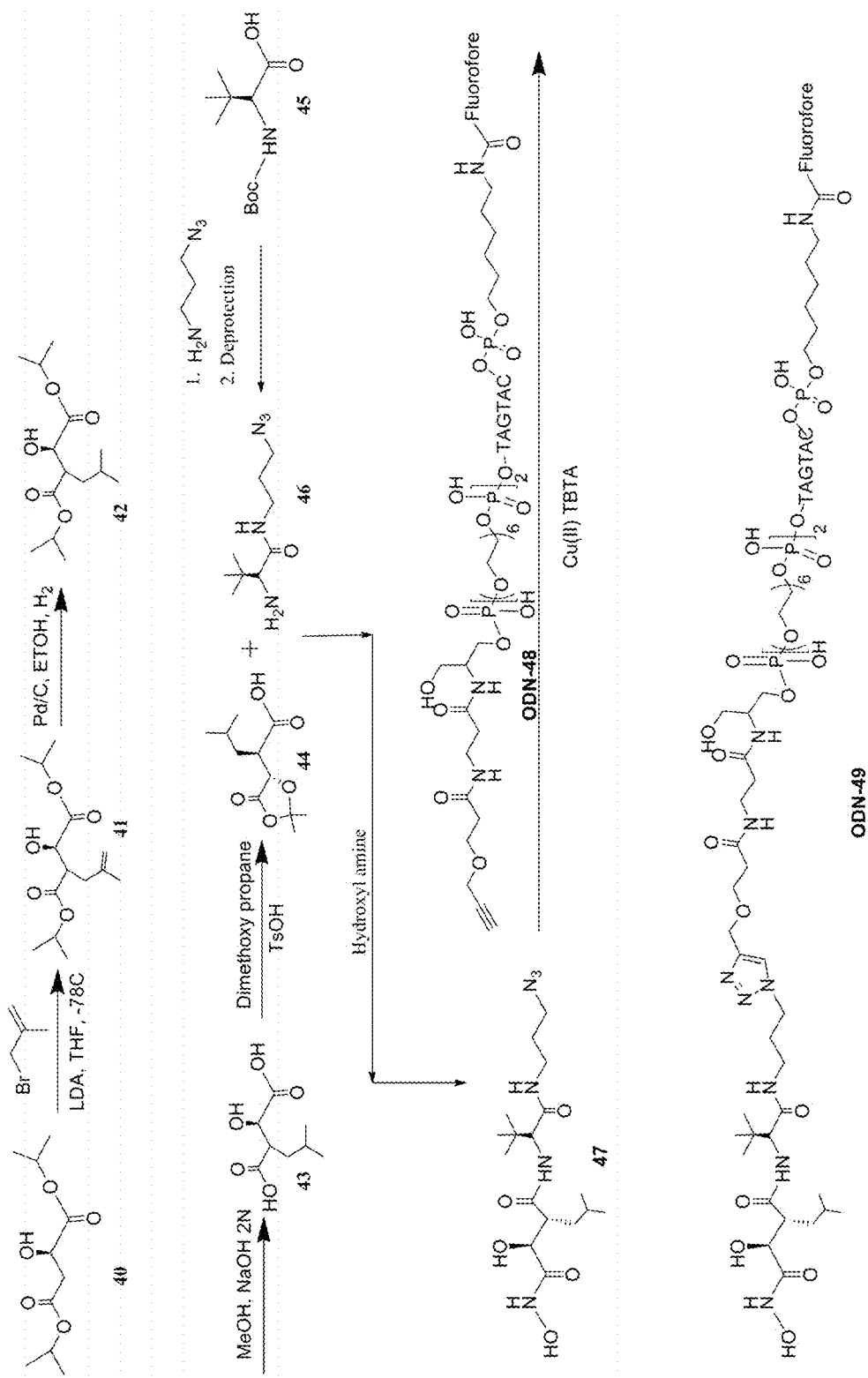

Synthesis of Selective ODN-49 (FIG. 13B)

2-Hydroxy-3-(2-methyl-allyl)-succinic acid diisopropyl ester (41)

Dry THF (30 mL) was added todiisoprpyl s(−) lactic acid (40, 1.8 g, 9.5 mmol) under argon. The solution was cooled to −78° C. using dry ice/acetone. Then, 10 mL LDA (2M, 10 mL, 20 mmol) was added dropwise. The mixture was stirred in ethylene glycol/dry ice bath (−15° C.) for 2 hours. The mixture was again cooled to 0° C., methallyl bromide (2.4 mL, 22.8 mmol) was added dropwise and stirred for 1 hour at −78° C., 2 hours at −10° C., and 1 hour at room temperature. The solution was quenched by adding 2.6 mL glacial acetic acid, then diluted by diethyl ether (160 mL) and water (40 mL). The organic layer was washed with saturated NaHCO$_3$ and saturated brine, dried over MgSO$_4$ and evaporated. The residue was purified using Combiflash chromatography and Hexane/EtOAc. The product eluted at 7% EtOAc. Yield 738 mg, 29%. $^1$H NMR (300 MHz, CDCl$_3$): δ 5.11-4.97 (m, 2H), 4.81 (d, J=10.5 Hz, 2H), 4.17 (d, J=3.6 Hz, 1H), 3.22 (d, J=6.9 Hz, 1H), 3.02 (m. 1H), 2.56-2.34 (m, 2H), 1.74 (s, 3H), 1.28 (d, J=2.7 Hz, 3H), 1.26 (d, J=5.1 Hz, 3H), 1.20 (s, 3H), 1.18 (s, 3H). ESI-MS: calcd. 272.3. found 273.3 (M+H), 295.3 (M+Na), 311.3 (M+K).

2-Hydroxy-3-isobutyl-succinic acid diisopropyl ester (42)

Compound 41 (738 mg, 2.71 mmol) was dissolved in ethanol (10 mL) and degassed with argon. Then 10% Pd/C (240 mg) was added. The resulting black suspension was exposed to hydrogen at 1 atm of pressure overnight. Then, the catalyst was removed by filtration, and the filtrate was concentrated to a colorless gum (used for the next step without weighting). $^1$H NMR (300 MHz, CDCl$_3$): δ 5.09-4.93 (m, 2H), 4.14 (d, J=6.0 Hz, 1H), 3.18 (s, br, 1H), 2.82 (m. 1H), 1.73-1.57 (m, 2H), 1.42 (m, 1H), 1.25 (s, 3H), 1.22 (s, 3H), 1.18 (s, 3H), 1.16 (s, 3H), 0.89 (q, J=3 Hz, 6H). ESI MS: [M+H]=275.2 (275.2), [M+Na]=297.2, and [M+K]=313.1.

(2R)-2-hydroxy-3-isobutylsuccinic acid (43)

Compound 42 (crude from previous step) was dissolved in methanol (16 mL) and sodium hydroxide (2N, 16 mL) was added at 0° C. The mixture was stirred at room temperature overnight. The solution was quenched by adding 6 N HCl to pH=1. The mixture was extracted with EtOAc (20 mL×8). The combined organic extracts were dried over anhydrous MgSO$_4$ and evaporated to yield a pale yellow gum. The product, analyzed by mass spectroscopy and $^1$H NMR, was found to be composed of a mixture of mono-isopropyl ester and the di-acid product. Therefore, this procedure was repeated again. An alternative option: use dioxane (15 mL) and KOH, (15 mL2N) to yield the desired product after a workup. Yield: 340 mg, 66%. $^1$H NMR (300 MHz, MeOD): δ 4.23 (d, J=5.7 Hz, 1H), 2.91-2.88 (m, 1H), 1.73-1.61 (m, 2H), 1.41-1.36 (m, 1H), 0.94 (d, J=6 Hz, 6H). ESI MS: calcd. 189.2. found 188.9=(M−H), 213.0 (M+Na), 229.0 (M+K).

(S)-2-((R)-2,2-dimethyl-5-oxo-1,3-dioxolan-4-yl)-4-methylpentanoic acid (44)

Compound 43 (275 mg, 1.45 mol) and TsOH hydrate (52 mg, 0.27 mmol) were dissolved in dimethoxypropane (6 mL). The mixture was stirred for 6 hours at room temperature (3-6 hours) and then concentrated (during evaporation the colorless solution turned red-brown). Purification was performed by Combiflash chromatography using Hexane/EtOAc. The product eluted at 7% EtOAc. Yield: 30 mg, 9%. $^1$H NMR (300 MHz, CDCl$_3$): δ 4.46 (d, J=6 Hz, 1H), 3.04-2.98 (m, 1H), 1.82-1.62 (m, 3H), 1.60 (s, 3H), 1.54 (s, 3H), 0.96 (s, 3H), 0.94 (s, 3H). ESI MS: calcd 230.3. found 228.9 (M−H), 253.0 (M+Na), 269.0 (M+K).

(R)-2-amino-N-(3-azidopropyl)-3,3-dimethylbutanamide (46)

Boc-tert-Leu-OH (45, 75 mg, 0.325 mmol, 1 eq) and 3-azidopropane amine (39 mg, 0.39 mmol, 1.2 eq) were dissolved in 5 mL DCM, followed by addition of EDC (124.6 mg, 0.65 mmol, 2 eq). After being stirred overnight, the reaction mixture was diluted with 20 mL DCM and washed with 10% HCl and Brine. The organic layer was dried with MgSO$_4$ and concentrated under reduced pressure by rotary evaporator. The residue was purified by Combiflash chromatography using Hexane/EtOAc. Yield 66 mg, 65%.

Deprotection of BOC protecting group: HCl (4.0M) in dioxane (2.5 mL) was added to a round bottom flask containing 46 (66 mg) under argon with an ice-water bath at 0° C. and stirred for 30 min. Then, the reaction mixture was stirred at room temperature for 3 hours. 15 mL of DCM were added and the solvent was evaporated. Yield: 30.5 mg 68%. $^1$H NMR (300 MHz, CDCl$_3$): δ 1.18 (s, 9H), 1.89-1.94 (m, 2H), 3.40-3.45 (m, 4H), 4.14 (s, 1H), 8.15 (s, 2H), 8.42 (s, 1H). ESI MS: calcd. 213.3. found 214.0 (M+H), 236.0 (M+Na), 427.2 (2M+H).

(2R,3S)—N1-((R)-1-((3-azidopropyl)amino)-3,3-dimethyl-1-oxobutan-2-yl)-N4,3-dihydroxy-2-isobutylsuccinamide (47)

Compound 44 (25 mg, 0.11 mmol) was dissolved in anhydrous DMF (1.2 mL), followed by the addition of 46 (25.5 mg, 0.12 mmol), HBTU (41.1 mg, 0.11 mmol), and DIPEA (100 μL, pH ~8). After 1 hour, the reaction was diluted in ethyl acetate (25 mL) and washed with HCl (1N×3). The organic layer was then dried with MgSO$_4$ and concentrated under reduced pressure by using a rotary evaporator and oil pump. Combiflash chromatography and Hexane/EtOAcused for purification (product eluted at 39% EtOAc). Yield 20 mg, 48%. $^1$H NMR (300 MHz, CDCl$_3$): δ 0.99 (s, 9H), 1.43 (s, 9H), 1.73-1.85 (m, 2H), 3.27-3.39 (m, 4H), 3.85 (d, J=9 Hz, 1H), 5.35 (d, J=9 Hz, 1H), 6.62 (s, 1H). ESI MS: calcd. 313.4. found 336.1 (M+Na), 352.1 (M+K), 649.3 (2M+Na).

THF was added to a round bottom flask containing the resulting product (18 mg, 0.042 mmol), followed by hydroxylamine (1.5 mL 50% in water). This solution was then refluxed at 80° C. for 3 hours (analyzed by analytical HPLC). The reaction was concentrated under reduced pressure using a rotary evaporator. This residue was then purified by HPLC to afford 47. Yield: 10.8 mg, 64%. $^1$H NMR (300 MHz, CDCl$_3$): 0.93-1.00 (m, 15H), 1.21 (m, 2H), 1.27 (m, 1H), 3.18 (m, 1H), 3.39 (m, 4H), 4.17 (d, J=9 Hz, 1H), 4.32 (s, 1H), 7.04 (s, 1H), 7.65 (d, J=3 Hz, 1H). ESI MS: calcd. 400.47. found 399.14 (M−H), 423.17 (M+Na), 439.15 (M+K).

FAM-DNA-Marimastat (ODN-49)

ODN-48 (Prepared by automated DNA synthesizer using the suitable phosphoamidite). 75 μL, 247 nmol) was mixed with compound 47 (1.4 μmol, about 6 eq). Then TEAA buffer (2M, 10 μL) and ascorbic acid (20 μL in H$_2$O, 5 mM) were added. The mixture was degassed with argon, and Cu-TBTA (10 μL, 10 mM in 55% DMSO) was added and stirred overnight. Note: the total volume was 200 μL, H$_2$O:DMSO, 1:1. The product was purified using HPLC. Yield: 40%. Maldi: calcd. 4440. found 4442.

Example 10

Figure 13C:
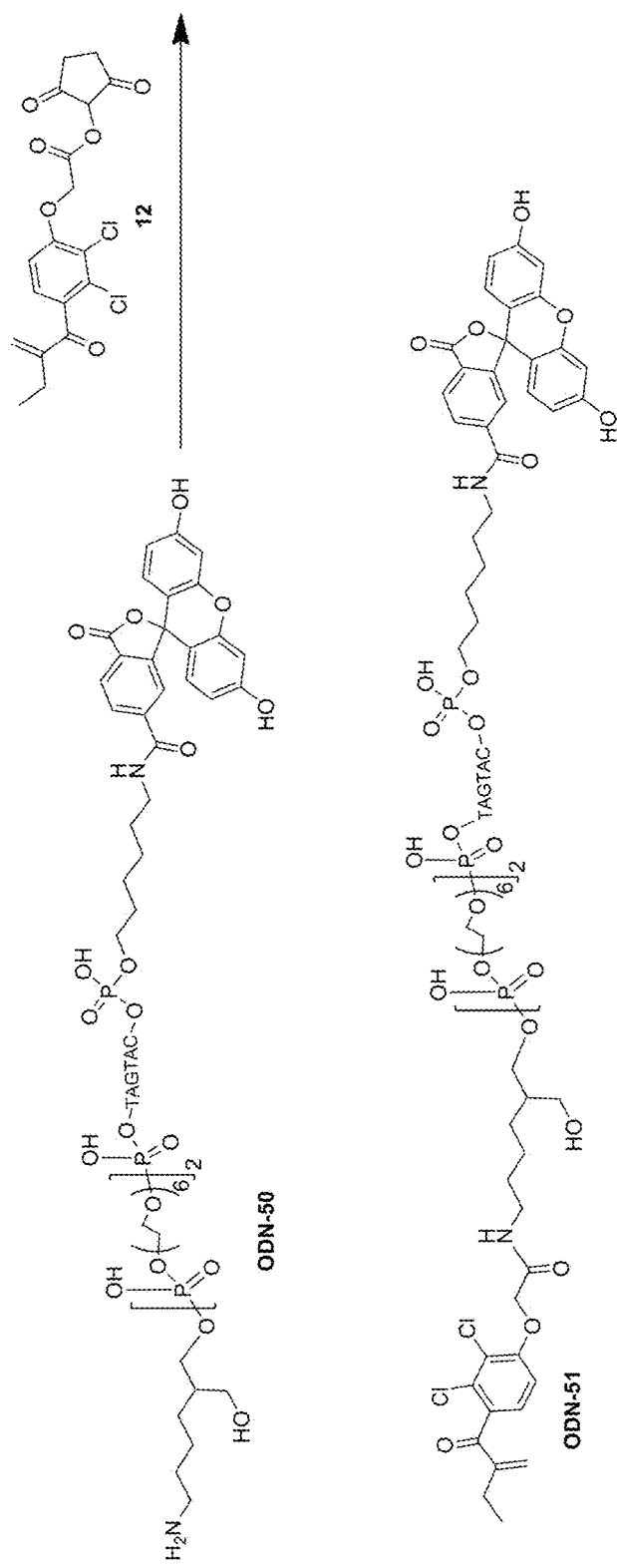

Synthesis of Selective ODN-51 (FIG. 13C)

ODN-50 (Prepared by automated DNA synthesizer using the suitable phosphoamidite) (100 μL, 350 nmol) was added to 250 μL, NaHCO$_3$/Na$_2$CO$_3$ buffer (pH=8.75). NHS ester of ethacrynic acid (12, 12 mg, 30 μmol) was dissolved in 350 μL, DMSO. Then DMSO and buffer solutions were mixed and white precipitate was formed. The reaction mixture was stirred overnight at room temperature. The sediment was removed by centrifugation and then 1 mL milli-Q water was added and the sample was lyophilized. The DNA was re-suspended in 300 μL milli-Q water, desalted using MicroSpin G-25 columns according to the manufacturer's instructions (GE Healthcare), and purified HPLC. Yield: 30%. Maldi: calcd. 4200. found 4202.

Example 11

Figure 13D:
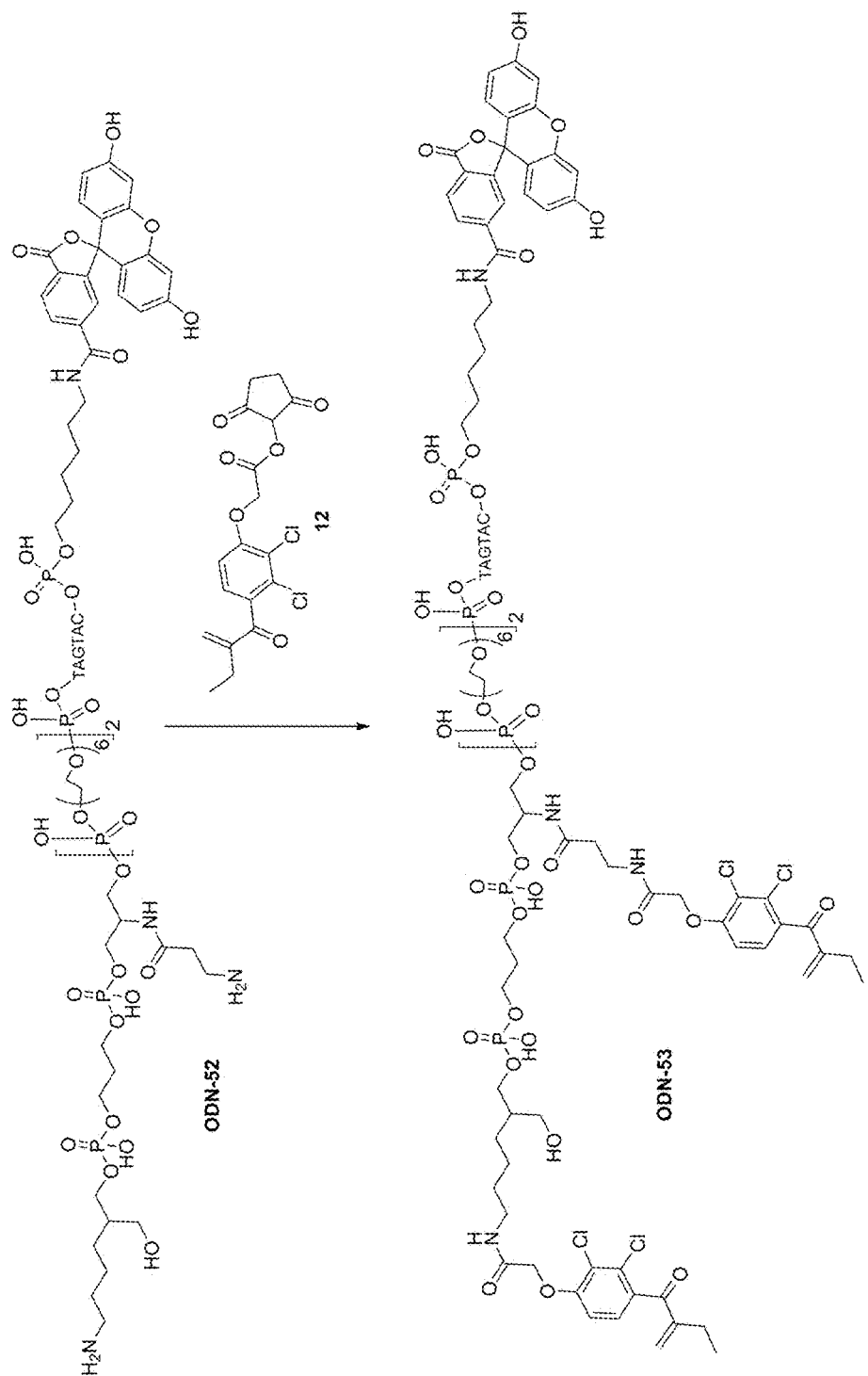

Synthesis of Selective ODN-53 (FIG. 13D)

ODN-52 (100 μL, 350 nmol,) was added to 250 μL, NaHCO$_3$/Na$_2$CO$_3$ buffer (pH=8.75). NHS ester of ethacrynic acid (12.44 mg, 110 μmol) was dissolved in 350 μL, DMSO. Then, DMSO and buffer solutions were mixed and white precipitate was formed. The reaction mixture was stirred overnight at room temperature. The sediment was removed by centrifugation and then 1 mL milli-Q water was added and the sample was lyophilized. The DNA was re-suspended in 300 μL, milli-Q water, desalted using MicroSpin G-25 columns according to the manufacturer's instructions (GE Healthcare), and purified by HPLC. Yield: 40%. Maldi: calcd. 4847. found 4847.

Example 12

MMP Kinetic Measurements

Figure 14:
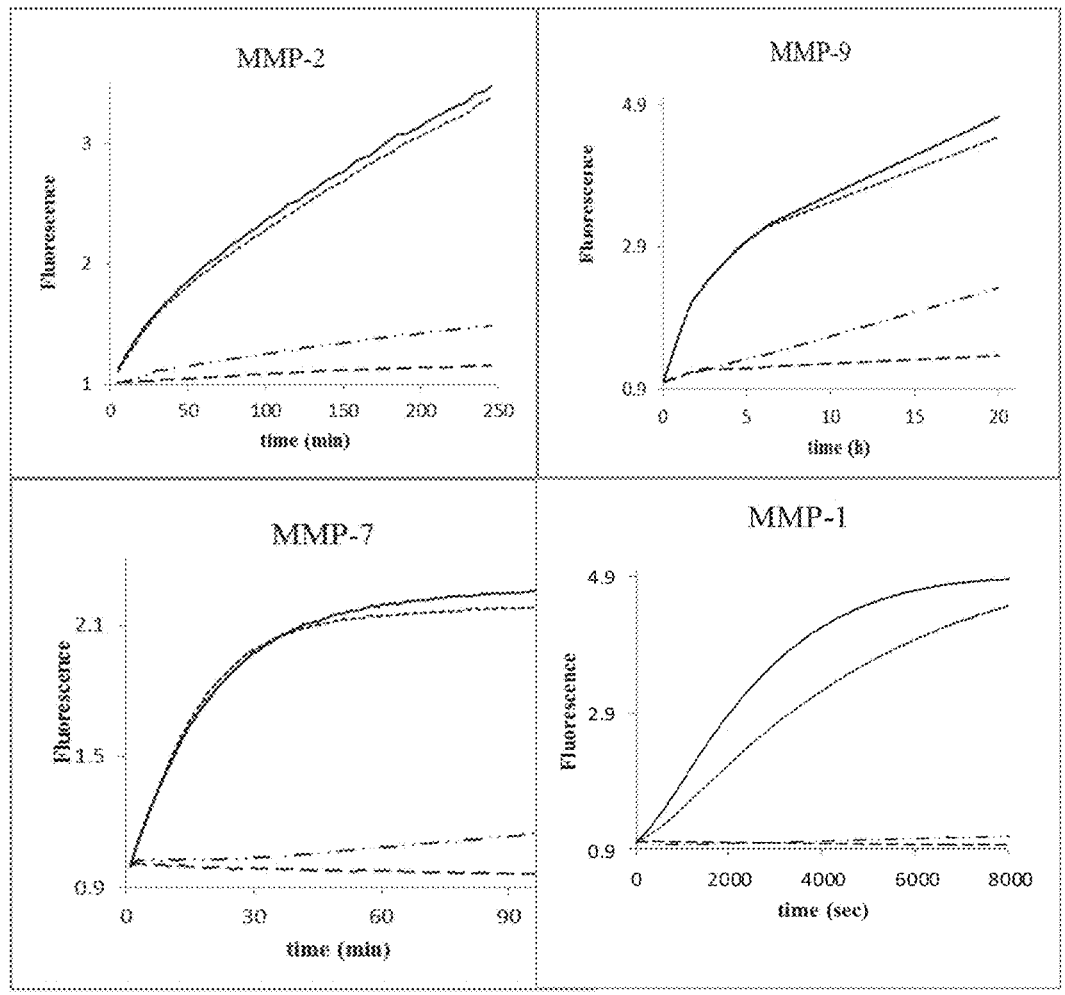
FIG. 14 depicts enzymatic activity of four MMPs (8 nM) in the absence (solid line) and presence of 50 nM 'marimastat' (dashed line), ODN-49 (dash-dotted line), and ODN-48 (dotted line). The changes in emission were followed using 310/20 and 400/30 excitation and emission filters, respectively.

Enzymatic inhibition assays were performed to confirm the binding of the marimastat-ODN conjugate (ODN 49) to four MMP isoforms (FIG. 14) and to obtain the corresponding inhibition constants (Ki) (FIG. 15A-15E). Marimastat is a highly potent broad-spectrum inhibitor of MMP isoforms, with K$_i$ values in the low nanomolar range.

MMP-2, MMP-9, and MMP-1 (1 μM final concentration) were activated using APMA (1 mM final concentration) in Tris buffer (100 mM Tris, pH 7.5, 100 mM NaCl, 10 mM CaCl$_2$), at 37° C. for 1, 2 and 3 hours, respectively. MMP 7 does not need any activation Inhibition of MMP-1, MMP-2, MMP-7, and MMP-9 by ODN-49 was followed by using a fluorescently labeled peptide, namely, Mca-Pro-Leu-Gly-Leu-Dap(Dnp)-Ala-Arg-OH, as the substrate. This peptide contains a fluorophore (Mca) whose emission is intramolecularly quenched by the Dnp group. Therefore cleavage of this substrate by MMP results in an increase in the fluorescence signal at λ$_{em}$=393 nm. The reaction was followed by monitoring the emission at 393 nm over several hours. As control experiments, the change in emission was also followed in the presence of an unmodified 'marimastat', ODN-48, as well as without any inhibitor (FIG. 15A-15E). MMP (8 nM final concentration) was incubated with commercial marimastat (50 nM), ODN-48 (50 nM), and ODN-49 (50 nM) for 10 min at room temperature. The peptide substrate was then added (5 µM final concentration) and the fluorescence emission was monitored using a plate reader with 310/20 and 400/30 excitation and emission filters, respectively. After selective binding was established, the $K_i$ values were determined by incubating 5 nM of each MMP with 7-8 different concentrations of ODN-49 (0, 0.05, 0.1, 0.5, 1, 2, 5, and 12.5 nM) for 10 min at room temperature. The peptide substrate was then added (5 µM final concentration) and the reaction emission was monitored using a plate reader 310/20 and 400/30 excitation and emission filters, respectively.

To obtain $K_i$ values, eight different concentrations of ODN-49, ranging from 0.1 nM to 15 nM, were added to 5 nM MMP, followed by the addition of 5 µM substrate. The fluorescence emission was monitored using a microplate reader with 310/20 nm and 400/30 nm excitation and emission filters, respectively. The Ki values (Table 4) were obtained by fitting initial velocities into the equation:

$$V = \frac{V_o}{1 + \frac{[I]}{K_i}}$$

using Sigmaplot 12.0 statistical software (Systat) (FIG. 15A-15D, Table 4).

These experiments showed that the inhibition of the four MMPs by ODN-49 is comparable to that of the highly potent 'marimastat' and that ODN-48, which lacks the 'marimastat' group, does not inhibit their function. Thus, ODN-49 binds the enzymes via a derivative at the active site, as expected from our design.

Example 13

Fluorescence Polarization Measurements

Fluorescence polarization was measured using a Synergy H4 hybrid multi well plate reader using black flat-bottom polystyrene NBS 384-well microplates in Tris buffer (100 mM Tris, pH 7.5, 100 mM NaCl, 10 mM $CaCl_2$). The optimal concentrations of ODN-48 and ODN-49 were determined by measuring the fluorescence anisotropy of 50 µl of various concentrations of ODN (0.01-1000 nM) in triplicate. The measurements were performed using 485/20 and 528/20 excitation and emission filters, respectively, with a 510-nm cut-off mirror. In order to monitor the interaction between MMP-7 and ODN-49, ODN-49 (1 nM, 200 µl) and different concentrations of MMP-7 (0, 1, 2, 3, 4, 5, 10, 20, 40, 60, 75, 100, and 150 nM) were incubated at room temperature for 20 min and then divided into 60 µL, triplicates.

Figure 15A:
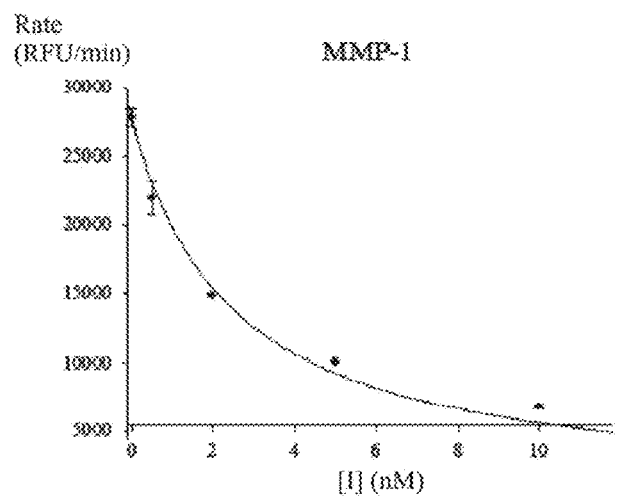
FIG. 15A-15E depicts inhibition of MMP activity by marimastat-DNA conjugate (ODN-49).
Figure 15B:
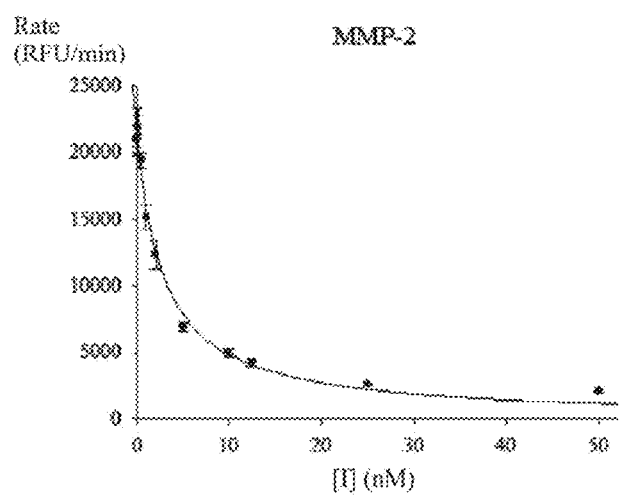
Figure 15C:
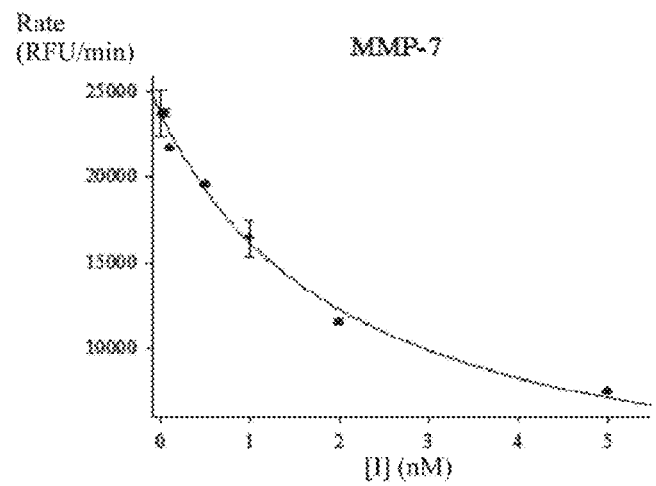
Figure 15D:
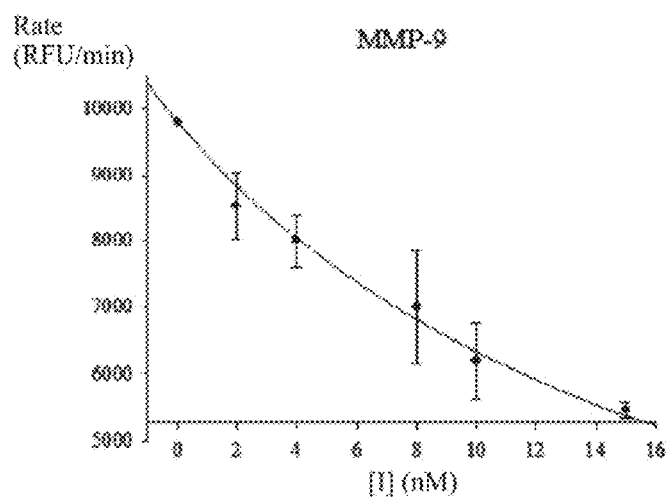
Figure 15E:
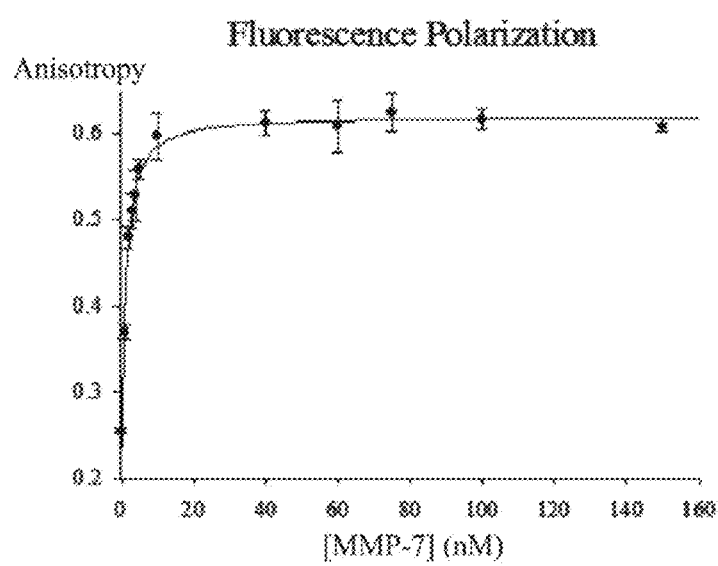
Figure 16:
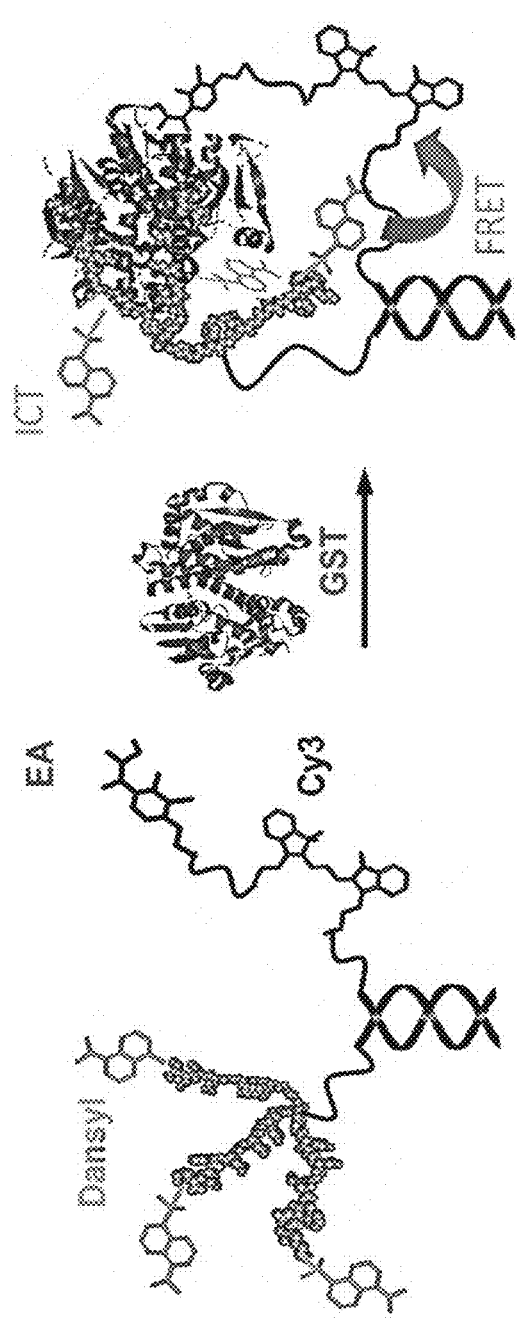
FIG. 16 depicts a schematic sensing with self-assembled synthetic receptors integrating selective and non-selective GST binders. Changes in the emission of each dye can result from changes in the distance between the donor and acceptor, as well as from changes in dansyl's microenvironment.

The $K_d$ value for the interaction between MMP-7 and ODN-49 was obtained by performing fluorescence polarization (FP) measurements (FIG. 15E). Fluorescein has been widely used in FP assays owing to its short excited state lifetime (~4 ns); thus, a binding curve for the MMP-7-ODN-49 interaction could be obtained by following the change in the anisotropy signal of ODN-49 upon addition of MMP-7 in increasing concentrations (0-120 nM).

A dissociation constant of $K_d$=0.98 nM was obtained by fitting the data (FIG. 15E) to a known FP equation:

$$A = A_f + (A_b - A_f) \times \frac{(L_T + K_d + R_T) - \sqrt{(L_T - K_d - R_T)^2 - 4L_T R_T}}{2L_T}$$

where $A_f$ is the anisotropy of the free ligand, $A_b$ is the anisotropy of the fully bond ligand, $L_T$ is the concentration of the ligand, and $R_T$ is the concentration of the receptor.

Example 14

GST Kinetic Measurements

Inhibition of GST A1-1, GST A2-2, GST M1-1, and GST P1-1 activity by ODN modified with one (ODN-51) or two (ODN-53) ethacrynic acids (EAs) was followed using a GST activity assay developed by Habig et al. all GST isozymes (20 nM final concentration) were incubated with 1 µM EA, ODN-50, and ODN-51 (GST A1-1 was incubated with 50 µM EA, 50 µM DNA, and 1 µM ODN-53) in a phosphate buffer at pH 6.5.

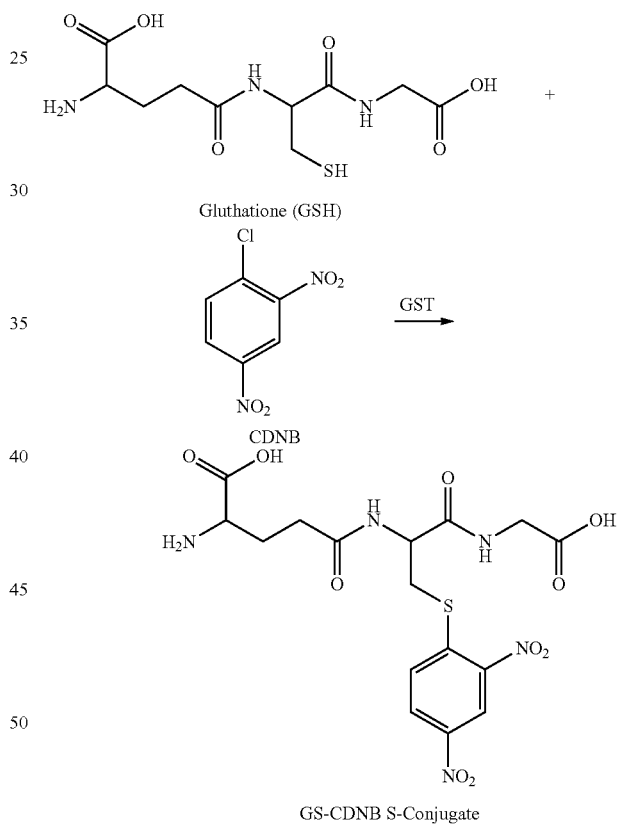

After incubation for 10 min at 30° C., GSH (350 µM final concentration) and CDNB (720 µM final concentration) were added and the absorbance at λ=340 nm was monitored using a plate reader. The uninhibited reaction contained GST, GSH, and CDNB without ODN-53.

Figure 17:
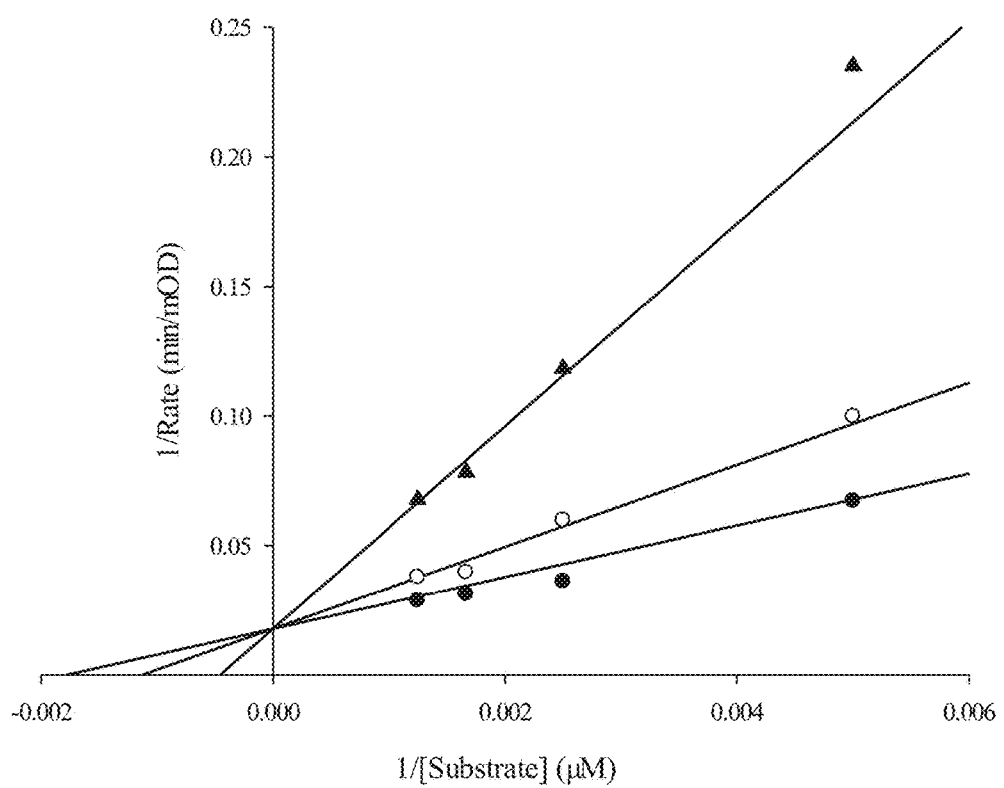
FIG. 17 depicts a Lineweaver-Burk plot of inhibition of GST A1-1 enzymatic activity with no inhibitor (●), 10 μM (○), and 50 μM (▲) ODN-53 and with increasing concentrations of CDNB: 200, 400, 600, and 800 μM. The reaction was followed by monitoring the absorbance at λ=340 nm.

The uninhibited reaction contained GST, GSH, and CDNB. After selective binding was established, the $K_i$ values were determined by incubating GST A1-1 (20 nM) with 4 different concentrations of ODN-51 (0, 1, 10, and 50 µM) and with 4-6 concentrations of ODN-53 (0, 10, 30, 60, 100, 500, 800, and 1200 nM) for 10 min at 30° C. GSH (1 mM final concentration) and CDNB (200, 400, 600, 800 µM final concentrations) were then added and the absorbance at λ=340 nm was monitored using a plate reader. The initial velocities were fitted to a LineweaverBurk competitive inhibition model using Sigmaplot 12.0 statistical software (Systat) (FIG. 17) and the $K_i$ values were derived according to the fitting parameters, namely, according to the highest determination coefficient ($R^2$) and the lowest Akaike Information criterion correction (AICc). The LineweaverBurk competitive inhibition model was chosen.

Figure 18:
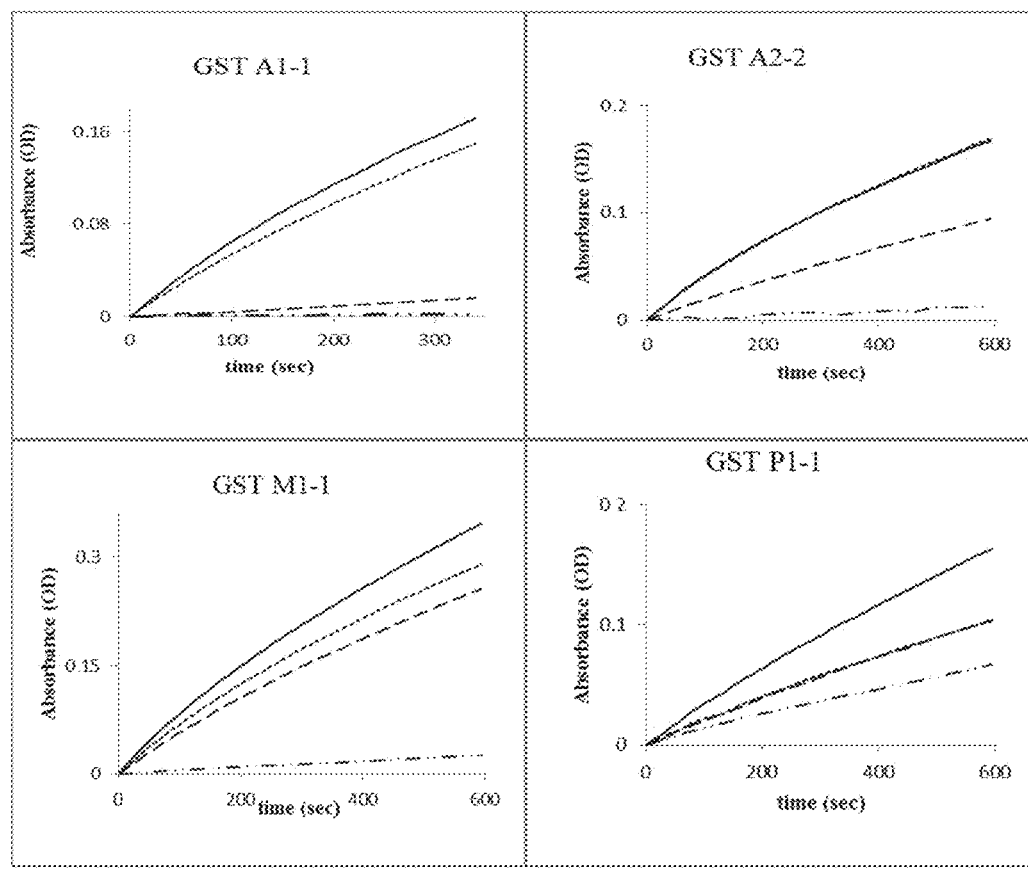
FIG. 18 depicts the enzymatic activity of four GST isozymes (20 nM) in the absence (solid line) and presence of 50 μM commercial ethacrynic acid (dashed line), ODN-53 (dash-dotted line), and ODN-52 (dotted line). The reaction was followed by monitoring the absorbance at λ=340 nm.

Monofunctionalized ODN-53, inhibited the GST-A1-1 with a Ki value of ~14 μM (Table 4). This value is consistent with reported values for the inhibition of GSTs by EA in the low micromolar range. ODN-53 inhibited all GST isozymes at the nanomolar range. To ensure that the inhibition is induced by the EA derivatives, a control experiment was performed in which GST activity was followed in the presence of ODN-52, which lacks the EA moieties (FIG. 18). As expected, ODN-52 displayed no inhibition activity.

The resulting $K_i$ values of ODN-53 were obtained for GST A1-1, A2-2, M1-1, and P1-1 were 33 nM, 3 nM, 3 nM, and 230 nM, respectively, indicating that the bivalent inhibitor binds these enzymes with high affinity.

TABLE 4

Inhibition constants of the DNA-based GSTs and MMPs binders.

| Isozyme | $K_i$ (nM) | $R^2$ | Isozyme | $K_i$ (nM) | $R^2$ |
| --- | --- | --- | --- | --- | --- |
| GST A1-1 & ODN-51 | 13763 ± 1992 | 0.99 | MMP-1 & ODN-49 | 0.40 ± 0.07 | 0.95 |
| GST A1-1 & ODN-53 | 33.05 ± 6.50 | 0.97 | MMP-2 & ODN-49 | 0.33 ± 0.03 | 0.99 |
| GST A2-2 & ODN-53 | 2.75 ± 0.67 | 0.97 | MMP-7 & ODN-49 | 1.21 ± 0.11 | 0.99 |
| GST P1-1 & ODN-53 | 228.36 ± 42.47 | 0.97 | MMP-9 & ODN-49 | 0.06 ± 0.01 | 0.99 |
| GST M1-1 & ODN-53 | 2.94 ± 0.80 | 0.97 | | | |

Example 14

MMP Differentiation Assay

Figure 19A:
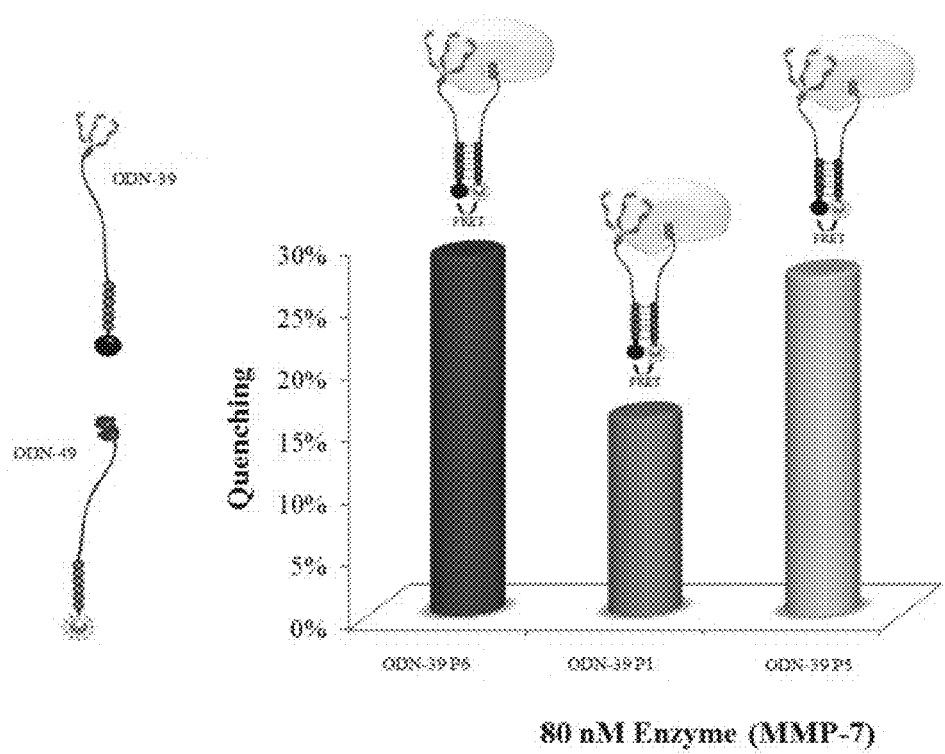
FIG. 19A-19B present changes in the fluorescence upon addition of MMP-7 (80 nM) to three distinct MBs consisting of ODN-49 (60 nM) and ODN-39-P1, ODN-39-P5, or ODN-39-P6 (7 μM each) (FIG. 19A).

Molecular beacons (MBs) of this invention were prepared by incubating three non-selective ODN-peptide conjugates (ODN-39-P1, P5, and P6) with ODN-49 and recording the changes in their fluorescence upon addition of MMP-7 (FIG. 19A). The different fluorescence responses confirm that distinct, non-selective peptide binders (i.e., P1, P5, and P6) interact differently with the same protein surface.

The ODN-39 peptide conjugate (ODN-39-P1, . . . ODN-39-$P_9$, 1-25 μM final concentration) was added to ODN-49 (20 nM final concentration) in Tris buffer (100 Mm Tris, pH 7.5, 100 mM NaCl, 10 Mm $CaCl_2$). Then the mixture was dispensed into 5 wells (50 μL, each well). MMP (activated as described before and dialyzed for 4 hours against Slide-A-Lyzer MINI Dialysis Device, 10K MWCO, 0.1 mL 1 L Tris buffer, to remove all APMA) was added to each well (100 nM final concentration). Control experiments were performed by addition of Tris buffer to each ODN-39 peptide conjugates. The change in the fluorescence upon the addition of MMP was monitored using a plate reader with 485/20 and 528/20 excitation and emission filters, respectively. The fluorescence value of each well was subtracted from the respective control well and then divided by the fluorescence of the control well.

Figure 19B:
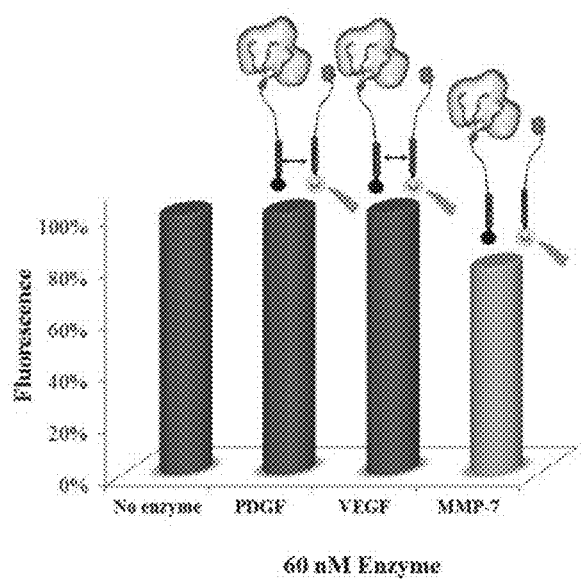

The MB that showed the most profound change in emission signal (FIG. 19A, ODN-49/ODN-39-P1) was incubated with other cancer biomarkers, namely, with vascular endothelial growth factor (VEGF) and platelet-derived growth factor (PDGF) (FIG. 19B). A change in the fluorescence was observed only upon addition of MMP-7, indicating the system is selective towards MMPs.

The response of each MB to different proteins was tested in Tris, PBS, and HEPES buffers containing different concentration salts such as NaCl, $MgCl_2$, $ZnCl_2$, and $CaCl_2$. Different temperatures and incubation times were also tested.

Figure 20:
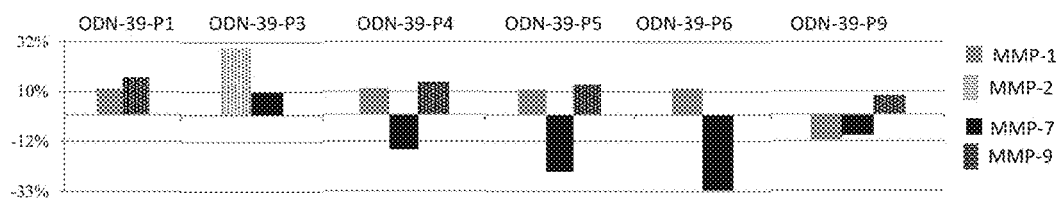
FIG. 20 depicts the fluorescence responses of different MBs of this invention to the presence of different enzymes.

FIG. 20 shows representative emission signals obtained from different MB-enzyme combinations. While in the presence of MMP-1, MMP-9, and MMP-2, an increase in fluorescence intensity (8-30%) was observed for the different MBs; MMP-7 induced a decrease (13-33%) in their emission. MMP-7 is the only isozyme with a basic isoelectric point (pI=9.63); therefore, at pH=7 positively charged domains on the protein's surface may interact with the negatively charged sugar-phosphate backbone of the MBs. This could lead to a direct interaction between 6-FAM and peptide side chains on the surface of MMP-7 and, as a result, to quenching of fluorescence.

Figure 21A:
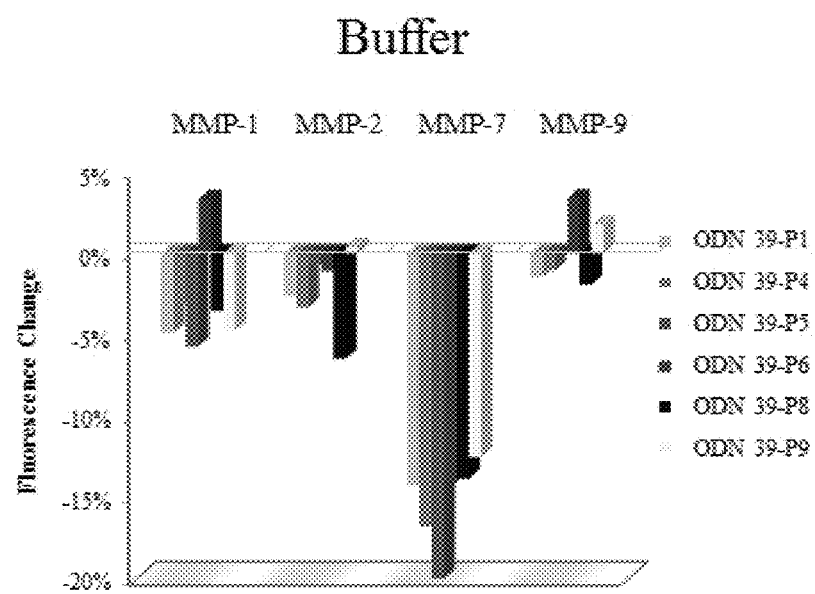
FIG. 21A-21D depicts the fluorescence response of an array of MBs to the addition of MMPs in Tris buffer (FIG. 21A), and Human urine (FIG. 21B).
Figure 21B:
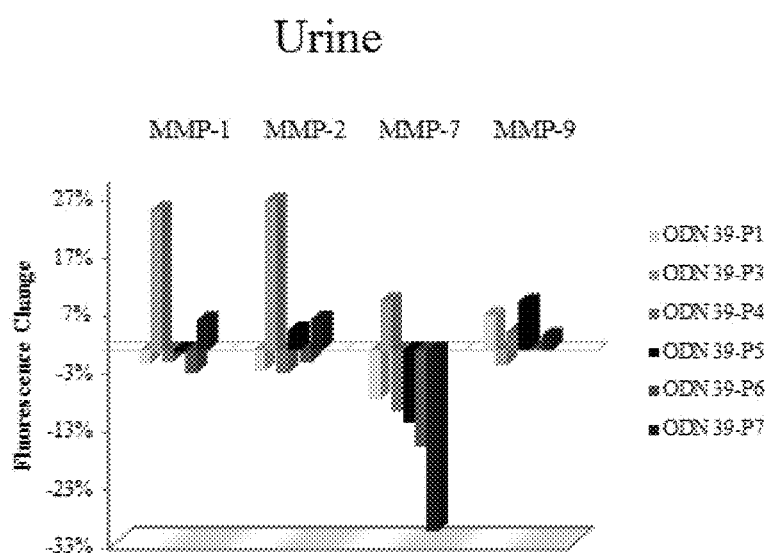

In addition, the different MBs were arrayed on a microwell plate and incubated with the four MMP isoforms. FIGS. 21A and 21B show the fluorescence response of this cross-reactive sensor array to the addition of these enzymes in Tris buffer and human urine, respectively. For experiments with urine, two aliquots were rapidly thawed in 37° C., centrifuged for 1 min at 1000×g, and then centrifuged for 15 minutes at 4500×g, 4° C. using A micon Ultra 2 mL 10,000 MWCO, followed by addition of 1.5 mL Tris buffer and centrifuging for 15 minutes at 4500×g, 4° C. Finally, Tris buffer was added up to a volume of 1.5 mL. The differentiation experiment with urine samples was carried out similarly to the experiments in Tris buffer.

Figure 21C:
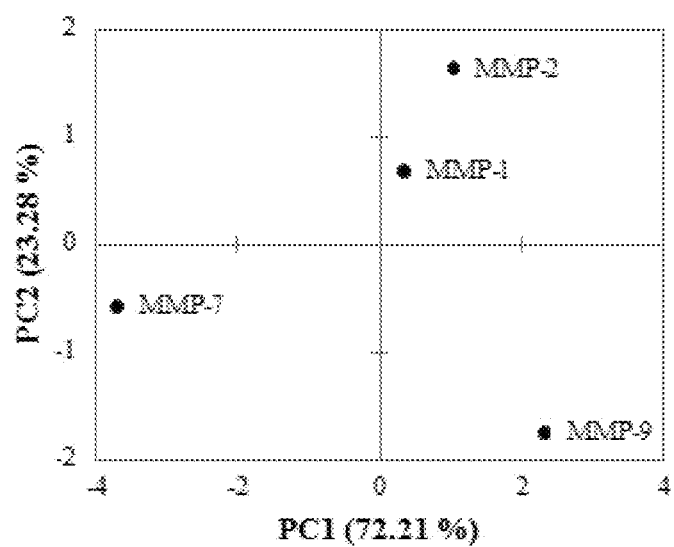
Figure 21D:
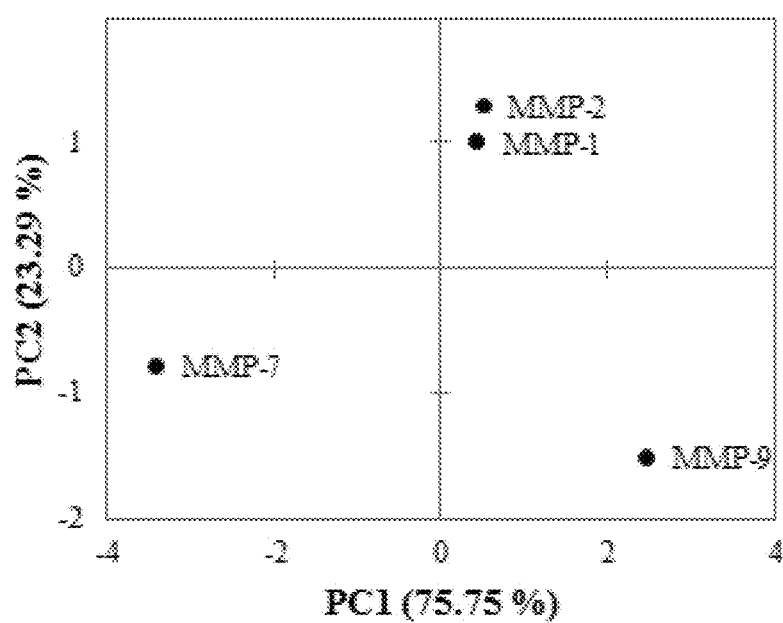

In this experiment, the conditions that maximize the response of the MBs to MMP-7 were selected. As a result, MMP-1, MMP-2, and MMP-9 induced relatively small changes in the emission signals. Principal component analysis (PCA) mapping of these patterns shows a clear differentiation between the four isoforms (FIGS. 21C and 21D).

Example 15

GST Differentiation Assay

The ODN-39 peptide conjugate (ODN-39-P1, . . . ODN-39-$P_9$, 1-25 μM final concentration) was added to ODN-53 (20 nM final concentration, in PBS buffer (100 mM, pH=6.5). Then the mixture was dispensed into 5 wells (50 μL in each well). GST was added to each well (100 nM final concentration). Control experiments were performed by addition of PBS buffer to each ODN-39-peptide conjugate. The change in the fluorescence upon the addition of the GST was monitored using a plate reader with 485/20 and 528/20 excitation and emission filters, respectively. The fluorescence value of each well was subtracted for the respective control well divided by the fluorescence of the control well. GST differentiation was observed using the ODN-39-$P_1$-$P_9$ and ODN-53 hybridized forms (not shown).

Example 16

Figure 22A:
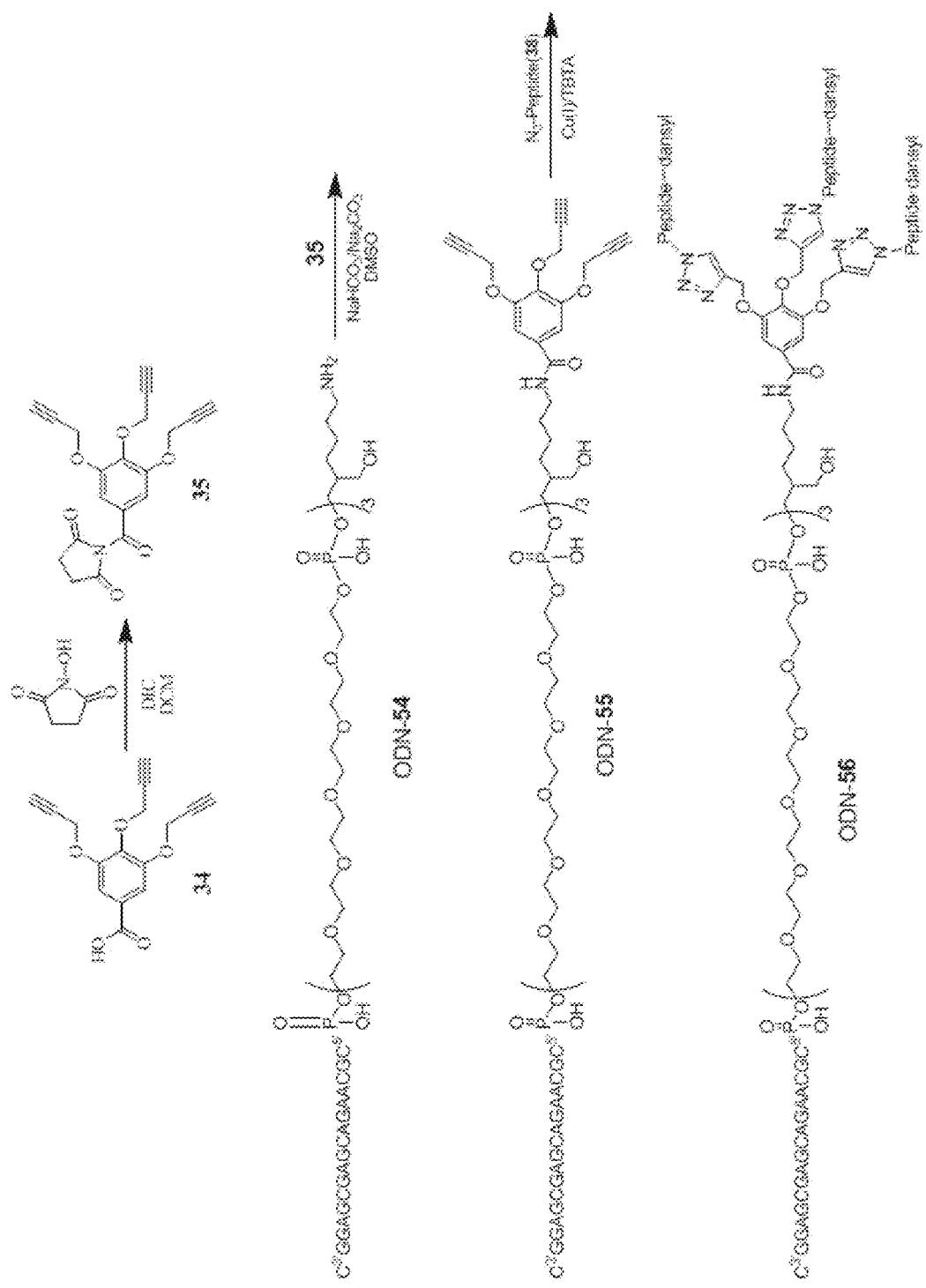
FIG. 22A-22B depicts a synthetic scheme of the molecular beacons of this invention.

Synthesis of Non-Selective ODN-56 (FIG. 22A)

Synthesis of 2,5-dioxopyrrolidin-1-yl 3,4,5-tris(prop-2-yn-1-yloxy)benzoate (35)

Compound 34 (1.5 g, 5.28 mmol) was suspended in dry DCM, and N-hydroxysuccinimide (0.06 g, 5.28 mmol) and DIC (818 µl, 5.28 mmol) were added to the solution. The mixture was stirred overnight and TLC (3% MeOH in DCM) was used to monitor the reaction progress. The reaction mixture was washed with HCl (0.1 N) and brine solution, then the product was purified by combiflash using silica gel column chromatography (eluent: 1.5% MeOH in DCM). Yield: 75.7%. 1H NMR (CDCl$_3$, 300 MHz): δ 2.49 (t, J=3.0 Hz, 1H); 2.57 (t, J=3.0 Hz, 2H); 2.93 (s, 4H); 4.83 (d, J=2.0 Hz, 4H); 4.89 (d, J=3.0 Hz, 2H); 7.57 (s, 2H). ES-MS (m/z): calcd. 381.34. found 404.04 (M+Na), 785.17 (2M+Na).

Synthesis of 3-azidopropanoic acid

3-Bromopropionic acid (3 g, 20 mmol) was suspended in 30 mL acetonitrile and cooled in an ice bath. Then sodium azide (1.5 g, 20 mmol) was added under an argon atmosphere. The mixture was stirred overnight at 75° C., and product formation was monitored by TLC. The solvent was evaporated in vacuum, re-suspended in EtOAc and washed with 1N HCL and brine. The organic phase was dried over MgSO$_4$ and dried under vacuum. Yield: 50%. $^1$H NMR (CDCl$_3$, 300 MHz): δ 2.62 (t, J=6.0 Hz, 2H); 3.56 (t, J=6.0 Hz, 2H); 11.52 (bs, 1H). Compound 16 is coupled to the peptide (see for example Scheme 1 below with a terminal azide group to yield 38-P1-P5).

Synthesis of ODN-55

300 nmol of the oligonucleotide was dissolved in 80 µL milli-Q water and 40 µL of Na$_2$CO$_3$/NaHCO buffer (1 M, pH 8.75) was added to maintain basic conditions of the reaction. Then compound 35 (11.5 mg, 30 µmol) in 40 µl of DMSO was added and the mixture was stirred for 3 h. Additional portion of compound 35 (15 µmol in 20 µL DMSO) was added and the mixture was allowed to stir for another 2 h. Reaction progress was monitored using HPLC. The sediment was removed by centrifugation and then 1 mL milli-Q water was added and the sample was lyophilized. The DNA was re-suspended in 300 µl milli-Q water and desalted using MicroSpin G-25 columns according to the manufacturer's instructions (GE Healthcare). The HPLC analysis of the product showed minor traces of ODN-54 (~11% peak area) and the product with a major peak (89% peak area). Yield: 55%. MALDI-TOF MS (m/z): calcd. 6722. found: 6710.

Synthesis of ODN-56

A solution of alkyne modified oligonucleotide ODN-55 (30 nmol) in 90 µl milli-Q water and a solution of ascorbic acid in milli-Q water (40 µL, 50 mM) were mixed and buffered with TEAA (10 µL, pH 7.0) to maintain neutral pH. After addition of the azide functionalized peptide (12 equiv. in 90 µl DMSO), the solution was degassed by argon bubbling for 1 min. Then a solution of CuSO$_4$/TBTA (10 mM, 25 µl) was added. The reaction was stirred for ½ h at 35° C., and for additional 3 h at 25° C.

The azide functionalized peptides 38-P1-P5 (Table 5) that differ in their charge, polarity, and position of the solvatochromic dansyl fluorescent group were prepared using standard Fmoc solid phase peptide synthesis on a Rink amide resin. Their N-termini were functionalized with 3-azidopropanoic acid, whereas dansyl was incorporated into their structures by removing the Mtt protecting group and reacting the ε-amino side chain of lysine with dansyl chloride (Scheme 1). The modified peptides were purified by RP-HPLC and characterized by ES-MS.

Scheme 1: Introducing a dansyl group to peptide 5 from Table 5 below.

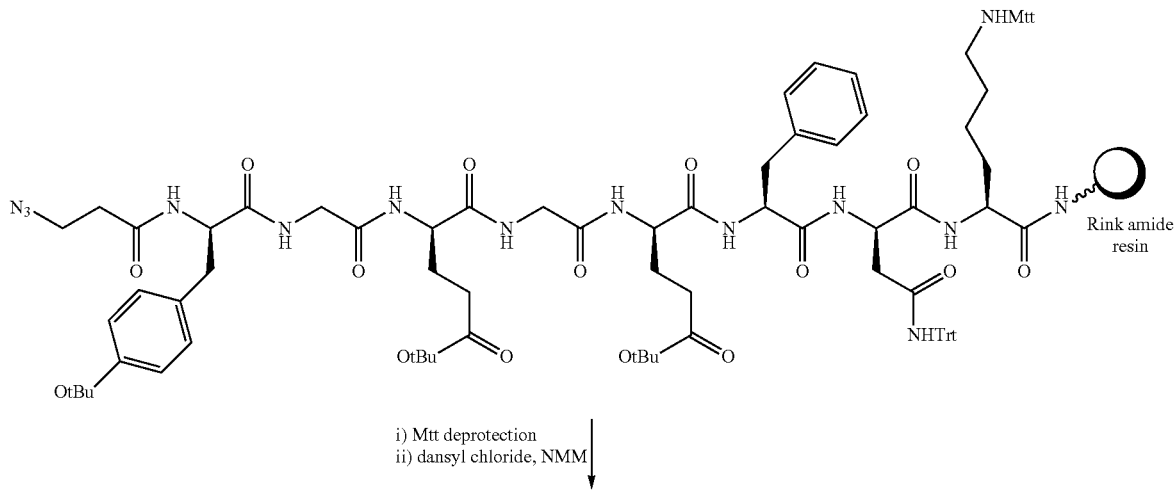

i) Mtt deprotection
ii) dansyl chloride, NMM

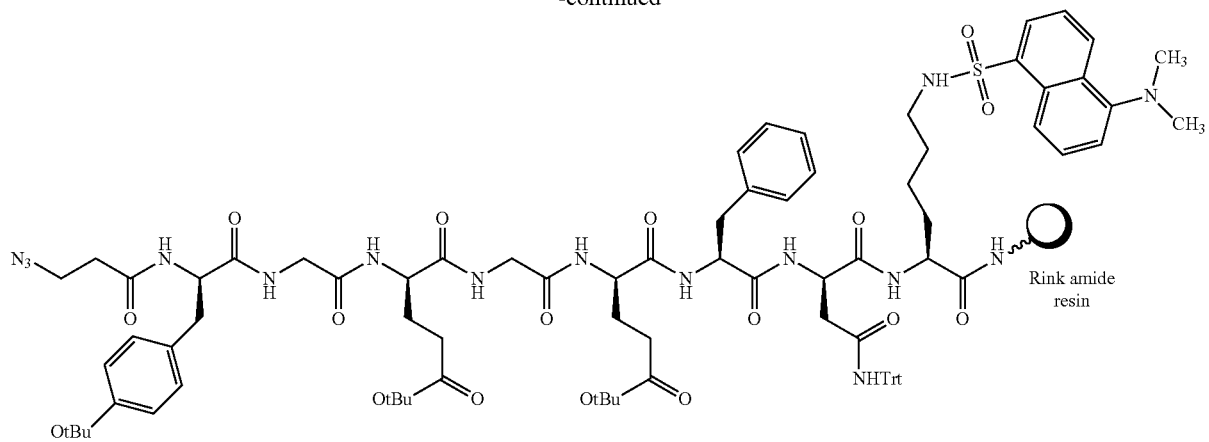

The ODN-peptide conjugates were purified using HPLC, eluted at 65%-95% B depending on peptide sequence.

TABLE 5

Peptide sequences used for preparing different oligonucleotide-peptide conjugates

| Peptide | Peptide Sequence | Oligonucleotide-Peptide Conjugate | |
|---|---|---|---|
| 1 | $N_3$—$(CH_2)_3$-I-E-A-D-K(dansyl)-G-I-D | ODN56-P1 | (Seq. ID. 19) |
| 2 | $N_3$—$(CH_2)_3$-K(dansyl)-F-D-S-E-F-D-S-E | ODN56-P2 | (Seq. ID. 5) |
| 3 | $N_3$—$(CH_2)_3$-K(dansyl)-S-T-G-V-S-T-G-V | ODN56-P3 | (Seq. ID. 6) |
| 4 | $N_3$—$(CH_2)_3$-S-T-A-F-A-Y-G-K(dansyl) | ODN56-P4 | (Seq. ID. 20) |
| 5 | $N_3$—$(CH_2)_3$-Y-G-E-G-E-F-N-K(dansyl) | ODN56-P5 | (Seq. ID. 7) |

ODN-56-P1: yield: 30%. MALDI-TOF MS (m/z): calcd. 11020. found 11011.

ODN-56-P2: yield: 48%. MALDI-TOF MS (m/z): calcd. 10345. found 10376 (M+Na).

ODN-56-P3: yield: 14%. MALDI-TOF MS (m/z): calcd. 10270. found 10319 (M+2Na).

ODN-56-P4: yield: 30%. MALDI-TOF MS (m/z): calcd. 10242.6. found 10247.3.

ODN-56-P5: yield: 55%. MALDI-TOF MS (m/z): calcd. 10597.69. found 10578.4.

Example 17

Figure 22B:
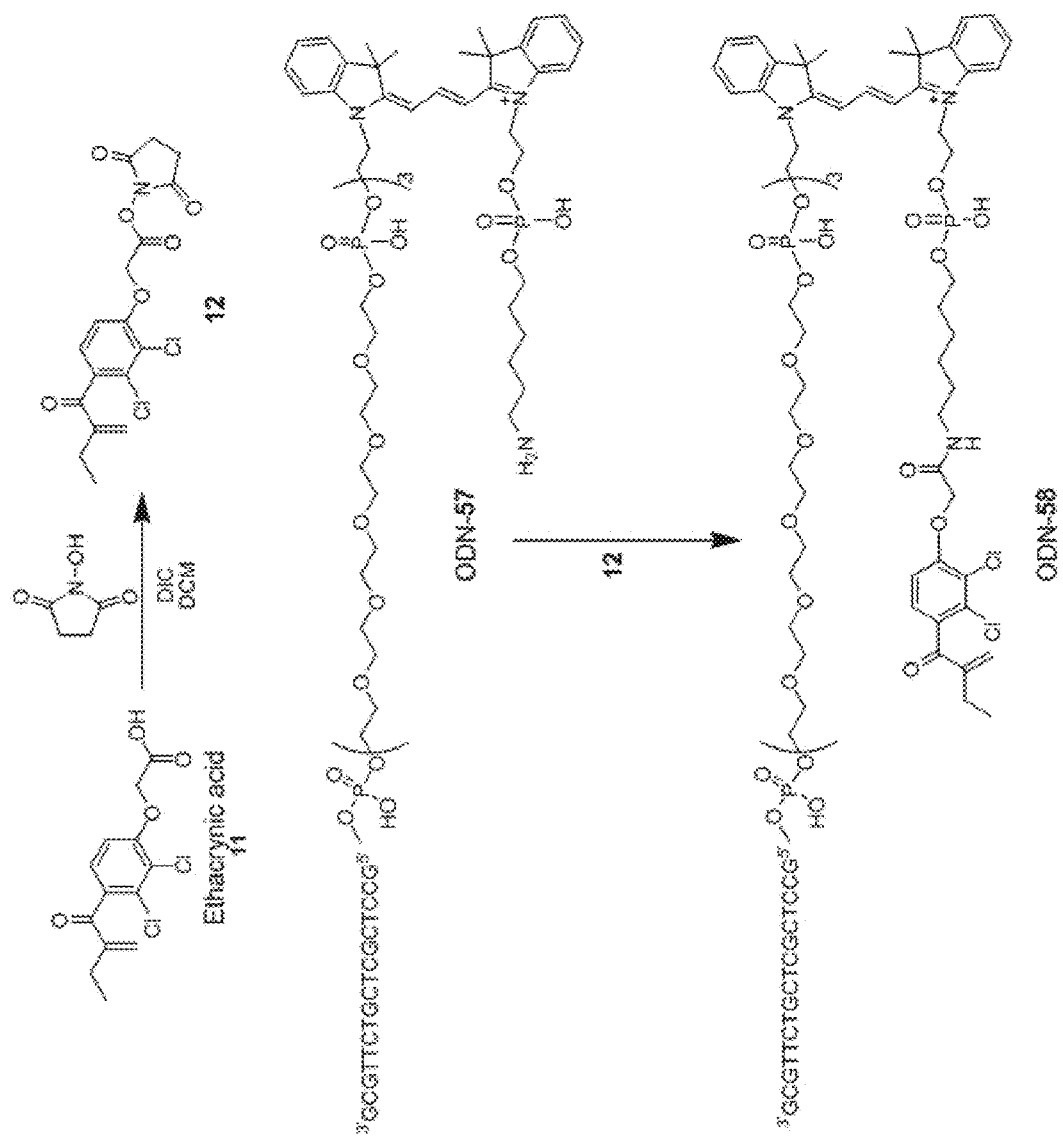

Synthesis of Selective ODN-58-(FIG. 22B)

Synthesis of ODN-58. The amine modified ODN-57 (250 nmol)[ODN-57 prepared by automated DNA synthesizer using the suitable phosphoamidite] was dissolved in 80 μl milli-Q water. Then 40 μl of $Na_2CO_3/NaHCO_3$ buffer (1M, pH 8.75) was added to maintain basic conditions of the reaction. The NHS-ester of ethacrynic acid 12 (see below) (10 mg, 25 μmol) in DMSO (40 μl) was added and the mixture was stirred overnight. Reaction progress was monitored using HPLC. The sediment was removed by centrifugation and then milli-Q water (1 mL) was added and the sample was lyophilized. The oligonucleotide was re-suspended in 300 μL, milli-Q water and desalted using MicroSpin G-25 columns according to the manufacturer's instructions (GE Healthcare). The HPLC analysis of the product showed minor traces of ODN-57 (~11% peak area, eluted at 5% B) and the product as a major peak (89% peak area, eluted at 30-35% B). MALDI-TOF MS (m/z): calcd. 7134.05. found 7134.67, 7187.5 (M+2Na).

NHS-Ester of Ethacrynic Acid (12)

Ethacrynic acid (11) (0.9 g, 3 mmol) was suspended in dry DCM, and N-hydroxysuccinimide (0.42 g, 3.6 mmol) and DIC (465 μl, 3 mmol) were added to the solution. The reaction mixture was stirred overnight and TLC (3% MeOH in DCM) was used to monitor the reaction progress. The reaction mixture was washed with HCl (0.1 N) and brine. The product was purified by combiflash using silica gel column chromatography (eluent: 2% MeOH in DCM). Yield: 36%. $^1$H NMR ($CDCl_3$, 300 MHz): δ 2.49 (t, J=3.0 Hz, 1H); 2.57 (t, J=3.0 Hz, 2H); 2.93 (s, 4H); 4.83 (d, J=2.0 Hz, 4H); 4.89 (d, J=3.0 Hz, 2H); 7.57 (s, 2H). ES-MS (m/z): calcd. 400.21. found 400.16, 422.10 (M+Na), 823.14 (2M+Na).

Example 18

GST Kinetic Measurements of ODN-57 and ODN-58

The GST activity was measured spectrophotometrically at 25° C. using duplicate samples of chloro-2,4-dinitrobenzene (CDNB) and GSH as substrates, in phosphate buffer (50 μl, 1 M, pH 6.5). In a typical experiment, GST, GSH, and ODN were incubated for 10 min and then CDNB was added and formation of S-(2,4-dinitrophenyl)-glutathione was monitored using the plate reader at λ=340 nm Concentration of GST-A1-1, GST-M1-1, GST-A2-2 and GST-P1-1 were 15 nM, 15 nM, 45 nM and 75 nM, respectively. The GSH concentration (1 mM) was kept constant and the concentration of CDNB was varied from 0.05 mM to 1.5 mM. The initial velocities were calculated by subtracting the spontaneous (non GST catalyzed) reaction of GSH and CDNB. In order to determine the $K_i$ and the inhibition model, similar assay was carried out using two concentrations (0.1 and 1 μM) of ODN-58. Control experiments were performed with ODN-57 (10 μM). The data was analyzed using Sigmaplot version 12.0 statistical software (Systat) and the values of $V_{max}$, $K_m$ and $K_i$ were determined from the experimental fitting of the data to partial competitive inhibition model.

Results demonstrated inhibition activity of ODN-58 as opposed to ODN-57-(not shown).

Example 19

Hybridization of Complementary DNA Strands

Hybridization of ODN-56 conjugates with the complementary sequence ODN-58 was performed as following: Solutions of the oligonucleotides in 50 µl phosphate buffer (100 mM, pH 7.4) were heated to 98° C. for 1 min, held at 90° C. for 2 min and then slowly cooled to 25° C. at a rate of 1° C./min. The hybridization was confirmed by gel electrophoresis using 5% agarose gel and ethidium bromide as intercalating agent. The gel ran at a constant voltage of 60 V for 1 hour. The gel was scanned by ChemiDoc XRC UV scanner and analyzed by Image Lab software.

Figure 23:
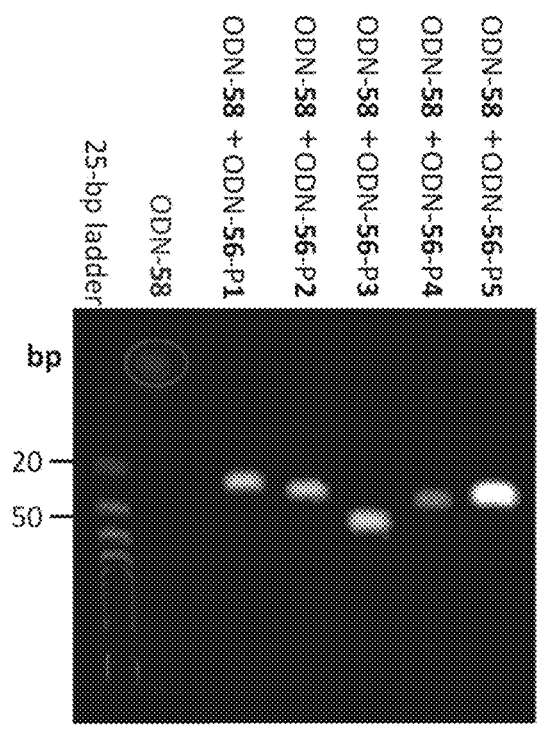
FIG. 23 depicts a gel electrophoresis migration pattern of double-stranded ODN-56-peptides and ODN-58.

The ODN-56 and ODN-EA (ODN-58) conjugates were hybridized in PBS buffer (0.1 M, pH 7.4). The mixtures were heated to 98° C. for 1 min, held at 90° C. for 2 min, and then cooled down slowly to 25° C. at a constant rate of −1° C./min. The hybridization products were analyzed by 5% agarose gel electrophoresis using ethidium bromide staining and visualized by autoradiography (FIG. 23). The formation of double-stranded ODNs was confirmed by the appearance of strong bands at ~20-base-pair (bp) position, which migrate slower than a single-stranded ODN-58. The lower intensity of control ODN-58 is due to the poor intercalation of ethidium bromide into a single strand.

Fluorescence Resonance Energy Transfer Measurements

Equimolar concentrations of each of the complementary DNA strands in 50 mM phosphate buffer, pH 7.4 were incubated at 95° C. for 5 mM and then slowly cooled to room temperature. All FRET experiments were carried out with single- or double-stranded DNA (1.5 nM, 60 µl) in phosphate buffer (50 Mm, pH 7.4). Fluorescence emission spectra were recorded using $\lambda_{ex}$=325 nm and excitation and emission slit widths of 20 nm in quartz cuvettes.

Example 20

GST Differentiation Assay

Following hybridization, five self-assembled synthetic receptors were arrayed on a microwell plate, and four GST isozymes, namely, A1-1, A2-2, M1-1, and P1-1 were incubated with each of the receptors.

50 µL of the receptor (50 nM) in phosphate buffer (50 mM, pH 7.4) was dispensed into 384-well microplates. The emission spectra and fluorescence intensity were recorded following excitation at 333 nm and using Ex: 325/15 and Em: 620/40 filters along with a 50% cut-off mirror. Then, 1 µL of GST isoform (200 nM) was added to the appropriate wells, incubated for 30 min at room temperature, and the fluorescence was recorded again. The fluorescence intensity from triplicate samples was averaged.

Figure 24:
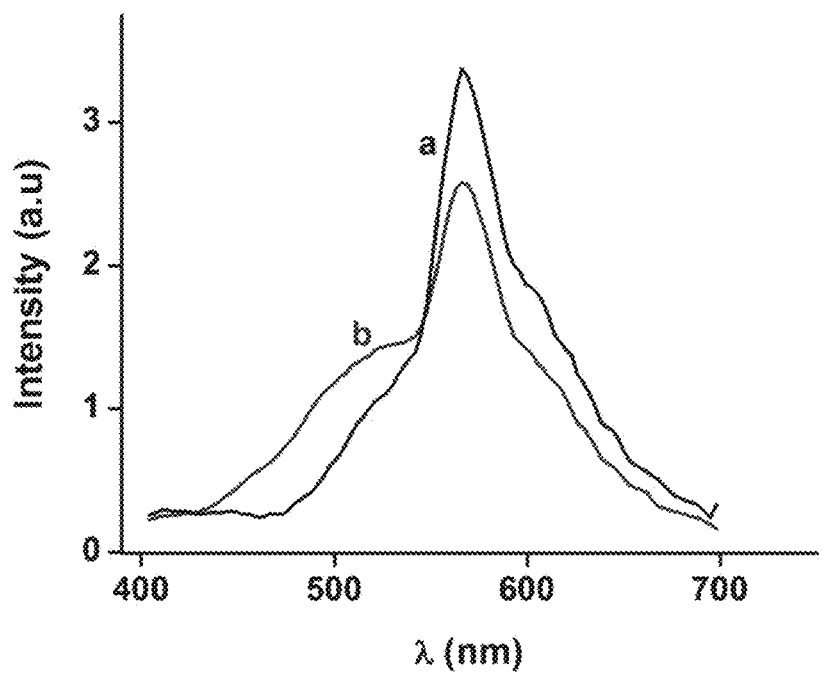
FIG. 24 depicts a fluorescence emission spectrum of ODN-56-P5 and ODN-58 (500 nM) (a) before and (b) after the addition of GST-A2-2 (800 nM) in phosphate buffer (50 mM, pH 7.4).
Figure 25:
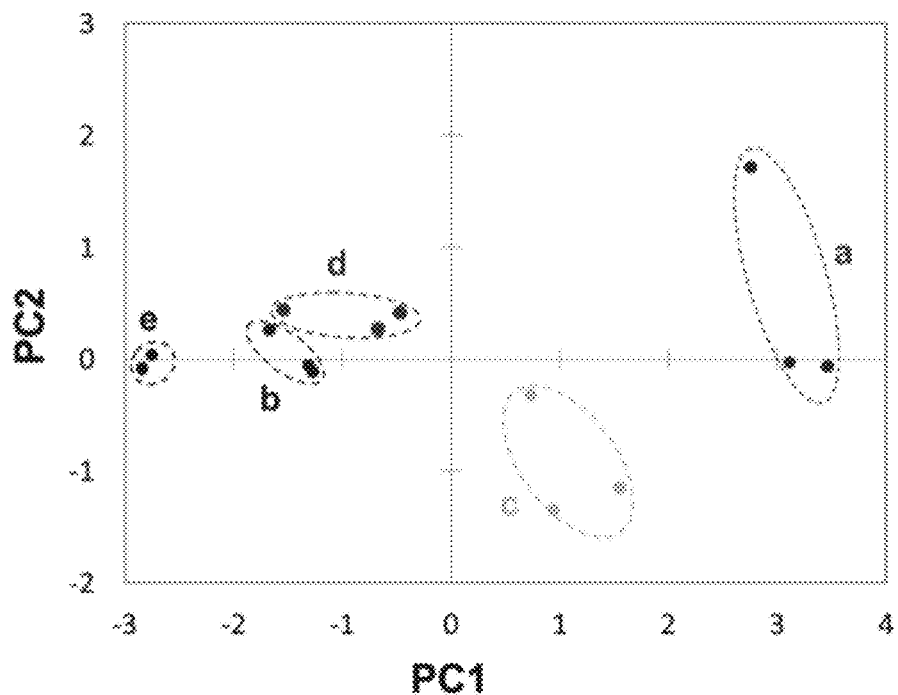
FIG. 25 depicts PCA mapping of the emission patterns generated by the self-assembled synthetic receptors ODN- 56 (P1-P5) and ODN-58 (50 nM) (a) GST-A1-A, (b) GST-A2-2, (c) GST-M1-1, (d) GST-P1-1, and (e) none.

FIG. 24 shows a representative emission spectrum of ODN-56-P5 and ODN-58 prior to and after the addition of GST-A2-2. Interaction with the protein induced a change in the emissions of both dansyl and Cy3 Similarly, emission spectra were recorded from all wells, and the optical patterns resulting from variations in Cy3 emission intensities were analyzed using principal component analysis (PCA). The PCA plot confirms the ability of the system to differentiate between structurally related proteins (FIG. 25).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An oligodeoxyribose nucleotide (ODN) derivatives duplex, which consists of
   a first ODN derivative comprising a first ODN sequence, at least one selective protein binder and a donor or acceptor; and
   a second ODN derivative comprising a second ODN sequence, which is complementary to said first ODN sequence, at least one non-selective protein surface binder and a donor or acceptor;
   wherein if one ODN derivative comprises a donor, the other one comprises an acceptor,
   at least one of the donor or acceptor is a fluorophore; and
   wherein said non-selective protein surface binder comprises a peptide tripod, represented by the structure of formula A:

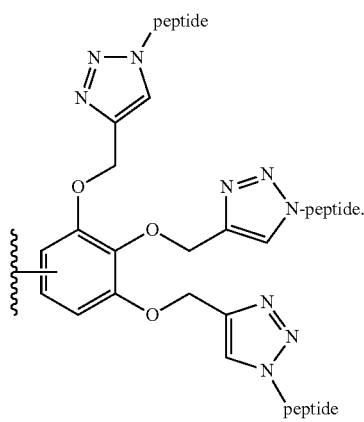

A

2. The oligodeoxyribose nucleotide (ODN) derivatives duplex of claim 1, wherein said selective protein binder is marimastat, ethacrynic acid (EA), bis ethacrynic acid, Ni-nitrilotriacetic acid (Ni-NTA), bis-Ni-NTA, tris-Ni-NTA, PDGF-BB aptamer, heparin derivative, FGF aptamer, or estrogen.

3. The oligodeoxyribose nucleotide (ODN) derivatives duplex of claim 1, wherein "peptide" is an amino acid sequence or an amino acid sequence connected to a linker.

4. The oligodeoxyribose nucleotide (ODN) derivatives duplex according to claim 3, wherein said linker is a $C_1$-$C_6$ alkyl.

5. The oligodeoxyribose nucleotide (ODN) derivatives according to claim 1, wherein said donor or acceptor is fluorescein (6-FAM), Cy3, nile red, rhodamine, dansyl, dabcyl, perylene, fluorenyl, coumarin, 7-methoxycoumarin or Cy5.

6. The oligodeoxyribose nucleotide (ODN) derivatives duplex according to claim 1, wherein said first ODN derivative is represented by the structure of formula IA, IB or IC:

$$ODN1\text{-}X^2\text{—}Y\text{—}X^1\text{—}(R^1)_k \quad (IA);$$

$$Y\text{—}X^2\text{—}ODN1\text{-}X^1\text{—}(R^1)_k \quad (IB);$$

$$ODN1\text{-}X^2\text{—}R^1\text{—}X^1\text{—}(Y)_k \quad (IC);$$

wherein
ODN 1 is a first ODN sequence;
$X^1$ and $X^2$ are each independently a linker or a bond, wherein said linker comprises at least one moiety selected from: $C_1$-$C_{20}$ alkyl, $C_1$-$C_{20}$ alkylether, $C_1$-$C_{20}$ alkylamide, $C_1$-$C_{20}$ alkylphsophate, $C_1$-$C_{20}$ alkyl-NH, $C_1$-$C_{20}$ alkyl-O, $C_1$-$C_{20}$ alkyl-diamide, phosphate, $C_1$-$C_{20}$ alkylamine, NH, O, PEG, triazole, and NHC(O); wherein alkyl is optionally substituted, wherein substitutions include one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol and thioalkyl;
Y is a donor or acceptor;
k is an integer between 1 and 5; and
$R^1$ is a selective protein binder.

7. The oligodeoxyribose nucleotide (ODN) derivatives duplex according to claim 1, wherein said second ODN derivative is represented by the structure of formula IIA, IIB or IIC:

$$ODN2\text{-}X^{2'}\text{—}Y'\text{—}X^{1'}\text{—}R^{1'} \quad (IIA);$$

$$Y'\text{—}X^{2'}\text{-}ODN2\text{-}X^{1'}\text{—}R^{1'} \quad (IIB);$$

$$ODN2\text{-}X^{2'}\text{—}R^{1'}\text{—}(X^{1'}\text{—}Y')_{k'} \quad (IIC);$$

wherein
ODN2 is a second ODN sequence;
$X^{1'}$ and $X^{2'}$ are each independently a linker or a bond, wherein said linker comprises at least one moiety selected from: $C_1$-$C_{20}$ alkyl, $C_1$-$C_{20}$ alkylether, $C_1$-$C_{20}$ alkylamide, $C_1$-$C_{20}$ alkylphsophate, $C_1$-$C_{20}$ alkyl-NH, $C_1$-$C_{20}$ alkyl-O, $C_1$-$C_{20}$ alkyl-diamide, phosphate, $C_1$-$C_{20}$ alkylamine, NH, O, PEG, triazole, and NHC(O); wherein alkyl is optionally substituted, wherein substitutions include one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol and thioalkyl;
Y' is a donor or acceptor;
k' is an integer between 1 and 5; and
$R^{1'}$ is a non-selective protein surface binder.

8. The oligodeoxyribose nucleotide (ODN) derivatives duplex according to claim 6, wherein said first ODN derivative of formula IA is represented by the structure of formula III:

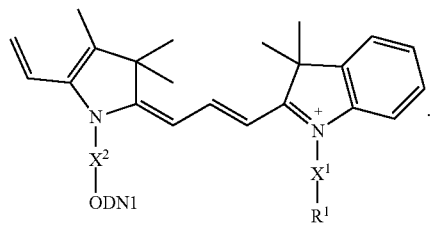

III

9. The oligodeoxyribose nucleotide (ODN) derivatives of claim 8, wherein said first ODN derivative is represented by the structure of formula ODN-58:

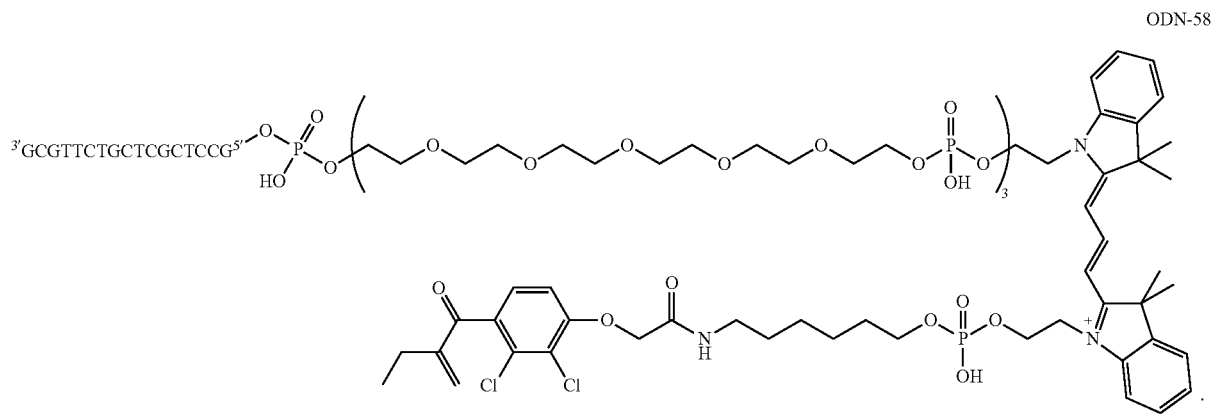

10. The oligodeoxyribose nucleotide (ODN) derivatives of claim 8, wherein said first ODN derivative is represented by the structure of formula ODN-20:

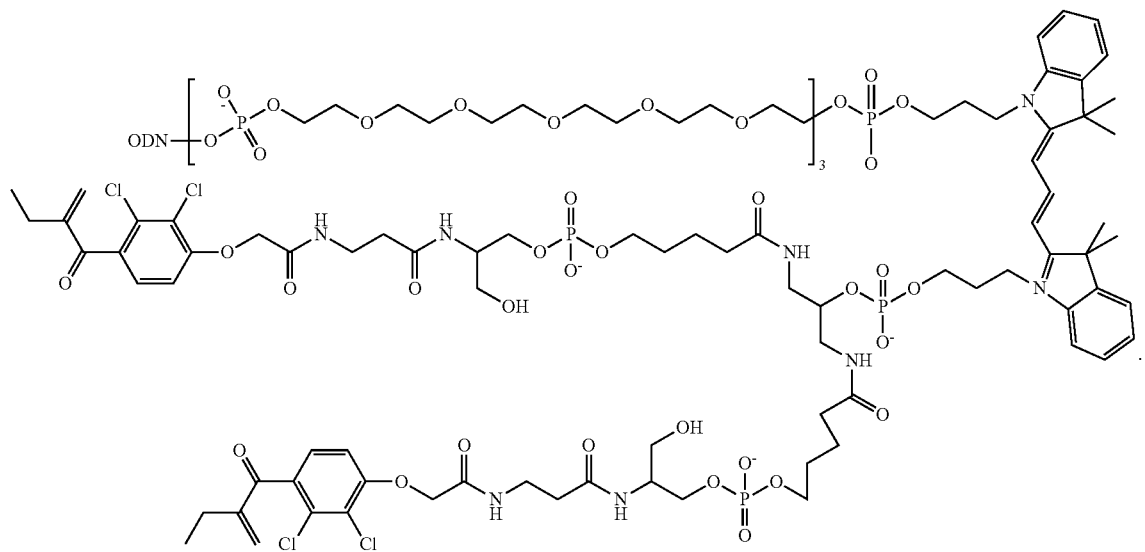

11. The oligodeoxyribose nucleotide (ODN) derivatives of claim 6, wherein said first ODN derivative of formula IB is represented by the structure of formula ODN-49, ODN-51 or ODN-53:

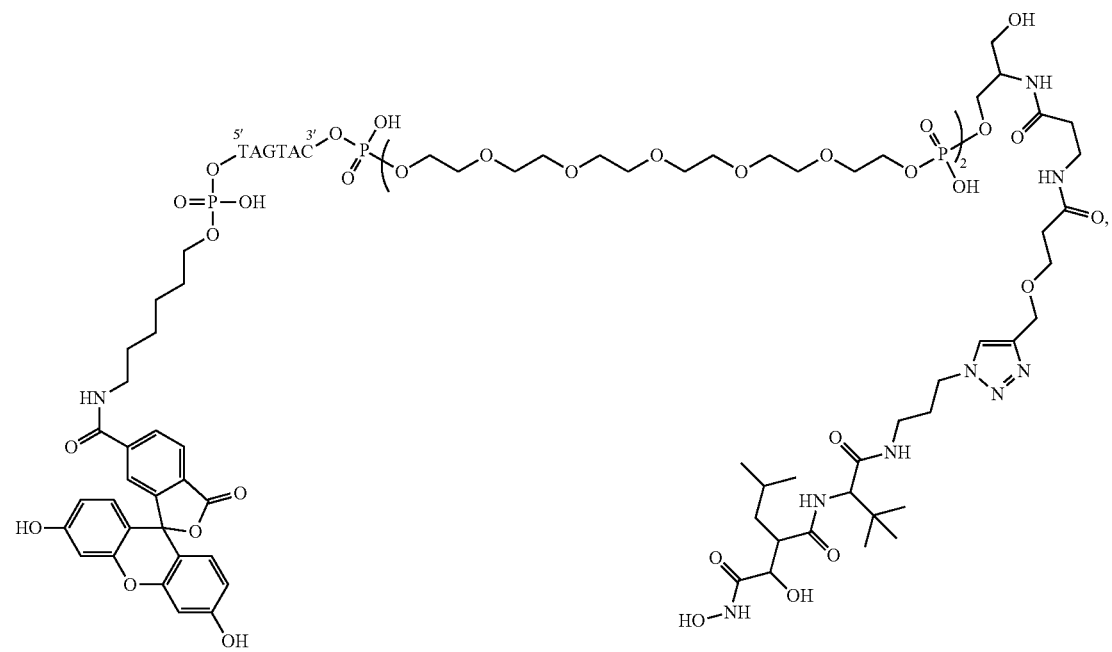
ODN-49
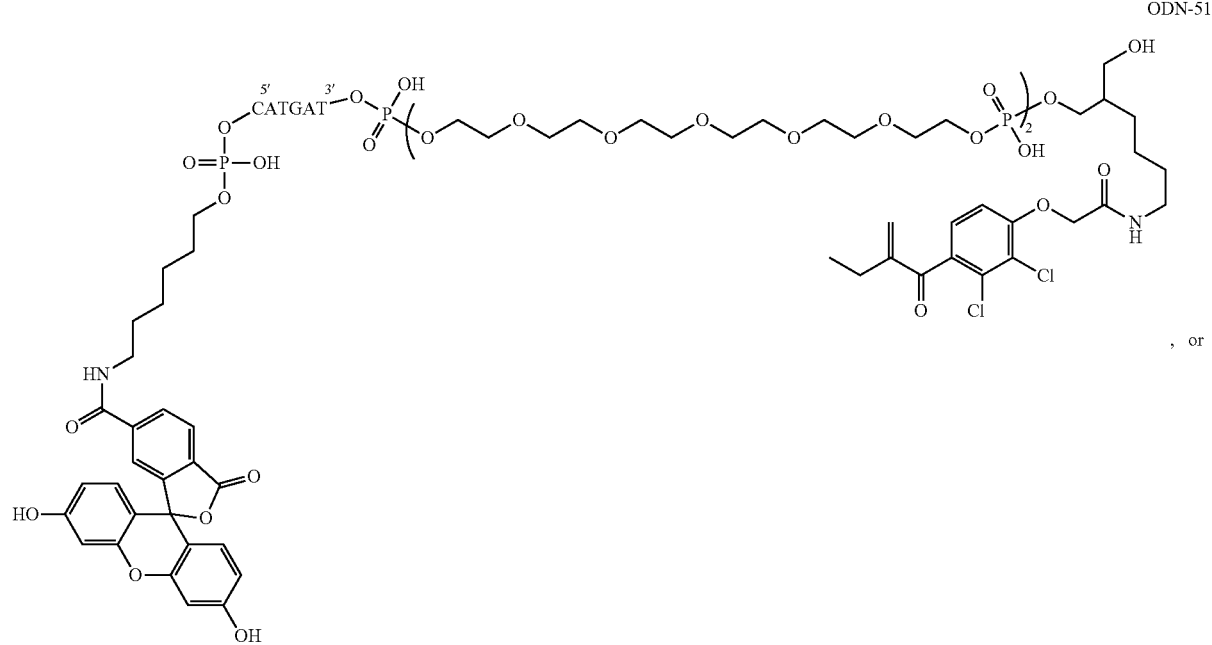
ODN-51
, or

-continued

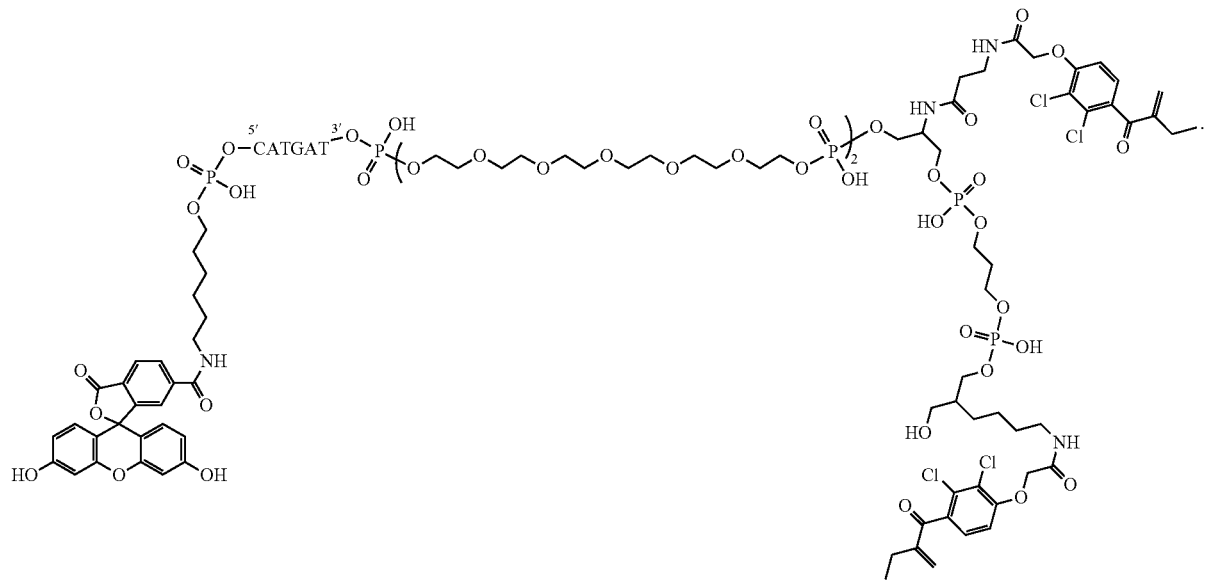

ODN-53

12. The oligodeoxyribose nucleotide (ODN) derivatives of claim 7, wherein said second ODN derivative of formula IIA is represented by the structure of formula IV:

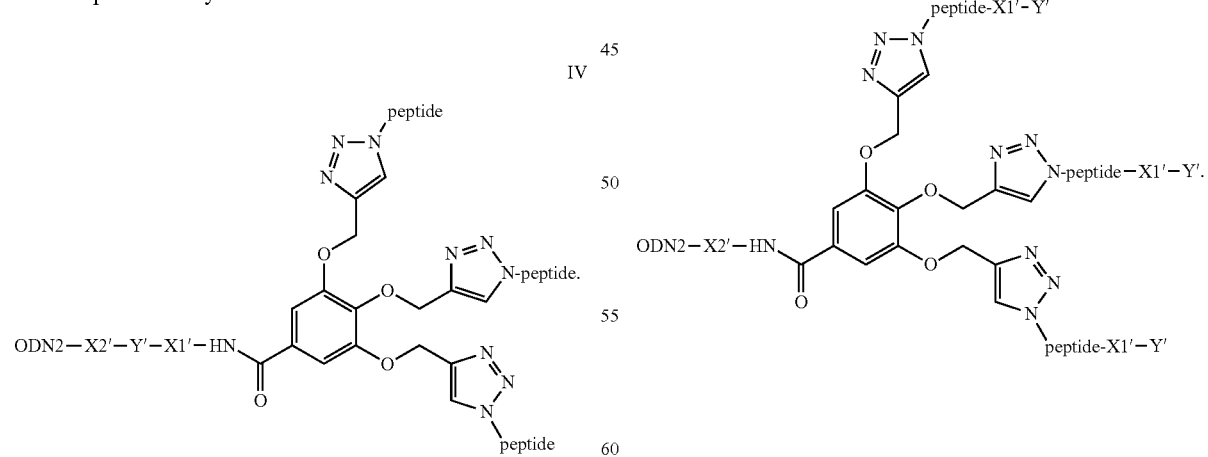

13. The oligodeoxyribose nucleotide (ODN) derivatives of claim 7, wherein said second ODN derivative of formula IIC is represented by the structure of formula V:

14. The oligodeoxyribose nucleotide (ODN) derivatives of claim 7, wherein said second ODN derivative of formula IIB is represented by the structure of formula ODN-39:

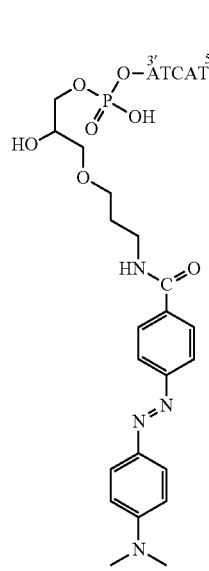
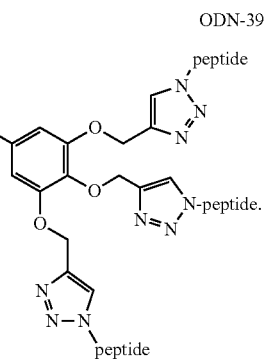
15. The oligodeoxyribose nucleotide (ODN) derivatives of claim 7, wherein said second ODN derivative of IIC is represented by the structure of formula ODN-56:
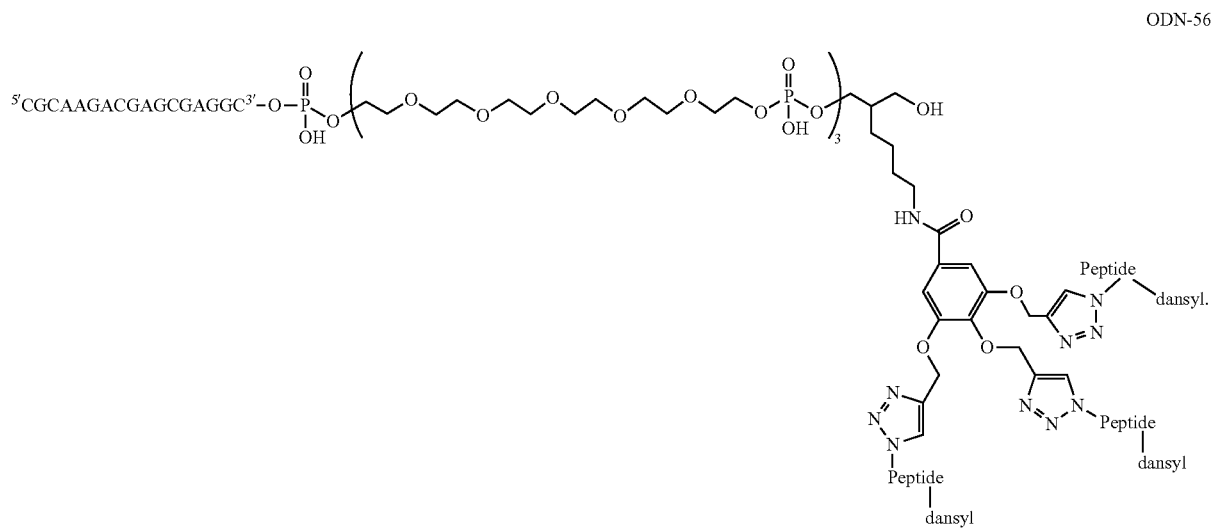
16. The oligodeoxyribose nucleotide (ODN) derivatives of claim 7, wherein said second ODN derivative of IIC is represented by the structure of formula ODN-5, ODN-6, ODN-7, ODN-8 and/or ODN-9:

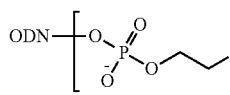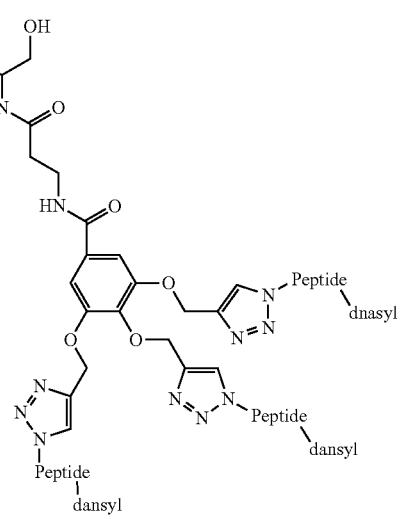

wherein
the peptide of ODN-5 is $(CH_2)_3$—Seq. ID. 5, the peptide of ODN-6 is $(CH_2)_3$—Seq. ID. 6,
the peptide of ODN-7 is $(CH_2)_3$—Seq. ID. 7, the peptide of ODN-8 is $(CH_2)_3$—Seq. ID. 8
and the peptide of ODN-9 is $(CH_2)_3$—Seq. ID. 9; and wherein solvatochromic dansyl group is covalently attached to K residue in all sequences.

17. The oligodeoxyribose nucleotide (ODN) derivatives duplex of claim 1, wherein said first ODN derivative is represented by the structure of formula IIA, IIIB or IIIC:

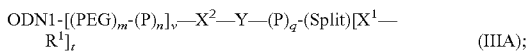 (IIIA);

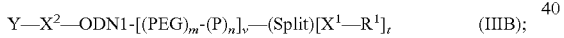 (IIIB);

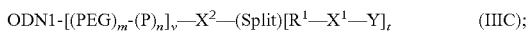 (IIIC);

wherein
ODN1 is a first oligodeoxyribose nucleotide sequence;
$X^1$ and $X^2$ are each independently a linker or a bond, wherein each of said linkers comprises at least one moiety selected from: $C_1$-$C_{20}$ alkyl, $C_1$-$C_{20}$ alkyl-NH, $C_1$-$C_{20}$ alkylether-NH, $C_1$-$C_{20}$ alkylether, $C_1$-$C_{20}$ alkylamide, $C_1$-$C_{20}$ alkyl-diamide, $C_1$-$C_{20}$ alkyl-O, $C_1$-$C_{20}$ alkylamine, phosphate, NH, O, triazole, and NHC(O); wherein alkyl is optionally substituted, wherein substitutions include one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol and thioalkyl;
each P is independently $PO_3$, $PO_2OH$, $PO(OH)_2$, $PO_4$, $PO_3OH$ or $PO_2(OH)_2$;
n and q are each 0 or 1;
PEG is $OCH_2CH_2$;
m is an integer between 0 and 10;
v is an integer between 1 and 10;
Split is C, CH, $CH_2$—C, $CH_2$—CH or absent;
t is 1, 2 or 3; wherein if Split is C or $CH_2$—C then t is 3, if Split is CH or $CH_2$—CH then t is 2 and if Split is absent than t is 1;

Y is a donor or acceptor;
$R^1$ is a selective protein binder; and
wherein, if t is 2 or 3, then each of $X^1$, $R^1$, and Y can be same or different.

18. The oligodeoxyribose nucleotide (ODN) derivatives duplex of claim 17, wherein said second ODN derivative is represented by the structure of formula IVA, IVB or IVC:

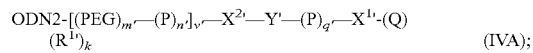 (IVA);

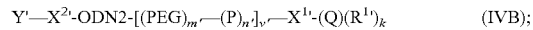 (IVB);

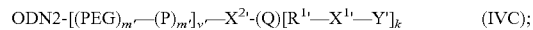 (IVC);

wherein
ODN2 is a second oligodeoxyribose nucleotide sequence;
$X^{1'}$ and $X^{2'}$ are each independently a linker or a bond, wherein each of said linkers comprises at least one moiety selected from: $C_1$-$C_{20}$ alkyl, $C_1$-$C_{20}$ alkyl-NH, $C_1$-$C_{20}$ alkylether-NH, $C_1$-$C_{20}$ alkylether, $C_1$-$C_{20}$ alkylamide, $C_1$-$C_{20}$ alkyl-diamide, $C_1$-$C_{20}$ alkyl-O, $C_1$-$C_{20}$ alkylamine, phosphate, NH, O, triazole, and NHC(O); wherein alkyl is optionally substituted, wherein substitutions include one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol and thioalkyl;
each P is independently $PO_3$, $PO_2OH$, $PO(OH)$, $PO_4$, $PO_3OH$ or $PO_2(OH)_2$;
n' and q' are each 0 or 1;
each PEG is $OCH_2CH_2$;
m' is an integer between 0 and 10;
v' is an integer between 1 and 10;
Q is either absent, alkyl triazole or represented by the structure of formula B:

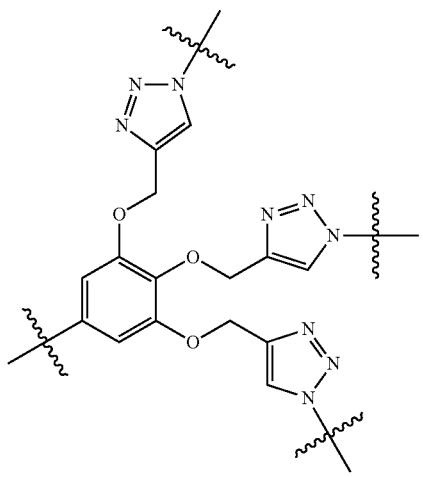

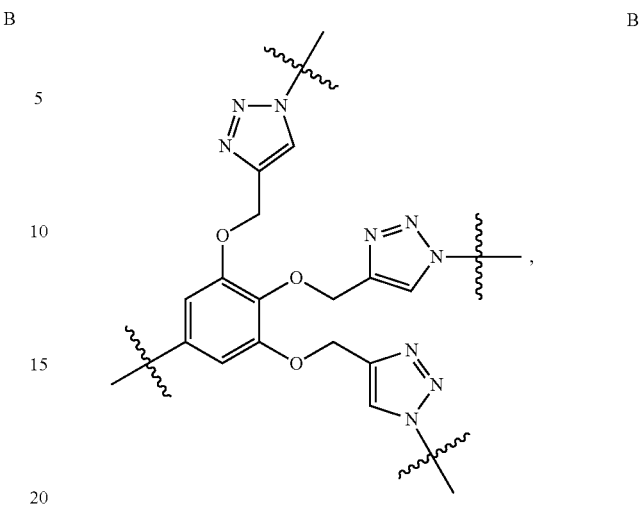

k is either 1 or 3; wherein if Q is B then k is 3, otherwise k is 1;
Y' is a donor or acceptor; and
R¹' is a peptide.

19. The oligodeoxyribose nucleotide (ODN) derivatives duplex of claim 17, wherein n is 1, m is 6, v is 1, 2 or 3, $X^2$ is a bond, NH-alkyl or $C_1$-$C_{20}$ alkyl, Y is Cy3 or FAM, q is 1, Split is absent, CH or $CH_2CH$, and each $X^1$ is independently a substituted or unsubstituted $C_1$-$C_{20}$ alkyl; a substituted or unsubstituted $C_1$-$C_{20}$ alkyl-NH; a substituted or unsubstituted $C_1$-$C_{20}$ amide-alkyl-NH; substituted or unsubstituted $C_1$-$C_{20}$ alkyl ether, substituted or unsubstituted $C_1$-$C_{20}$ alkyl ether-alkylphosphate, substituted or unsubstituted $C_1$-$C_{20}$ alkyl di-amide-alkylether-triazole-alkyl, substituted or unsubstituted $C_1$-$C_{20}$ alkyl di-amide, substituted or unsubstituted alkyl-phosphate-alkyl-phosphate-alkyl-NH—, substituted or unsubstituted alkylamide-alkyl-phosphate-alkylamide-alkyl-NH—; wherein said substitutions are selected from hydroxyl, methylene-hydroxyl, halogen, CN, $NO_2$, linear or branched $C_1$-$C_6$ alkyl, linear or branched $C_1$-$C_6$ alkoxy, linear or branched $C_1$-$C_6$ haloalkyl, or any combination thereof, $R^1$ is EA or Marimastat, and t is 1 or 2.

20. The oligodeoxyribose nucleotide (ODN) derivatives duplex of claim 18, wherein Y' is dabcyl or dansyl, $X^{2'}$ is a bond, a substituted or unsubstituted $C_1$-$C_{20}$ alkylether-NH, a substituted or unsubstituted $C_1$-$C_{20}$ alkyl-NH, a substituted $C_1$-$C_{20}$ alkyl di-amide, or a substituted or unsubstituted $C_1$-$C_{20}$ alkylamide, n' is 1, m' is 6, v' is 1, 2 or 3, $X^{1'}$ is a bond, a substituted or unsubstituted $C_1$-$C_{20}$ alkylamide, a substituted or unsubstituted $C_1$-$C_{20}$ alkyl-NH, Q is represented by formula B:

and k is 3.

21. A method of differentiating between proteins and protein isoforms in a biological medium comprising:
   (i) incubating an array of complementary two oligodeoxyribose nucleotide (GDN) derivatives duplexes with a biological medium comprising said proteins and/or protein isoforms;
   wherein each of said duplexes is the oligodeoxyribose nucleotide (ODN) derivatives duplex of claim 1, wherein said "peptide" is different for each ODN derivative duplex;
   wherein binding said protein and/or protein isoforms with each of said duplexes results in a conformational change of said duplex and thereby to a unique optical signature for each duplex; and
   (ii) measuring said optical signature obtained by said binding of step (1); and thereby, differentiating between proteins and/or protein isoforms in said biological medium.

22. A method of diagnosing a disease or disorder in a subject, wherein said diagnosis comprises detection of a protein biomarker; said method comprises:
   (i) collecting a biological sample from a subject;
   (ii) optionally isolating components from said biological sample;
   (iii) incubating an array of complementary oligodeoxyribose nucleotide (ODN) derivatives duplexes with said biological sample;
   wherein each of said duplexes is the oligodeoxyribose nucleotide (ODN) derivatives duplex of claim 1, wherein said "peptide" is different for each ODN derivative duplex;
   wherein binding of said protein biomarker with each of said duplexes results in a conformational change of said duplex and thereby to a unique optical signature for each duplex;
   (iv) measuring said optical signature obtained by said binding of step (iii); and
   (v) identifying a protein biomarker in said sample based on the measurement of a unique optical signature, which characterizes the specific protein biomarker, wherein said protein biomarker being characteristic of a disease or disorder; thereby, diagnosing a disease or disorder in a subject.

23. The methods of claim 22, wherein said protein is matrix metalloproteases (MMPs) protein and its isoforms, glutathione S-Transferase (GSTs) protein and its isoforms, platelet derived growth factor, Histidine-tag proteins, estrogen receptor, or fibroblast growth factor (FGF).

24. The methods of claim 22, wherein said selective protein binder is marimastat, ethacrynic acid, bis ethacrynic acid, Ni-nitrilotriacetic acid (Ni-NTA), bis-Ni-NTA, tris-Ni-NTA, PDGF-BB, heparin or estrogen which is selective to matrix metalloproteases (MMPs) protein.

25. The method of claim 22, wherein said unique optical signature is a fluorescence pattern of said binding said duplex with said protein; and said fluorescence pattern is obtained following irradiation of said donor of said ODN derivative duplex at a wavelength that causes the excitation of said donor species.

26. The method of claim 22, wherein said fluorescence pattern indicates that said protein is present in said biological medium.

27. The method of claim 22, wherein said biological medium is blood, tissue, serum or urine.

28. The method of claim 22, wherein said disease or disorder is breast cancer, lung cancer, colorectal cancer, pancreatic cancer, bladder cancer, ovarian cancer, prostate cancer, brain cancer, clear cell renal cell carcinoma, gastric cancer, renal tubular injury or any combination thereof.

29. The method of claim 21, wherein said protein is glutathione S-Transferase (GSTs), wherein said GST is a biomarker for monitoring graft failure or regeneration following living donor liver transplantation.

30. A protein sensor, said sensor comprises an array of synthetic receptors, wherein each of said synthetic receptors comprises the ODN derivative duplex of claim 1, and wherein said synthetic receptors differ from each other in their non-selective protein surface binder.

31. The sensor of claim 30, wherein the non-selective protein surface binder comprises a peptide tripod, represented by the structure of formula A:

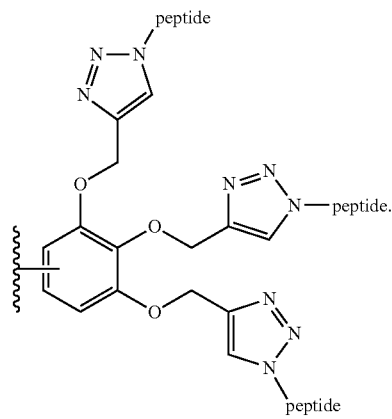

32. A protein sensor, said sensor comprises a non-selective protein surface binder represented by the structure of formula A:

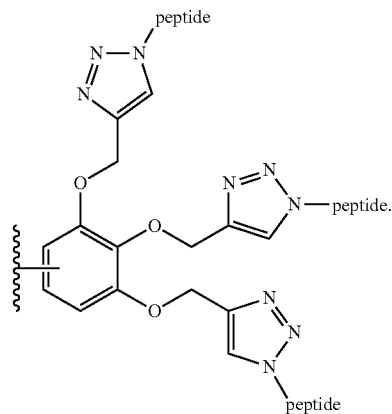

33. The protein sensor of claim 32, further comprising a selective protein binder.

34. The protein sensor of claim 33, further comprising a fluorophore.

35. The protein sensor of claim 33, further comprising a donor and an acceptor, wherein at least one of the donor or acceptor is a fluorophore.

36. The protein sensor of claim 33, wherein each donor or acceptor is attached to or in close proximity to one of the selective and non-selective binders of said sensor.

* * * * *